United States Patent [19]

Ohmori et al.

[11] Patent Number: 5,650,428
[45] Date of Patent: Jul. 22, 1997

[54] ARYLSULFONAMIDE DERIVATIVE AND PHARMACEUTICAL COMPOSITIONS AND USE THEREOF

[75] Inventors: Masayuki Ohmori; Shin-Ichi Sawamura; Takehiro Yamamoto; Yoshiko Kawada; Shihoko Maeda; Takeshi Yago; Akihiro Nakajima; Masatsugu Mizuguchi; Yasuo Miyoshi, all of Tokyo, Japan

[73] Assignee: NKK Corporation, Tokyo, Japan

[21] Appl. No.: 392,793

[22] PCT Filed: Jul. 1, 1994

[86] PCT No.: PCT/JP94/01073

§ 371 Date: Feb. 28, 1995

§ 102(e) Date: Feb. 28, 1995

[87] PCT Pub. No.: WO95/01332

PCT Pub. Date: Jan. 12, 1995

[30]    Foreign Application Priority Data

| Jul. 1, 1993 | [JP] | Japan | 5-189236 |
| Dec. 27, 1993 | [JP] | Japan | 5-351660 |
| Mar. 11, 1994 | [JP] | Japan | 6-067792 |
| Mar. 14, 1994 | [JP] | Japan | 6-069031 |

[51] Int. Cl.$^6$ ............ G07D 209/20; G07D 309/12; A61K 31/35; A61K 31/405
[52] U.S. Cl. ............ 514/419; 514/351; 514/398; 514/460; 514/538; 514/562; 548/320.1; 548/495; 546/293; 549/419; 560/16; 562/426
[58] Field of Search ............ 560/16; 548/320.1, 548/495; 514/538, 460, 398, 351, 562; 546/293; 562/426; 549/419

[56]        References Cited

PUBLICATIONS

Chemical Abstracts, vol. 97, abstract 6774e (1982).
Chemical Abstracts, vol. 120, abstract 299279r (1994).

Primary Examiner—David B. Springer
Attorney, Agent, or Firm—Sughrue, Mion, Zinn, Macpeak & Seas

[57]        ABSTRACT

An arylsulfonamide derivative of the formula (I):

$$R^1-SO_2NH-(CH_2)_p-\underset{O}{\overset{}{\underset{\|}{C}}}\begin{matrix}(CH_2)_n-R^2\\ \\N-X-COO-R^3\\|\\H\end{matrix} \quad (I)$$

wherein $R^1$ is unsubstituted phenyl or naphthyl, or phenyl substituted by 1 to 3 same or different substituents selected from the group consisting of halogen, alkyl, nitro and alkoxy, $R^2$ is straight, branched, or branched cyclic alkyl with 1 to 15 carbon atoms, phenyl, phenyloxyl, phenyloxy substituted by one or more halogen atoms, cycloalkyl with 5 to 7 carbon atoms, indolyl, alkylthiol with 1 to 4 carbon atoms, hydroxyl, protected hydroxyl, imidazolyl, pyridyloxyl, or $—OSO_2R^4$, $R^4$ is straight or branched alkyl with 1 to 15 carbon atoms, or unsubstituted phenyl or thienyl, or phenyl or thienyl substituted by 1 to 3 same or different substituents of halogen, alkyl, nitro and alkoxy, $R^3$ is hydrogen or straight or branched alkyl with 1 to 20 carbon atoms, n is an integer of 0 to 10, p is an integer of 0 to 10, X is a group of the formula —$(CH_2)_m$-A-$(CH_2)_q$-, m and q are independently an integer of 0 to 8, and A is a direct bond or phenylene, or a salt thereof; a process for manufacture thereof and a pharmaceutical composition containing same.

The above compound exhibits thromboxane $A_2$ antagonism.

9 Claims, No Drawings

ARYLSULFONAMIDE DERIVATIVE AND PHARMACEUTICAL COMPOSITIONS AND USE THEREOF

TECHNICAL FIELD

The present invention relates to a novel arylsulfonamide derivative having antagonism specific to a thromboxane $A_2$ receptor and a pharmaceutical composition, particularly, a thromboxane $A_2$ antagonist, containing said arylsulfonamide derivative as an effective ingredient.

BACKGROUND ART

It is known that thromboxane $A_2$ (Tx$A_2$) is an autacoid synthesized in cells such as platelets and exhibits a strong platelet agglutination of platelets, constriction of smooth muscle or the like. Accordingly, it is suggested that a Tx$A_2$ receptor antagonist would be effective in the treatment and prevention of diseases relating to Tx$A_2$ action [Japanese Unexamined Patent Publication (Kokai) No. 4-257556, Japanese Examined Patent Publication (Kokoku) No. 57-35910 and so on]. As examples of such diseases, there may be mentioned cardiac infarction, cerebral infarction, pneumobstruction, thrombosis, renal insufficiency, gestational toxemia and asthma due to bronchoconstriction. Efficacy is expected in the treatment and prevention of various diseases as mentioned above, and thus, development of more excellent novel Tx$A_2$ receptor antagonists was desired.

DISCLOSURE OF INVENTION

Under the circumstances, the inventors of the present invention first analyzed and considered the three-dimensional structural elements of Tx$A_2$ and Tx$A_2$ receptor antagonists by means of the techniques of computer graphics and molecular force field calculation. Then, various compounds, which were designed using the techniques of computer graphics and molecular force field calculation, in view of the above results, were synthesized. Further, the physiological activities of various synthesized compounds were evaluated to find novel arylsulfonamide derivatives having Tx$A_2$ receptor antagonism, and the present invention was completed.

Accordingly, the present invention relates to an arylsulfonamide derivative of the general formula (I):

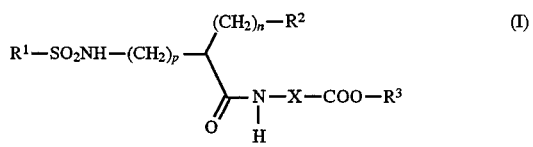

wherein $R^1$ is an unsubstituted phenyl or naphthyl group, or a phenyl group substituted by 1 to 3 (preferably 1 or 2) same or different substituents selected from the group consisting of a halogen atom, alkyl group (preferably straight or branched alkyl group with 1 to 10, more preferably 1 to 3 carbon atoms), nitro group and alkoxy group (preferably straight or branched alkoxy group with 1 to 10, more preferably 1 to 3 carbon atoms), $R^2$ is a straight, branched, or branched cyclic alkyl group with 1 to 15 (preferably 1 to 8) carbon atoms, phenyl, phenyloxyl group, phenyloxy group substituted by one or more halogen atoms, cycloalkyl group with 5 to 7 carbon atoms (preferably, cyclohexyl group), indolyl group (preferably, 3-indolyl group), alkylthiol group with 1 to 4 (preferably 1 to 2) carbon atoms, hydroxyl group, protected hydroxyl group (for example, tetrahydropyranyloxy, preferably 2-tetrahydropyranyloxy group), imidazolyl group (preferably, 1-imidazolyl group), pyridyloxyl group (preferably, 3-pyridyloxy group), or —$OSO_2R^4$ group. $R^4$ is a straight or branched alkyl group with 1 to 15 (preferably, 1 to 8, more preferably 1 to 3) carbon atoms, or unsubstituted phenyl or thienyl group, or a phenyl or thienyl group substituted by 1 to 3 same or different substituents selected from the group consisting of a halogen atom, alkyl group (preferably straight or branched alkyl group with 1 to 10, more preferably 1 to 3 carbon atoms), nitro group and alkoxy group (preferably straight or branched alkoxy group with 1 to 10, more preferably 1 to 3 carbon atoms), $R^3$ is a hydrogen atom or straight or branched alkyl group with 1 to 20 (preferably 1 to 5, more preferably 1 to 3) carbon atoms, n is an integer of 0 to 10 (preferably 0 to 2), p is an integer of 0 to 10 (preferably 0 or 1), X is a group of the general formula

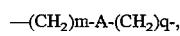

m and q are independently an integer of 0 to 8 (preferably 0 to 5), and A is a direct bond or phenylene group (that is, 1,2-, 1,3- or 1,4-phenylene group), or a salt thereof.

Further, the present invention relates to a pharmaceutical composition, particularly an antagonist to thromboxane $A_2$, characterized by containing an arylsulfonamide derivative of the above-mentioned general formula (I) or pharmaceutically acceptable salt thereof.

BEST MODE FOR CARRYING OUT THE INVENTION

In the present specification, the straight or branched alkyl group means, for example, methyl, ethyl, propyl, isopropyl, n-butyl, isobutyl, sec-butyl, t-butyl, n-pentyl, isopentyl, neopentyl, t-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-2-methylpropyl, or the like.

The branched cyclic alkyl group is, for example, an alkyl group with 1 to 9 carbon atoms substituted by a cycloalkyl group with 5 to 7 carbon atoms, for example, 1-cyclopentylmethyl, 2-cyclopentylethyl, 1-cyclohexylmethyl or 2-cyclohexylethyl group. The cycloalkyl group with 5–7 carbon atoms is cyclopentyl, cyclohexyl, or cycloheptyl group.

As the alkoxy group, there may be mentioned, for example, a straight or branched alkoxy group, such as, methoxy, ethoxy, n-propoxy, isopropoxy, n-butoxy, isobutoxy, t-butoxy, n-pentyloxy, n-hexanoxy, or the like. The alkylthio group is, for example, methylthiol or ethylthiol group. As the halogen atom, there may be mentioned, for example, fluorine, chlorine, bromine, or iodine atom.

The protected hydroxyl group is, for example, tetrahydropyranyloxy group.

In the above-mentioned general formula (i), phenyl or naphthyl group as the group $R^1$ may be unsubstituted or mono-, di-, or tri-substituted. The substituents may be the same or different.

The preferable compounds of the above-mentioned general formula (I) are the compounds wherein $R^1$ is an unsubstituted phenyl or naphthyl group, or a phenyl group substituted by 1 to 3 same or different substituents selected from the group consisting of a halogen atom, straight or branched alkyl group with 1 to 10 carbon atoms, nitro group and straight or branched alkoxy group with 1 to 10 carbon atoms, $R^2$ is a straight, branched or branched cyclic alkyl group with 1 to 8 carbon atoms, phenyl, phenyloxy, phenyloxy group substituted by one or more halogen atoms, cyclohexyl, indolyl, alkylthiol groups with 1 to 3 carbon atoms, hydroxyl, tetrahydropyranyloxy, imidazolyl, pyridyloxy or —$OSO_2R^4$ group, $R^4$ is a straight or branched alkyl group with 1 to 8 carbon atoms, $R^3$ is a hydrogen atom or straight or branched alkyl group with 1 to 5 carbon atoms, n is an integer of 0 to 2, p is 0 or 1, X is a group of the general formula

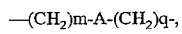

m and q are independently an integer of 0 to 5, and A is a direct bond or 1,2-, 1,3-, or 1,4-phenylene group.

Further, the preferable compounds of the above-mentioned general formula (I) are the compounds in which $R^1$ is an unsubstituted phenyl or naphthyl group or a phenyl group substituted by 1 or 2 same or different substituents selected from the groups consisting of a halogen atom, straight alkyl group with 1 to 2 carbon atoms, nitro group and straight alkoxy group with 1 to 2 carbon atoms, $R^2$ is a straight or branched alkyl group with 1 to 6 carbon atoms, phenyl, phenyloxy, phenyloxy group substituted by one or more halogen atoms, cyclohexyl, 3-indolyl, alkylthio group with 1 to 2 carbon atoms, hydroxyl, 2-tetrahydropyranyloxy, 1-imidazolyl, 3-pyridyloxy or —$OSO_2CH_3$ group, $R^3$ is a hydrogen atom or alkyl group with 1 to 3 carbon atoms, n is an integer of 0 to 2, p is 0 or 1, X is a group of the general formula

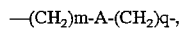

m and q are independently an integer of 0 to 5, and A is a direct bond or 1,3- or 1,4-phenylene group.

The compound of the formula (I) according to the present invention may be one of geometrical isomers, optical isomers or tautomers. One of the above isomers or a mixture thereof is involved in the scope of present invention.

The salts of the arylsulfonamide derivatives of the present invention are not particularly limited, but are preferably pharmaceutically acceptable salts. When the group $R^2$ is 1-imidazolyl or 3-pyridyloxy group in the general formula (I), an acid addition salt may be formed, and when the group $R^3$ is a hydrogen atom, a salt wherein the hydrogen atom is replaced by a metal ion or organic base may be formed.

Pharmaceutically acceptable acid addition salts are, for example, salts containing a pharmaceutically acceptable anion with organic and inorganic acid, such as hydrochloric, hydrobromic, sulfuric, sulfurous, phosphoric, phosphorous, acetic, maleic, fumaric, lactic, tataric, citric, gluconic, succinic, benzoic, or p-toluene sulfonic acid, and the like.

Preferable metal salts are salts of alkali metals such as lithium, sodium or potassium, or alkali earth metals such as calcium or magnesium.

Preferable salts of organic bases are salts of triethylamine, 2-aminobutane, tert-butylamine, diisopropylethylamine, n-butylmethylamine, n-butyldimethylamine, tri-n-butylamine, dicyclohexylamine, morpholine, N-methylmorpholine, tromethamine, or the like.

The arylsulfonamide derivative of the general formula (I) of the present invention may be prepared by various methods. A typical process of preparation will be explained hereinafter.

(1) A process wherein a sulfonylaminocarboxylic acid compound of the general formula (II):

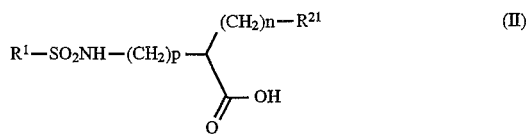

wherein $R^{21}$ is a straight, branched or branched cyclic alkyl group with 1 to 15 carbon atoms, phenyl group, cycloalkyl group with 5 to 7 carbon atoms, indolyl group, alkylthio group with 1 to 4 carbon atoms, protected hydroxyl group, or imidazolyl group, and $R^1$, n, and p have the same meanings as the above, is used as a starting material.

The sulfonylaminocarboxylic acid compound of the general formula (II) is reacted with an amino acid ester compound of the general formula (III):

wherein $R^{31}$ is a straight or branched alkyl group with 1–20 (preferably 1 to 5, more preferably 1 to 3) carbon atoms, and X has the same meaning as above, for example, in an appropriate solvent (for example, chloroform), in the presence of appropriate condensation agent (for example, pivaloyl chloride, 2-chloro-1-methylpyridinium iodide, N,N'-dicyclohexylcarbodiimide) and appropriate base (for example, triethylamine) to obtain an arylsulfonamide derivative of the general formula (I), wherein $R^2$ is the group $R^{21}$, $R^3$ is the group $R^{31}$, and then, the group $R^{21}$ and/or $R^{31}$ may be converted into another group $R^2$ and/or $R^3$ by a known method.

A sulfonylaminocarboxylic acid compound of the general formula (II) in which $R^{21}$ is a protected hydroxyl group may be prepared by protecting the OH group of the —$(CH_2)$n-OH group of the sulfonylaminocarboxylic acid compound of the general formula (IV):

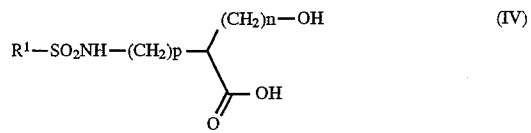

wherein $R^1$, n and p have the same meanings as the above. The OH group may be protected by a known method. For example, a sulfonylaminohydroxycarboxylic acid of the general formula (IV) may be treated with dihydropyran in an appropriate solvent (for example, chloroform) in the presence of an appropriate acid catalyst (for example, p-toluenesulfonic acid) to convert the OH group of the —$(CH_2)$n-OH group in the general formula (IV) to tetrahydropyranyl and obtain a sulfonylaminocarboxylic acid compound of the general formula (II) wherein $R^{21}$ is 2-tetrahydropyranyloxy group (hereinafter, sometimes referred to as OTHP). The resulting sulfonylaminocarboxylic acid compound may be reacted in the same reaction vessel with an amino acid ester of the general formula (III).

The arylsulfonamide derivative obtained by the above-mentioned method of the general formula (I) wherein $R^2$ is a protected hydroxyl group (for example, OTHP) may be hydrolyzed in a an appropriate solvent (for example, aqueous ethanol) in the presence of a an appropriate acid catalyst [for example, p-toluenesulfonic acid, pyridinium p-toluenesulfonate (hereinafter referred to as PPTS)], to obtain an arylsulfonamide derivative of the general formula (I) wherein $R^2$ is hydroxyl group.

Further, the arylsulfonamide derivative obtained by hydrolysis of the general formula (I) wherein $R^2$ is OH may be sulfonated by treatment with methanesulfonyl chloride in an appropriate solvent (for example, chloroform) in the presence of an appropriate base (for example, pyridine or triethylamine) to obtain an arylsulfonamide derivative of the general formula (I) wherein $R^2$ is —$OSO_2R^4$ (for example, —$OSO_2CH_3$).

Further, the arylsulfonamide derivative obtained by sulfonation of the general formula (I) wherein $R^2$ is —$OSO_2R^4$ may be condensed with imidazole in an appropriate solvent [for example, dimethylformamide (hereinafter referred to as DMF)] in the presence of an appropriate base (for example, NaH), to obtain an arylsulfonamide derivative of the general formula (I) wherein $R^2$ is an imidazolyl group.

Further, the arylsulfonamide derivative obtain by sulfonation of the general formula (I) wherein $R^2$ is —$OSO_2R^4$ may be condensed with 3-hydroxypyridine in an appropriate solvent (for example, DMF) in the presence of an appropriate base (for example, NaH), to obtain an arylsulfonamide derivative of the general formula (I) wherein $R^2$ is a pyridyloxyl group.

Further, the arylsulfonamide derivative obtained by sulfonation of the general formula (I) wherein $R^2$ is —$OSO_2R^4$ may be condensed with phenol or phenol substituted by one or more halogen atoms in an appropriate solvent (for example, DMF) in the presence of an appropriate base (for example, NaH) to obtain an arylsulfonamide derivative of the general formula (I) wherein $R^2$ is a phenyloxy group or a phenyloxy group substituted by one or more halogen atoms.

(2) A process wherein the carbonylaminocarboxylic acid compound of the general formula (v):

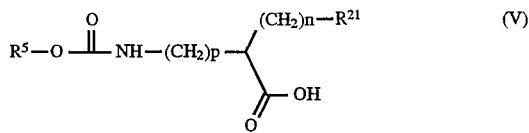

wherein $R^5$ is a straight or branched alkyl group with 1 to 20 carbon atoms, or unsubstituted benzyl group or a benzyl group substituted by 1 to 3 same or different substituents selected from the group consisting of a halogen atom, alkyl group (preferably, straight or branched alkyl group with 1 to 6 carbon atoms), nitro group, alkoxy group (preferably straight or branched alkoxy group with 1 to 6 carbon atoms) or hydroxyl group, $R^{21}$, n and p have the same meanings as above, is used as a starting material.

The carbonylaminocarboxylic acid compound of the general formula (V) may be reacted with the amino acid ester compound of the general formula (III):

$$H_2N—X—COO—R^{31} \quad (III)$$

wherein $R^{31}$ and X have the same meanings as above, in the presence of, for example, an appropriate condensing agent (for example, pivaloyl chloride, 2-chloro-1-methylpyridinium iodide, N,N'-dicyclohexylcarbodiimide) and an appropriate base (for example, triethylamine) to obtain a carbonylamine derivative of the general formula (VI):

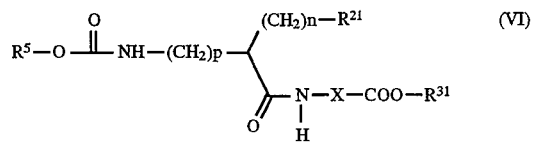

wherein $R^5$, $R^{21}$, $R^{31}$ and X have the same meanings as above.

Then, the carbonylamine derivative of the general formula (VI) obtained by condensation reaction may be hydrogenolyzed in the presence of, for example, an appropriate catalyst (for example, palladium-carbon) to remove the $R^5$—O—CO—group and obtain an amine derivative of the general formula (VII):

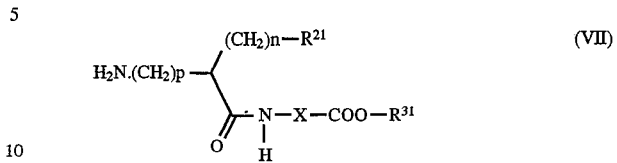

wherein $R^5$, $R^{21}$, $R^{31}$ and X have the same meanings as above, and then, the resulting derivative may be sulfonated with an appropriate sulfonating agent (for example, p-chlorobenzenesulfonyl chloride or toluenesulfonyl chloride) in an appropriate solvent (for example, chloroform) in the presence of an appropriate base (for example, pyridine, triethylamine) to produce an arylsulfonamide derivative of the general formula (I) wherein $R^2$ is the group $R^{21}$ and $R^3$ is the group $R^{31}$, and then, convert the group $R^{21}$ and/or $R^{31}$ by a known method to another group $R^2$ and/or $R^3$.

A carbonylaminocarboxylic acid compound of the general formula (V) wherein $R^{21}$ is a protected hydroxyl group may be prepared by protecting the OH group of the —$(CH_2)n$-OH group of the carbonylaminohydroxycarboxylic acid compound of the general formula (VIII):

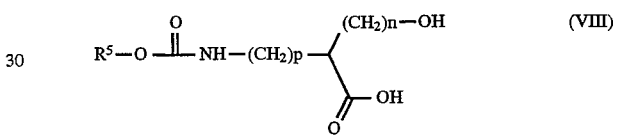

wherein $R^5$, n and p have the same meanings as the above. The OH group may be protected by a known method. For example, the carbonylaminohydroxycarboxylic acid compound of the general formula (IV) may be treated with dihydropyran in an appropriate solvent (for example, chloroform) in the presence of an appropriate acid catalyst (for example, p-toluenesulfonic acid) to convert the OH group of the —$(CH_2)n$-OH group in the general formula (VIII) to tetrahydropyranyl and produce a carbonylaminocarboxylic acid compound of the general formula (V) wherein $R^{21}$ is 2-tetrahydropyranyloxy group. The resulting carbonylaminocarboxylic acid compound may be reacted in the same reaction vessel with the amino acid ester of the general formula (III).

If desired, the ester of the arylsulfonamide derivative of the general formula (I) wherein $R^3$ is an alkyl group may be hydrolyzed, in an appropriate solvent (for example, ethanol or methanol) by treatment with an appropriate base (for example, sodium hydroxide or potassium carbonate), and then, treated by an ordinary method to obtain an arylsulfonamide derivative of the general formula (I) wherein $R^3$ is a hydrogen atom, that is a derivative having a free carboxyl group. If desired, the arylsulfonamide derivative having the free carboxyl group of the general formula (I) wherein $R^3$ is H may be treated with one equivalent of an appropriate base (for example, sodium hydroxide, potassium hydroxide, triethylamine, 2-aminobutane, tert-butylamine or diisopropylethylamine) in an appropriate solvent (for example, ethanol or methanol) to obtain a salt of a metal or organic base.

The arylsulfonamide derivative of the general formula (I) according to the present invention was evaluated for physiological activities in the working Examples by the following methods to find remarkable advantages:

(1) measurement of TxA$_2$ antagonism by binding assay, (2) measurement of inhibitory activity of vasoconstriction, and (3) measurement of inhibitory activity of platelet agglutination.

Accordingly, an arylsulfonamide derivative of the general formula (I) according to the present invention exhibits an antagonism specific to a TxA$_2$ receptor and can be used as an effective ingredient of a pharmaceutical composition on the basis of its TxA$_2$ receptor antagonism, inhibitory action of vasoconstriction or platelet agglutination. Specifically, for example, there may be mentioned cardiac infarction, cerebral infarction, pneum-obstruction, thrombosis, gestational toxemia, renal insufficiency and asthma due to bronchoconstrictive action. Further, the above derivative is effective for prevention of vasoconstriction followed by subarachnoid hemorrhage, prevention of shock due to TxA$_2$ after arterial re-perfusion of the circulatory or digestive system, large amount of blood loss, septicemia, trauma, cardiac function failure, endotoxins, acute pancreatitis or burns, or prevention of reduction of platelets in extracorporeal circulation.

The arylsulfonamide derivative of the general formula (I) used as the effective ingredient in the pharmaceutical composition of the present invention includes all pure stereo isomers and a mixture thereof in any ratio, and further include a pharmaceutically acceptable salt thereof.

The pharmaceutical composition of the present invention may be administered oral by or parenterally, for example, intravenously, subcutaneously, per rectum, or percutaneously. Depending on its administration route, the composition may be formulated into an oral agent, injection, inhalant, suppository, and the like. When administered orally, the composition may be used as a normal preparation, for example, solid preparations, such as tablets, dispersions, capsules, or granules, liquid preparations, such as aqueous or oil suspensions, syrups, elixers. When administered parenterally, the composition may be used as aqueous or oil injection, or suppositories.

The pharmaceutical composition of the present invention may contain, in addition to the above-mentioned effective ingredient, a pharmaceutically acceptable diluent or carrier. As the diluent or carrier, for example, any of ordinary excipients, binding agents, lubricants, aqueous solvents, oil solvent, emulsifying agent, suspending agent, or the like may be used. Further, other additives, such as, preservatives or stabilizers may be contained. The dose of the effective ingredient varies with the desired therapeutic effect, the method of administration, age, body weight, or the like, and cannot be determined generally. However, in the case of oral administration, the dose is usually approximately 0.1 mg to approximately 500 mg, preferably approximately 0.5 mg to approximately 2000 mg, per day per 1 kg body weight for adult, and in the case of parenteal administration, the dose is approximately 0.001 mg to approximately 500 mg, preferably approximately 0.5 mg to approximately 100 mg per day per 1 kg body weight for adult. The dose may be divided into 1 to 5 dosages.

EXAMPLES

The present invention now will be illustrated by, but by no means limited to, the following Examples.

Example 1

Preparation of (S)-2-(4-chlorobenzenesulfonylamino)-N-(4-ethoxycarbonylphenyl)-3-(tetrahydropyran-2-yloxy)propanamide Dihydropyran (245 µl), p-toluene sulfonic acid (20 mg) and chloroform (5 ml) were successively added to a solution of (S)-2-(4-chlorobenzenesulfonylamino)-3-hydroxypropanoic acid (500 mg) in THF (5 ml). The mixture was stirred at room temperature for 4 hours under argon. Triethylamine (327 µl) and pivaloyl chloride (241 µl) were added to the reaction mixture. After stirring for 30 minutes, ethyl p-aminobenzoate (345 mg) was added, and the mixture was stirred at room temperature overnight. The reaction mixture was poured into saturated saline solution and extracted with ethyl acetate. The combined ethyl acetate layers were washed with saturated saline solution, and dried over Na$_2$SO$_4$. The solvent was evaporated under reduced pressure to obtain 1.27 g of a yellow oil. The crude product was purified by column chromatography (silica gel=23 g, hexane/ethyl acetate=5/2) to obtain (S)-2-(4-chlorobenzenesulfonylamino)-N-(4-ethoxycarbonylphenyl)-3-(tetrahydropyran-2-yloxy)propanamide (595 mg).

IR vmax cm$^{-1}$ (KBr): 3359, 3205, 1710, 1693, 1278, 1168

$^1$H-NMR δ ppm (CDCl$_3$): 1.38 (3H, t, J=7 Hz), 1.4–1.8 (6H, m), 3.3–4.1 (4H, m), 4.35 (2H, q, J=7 Hz), 4.40 (1H, m), 7.3–7.7 (4H, m), 7.85 (2H, d, J=8.5 Hz), 7.97 (2H, d, J=8.5 Hz)

Fab-MS m/z: 514, 513, 512, 511 (MH$^+$), 510, 427

Example 2

Preparation of (RS)-2-(4-chlorobenzenesulfonylamino)-N-(4-ethoxycarbonylphenyl)-3-(tetrahydropyran-2-yloxy)propanamide The procedure described in Example 1 was repeated, except that dihydropyran (2.7 g) and ethyl p-aminobenzoate (2.13 g) were successively reacted with (RS)-2-(4-chlorobenzenesulfonylamino)-3-hydroxypropanoic acid (3 g) to obtain (RS)-2-(4-chlorobenzenesulfonylamino)-N-(4-ethoxycarbonylphenyl)-3-(tetrahydropyran-2-yloxy)propanamide (1.962 g).

IR vmax cm$^{-1}$ (KBr): 3359, 1710, 1693, 1278, 1168

$^1$H-NMR δ ppm (CDCl$_3$): 1.38 (3H, t, J=7 Hz), 1.4–1.8 (6H, m), 3.3–4.1 (4H, m), 4.35 (2H, q, J=7 Hz), 4.40 (1H, m), 7.3–7.7 (4H, m), 7.85 (2H, d, J=8.5 Hz), 7.97 (2H, d, J=8.5 Hz)

Fab-MS m/z: 514, 513, 512, 511 (MH$^+$), 510, 427

Example 3

Preparation of (RS)-2-(4-chlorobenzenesulfonylamino)-N-(4-(ethoxycarbonylmethyl)phenyl)-3-(tetrahydropyran-2-yloxy)propanamide The procedure described in Example 1 was repeated, except that dihydropyran (1.4 ml) and ethyl p-aminophenyl acetate (2.02 g) were successively reacted with (RS)-2-(4-chlorobenzenesulfonylamino)-3-hydroxypropanoic acid (2.8 g) to obtain (RS)-2-(4-chlorobenzenesulfonylamino)-N-(4-(ethoxycarbonylmethyl)phenyl)-3-(tetrahydropyran-2-yloxy)propanamide (3.4 g).

Melting point: 100°–110° C.

IR vmax cm$^{-1}$ (KBr): 3359, 1734, 1672, 1338, 1168

$^1$H-NMR δ ppm (CDCl$_3$): 1.242 (3H, t, J=7.2 Hz), 1.35–1.9 (6H, m), 3.50 (2H, m), 3.569 (2H, s), 3.714 (1H, dd, J=12.8 Hz, J=9.2 Hz), 3.95 (2H, m), 4.137 (2H, q, J=7.2 Hz), 4.40 (1H, m), 7.230 and 7.238 (2H, d, J=8.5 Hz), 7.394 and 7.444 (2H, d, J=8.5 Hz), 7.484 and 7.504 (2H, d, J=8.5 Hz), 7.834 (2H, d, J=8.5 Hz)

$^{13}$C-NMR δ ppm (CDCl$_3$): 14.13, 20.56 and 20.75, 24.89 and 25.02, 26.98 and 27.09, 30.61 and 30.89, 40.82, 56.39 and 56.65, 60.85, 64.57 and 64.86, 68.31 and 68.71, 101.08 and 101.81, 119.95 and 120.03, 128.74 and 128.91, 129.45 and 129.61, 129.70 and 129.83, 130.54 and 130.61, 136.10, 137.33 and 137.58, 139.76 and 139.86, 166.53 and 166.72, 171.43

Fab-MS m/z: 525 (MH$^+$), 524(MH$^+$), 441 (MH$^+$-DHP)

Example 4

Preparation of (RS)-2-(4-chlorobenzenesulfonylamino)-N-(4-(2-methoxycarbonylethyl)phenyl)-3-(tetrahydropyran-2-yloxy)propanamide The procedure described in Example 1 was repeated, except that dihydropyran (1.4 ml) and methyl p-aminophenylpropionate (2.15 g) were successively reacted with (RS)-2-(4-chlorobenzenesulfonylamino)-3-hydroxypropanoic acid (2.8 g) to obtain (RS)-2-(4-chlorobenzenesulfonylamino)-N-(4-(2-methoxycarbonylethyl)phenyl)-3-(tetrahydropyran-2-yloxy)propanamide (2.1 g)

Melting point: 102°–107° C.

IR vmax cm$^{-1}$ (KBr): 3700–2500(br), 3265, 1736, 1662, 1340, 1164

$^1$H-NMR δ ppm (CDCl$_3$): 1.3–1.9 (6H, m), 2.598 (2H, t, J=7.7 Hz), 2.911 (2H, t, J=7.7 Hz), 3.50 (2H, m), 3.660 (3H, s), 3.95 (2H, m), 4.16 (1H, m), 4.42 (1H, m), 7.139 and 7.146 (2H, d, J=8.5 Hz), 7.347 and 7.396 (2H, d, J=8.5 Hz), 7.479 and 7.498 (2H, d, J=8.5 Hz), 7.833 (2H, d, J=8.5 Hz)

$^{13}$C-NMR δ ppm (CDCl$_3$): 20.53 and 20.71, 24.89 and 25.02, 30.34, 30.59 and 30.87, 35.63, 51.57, 56.39 and 56.65, 64.51 and 64.81, 68.29 and 68.71, 101.02 and 101.74, 120.05 and 120.14, 128.74 and 128.80, 128.89, 129.46 and 129.59, 135.35, 137.01 and 137.09, 137.34 and 137.60, 139.75 and 139.82, 166.50 and 166.68, 173.17

Fab-MS m/z: 525 (M$^+$), 524 (M$^+$), 441 (MH-DHP)

Example 5

Preparation of (S)-2-(4-chlorobenzenesulfonylamino)-N-(3-ethoxycarbonylphenyl)-3-(tetrahydropyran-2-yloxy)propanamide The procedure described in Example 1 was repeated, except that dihydropyran (1.46 ml) and ethyl m-aminobenzoate (2.13 g) were successively reacted with (S)-2-(4-chlorobenzenesulfonylamino)-3-hydroxypropanoic acid (3 g) to obtain (S)-2-(4-chlorobenzenesulfonylamino)-N-(3-ethoxycarbonylphenyl)-3-(tetrahydropyran-2-yloxy)propanamide (2.3 g).

IR vmax cm$^{-1}$ (KBr): 3336, 1716, 1695, 1288, 1168

$^1$H-NMR δ ppm (CDCl$_3$): 1.38 (3H, t, J=7.1 Hz), 1.4–1.8 (6H, m), 3.3–4.1 (5H, m), 4.37 (2H, q, J=7.1 Hz), 4.40 (1H, m), 7.2–7.6 (3H, m), 7.7–7.9 (1H, m), 7.85 (2H, d, J=7.6 Hz), 8.01 (2H, d, J=7.1 Hz), 8.83 (2H, d, J=3.4 Hz)

Fab-MS m/z: 511 (MH$^+$)

Example 6

Preparation of (RS)-2-(4-chlorobenzenesulfonylamino)-N-(3-ethoxycarbonylphenyl)-3-(tetrahydropyran-2-yloxy)propanamide The procedure described in Example 1 was repeated, except that dihydropyran (2.7 g) and m-aminobenzoic acid (2.13 g) were successively reacted with (RS)-2-(4-chlorobenzenesulfonylamino)-3-hydroxypropanoic acid (3 g) to obtain (RS)-2-(4-chlorobenzenesulfonylamino)-N-(3-ethoxycarbonylphenyl)-3-(tetrahydropyran-2-yloxy)propanamide (2.725 g).

IR vmax cm$^{-1}$ (KBr): 3336, 1716, 1695, 1288, 1168

$^1$H-NMR δ ppm (CDCl$_3$): 1.38 (3H, t, J=7.1 Hz), 1.4–1.8 (6H, m), 3.3–4.1 (5H, m), 4.37 (2H, q, J=7.1 Hz), 4.40 (1H, m), 7.2–7.6 (3H, m), 7.7–7.9 (1H, m), 7.85 (2H, d, J=7.6 Hz), 8.01 (2H, d, J=7.1 Hz), 8.83 (2H, d, J=3.4 Hz)

Fab-MSm/z: 511 (MH$^+$)

Example 7

Preparation of (RS)-2-(4-chlorobenzenesulfonylamino)-N-(3-(methoxycarbonylmethyl)phenyl)-3-(tetrahydropyran-2-yloxy)propanamide The procedure described in Example 1 was repeated, except that dihydropyran (0.4 ml) and methyl m-aminophenylacetate (604 mg) were successively reacted with (RS)-2-(4-chlorobenzenesulfonylamino)-3-hydroxypropanoic acid (893 mg) to obtain (RS)-2-(4-chlorobenzenesulfonylamino)-N-(3-(methoxycarbonylmethyl)phenyl)-3-(tetrahydropyran-2-yloxy)propanamide (624 mg).

IR vmax cm$^{-1}$ (neat): 3336, 1723, 1691, 1346, 1167

Fab-MS m/z: 497 (MH$^+$), 413

Example 8

Preparation of (RS)-2-(4-Chlorobenzenesulfonylamino)-N-(3-(2-methoxycarbonylethyl)phenyl)-3-(tetrahydropyran-2-yloxy)propanamide The procedure described in Example 1 was repeated, except that dihydropyran (2.74 ml) and methyl p-aminophenylpropionate (3.94 g) were successively reacted with (RS)-2-(4-chlorobenzenesulfonylamino)-3-hydroxypropanoic acid (5.59 g) to obtain (RS)-2-(4-chlorobenzenesulfonylamino)-N-(3-(2-methoxycarbonylethyl)phenyl)-3-(tetrahydropyran-2-yloxy)propanamide (7.60 g).

IR vmax cm$^{-1}$ (neat): 3340, 1733, 1689, 1344, 1165

$^1$H-NMR δ ppm (CDCl$_3$): 1.3–1.9 (6H, m), 2.621 (2H, t, J=7.7 Hz), 2.925 (2H, t, J=7.7 Hz), 3.4–3.6 (2H, m), 3.670 (3H, s), 4.15 (1H, m), 4.44 (2H, m), 6.960 (1H, d, J=7.1 Hz), 7.1–7.4 (3H, m), 7.45–7.75 (2H, m), 7.842 (2H, d, J=8.6 Hz), 8.568 (1H, d, J=15.4 Hz)

$^{13}$C-NMR δ ppm (CDCl$_3$): 20.54, 24.89, 30.61, 35.47, 51.59, 56.46, 64.55, 68.29, 101.06, 117.80, 119.70, 124.66, 137.29, 139.75, 141.60, 166.53, 173.12

Fab-MS M/z: 525 (MH$^+$), 441(MH$^+$-DHP), 85

Example 9

Preparation of (RS)-2-(4-chlorobenzenesulfonylamino)-N-(3-methoxycarbonylpropyl)-3-(tetrahydropyran-2-yloxy)propanamide The procedure described in Example 1 was repeated, except that dihydropyran (1.37 ml) and methyl 4-aminobutanate hydrochloride (1.69 g) were successively reacted with (RS)-2-(4-chlorobenzenesulfonylamino)-3-hydroxypropanoic acid (2.80 g) to obtain (RS)-2-(4-chlorobenzenesulfonylamino)-N-(3-methoxycarbonylpropyl)-3-(tetrahydropyran-2-yloxy)propanamide (3.12 g).

IR vmax cm$^{-1}$ (neat): 3369, 3292, 1736, 1660, 1340, 1167

$^1$H-NMR δ ppm (CDCl$_3$): 1.4–1.9 (6H, m), 1.807 (2H, t, J=7.2 Hz), 2.340 (2H, q, J=7.2 Hz), 3.25 (2H, m), 3.45 (2H, m), 3.682 (3H, s), 3.85 (2H, m), 4.35 (1H, m), 4.10 (1H, m), 6.90 (1H, m), 7.503 (2H, d, J=8.3 Hz), 7.813 (2H, d, J=8.3 Hz)

$^{13}$C-NMR δ ppm (CDCl$_3$): 24.52, 25.00, 27.53, 30.57, 31.05, 38.94, 51.62, 56.39, 64.46, 68.35, 100.91, 128.71, 129.33, 137.44, 139.64, 168.79, 173.45

Fab-MS m/z: 463 (MH$^+$), 379 (MH$^+$–DHP)

Example 10

Preparation of (RS)-2-(4-chlorobenzenesulfonylamino)-N-(4-methoxycarbonylbutyl)-3-(tetrahydropyran-2-yloxy)propanamide The procedure described in Example 1 was repeated, except that dihydropyran (2.9 ml) and methyl 5-aminopentanate hydrochloride (2.158 g) were successively reacted with (RS)-2-(4-chlorobenzenesulfonylamino)-3-hydroxypropanoic acid (3 g) to obtain (RS)-2-(4-chlorobenzenesulfonylamino)-N-(4-methoxycarbonylbutyl)-3-(tetrahydropyran-2-yloxy)propanamide (2.059 g).

IR νmax cm$^{-1}$ (neat): 3373, 3305, 2945, 1736, 1655, 1439, 1340, 1167, 1124, 1086

$^1$H-NMR δ ppm (CDCl$_3$): 1.259 (2H, t, J=7.1 Hz), 1.4–1.9 (8H, m), 2.329 (2H, t, J=7.1 Hz), 3.1–3.3 (2H, m), 3.3–3.5 (2H, m), 3.673 (3H, s), 3.7–3.9 (2H, m), 4.122 (1H, dd, J=14.4 Hz, J=7.1 Hz), 4.3–4.4 (1H, m), 7.4–7.6 (2H, m), 7.7–7.9 (2H, m)

$^{13}$C-NMR δ ppm (CDCl$_3$): 14.15, 20.53, 24.93 and 25.00, 28.74, 30.57 and 30.65, 33.40, 39.23, 56.17 and 56.35, 64.42, 68.31, 100.91 and 101.06, 128.71 and 128.93, 137.44 and 137.84, 139.56 and 139.64, 168.46 and 168.68, 173.74

Fab-MS m/z: 477 (MH$^+$), 393 (MH$^+$–THP)

Example 11

Preparation of (RS)-2-(4-chlorobenzenesulfonylamino)-N-(5-methoxycarbonylpentyl)-3-(tetrahydropyran-2-yloxy)propanamide The procedure described in Example 1 was repeated, except that dihydropyran (2.56 ml) and methyl 6-aminohexanate hydrochloride (3.41 g) were successively reacted with (RS)-2-(4-chlorobenzenesulfonylamino)-3-hydroxypropanoic acid (4.94 g) to obtain (RS)-2-(4-chlorobenzenesulfonylamino)-N-(5-methoxycarbonylpentyl)-3-(tetrahydropyran-2-yloxy)propanamide (0.87 g).

Melting point: 59°–60° C.

IR νmax cm$^{-1}$ (neat): 3377, 3305, 1736, 1662, 1342, 1167, 754

$^1$H-NMR δ ppm (CDCl$_3$): 1.2–1.9 (12H, m), 2.310 (2H, t, J=7.4 Hz), 3.230 (2H, dd, J=13.3 Hz, J=6.7 Hz), 3.3–4.2 (5H, m), 3.670 (3H, s), 6.90 (1H, m), 7.490 (2H, d, J=8.3 Hz), 7.813 (2H, d, J=8.3 Hz)

Fab-MS m/z: 491 (MH$^+$), 407

Example 12

Preparation of (RS)-2-(4-chlorobenzenesulfonylamino)-N-(6-methoxycarbonylhexyl)-3-(tetrahydropyran-2-yloxy)propanamide The procedure described in Example 1 was repeated, except that dihydropyran (1.93 ml) and methyl 7-aminoheptanate hydrochloride (1.679 g) were successively reacted with (RS)-2-(4-chlorobenzenesulfonylamino)-3-hydroxypropanoic acid (2 g) to obtain (RS)-2-(4-chlorobenzenesulfonylamino)-N-(6-methoxycarbonylhexyl)-3-(tetrahydropyran-2-yloxy)propanamide (1. 497 g).

IR νmax cm$^{-1}$ (neat): 3371, 2941, 2866, 1738, 1660, 1441, 1342, 1167, 1124, 1093

$^1$H-NMR δ ppm (CDCl$_3$): 1.2–1.4 (4H, m), 1.4–1.8 (10H, m), 2.308 (2H, t, J=7.4 Hz), 3.1–3.3 (2H, m), 3.4–3.5 (2H, m), 3.669 (3H, s), 3.7–3.9 (2H, m), 4.0–4.2 (1H, m), 4.3–4.4 (1H, m), 7.495 (2H, dd, J=8.8 Hz, J=3.7 Hz), 7.812 (2H, dd, J=8.8 Hz, J=1.2 Hz)

$^{13}$C-NMR δ ppm (CDCl$_3$): 20.42, 24.71 and 24.93, 26.25, 27.46 and 27.53, 28.59, 29.07, 30.57 and 30.65, 33.87, 39.56, 50.63, 51.44, 56.17 and 56.39, 64.31 and 64.39, 68.27, 100.87, 128.67 and 128.89, 129.33 and 129.48, 137.51 and 137.84, 139.53 and 139.60, 168.46 and 168.64, 174.18

Fab-MS m/z: 505 (MH$^+$), 421 (MH$^+$–THP)

Example 13

Preparation of (RS)-2-(4-chlorobenzenesulfonylamino)-N-(7-methoxycarbonylheptyl)-3-(tetrahydropyran-2-yloxy)propanamide The procedure described in Example 1 was repeated, except that dihydropyran (2.9 ml) and methyl 6-aminooctanate hydrochloride (2.699 g) were successively reacted with (RS)-2-(4-chlorobenzenesulfonylamino)-3-hydroxypropanoic acid (3 g) to obtain (RS)-2-(4-chlorobenzenesulfonylamino)-N-(7-methoxycarbonylheptyl)-3-(tetrahydropyran-2-yloxy)propanamide (2.026 g).

IR νmax cm$^{-1}$ (neat): 3369, 3305, 2939, 1738, 1660, 1441, 1342, 1167, 1122, 1086

$^1$H-NMR δ ppm (CDCl$_3$): 1.2–1.4 (6H, m), 1.4–1.8 (10H, m), 2.301 (2H, t, J=7.6 Hz), 3.4–3.6 (2H, m), 3.664 (3H, s), 3.7–3.9 (2H, m), 4.0–4.1 (1H, m), 4.3–4.4 (1H, m), 7.484 (2H, d, J=8.6 Hz), 7.812 (2H, d, J=8.6 Hz)

$^{13}$C-NMR δ ppm (CDCl$_3$): 20.38, 24.71 and 24.89, 26.43, 28.70 and 28.85, 29.14, 30.54 and 30.61, 31.89, 33.91, 39.60, 51.37, 56.10 and 56.28, 63.76, 64.24, 68.24, 100.76 and 100.87, 128.67 and 128.85, 129.26 and 129.44, 137.84, 139.45, 168.39 and 168.57, 174.14

Fab-MS m/z: 519 (MH$^+$), 435 (MH$^+$–THP)

Example 14

Preparation of (RS)-2-(benzyloxycarbonylamino)-N-(4-(ethoxycarbonylmethyl)phenyl)-3-(tetrahydropyran-2-yloxy)propanamide Dihydropyran (2.27 ml) and p-toluenesulfonic acid (500 mg) were added to a suspension of N-benzyloxycarbonyl-DL-serine (5 g) in chloroform, and the mixture was stirred at room temperature overnight under argon. Triethylamine (11.65 ml), ethyl p-aminophenylacetate hydrochloride (4.5 g) and 2-chloro-1-methylpyridinium iodide (6.4 g) were added to the reaction mixture and the whole was refluxed for 3 hours. The reaction mixture was concentrated under reduced pressure. The residue was dissolved in ethyl acetate, washed with 1N HCl, 5% NaHCO$_3$, and saturated saline solution, and dried over Na$_2$SO$_4$. The solvent was evaporated under reduced pressure. The residue was purified by column chromatography (silica gel=300 g, hexane/ethyl acetate=20/9) to obtain (RS)-2-(benzyloxycarbonylamino)-N-(4-(ethoxycarbonylmethyl)phenyl)-3-(tetrahydropyran-2-yloxy)propanamide (6.847 g).

IR νmax cm$^{-1}$ (KBr): 3315, 1734, 1685, 1369, 1159

$^1$H-NMR δ ppm (CDCl$_3$-CD$_3$OD): 1.241 (3H, t, J=7.08 Hz), 1.4–1.9 (6H, m), 3.567 (2H, s), 3.5–4.0 (3H, m), 4.135 (2H, q, J=7.08 Hz), 4.61 (1H, m), 5.137 (2H, s), 7.225 (2H, d, J=8.30 Hz), 7.35 (5H, m), 7.453 (2H, d, J=8.30 Hz)

$^{13}$C-NMR δ ppm (CDCl$_3$-CD$_3$OD): 14.16, 19.98, 25.13, 30.52, 40.82, 60.87, 63.34, 67.23, 68.41, 120.07, 128.11, 128.28, 128.57, 129.81, 130.18, 136.08, 136.57, 156.13, 167.96, 171.53

Fab-MS m/z: 458 (MH$^+$), 401

Example 15

Preparation of (RS)-2-(benzenesulfonylamino)-N-(4-(ethoxycarbonylmethyl)phenyl)-3-(tetrahydropyran-2-yloxy)propanamide 10% palladium-carbon (100 mg) was added to a solution of (RS)-2-(benzyloxycarbonylamino)-N-(4-(ethoxycarbonylmethyl)phenyl)-3-(tetrahydropyran-2-yloxy)propanamide (1 g) in methanol (30 ml), and the mixture was stirred under hydrogen at room temperature overnight. The reaction mixture was filtered, and the filtrate was concentrated under reduced pressure. The residue was dissolved in pyridine (3 ml). Benzenesulfonyl chloride (521 μl) was added to the solution, and the mixture was stirred at room temperature overnight under argon. The reaction mixture was poured in 1N HCl and extracted with ethyl acetate. The combined ethyl acetate layers were washed with 1N HCl, 5% NaHCO$_3$, and a saturated saline solution, and dried over Na$_2$SO$_4$. The solvent was evaporated under reduced pressure. The residue was purified by column chromatography (silica gel=25 g, hexane/ethyl acetate=5/4) to obtain (RS)-2-(benzene-sulfonylamino)-N-(4-(ethoxycarbonylmethyl)phenyl)-3-(tetrahydropyran-2-yloxy)propanamide (0.96 g).

Melting point: 113°–122° C.

IR vmax cm$^{-1}$ (KBr): 3350, 3265, 1736, 1666, 1333, 1166, 729, 688

$^1$H-NMR δ ppm (CDCl$_3$): 1.239 (3H, t, J=7.08 Hz), 1.3–1.8 (6H, m), 3.4–3.7 (2H, m), 3.562 (2H, s), 3.8–4.05 (3H, m), 4.136 (2H, q, J=7.08 Hz), 4.3–4.5 (1H, m), 7.2–7.7 (7H, m), 7.903 (2H, d, J=8.3 Hz)

$^{13}$C-NMR δ ppm (CDCl$_3$): 14.15, 20.53, 30.61, 30.76, 40.81, 56.43, 56.76, 60.83, 64.50, 68.31, 101.06, 101.35, 119.94, 120.02, 127.24, 127.39, 129.18, 129.33, 129.77, 130.43, 130.50, 133.18, 133.25, 136.19, 138.79, 139.05, 166.74, 166.92, 171.47

Fab-MS m/z: 490 (M$^+$), 407

Example 16

Preparation of (RS)-N-(4-(ethoxycarbonylmethyl) phenyl)-2-(4-fluorobenzenesulfonylamino)-3-(tetrahydropyran-2-yloxy)propanamide The procedure described in Example 15 was repeated, except that (RS)-2-(benzyloxycarbonylamino)-N-(4-(ethoxycarbonylmethyl)phenyl)- 3-(tetrahydropyran-2-yloxy)propanamide (2.0 g) was hydrogenolyzed in the presence of 10% Pd-C, and then, reacted with 4-fluorobenzenesulfonyl chloride (1.72 g) to obtain (RS)-N-(4-(ethoxycarbonylmethyl)phenyl)-2-(4-fluorobenzenesulfonylamino)-3-(tetrahydropyran-2-yloxy) propanamide (1.59 g).

Melting point: 117°–119° C.

IR vmax cm$^{-1}$ (KBr): 3338, 3261, 1732, 1657, 1338, 1171, 1155, 1036, 841

$^1$H-NMR δ ppm (CDCl$_3$): 1.246 (3H, t, J=7.08 Hz), 1.3–1.9 (6H, m), 3.4–3.6 (2H, m), 3.567 (2H, s), 3.8–4.0 (3H, m), 4.137 (2H, q, J=7.08 Hz), 4.40 (1H, m), 7.1–7.3 (4H, m), 7.3–7.5 (2H, m), 7.918 (2H, dd, J=9.03 Hz, J=4.88 Hz)

$^{13}$C-NMR δ ppm (CDCl$_3$): 14.15, 20.56, 20.71, 24.89, 25.00, 30.61, 30.87, 40.81, 56.43, 56.65, 60.86, 64.53, 64.83, 68.27, 68.64, 101.06, 101.75, 116.28, 116.42, 116.61, 116.75, 119.94, 120.02, 129.81, 129.99, 130.14, 130.28, 130.58, 134.87, 135.09, 136.12, 163.47, 166.63, 166.81, 167.25, 171.43

Fab-MS m/z: 508 (M$^+$), 425

Example 17

Preparation of (RS)-2-(4-chlorobenzenesulfonylamino)-N-(4-(ethoxycarbonylmethyl)phenyl)-3-(tetrahydropyran-2-yloxy)propanamide The procedure described in Example 15 was repeated, except that (RS)-2-(benzyloxycarbonylamino)-N-(4-(ethoxycarbonylmethyl)phenyl)-3-(tetrahydropyran-2-yloxy) propanamide (4.34 g) was hydrogenolyzed in the presence of 10% Pd-C, and then, reacted with 4-chlorobenzenesulfonyl chloride (3.87 g) to obtain (RS)-2-(4-chlorobenzenesulfonylamino)-N-(4-(ethoxycarbonylmethyl)phenyl)-3-(tetrahydropyran-2-yloxy)propanamide (3.07 g).

Melting point: 100°–110° C.

IR vmax cm$^{-1}$ (KBr): 3359, 1734, 1672, 1338, 1168

$^1$H-NMR δ ppm (CDCl$_3$): 1.242 (3H, t, J=7.2 Hz), 1.35–1.9 (6H, m), 3.50 (2H, m), 3.569 (2H, s), 3.714 (1H, dd, J=12.8 Hz, J=9.2 Hz), 3.95 (2H, m), 4.137 (2H, q, J=7.2 Hz), 4.40 (1H, m) 7.230 and 7.238 (2H, d, J=8.5 Hz), 7.394 and 7.444 (2H, d, J=8.5 Hz), 7.484 and 7.504 (2H, d, J=8.5 Hz), 7.834 (2H, d, J=8.5 Hz)

$^{13}$C-NMR δ ppm (CDCl$_3$): 14.13, 20.56 snd 20.75, 24.89 and 25.02, 26.98 and 27.09, 30.61 and 30.89, 40.82, 56.39 and 56.65, 60.85, 64.57 and 64.86, 68.31 and 68.71, 101.08 and 101.81, 119.95 and 120.03, 128.74 and 128.91, 129.45 and 129.61, 129.70 and 129.83, 130.54 and 130.61, 136.10, 137.33 and 137.58, 139.76 and 139.86, 166.53 and 166.72, 171.43

Fab-MS m/z: 525 (MH$^+$), 524(M$^+$), 441(MH$^+$–DHP)

Example 18

Preparation of (RS)-2-(4-bromobenzenesulfonylamino)-N-(4-(ethoxycarbonylmethyl)phenyl)-3-(tetrahydropyran-2-yloxy)propanamide The procedure described in Example 15 was repeated, except that (RS)-2-(benzyloxycarbonylamino)-N-(4-(ethoxycarbonylmethyl)phenyl)-3-(tetrahydropyran-2-yloxy)propanamide (2.0 g) was hydrogenolyzed in the presence of 10% Pd-C, and then, reacted with 4-bromobenzenesulfonyl chloride (2.08 g) to obtain (RS)-2-(4-bromobenzenesulfonyl-amino)-N-(4-(ethoxycarbonylmethyl) phenyl)-3-(tetrahydro-pyran-2-yloxy)propanamide (1.58 g).

Melting point: 115°–126° C.

IR vmax cm$^{-1}$ (KBr): 3334, 3278, 1734, 1684, 1338, 1167, 742

$^1$H-NMR δ ppm (CDCl$_3$): 1.243 (3H, t, J=7.08 Hz), 1.3–1.9 (6H, m), 3.4–4.0 (5H, m), 3.569 (2H, s), 4.137 (2H, q, J=7.08 Hz), 4.42 (1H, m), 7.15–7.5 (4H, m), 7.649 (1H, d, J=8.79 Hz), 7.668 (1H, d, J=8.79 Hz), 7.758 (2H, d, J=8.79 Hz)

$^{13}$C-NMR δ ppm (CDCl$_3$): 14.15, 20.56, (20.75), 24.89, (25.00), 30.61, (30.87), 56.39, (56.65), 60.86, 64.57, (64.86), 68.31, (68.71), 101.06, (101.79), 119.98, (120.05), 128.27, 128.34, 128.82, 128.96, 129.84, 130.54, 130.61, 132.45, 132.59, 136.08, 137.88, 138.10, 166.52, (166.74), 171.40

Fab-MS m/z: 569 (MH$^+$+2), 567 (MH$^+$)

Example 19

Preparation of (RS)-N-(4-(ethoxycarbonylmethyl) phenyl)-2-(4-iodobenzenesulfonylamino)-3-(tetrahydropyran-2-yloxy)propanamide The procedure described in Example 15 was repeated, except that (RS)-2-(benzyloxycarbonylamino)-N-(4-(ethoxycarbonylmethyl)phenyl)-3-(tetrahydropyran-2-yloxy)propanamide (1.0 g) was hydrogenolyzed in the presence of 10% Pd-C, and then, reacted with 4-iodobenzenesulfonyl chloride (1.31 g) to obtain (RS)-N-(4-(ethoxycarbonyl-methyl)phenyl)-2-(4-iodobenzenesulfonylamino)-N-(3-(tetrahydropyran-2-yloxy)propanamide (1.10 g).

Melting point: 146°–147.3° C.

IR vmax cm$^{-1}$ (KBr): 3278, 1732, 1674, 1338, 1167

$^1$H-NMR δ ppm (CDCl$_3$): 1.243 (3H, t, J=7.08 Hz), 1.3–1.9 (6H, m), 3.50 (2H, m), 3.570 (2H, s), 3.6–4.1 (3H, m), 4.137 (2H, q, J=7.08 Hz), 4.40 (1H, m), 7.1–8.0 (8H, m)

$^{13}$C-NMR δ ppm (CDCl$_3$): 14.14, 20.53, 20.70, 24.91, 24.99, 30.61, 30.84, 40.80, 56.44, 56.70, 60.87, 64.53, 64.79, 68.27, 68.62, 100.70, 100.76, 101.02, 101.71, 120.02, 120.11, 120.20, 128.52, 128.60, 128.78, 129.84, 130.53, 136.06, 138.42, 138.57, 138.77, 166.59, 166.79, 171.48

Fab-MS m/z: 616 (M$^+$), 533

Example 20

Preparation of (RS)-N-(4-(ethoxycarbonylmethyl) phenyl)-2-(4-methylbenzenesulfonylamino)-3-(tetrahydropyran-2-yloxy)propanamide The procedure described in Example 15 was repeated, except that (RS)-2-(benzyloxycarbonylamino)-N-(4-(ethoxycarbonylmethyl)phenyl)-3-(tetrahydropyran-2-yloxy) propanamide (1.0 g) was hydrogenolyzed in the presence of 10% Pd-C, and then, reacted with 4-methylbenzenesulfonyl chloride (778 mg) to obtain (RS)-N-(4-(ethoxycarbonylmethyl)phenyl)-2-(4-methylbenzenesulfonylamino)-3-(tetrahydropyran-2-yloxy) propanamide (540 mg).

Melting point: 119°–128° C.

IR vmax cm$^{-1}$ (KBr): 1735, 1666, 1333, 1165, 1034, 667, 550

$^1$H-NMR δ ppm (CDCl$_3$): 1.241 (3H, t, J=7.08 Hz), 1.3–1.8 (6H, m), 2.404 (3/2H, s), 2.420 (3/2H, s), 3.565 (2H, s), 3.35–3.66 (2H, m), 3.75–4.2 (2H, m), 4.135 (2H, q, J=7.08 Hz), 4.3–4.5 (1H, m), 7.1–7.5 (6H, m), 7.777 (2H, d, J=8.05 Hz)

$^{13}$C-NMR δ ppm (CDCl$_3$): 14.15, 20.49, 21.52, 24.93, 25.00, 30.61, 30.72, 40.84, 56.46, 56.76, 60.83, 64.42, 68.20, 68.31, 101.02, 101.24, 119.94, 120.02, 127.31, 127.46, 129.77, 129.92, 130.36, 130.43, 135.75, 136.19, 144.15, 144.22, 166.85, 167.03, 171.47

Fab-MS m/z: 504 (M$^+$), 421

Example 21

Preparation of (RS)-N-(4-(ethoxycarbonylmethyl) phenyl)-2-(4-methoxybenzenesulfonylamino)-3-(tetrahydropyran-2-yloxy)propanamide The procedure described in Example 15 was repeated, except that (RS)-2-(benzyloxycarbonylamino)-N-(4-(ethoxycarbonylmethyl)phenyl)-3-(tetrahydropyran-2-yloxy)propanamide (0.68 g) was hydrogenolyzed in the presence of 10% Pd-C, and then, reacted with 4-methoxybenzenesulfonyl chloride (575 mg) to obtain (RS)-N-(4-(ethoxycarbonylmethyl)phenyl)-2-(4-methoxybenzenesulfonylamino)-3-(tetrahydropyran-2-yloxy)propanamide (3 19 mg).

Melting point: 113°–115° C.

IR vmax cm$^{-1}$ (KBr): 3342, 3261, 1730, 1660, 1335, 1160, 1032, 559

$^1$H-NMR δ ppm (CDCl$_3$): 1.243 (3H, t, J=7.08 Hz), 1.3–1.9 (6H, m), 3.3–3.7 (2H, m), 3.567 (2H, s), 3.848 (3/2H, s), 3.864 (3/2H, s), 3.8–4.1 (3H, m), 4.137 (2H, q, J=7.08 Hz), 4.2–4.4 (1H, m), 6.9–7.0 (2H, m), 7.15–7.28 (2H, m), 7.4–7.5 (2H, m), 7.825 (2H, d, J=8.79 Hz)

$^{13}$C-NMR δ ppm (CDCl$_3$): 14.15, 20.53, 25.00, 30.61, 30.79, 40.84, 55.62, 56.46, 56.76, 60.83, 64.46, 68.27, 101.06, 144.37, 144.48, 119.94, 120.02, 129.48, 129.62, 129.77, 130.39, 134.91, 136.26, 160.76, 163.36, 166.88, 167.07, 171.47

Fab-MS m/z: 520 (M$^+$), 437

Example 22

Preparation of (RS)-2-(4-chloro-3-nitrobenzenesulfonylamino)-N-(4-(ethoxycarbonylmethyl)phenyl)-3-(tetrahydropyran-2-yloxy)propanamide The procedure described in Example 15 was repeated, except that (RS)-2-(benzyloxycarbonylamino)-N-(4-(ethoxycarbonylmethyl)phenyl)-3-(tetrahydropyran-2-yloxy)propanamide (500 mg) was hydrogenolyzed in the presence of 10% Pd-C, and then, reacted with 4-chloro-3-nitrobenzenesulfonyl chloride (524 mg) to obtain (RS)-2-(4-chloro-3-nitrobenzenesulfonylamino)-N-(4-(ethoxycarbonylmethyl) phenyl)-3-(tetrahydropyran-2-yloxy)propanamide (198.2 mg).

Melting point: 108°–111° C.

IR vmax cm$^{-1}$ (KBr): 3275, 1736, 1684, 1659, 1539, 1354, 1174, 1030

$^1$H-NMR δ ppm (CDCl$_3$): 1.244 (3H, t, J=7.08 Hz), 1.4–1.9 (6H, m), 3.572 (2H, s), 3.3–3.7 (2H, m), 3.8–4.1 (3H, m), 4.139 (2H, q, J=7.08 Hz), 4.45 (1H, m), 7.23 (2H, m), 7.40 (2H, m), 7.71 (1H, m), 8.05 (1H, m), 8.400 (1H, t, J=1.71 Hz)

$^{13}$C-NMR δ ppm (CDCl$_3$): 14.19, 20.72, 21.16, 24.90, 25.01, 30.69, 31.06, 40.85, 56.62, 60.95, 64.95, 65.72, 68.32, 69.49, 101.25, 102.75, 119.99, 120.06, 124.65, 124.90, 129.96, 130.81, 130.88, 131.32, 131.54, 132.16, 133.05, 133.16, 135.98, 139.13, 166.09, 166.31, 171.48

Fab-MS m/z: 569 (M$^+$), 486

Example 24

Preparation of (RS)-N-(4-(ethoxycarbonylmethyl) phenyl)-2-(2-naphthalenesulfonylamino)-3-(tetrahydropyran-2-yloxy)propanamide The procedure described in Example 15 was repeated, except that (RS)-2-(benzyloxycarbonylamino)-N-(4-(ethoxycarbonylmethyl)phenyl)-3-(tetrahydropyran-2-yloxy)propanamide (500 mg) was hydrogenolyzed in the presence of 10% Pd-C, and then, reacted with 2-naphthalenesulfonyl chloride (463 mg) to obtain (RS)-N-(4-(ethoxycarbonyl-methyl)phenyl)-2-(2-naphthalenesulfonylamino)-3-(tetrahydropyran-2-yloxy) propanamide (345.7 mg).

Melting point: 132°–136° C.

IR vmax cm$^{-1}$ (KBr): 1734, 1674, 1336, 1163, 1132, 1074, 1034, 661, 550

$^1$H-NMR δ ppm (CDCl$_3$): 1.237 (3H, t, J=7.08 Hz), 1.3–1.9 (6H, m), 3.3–3.5 (2H, m), 3.548 (2H, s), 3.8–4.1

(3H, m), 4.132 (2H, q, J=7.08 Hz), 4.3–4.45 (1H, m), 7.1–8.0 (10H, m), 8.473 (1H, s), 8.641 (1H, d, J=2.19 Hz)

$^{13}$C-NMR δ ppm (CDCl$_3$): 14.15, 20.53, 24.89, 25.00, 30.61, 30.68, 40.84, 56.54, 56.87, 60.83, 64.53, 68.24, 68.38, 101.09, 101.28, 119.98, 120.05, 122.07, 122.33, 127.72, 127.83, 127.94, 129.00, 129.07, 129.18, 129.26, 129.73, 130.39, 130.47, 132.04, 135.02, 135.46, 136.15, 166.77, 166.99, 171.47

Fab-MS m/z: 540 (M$^+$), 457

Example 25

Preparation of (S)-2-(4-chlorobenzenesulfonylamino)-N-(4-ethoxycarbonylphenyl)-3-hydroxypropanamide A mixture of (S)-2-(4-chlorobenzenesulfonylamino)-N-(4-ethoxycarbonylphenyl)-3-(tetrahydropyran-2-yloxy) propanamide (385 mg), PPTS (140 mg) and ethanol (25 ml) was refluxed for 1 hour under argon. The reaction mixture was concentrated under reduced pressure, poured into a saturated saline solution, and extracted with ethyl acetate. The combined ethyl acetate layers were washed with saturated saline solution and dried over Na$_2$SO$_4$. The solvent was evaporated under reduced pressure to obtain 339 mg of a yellow oil. The crude product was purified by column chromatography (silica gel=25 g, hexane/ethyl acetate=1/1) to obtain (S)-2-(4-chlorobenzenesulfonylamino)-N-(4-ethoxycarbonylphenyl)-3-hydroxypropanamide (145 mg).

Melting point: 157°–159.5° C.

IR vmax cm$^{-1}$ (KBr): 3455, 3261, 1708, 1693, 1280, 1168, 1110, 1093

$^1$H-NMR δ ppm (CDCl$_3$): 1.40 (3H, t, J=7.1 Hz), 3.63 (1H, dd, J=11.2 Hz, J=5.6 Hz), 3.85 (2H, m), 4.36 (2H, q, J=7.1 Hz), 7.43 (2H, d, J=8.8 Hz), 7.51 (2H, d, J=8.8 Hz), 7.82 (2H, d, J=8.8 Hz), 7.98 (2H, d, J=8.8 Hz)

Fab-MS m/z: 427 (MH$^+$)

Example 26

Preparation of (RS)-2-(4-chlorobenzenesulfonylamino)-N-(4-ethoxycarbonylphenyl)-3-hydroxypropanamide The procedure described in Example 25 was repeated, except that the THP was removed from the (RS)-2-(4-chlorobenzenesulfonylamino)-N-(4-ethoxycarbonylphenyl)-3-(tetrahydropyran- 2-yloxy)propanamide (1.496 g) to obtain (RS)-2-(4-chlorobenzenesulfonylamino)-N-(4-ethoxycarbonylphenyl)-3-hydroxypropanamide (1.078 g).

Melting point: 157°–159° C.

IR vmax cm$^{-1}$ (KBr): 3455, 3261, 1708, 1693, 1280, 1168, 1110, 1093

$^1$H-NMR δ ppm (CDCl$_3$): 1.40 (3H, t, J=7.1 Hz), 3.63 (1H, dd, J=11.2 Hz, J=5.6 Hz), 3.85 (2H, m), 4.36 (2H, q, J=7.1 Hz), 7.43 (2H, d, J=8.8 Hz), 7.51 (2H, d, J=8.8 Hz), 7.82 (2H, d, J=8.8 Hz), 7.98 (2H, d, J=8.8 Hz)

Fab-MS m/z: 427 (MH$^+$)

Example 27

Preparation of (RS)-2-(4-chlorobenzenesulfonylamino)-N-(4-(ethoxycarbonylmethyl)phenyl)-3-hydroxypropanamide The procedure described in Example 25 was repeated, except that the THP was removed from the (RS)-2-(4-chlorobenzenesulfonylamino)-N-(4-(ethoxycarbonylmethyl)phenyl)-3-(tetrahydropyran-2-yloxy)propanamide (2.1 g) to obtain (RS)-2-(4-chlorobenzenesulfonylamino)-N-(4-(ethoxycarbonylmethyl)phenyl)-3-hydroxypropanamide (1.36 g).

Melting point: 139°–140° C.

IR vmax cm$^{-1}$ (KBr): 3506, 3330, 3261, 1718, 1660, 1338, 1166

$^1$H-NMR δ ppm (CDCl$_3$-DMSO-d$_6$-d$_6$): 1.243 (3H, t, J=7.1 Hz), 3.555 (2H, s), 3.66 (1H, m), 3.90 (2H, m), 4.128 (2H, q, J=7.1 Hz), 7.190 (2H, d, J=8.5 Hz), 7.387 (2H, d, J=8.5 Hz), 7.418 (2H, d, J=8.5 Hz), 7.833 (2H, d, J=8.5 Hz)

$^{13}$C-NMR δ ppm (CDCl$_3$-DMSO-d$_6$-d$_6$): 14.17, 40.71, 58.88, 60.78, 62.78, 120.05, 128.72, 129.34, 129.63, 130.20, 136.49, 138.23, 139.26, 167.68, 171.48

Fab-MS m/z: 441 (MH$^+$)

Example 28

Preparation of (RS)-2-(4-chlorobenzenesulfonylamino)-N-(4-(2-methoxycarbonylethyl)phenyl)-3-hydroxypropanamide The procedure described in Example 25 was repeated, except that the THP was removed from the (RS)-2-(4-chlorobenzenesulfonylamino)-N-(4-(2-methoxycarbonylethyl)phenyl)-3-(tetrahydropyran-2-yloxy)propanamide (1.62 g) to obtain (RS)-2-(4-chlorobenzenesulfonylamino)-N-(4-(2-methoxycarbonylethyl)phenyl)-3-hydroxypropanamide (0.99 g).

IR vmax cm$^{-1}$ (KBr): 3388, 1716, 1674, 1344, 1165

$^1$H-NMR δ ppm (CDCl$_3$-CD$_3$OD): 2.588 (2H, d, J=7.3 Hz), 2.890 (2H, d, J=7.3 Hz), 3.654 (3H, s), 3.7 to 3.95 (3H, m), 7.097 (2H, d, J=8.4 Hz), 7.21 (1H, d, J=7.3 Hz), 7.329 (2H, d, J=8.4 Hz), 7.400 (2H, d, J=8.6 Hz), 7.831 (2H, d, J=8.6 Hz), 9.038 (1H, s)

$^{13}$C-NMR δ ppm (CDCl$_3$-CD$_3$OD): 29.91, 30.48, 35.27, 51.13, 58.68, 62.44, 119.67, 128.14, 128.29, 128.84, 135.49, 136.08, 138.08, 138.65, 167.23, 172.71

Fab-MS m/z: 441 (MH$^+$)

Example 29

Preparation of (S)-2-(4-chlorobenzenesulfonylamino)-N-(3-ethoxycarbonylphenyl)-3-hydroxypropanamide The procedure described in Example 25 was repeated, except that the THP was removed from the (S)-2-(4-chlorobenzenesulfonylamino)-N-(3-ethoxycarbonylphenyl)-3-(tetrahydropyran-2-yloxy)propanamide (2.3 g) to obtain (S)-2-(4-chlorobenzenesulfonylamino)-N-(3-ethoxycarbonylphenyl)-3-hydroxypropanamide (1.49g).

IR vmax cm$^{-1}$ (KBr): 3482, 3350, 3236, 1718, 1675, 1324, 1087

$^1$H-NMR δ ppm (CDCl$_3$-CD$_3$OD): 1.40 (3H, t, J=7.2 Hz), 3.63 (1H, dd, J=11.1 Hz, J=5.1 Hz), 3.88 (1H, dd, J=11.1 Hz, J=5.1 Hz), 3.95 (1H, t, J=5.1 Hz), 4.38 (2H, q, J=7.2 Hz), 7.37 (1H, t, J=7.6 Hz), 7.42 (2H, d, J=8.6 Hz), 7.71 (1H, d, J=7.6 Hz), 7.78 (1H, d, J=7.6 Hz), 7.83 (2H, d, J=8.6 Hz) 7.96 (1H, s)

$^{13}$C-NMR δ ppm (CDCl$_3$-CD$_3$OD): 14.07, 58.65, 61.21, 62.25, 120.88, 124.45, 125.63, 128.54, 128.88, 129.32, 130.90, 137.26, 137.93, 166.41, 168.13

Fab-MS m/z: 427 (MH$^+$)

Example 30

Preparation of (RS)-2-(4-chlorobenzenesulfonylamino)-N-(3-ethoxycarbonylphenyl)-3-hydroxypropanamide The procedure described in Example 25 was repeated, except that the THP was removed from the (RS)-2-(4-chlorobenzenesulfonylamino)-N-(3-ethoxycarbonylphenyl)-3-(tetrahydropyran-2-yloxy)propanamide (2.224 g) to obtain (RS)-2-(4-chlorobenzenesulfonylamino)-N-(3-ethoxycarbonylphenyl)-3-hydroxypropanamide (1.374 g).

Melting point: 142°–144° C.

IR vmax cm⁻¹ (KBr): 3482, 3350, 3236, 1718, 1675, 1324, 1087

¹H-NMR δ ppm (CDCl₃-CD₃OD): 1.40 (3H, t, J=7.2 Hz), 3.63 (1H, dd, J=11.1 Hz, J=5.1 Hz), 3.88 (1H, dd, J=11.1 Hz, J=5.1 Hz), 3.95 (1H, t, J=5.1 Hz), 4.38 (2H, q, J=7.2 Hz), 7.37 (1H, t, J=7.6 Hz), 7.42 (2H, d, J=8.6 Hz), 7.71 (1H, d, J=7.6 Hz), 7.78 (1H, d, J=7.6 Hz), 7.83 (2H, d, J=8.6 Hz), 7.96 (1H, s)

¹³C-NMR δ ppm (CDCl₃-CD₃OD): 14.07, 58.65, 61.21, 62.25, 120.88, 124.45, 125.63, 128.54, 128.88, 129.32, 130.90, 137.26, 137.93, 166.41, 168.13

Fab-MS m/z: 427 (MH⁺)

Example 31

Preparation of (RS)-2-(4-chlorobenzenesulfonylamino)-3-hydroxy-N-(3-methoxycarbonylpropyl)propanamide The procedure described in Example 25 was repeated, except that the THP was removed from the (RS)-2-(4-chlorobenzenesulfonylamino)-N-(3-methoxycarbonylpropyl)-3-(tetrahydropyran-2-yloxy)propanamide (1.99 g) to obtain (RS)-2-(4-chlorobenzenesulfonylamino)-3-hydroxy-N-(3-methoxycarbonylpropyl)propanamide (947 mg).

Melting point: 119°–121° C.

IR vmax cm⁻¹ (KBr): 3479, 3311, 3234, 2946, 1732, 1651, 1628, 1398, 1313, 1163, 1093

¹H-NMR δ ppm (DMSO-d₆): 1.576 (2H, qw, J=7.2 Hz), 2.220 (2H, t, J=7.4 Hz), 2.968 (2H, dd, J=12.7 Hz, J=6.8 Hz), 3.473 (2H, t, J=5.4 Hz), 3.598 (3H, s), 4.590 (1H, t, J=5.6 Hz), 7.550 (2H, d, J=8.4 Hz), 7.798 (2H, d, J=8.4 Hz)

¹³C-NMR δ ppm (CDCl₃): 23.92, 27.00, 30.33, 37.59, 58.28, 61.94, 128.10, 128.39, 138.40, 139.65, 163.96, 177.75

Fab-MS m/z: 379 (MH⁺)

Example 32

Preparation of (RS)-2-(4-chlorobenzenesulfonylamino)-3-hydroxy-N-(4-methoxycarbonylbutyl)propanamide The procedure described in Example 25 was repeated, except that the THP was removed from the (RS)-2-(4-chlorobenzenesulfonylamino)-N-(4-methoxycarbonylbutyl)-3-(tetrahydropyran-2-yloxy)propanamide (1.506 g) to obtain (RS)-2-(4-chlorobenzenesulfonylamino)-3-hydroxy-N-(4-methoxycarbonylbutyl)propanamide (997 mg).

Melting point: 92°–94° C.

IR vmax cm⁻¹ (KBr): 3296, 2954, 1733, 1637, 1618, 1398, 1313, 1165, 1093

¹H-NMR δ ppm (DMSO-d₆-d₆): 1.2–1.5 (4H, m), 2.248 (2H, t, J=7.3 Hz), 2.887 (2H, dd, J=12.7 Hz, J=6.6 Hz), 3.443 (2H, d, J=5.6 Hz), 3.582 (3H, s), 4.6–4.8 (1H, m), 7.573 (2H, d, J=8.6 Hz), 7.787 (2H, d, J=8.6 Hz)

¹³C-NMR δ ppm (CDCl₃): 21.53, 27.18, 27.99, 32.72, 37.96, 50.80, 62.09, 128.32, 128.65, 136.94, 139.91, 168.47, 172.86

Fab-MS m/z: 393 (MH⁺)

Example 33

Preparation of (RS)-2-(4-chlorobenzenesulfonylamino)-3-hydroxy-N-(5-methoxycarbonylpentyl)propanamide The procedure described in Example 25 was repeated, except that the THP was removed from the (RS)-2-(4-chlorobenzenesulfonylamino)-N-(5-methoxycarbonylpentyl)-3-(tetrahydropyran-2-yloxy)propanamide (1.755 g) to obtain (RS)-2-(4-chlorobenzenesulfonylamino)-3-hydroxy-N-(5-methoxycarbonylpentyl)propanamide (823 mg).

Melting point: 83°–86° C.

IR vmax cm⁻¹ (KBr): 3309, 1736, 1649, 1625, 1315, 1163, 823, 752

¹H-NMR δ ppm (CDCl₃): 1.2–1.8 (6H, m), 2.315 (2H, t, J=7.3 Hz), 3.201 (2H, dd, J=12.7 Hz, J=6.6 Hz), 3.403 (1H, dd, J=11.2 Hz, J=5.4 Hz), 3.673 (3H, s), 3.69 (1H, m), 3.896 (1H, dd, J=11.2 Hz, J=3.5 Hz), 6.901 (1H, m), 7.499 (2H, d, J=8.8 Hz), 7.817 (2H, d, J=8.8 Hz)

¹³C-NMR δ ppm (CDCl₃): 24.23, 25.99, 28.70, 33.69, 39.38, 51.59, 57.42, 62.22, 128.60, 129.55, 137.88, 139.67, 169.38, 174.33

Fab-MS m/z: 407 (MH⁺)

Example 34

Preparation of (RS)-2-(4-chlorobenzenesulfonylamino)-3-hydroxy-N-(6-methoxycarbonylhexyl)propanamide The procedure described in Example 25 was repeated, except that the THP was removed from the (RS)-2-(4-chlorobenzenesulfonylamino)-N-(6-methoxycarbonylhexyl)-3-(tetrahydropyran-2-yloxy)propanamide (1.163 g) to obtain (RS)-2-(4-chlorobenzenesulfonylamino)-3-hydroxy-N-(6-methoxycarbonylhexyl)propanamide (726 mg).

Melting point: 78°–81° C.

IR vmax cm⁻¹ (KBr): 3300, 2935, 1732, 1647, 1622, 1398, 1313, 1163, 1093

¹H-NMR δ ppm (CDCl₃): 1.2–1.3 (4H, m), 1.447 (2H, t, J=6.6 Hz), 1.605 (2H, t, J=7.3 Hz), 2.306 (2H, t, J=7.3 Hz), 3.180 (2H, q, J=6.6 Hz), 3.442 (2H, dd, J=11.2 Hz, J=5.4 Hz), 3.670 (3H, s), 3.938 (1H, dd, J=11.2 Hz, J=3.9 Hz), 6.200 (1H, d, J=7.6 Hz), 6.8–6.9 (1H, m), 7.498 (2H, d, J=8.8 Hz), 7.822 (2H, d, J=8.8 Hz)

¹³C-NMR δ ppm (CDCl₃): 24.63, 26.21, 29.48, 28.85, 33.84, 39.63, 51.55, 57.42, 62.44, 128.63, 129.59, 137.84, 139.75, 169.23, 174.40

Fab-MS m/z: 421 (MH⁺)

Example 35

Preparation of (RS)-2-(4-chlorobenzenesulfonylamino)-3-hydroxy-N-(7-methoxycarbonylheptyl)propanamide The procedure described in Example 25 was repeated, except that the THP was removed from the (RS)-2-(4-chlorobenzenesulfonylamino)-N-(7-methoxycarbonylheptyl)-3-(tetrahydropyran-2-yloxy)propanamide (1.835 g) to obtain (RS)-2-(4-chlorobenzenesulfonylamino)-3-hydroxy-N-(7-methoxycarbonylheptyl)propanamide (815 mg).

Melting point: 88°–92° C.

IR vmax cm⁻¹ (KBr): 3311, 2926, 1734, 1649, 1626, 1398, 1313, 1163, 1093

¹H-NMR δ ppm (CD₃OD): 1.2–1.4 (8H, m), 1.604 (2H, t, J=7.3 Hz), 2.319 (2H, t, J=7.3 Hz), 2.997 (2H, t, J=6.8 Hz), 3.5–3.6 (2H, m), 3.651 (3H, s), 3.776 (1H, t, J=5.6 Hz), 7.546 (2H, d, J=8.8 Hz), 7.838 (2H, d, J=8.8 Hz)

¹³C-NMR δ ppm (CD₃OD): 25.90, 27.62, 29.93, 30.00, 30.08, 34.77, 40.42, 51.97, 60.00, 63.74, 129.97, 130.30, 139.95, 140.72, 166.64, 171.45

Fab-MS m/z: 435 (MH⁺)

Example 36

Preparation of (RS)-N-(4-(ethoxycarbonylmethyl) phenyl)-2-(4-fluorobenzenesulfonylamino)-3-hydroxy propanamide The procedure described in Example 25 was repeated, except that the THP was removed from the (RS)-N-(4-(ethoxycarbonylmethyl)phenyl)-2-(4-fluorobenzenesulfonylamino)-3-(tetrahydropyran-2-yloxy) propanamide (2.50 g) to obtain (RS)-N-(4-(ethoxycarbonylmethyl)phenyl)-2-(4-fluorobenzenesulfonylamino)-3-hydroxypropanamide (1.96 g).

Melting point: 148.5°–150.5° C.

IR vmax cm$^{-1}$ (KBr): 3506, 3346, 3265, 1712, 1660, 1348, 1169

$^1$H-NMR δ ppm (CDCl$_3$-CD$_3$OD): 1.247 (3H, t, J=7.08 Hz), 3.569 (2H, s), 3.60 (1H, m), 3.80–3.95 (2H, m), 4.139 (2H, q, J=7.08 Hz), 7.140 (2H, t, J=8.79 Hz), 7.200 (2H, d, J=8.55 Hz), 7.365 (2H, d, J=8.55 Hz), 7.902 (2H, dd, J=8.79 Hz, J=5.0 Hz)

$^{13}$C-NMR δ ppm (CDCl$_3$-CD$_3$OD): 13.85, 40.63, 58.43, 60.87, 62.20, 62.31, 116.08, 116.39, 120.14, 120.22, 129.55, 129.73, 129.87, 130.39, 135.37, 135.92, 136.00, 167.94, 171.83

Fab-MS m/z: 425 (MH$^+$)

Example 37

Preparation of (RS)-2-(4-bromobenezenesulfonylamino)-N-(4-(ethoxycarbonylmethyl)phenyl)-3-hydroxy propanamide The procedure described in Example 25 was repeated, except that the THP was removed from the (RS)-2-(4-bromobenzenesulfonylamino)-N-(4-(ethoxycarbonylmethyl)phenyl)-3-(tetrahydropyran-2-yloxy)propanamide (2.21 g) to obtain (RS)-2-(4-bromobenzenesulfonylamino)-N-(4-(ethoxycarbonylmethyl)phenyl)-3-hydroxypropanamide (1.33 g).

Melting point: 149°–150° C.

IR vmax cm$^{-1}$ (KBr): 3506, 3265, 1734, 1670, 1325, 1171, 746

$^1$H-NMR δ ppm (CDCl$_3$-CD$_3$OD): 1.247 (3H, t, J=7.08 Hz), 3.48–3.63 (1H, m), 3.570 (2H, s), 3.88 (2H, m), 4.138 (2H, q, J=7.08 Hz), 7.208 (2H, d, J=8.55 Hz), 7.347 (2H, d, J=8.55 Hz), 7.598 (2H, d, J=8.79 Hz), 7.739 (2H, d, J=8.79 Hz)

$^{13}$C-NMR δ ppm (CDCl$_3$-CD$_3$OD): 14.00, 40.70, 58.22, 60.94, 62.22, 120.20, 120.31, 128.08, 128.60, 129.73, 130.58, 132.45, 135.82, 138.28, 167.65, 171.72

Fab-MS m/z: 487 (M+2), 485 (M$^+$)

Example 38

Preparation of (RS)-N-(4-(ethoxycarbonylmethyl) phenyl)-3-hydroxy-2-(4-iodobenzenesulfonylamino)propanamide The procedure described in Example 25 was repeated, except that the THP was removed from the (RS)-N-(4-(ethoxycarbonylmethyl)phenyl)-2-(4-iodobenzenesulfonylamino)-3-(tetrahydropyran-2-yloxy)propanamide (3.71 g) to obtain (RS)-N-(4-(ethoxycarbonylmethyl)phenyl)-3-hydroxy-2-(4-iodobenzenesulfonylamino)propanamide (2.66 g).

Melting point: 181°–182° C.

IR vmax cm$^{-1}$ (KBr): 3493, 3342, 3265, 1734, 1668, 1344, 1171, 739

$^1$H-NMR δ ppm (CDCl$_3$-DMSO-d$_6$-d$_6$): 1.243 (3H, t, J=7.1 Hz), 3.551 (2H, s), 3.61–3.73 (1H, m), 3.74–3.88 (1H, m), 3.968 (1H, t, J=5.4 Hz), 4.122 (2H, q, J=7.1 Hz), 7.172 (2H, d, J=8.6 Hz), 7.356 (2H, d, J=8.6 Hz), 7.598 (2H, d, J=8.5 Hz), 7.762 (2H, d, J=8.5 Hz)

$^{13}$C-NMR δ ppm (CDCl$_3$-DMSO-d$_6$-d$_6$): 13.52, 40.07, 58.70, 60.02, 62.22, 99.26, 119.36, 127.94, 128.89, 129.26, 136.12, 137.44, 139.38, 167.18, 170.73

Fab-MS m/z: 533 (MH$^+$)

Example 39

Preparation of (S)-N-(4-carboxyphenyl)-2-(4-chlorobenzenesulfonylamino)-3-(tetrahydropyran-2-yloxy) propanamide A mixture of (S)-2-(4-chlorobenzenesulfonylamino)-N-(4-ethoxycarbonylphenyl)-3-(tetrahydropyran-2-yloxy) propanamide (200 mg), ethanol (5 ml), and 2N NaOH (2 ml) was stirred at room temperature overnight under argon. The reaction mixture was concentrated under reduced pressure. It was repeated 3 times in order to remove ethanol completely that a small amount of purified water was added to the residue, and the whole was concentrated under reduced pressure. The residue was acidified with 1N HCl, and then extracted with ethyl acetate. The combined ethyl acetate layers were washed with saturated saline solution and dried over Na$_2$SO$_4$. The solvent was evaporated under reduced pressure to obtain (S)-N-(4-carboxyphenyl)-2-(4-chlorobenzenesulfonylamino)-3-(tetrahydropyran-2-yloxy)propanamide (147 mg).

Melting point: 139°–221° C.

IR vmax cm$^{-1}$ (KBr): 3365, 1689, 1319, 1168

$^1$H-NMR δ ppm (CDCl$_3$): 1.2–1.8 (6H, m), 3.42 (1, m), 3.58 (2H, m), 3.81 (1H, m), 4.167 and 4.173 (0.5H each, t, J=6.6 Hz), 4.49 and 4.59 (0.5H each, m), 7.43 and 7.44 (1H each, d, J=8.8 Hz), 7.40 and 7.49 (1H each, d, J=9.0 Hz), 7.84 (2H, d, J=9.0 Hz), 7.93 (2H, d, J=8.8 Hz)

Fab-MS m/z: 483 (MH$^+$), 399

Example 40

Preparation of (RS)-N-(4-carboxyphenyl)-2-(4-chlorobenzenesulfonylamino)-3-(tetrahydropyran-2-yloxy) propanamide The procedure described in Example 39 was repeated, except that (RS)-2-(4-chlorobenzenesulfonylamino)-N-(4-ethoxycarbonylphenyl)-3-(tetrahydropyran-2-yloxy) propanamide (160.8 mg) was hydrolyzed to obtain (RS)-N-(4-carboxyphenyl)-2-(4-chlorobenzenesulfonylamino)-3-(tetrahydropyran-2-yloxy)propanamide (112 mg).

Melting point: 136°–137° C.

IR vmax cm$^{-1}$ (neat): 3467, 1691, 1323, 1167

$^1$H-NMR δ ppm (CD$_3$OD): 1.2–1.8 (6H, m), 3.42 (1H, m), 3.72 (2H, m), 3.81 (1H, m), 4.17 (1H, m), 4.45 (1H, m), 7.44 (2H, d, J=8.8 Hz), 7.49 (2H, d, J=9.0 Hz), 7.84 (2H, d, J=9.0 Hz), 7.93 (2H, d, J=8.8 Hz)

Fab-MS m/z: 483 (MH$^+$), 399

Example 41

Preparation of (RS)-N-(4-(carboxyethyl)phenyl)-2-(4-chlorobenzenesulfonylamino)-3-(tetrahydropyran-2-yloxy) propanamide The procedure described in Example 39 was repeated, except that (RS)-2-(4-chlorobenzenesulfonylamino)-N-(4-(ethoxycarbonylmethyl)phenyl)-3-(tetrahydropyran-2-yloxy)propanamide (200 mg) was hydrolyzed to obtain (RS)-N-(4-(carboxymethyl)phenyl)-2-(4-chlorobenzenesulfonylamino)-3-(tetrahydropyran-2-yloxy) propanamide (80 mg).

Melting point: 146°–147° C.

IR νmax cm⁻¹ (KBr): 3440 (br), 3253, 1701, 1653, 1338, 1166

¹H-NMR δ ppm (DMSO-d₆-d₆): 1.2–1.7 (6H, m), 3.40 (2H, m), 3.481 (2H, s), 3.65 (2H, m), 4.145 (1H, m), 4.461 and 4.545 (1H, m), 7.157 (2H, d, J=8.5 Hz), 7.329 (2H, d, J=8.5 Hz), 7.525 (2H, d, J=8.6 Hz), 7.815 (2H, d, J=8.6 Hz)

¹³C-NMR δ ppm (DMSO-d₆-d₆): 18.21 and 18.34, 24.47, 29.47 and 29.51, 39.50, 56.59, 60.77 and 61.01, 66.38 and 66.58, 97.50 and 97.64, 119.26, 128.06, 128.50, 128.94, 130.02, 136.41, 136.92, 139.81, 166.84, 171.89

Fab-MS m/z: 497 (MH⁺)

Example 42

Preparation of (RS)-N-(4-(2-carboxyethyl) phenyl)-2-(4-chlorobenzenesulfonylamino)-3-(tetrahydropyran-2-yloxy) propanamide The procedure described in Example 39 was repeated, except that (RS)-2-(4-chlorobenzenesulfonylamino)-N-(4-(2-methoxycarbonylethyl)phenyl)-3-(tetrahydropyran-2-yloxy)propanamide (210 mg) was hydrolyzed to obtain (RS)-N-(4-(2-carboxyethyl)phenyl)-2-(4-chlorobenzenesulfonylamino)-3-(tetrahydropyran-2-yloxy)propanamide (130 mg).

Melting point: 150°–151° C.

IR νmax cm⁻¹ (KBr): 3255, 1695, 1658, 1342, 1167

¹H-NMR δ ppm (DMSO-d₆-d₆): 1.2–1.8 (6H, m), 2.489 (2H, t, J=7.5 Hz), 2.785 (2H, t, J=7.5 Hz), 3.3–3.8 (4H, m), 4.133 (1H, t, J=6.4 Hz), 4.460 and 4.542 (1H, m), 7.11 (2H, d, J=8.5 Hz), 7.30 (2H, d, J=8.5 Hz), 7.51 (2H, d, J=8.8 Hz), 7.812 (2H, d, J=8.8 Hz), 9.61 (1H, d, J=11.2 Hz)

¹³C-NMR δ ppm (DMSO-d₆-d₆): 18.19 and 18.34, 24.47, 29.49, 34.90, 56.59, 66.38 and 66.56, 97.50 and 97.63, 119.33, 127.71 and 127.81, 128.04 and 128.48, 135.84 and 135.87, 135.93, 136.90, 139.80, 166.71 and 166.82, 172.99

Fab-MS m/z: 511 (MH⁺), 510 (M⁺), 427 (MH⁺–DHP)

Example 43

Preparation of (S)-N-(3-carboxyphenyl)-2-(4-chlorobenzenesulfonylamino)-3-(tetrahydropyran-2-yloxy) propanamide The procedure described in Example 39 was repeated, except that (S)-2-(4-chlorobenzenesulfonylamino)-N-(3-ethoxycarbonylphenyl)-3-(tetrahydropyran-2-yloxy) propanamide (130 mg) was hydrolyzed to obtain (S)-N-(3-carboxyphenyl)- 2-(4-chlorobenzenesulfonylamino)-3-(tetrahydropyran-2-yloxy)propanamide (122 mg).

Melting point: 84°–124° C.

IR νmax cm⁻¹ (neat): 3800–2200 (br), 3240, 1702 (br), 1332, 1165

¹H-NMR δ ppm (CD₃OD): 1.2–1.8 (6H, t, m), 3.3–3.9 (4H, m), 4.17 (1H, m), 4.508 and 4.606 (1H, m), 7.379 (1H, t, J=8.1 Hz), 7.443 (1H, d, J=8.6 Hz), 7.448 (1H, d, J=8.6 Hz), 7.61 (1H, m), 7.754 (1H, dt, J=8.1 Hz, J=1.7 Hz) 7.857 (2H, d, J=8.6 Hz), 8.024 (1H, t, J=1.7 Hz)

Fab-MS m/z: 483 (MH⁺), 399

Example 44

Preparation of (RS)-N-(3-carboxyphenyl)-2-(4-chlorobenzenesulfonylamino)-3-(tetrahydropyran-2-yloxy) propanamide The procedure described in Example 39 was repeated, except that (RS)-2-(4-chlorobenzenesulfonylamino)-N-(3-ethoxycarbonylphenyl)-3-(tetrahydropyran-2-yloxy) propanamide (191 mg) was hydrolyzed to obtain (RS)-N-(3-carboxyphenyl)-2-(4-chlorobenzenesulfonylamino)-3-(tetrahydropyran-2-yloxy)propanamide (140.4 mg).

Melting point: 165°–166° C.

IR νmax cm⁻¹ (neat): 3800–2200 (br), 3240, 1702 (br), 1332, 1165

¹H-NMR δ ppm (CD₃OD): 1.2–1.8 (6H, m), 3.3–3.9 (4H, m), 4.17 (1H, m), 4.508 and 4.606 (1H, m), 7.379 (1H, t, J=8.1 Hz), 7.443 (1H, d, J=8.6 Hz), 7.448 (1H, d, J=8.6 Hz) 7.61 (1H, m), 7.754 (1H, dt, J=8.1 Hz, J=1.7 Hz) 7.857 (2H, d, J=8.6 Hz), 8.024 (1H, t, J=1.7 Hz)

Fab-MS m/z: 483 (MH⁺), 399

Example 45

Preparation of (RS)-N-(3-(carboxymethyl) phenyl)-2-(4chlorobenzenesulfonylamino)-3-(tetrahydropyran-2-yloxy)propanamide The procedure described in Example 39 was repeated, except that (RS)-2-(4-chlorobenzenesulfonylamino)-N-(3-(methoxycarbonylmethyl)phenyl)- 3-(tetrahydropyran-2-yloxy)propanamide (56 mg) was hydrolyzed to obtain (RS)-N-(3-(carboxymethyl)phenyl)-2-(4-chlorobenzenesulfonylamino)-3-(tetrahydropyran-2-yloxy)propanamide (17 mg).

IR νmax cm⁻¹ (KBr): 3263, 1710, 1690, 1338, 1167

¹H-NMR δ ppm (DMSO-d₆-d₆): 1.2–1.8 (6H, m), 3.499 (2H, s), 3.3–3.8 (4H, m), 4.146 (1H, m), 4.461 and 4.541 (0.5H each, m), 6.948 (1H, d, J=7.6 Hz), 7.195 (1H, t, J=7.6 Hz), 7.304 (1H, s), 7.527 (2H d, J=8.8 Hz), 7.813 (2H, d, J=8.8 Hz), 9.684 (1H, m)

Fab-MS m/z: 497 (MH⁺)

Example 46

Preparation of (RS)-N-(3-(carboxymethyl) phenyl)-2-(4-chlorobenzenesulfonylamino)-3-(tetrahydropyran-2-yloxy) propanamide The procedure described in Example 39 was repeated, except that (RS)-2-(4-chlorobenzenesulfonylamino)-N-(3-(2-methoxycarbonylethyl)phenyl)-3-(tetrahydropyran-2-yloxy) propanamide (525 mg) was hydrolyzed to obtain (RS)-N-(3-(carboxyethyl)phenyl)-2-(4-chlorobenzenesulfonylamino)-3-(tetrahydropyran-2-yloxy) propanamide (385 mg).

Melting point: 152°–154° C.

IR νmax cm⁻¹ (KBr): 3332, 3251, 1699, 1659, 1338, 1169

¹H-NMR δ ppm (DMSO-d₆): 1.2–1.7 (6H, m), 2.501 (2H, t, J=7.4 Hz), 2.801 (2H, t, 7.4 Hz), 3.4–3.9 (4H, m), 4.15 (1H, m), 4.5 (1H, m), 6.913 (1H, d, J=7.3 Hz), 7.1–7.3 (3H, m), 7.522 (2H, d, J=8.5 Hz), 7.824 (2H, d, J=8.5 Hz), 9.628 (1H, d, J=11.7 Hz)

Fab-MS m/z: 511 (MH⁺), 427 (MH⁺–DHP)

Example 47

Preparation of (RS)-N-(3-carboxypropyl)-2-(4-chlorobenzenesulfonylamino)-3-(tetrahydropyran-2-yloxy) propanamide The procedure described in Example 39 was repeated, except that (RS)-2-(4-chlorobenzenesulfonylamino)-N-(3-methoxycarbonylpropyl)-3-(tetrahydropyran-2-yloxy) propanamide (463 mg) was hydrolyzed to obtain (RS)-N-(3-carboxypropyl)- 2-(4-chlorobenzenesulfonylamino)-3-(tetrahydropyran-2-yloxy)propanamide (424 mg).

Melting point: 96°–101° C.

IR vmax cm⁻¹ (neat): 3369, 1716, 1652, 1338, 1167

¹H-NMR δ ppm (CDCl₃): 1.2–1.9 (8H, m), 2.382 (2H, t, J=7.0 Hz), 3.2–3.9 (6H, m), 4.05 (1H, m), 4.35 (1H, m), 6.268 (0.5H, d, J=5.4 Hz), 6.465 (0.5H, d, J=7.1 Hz), 7.014 (1H, dd, J=12.2 Hz, J=6.1 Hz), 7.491 (2H, d, J=8.5 Hz), 7.812 (2H, d, J=8.5 Hz)

Fab-MS m/z: 449 (MH⁺), 365 (MH⁺–DHP)

Example 48

Preparation of (RS)-N-(4-carboxybutyl)-2-(4-chlorobenzenesulfonylamino)-3-(tetrahydropyran-2-yloxy) propanamide The procedure described in Example 39 was repeated, except that -(RS)-2-(4-chlorobenzenesulfonyl-amino)-N-(methoxycarbonylbutyl)-3-(tetrahydropyran-2-yloxy)-propanamide (124.8 mg) was hydrolyzed to obtain (RS)-N-(4-carboxybutyl)-2-(4-chlorobenzenesulfonylamino)-3-(tetrahydropyran-2-yloxy)propanamide (95.7 mg).

IR vmax cm⁻¹ (neat): 3369, 3307, 2945, 1716, 1653, 1443, 1338, 1167, 1124, 1093

¹H-NMR δ ppm (CDCl₃): 1.258 (2H, t, J=7.1 Hz), 1.4–1.8 (8H, m), 2.360 (2H, t, J=7.0 Hz), 3.1–3.3 (2H, m), 3.4–3.6 (H, m), 3.8–3.9 (2H, m), 4.123 (1H, q, J=7.2 Hz), 4.3–4.4 (1H, m), 6.4–6.6 (1H, m), 6.964 (1H, d, J=5.4 Hz), 7.4–7.5 (2H, m), 7.815 (2H, d, J=8.3 Hz)

¹³C-NMR δ ppm (CDCl₃): 20.27, 21.63, 24.89 and 24.96, 28.56, 30.46, 33.29, 39.19, 56.28 and 56.46, 64.06 and 64.13, 68.09 and 68.16, 100.69, 128.67 and 128.85, 129.29 and 129.44, 137.62 and 137.88, 139.45 and 139.53, 168.86 and 169.08, 177.85

Fab-MS m/z: 463 (MH⁺), 379 (MH⁺–THP)

Example 49

Preparation of (RS)-N-(5-carboxypentyl)-2-(4-chlorobenzenesulfonylamino)-3-(tetrahydropyran-2-yloxy) propanamide The procedure described in Example 39 was repeated, except that (RS)-2-(4-chlorobenzenesulfonylamino)-N-(5-methoxycarbonylpentyl)- 3-(tetrahydropyran-2-yloxy) propanamide (103.7 mg) was hydrolyzed to obtain (RS)-N-(5-carboxypentyl)-2-(4-chlorobenzenesulfonylamino)-3-(tetrahydropyran-2-yloxy)propanamide (79.4 mg).

IR vmax cm⁻¹ (neat): 3500–3000 (br), 2941, 1711, 1653, 1396, 1340, 1167

¹H-NMR δ ppm (CDCl₃): 1.3–1.7 (12H, m), 2.343 (2H, t, J=7.2 Hz), 3.226 (2H, t, J=6.4 Hz), 3.4–3.5 (2H, m), 3.8–3.9 (2H, m), 4.3–4.4 (1H, m), 6.886 (1H, q, J=5.9 Hz), 7.483 (2H, dd, J=8.8 Hz, J=1.2 Hz), 7.7–7.9 (2H, m)

Fab-MS m/z: 477 (MH⁺), 393 (MH⁺–THP)

Example 50

Preparation of (RS)-N-(6-carboxyhexyl)-2-(4-chlorobenzenesulfonylamino)-3-(tetrahydropyran-2-yloxy) propanamide The procedure described in Example 39 was repeated, except that (RS)-2-(4-chlorobenzenesulfonylamino)-N-(6-methoxycarbonylhexyl)-3-(tetrahydropyran-2-yloxy) propanamide (107.3 mg) was hydrolyzed to obtain (RS)-N-(6-carboxyhexyl)-2-(4-chlorobenzenesulfonylamino)-3-(tetrahydropyran-2-yloxy)propanamide (83.2 mg).

Melting point: 86°–88° C.

IR vmax cm⁻¹ (neat): 3383, 2943, 2864, 1713, 1659, 1443, 1338, 1167, 1124, 1028

¹H-NMR δ ppm (CDCl₃): 1.2–1.4 (4H, m), 1.4–1.8 (10H, m), 2.341 (2H, t, J=7.3 Hz), 3.1–3.3 (2H, m), 3.4–3.5 (2H, m), 3.7–3.9 (2H, m), 4.008 (1H, dd, J=10.5 Hz, J=3.4 Hz), 4.3–4.4 (1H, m), 6.536 (1H, d, J=7.1 Hz), 6.865 (1H, d, J=4.6 Hz), 7.483 (2H, d, J=8.8 Hz), 7.811 (2H, d, J=8.8 Hz)

¹³C-NMR δ ppm (CDCl₃): 20.31 and 20.38, 24.41, 24.93 and 25.00, 26.21, 28.48, 28.92, 30.57, 30.76, 39.60, 56.24 and 56.43, 64.20 and 64.31, 68.13 and 68.24, 100.80, 128.71 and 128.89, 129.33 and 129.48, 137.58 and 137.88, 139.53 and 139.60, 168.75 and 168.97, 178.43

Fab-MS m/z: 491 (MH⁺), 407 (MH⁺–THP)

Example 51

Preparation of (RS)-N-(7-carboxyheptyl)-2-(4-chlorobenzenesulfonylamino)-3-(tetrahydropyran-2-yloxy) propanamide The procedure described in Example 39 was repeated, except that (RS)-2-(4-chlorobenzenesulfonylamino)-N-(7-methoxycarbonylheptyl)-3-(tetrahydropyran-2-yloxy) propanamide (108 mg) was hydrolyzed to obtain (RS)-N-(7-carboxyheptyl)-2-(4-chlorobenzenesulfonylamino)-3-(tetrahydropyran-2-yloxy)propanamide (72.6 mg).

IR vmax cm⁻¹ (neat): 3271, 3151, 2939, 1711, 1659, 1443, 1342, 1167, 1126, 1093

¹H-NMR δ ppm (CDCl₃): 1.2–1.8 (16H, m), 2.337 (2H, t, J=7.5 Hz), 3.1–3.3 (2H, m), 3.4–3.6 (2H, m), 3.7–3.9 (2H, m), 3.9–4.2 (1H, m), 4.3–4.4 (1H, m), 6.796 (1H, d, J=4.9 Hz), 7.495 (2H, d, J=8.5 Hz), 7.809 (2H, d, J=8.5 Hz)

¹³C-NMR δ ppm (CDCl₃): 20.34, 24.49, 25.04, 26.39, 28.67 and 28.81, 29.11, 30.61, 33.84, 39.63, 56.17, 56.39, 64.20 and 64.28, 68.20, 100.80, 128.71 and 128.89, 129.33 and 129.48, 137.58, 139.53 and 139.60, 168.64 and 168.83, 178.62

Fab-MS m/z: 505 (MH⁺), 421 (MH⁺–THP)

Example 52

Preparation of (RS)-2-(benzenesulfonylamino)-N-(4-(carboxymethyl)phenyl)-3-(tetrahydropyran-2-yloxy) propanamide The procedure described in Example 39 was repeated, except that (RS)-2-(benzenesulfonylamino)-N-(4-(ethoxycarbonylmethyl)phenyl)-3-(tetrahydropyran-2-yloxy) propanamide (100 mg) was hydrolyzed to obtain (RS)-2-(benzenesulfonylamino)-N-(4-(carboxymethyl) phenyl)-3-(tetrahydropyran-2-yloxy)propanamide (92.7 mg).

Melting point: 128.5°–135° C.

IR vmax cm⁻¹ (KBr): 3265, 1707, 1327, 1165, 1093, 1030, 688, 588

¹H-NMR δ ppm (CDCl₃-CD₃OD): 1.3–1.8 (6H, m), 3.4–3.7 (2H, m), 3.575 (2H, s), 3.8–4.1 (3H, m), 4.42 (1H, m), 7.2–7.6 (7H, m), 7.898 (2H, d, J=7.33 Hz)

¹³C-NMR δ ppm (CDCl₃-CD₃OD): 13.82, 19.83, 24.85, 40.40, 56.61, 56.90, 67.61, 67.83, 100.18, 100.32, 119.98, 120.05, 126.91, 127.02, 128.96, 129.07, 129.59, 130.54, 132.92, 135.86, 139.05, 167.18, 173.89

Fab-MS m/z: 462 (M⁺), 379

Example 53

Preparation of (RS)-N-(4-(carboxymethyl) phenyl)-2-(4-fluorobenzenesulfonylamino)-3-(tetrahydropyran-2-yloxy) propanamide The procedure described in Example 39 was repeated, except that (RS)-N-(4-(ethoxycarbonylmethyl)phenyl)-2-(4- fluorobenzenesulfonylamino)-3-(tetrahydropyran-2-yloxy) propanamide (223.9 mg) was hydrolyzed to obtain (RS)-N-(4-(carboxymethyl)phenyl)- 2-(4-fluorobenzenesulfonyl amino)-3-(tetrahydropyran-2-yloxy)propanamide (94.7 mg).

Melting point: 156°–157.2° C.

IR vmax cm$^{-1}$ (KBr): 3435, 1685, 1325, 1294, 1157, 841

$^1$H-NMR δ ppm (CDCl$_3$-CD$_3$OD): 1.3–1.9 (6H, m), 3.576 (2H, s), 3.3–4.2 (5H, m), 7.174 (2H, t, J=8.7 Hz), 7.239 (2H, d, J=8.4 Hz), 7.404 (2H, d, J=8.4 Hz), 7.920 (2H, dd, J=8.7 Hz, J=5.0 Hz)

$^{13}$C-NMR δ ppm (CDCl$_3$-CD$_3$OD): 19.92, 19.99, 25.27, 30.63, 40.86, 57.21, 57.47, 63.63, 63.74, 68.11, 100.30, 100.38, 116.33, 116.40, 116.66, 116.73, 120.44, 120.51, 129.86, 130.04, 130.15, 130.30, 131.15, 136.40, 167.41, 174.42

Fab-MS m/z: 481(MH$^+$), 480 (M$^+$), 397

Example 54

Preparation of (RS)-2-(4-bromobenzenesulfonylamino-N-(4-(carboxymethyl)phenyl)-3-(tetrahydropyran-2-yloxy) propanamide The procedure described in Example 39 was repeated, except that (RS)-2-(4-bromobenzenesulfonylamino)-N-(4-(ethoxycarbonylmethyl)phenyl)-3-(tetrahydropyran-2-yloxy)propanamide (348.2 mg) was hydrolyzed to obtain (RS)-2-(4-bromobenzenesulfonylamino)-N-(4-(carboxymethyl) phenyl)-3-(tetrahydropyran-2-yloxy) propanamide (132.1 mg).

Melting point: 155.5°–158° C.

IR vmax cm$^{-1}$ (KBr): 3348, 1689, 1336, 1167, 741, 611

$^1$H-NMR δ ppm (CDCl$_3$-CD$_3$OD): 1.35–1.9 (6H, m), 3.4–4.2 (5H, m), 3.572 (2H, s), 4.52 (1H, m), 7.239 (2H, d, J=8.54 Hz), 7.333 (1H, d, J=8.54 Hz), 7.355 (1H, d, J=8.54 Hz), 7.620 (2H, d, J=8.54 Hz), 7.768 (2H, d, J=8.30 Hz)

$^{13}$C-NMR δ ppm (CDCl$_3$-CD$_3$OD): 19.77, (19.92), 25.60, 30.77, 41.23, 57.66, (57.85), 63.23, (63.49), 68.11, (68.22), 100.01, (100.16), 120.80, 128.28, 129.27, 130.23, 131.55, 132.83, 136.68, 139.65, 168.33, 174.93

Fab-MS m/z: 543 (M+3), 542 (M+2), 541 (M+1), 540 (M$^+$)

Example 55

Preparation of (RS)-N-(4-(carboxymethyl) phenyl)-2-(4-iodobenzenesulfonylamino)-3-(tetrahydropyran-2-yloxy) propanamide The procedure described in Example 39 was repeated, except that (RS)-N-(4-(ethoxycarbonylmethyl)phenyl)-2-(4-iodobenzenesulfonylamino)-3-(tetrahydropyran-2-yloxy) propanamide (266.5 mg) was hydrolyzed to obtain (RS)-N-(4-(carboxymethyl)phenyl)-2-(4-iodobenzenesulfonylamino)-3-(tetrahydropyran-2-yloxy) propanamide (254.5 mg).

Melting point: 163°–165° C.

IR vmax cm$^{-1}$ (KBr): 3505, 3265, 1735, 1670, 1344, 1324, 1171

$^1$H-NMR δ ppm (CDCl$_3$): 1.2–1.9 (6H, m), 3.3–4.1 (5H, m), 3.577 (2H, s), 4.45 (1H, m), 7.239 (2H, d, J=8.7 Hz), 7.35 (2H, d, J=8.7 Hz), 7.595 (2H, d, J=8.85 Hz), 7.832 (2H, d, J=8.55 Hz)

$^{13}$C-NMR δ ppm (CDCl$_3$): 19.87, 24.89, 30.35, 40.48, 56.65, 63.76, 67.80, 100.36, 120.02, 128.45, 129.70, 130.58, 135.82, 138.17, 138.23, 138.90, 167.03, 173.92

Fab-MS m/z: 589 (MH$^+$), 505

Example 56

Preparation of (RS)-N-(4-(carboxymethyl) phenyl)-2-(4-methylbenzensulfonylamino)-3-(tetrahydropyran-2-yloxy) propanamide The procedure described in Example 39 was repeated, except that (RS)-N-(4-(ethoxycarbonylmethyl)phenyl)-2-(4-methylbenzenesulfonylamino)-3-(tetrahydropyran-2-yloxy) propanamide (100 mg) was hydrolyzed to obtain (RS)-N-(4-(carboxymethyl)phenyl)-2-(4-methylbenzenesulfonylamino)-3-(tetrahydropyran-2-yloxy) propanamide (69.0 mg).

Melting point: 115°–171° C.

IR vmax cm$^{-1}$ (KBr): 3325, 1668, 1323, 1163, 1092, 814, 667, 552

$^1$H-NMR δ ppm (CDCl$_3$): 1.3–1.8 (6H, m), 2.322 (3H, s), 3.3–3.7 (2H, m), 3.8–4.1 (3H, m), 4.390 (1H, m), 7.1–7.6 (6H, m), 7.752 (2H, d, J=8.30 Hz)

$^{13}$C-NMR δ ppm (CDCl$_3$): 19.90, 20.01, 21.30, 24.82, 24.89, 30.39, 40.40, 56.90, 58.30, 62.15, 63.95, 67.69, 67.98, 100.36, 119.98, 120.05, 120.16, 120.27, 127.02, 127.09, 127.20, 129.66, 129.73, 130.39, 130.50, 135.86, 135.93, 136.08, 144.04, 167.98, 174.14

Fab-MS m/z: 477 (MH$^+$), 393

Example 57

Preparation of (RS)-N-(4-(carboxymethyl) phenyl)-2-(4-methoxybenzenesulfonylamino)-3-(tetrahydropyran-2-yloxy)propanamide The procedure described in Example 39 was repeated, except that (RS)-N-(4-(ethoxycarbonylmethyl)phenyl)-2-(4-methoxy-benzenesulfonylamino)-3-(tetrahydropyran-2-yloxy) propanamide (101.6 mg) was hydrolyzed to obtain (RS)-N-(4-(carboxymethyl)phenyl)-2-(4-methoxybenzenesulfonylamino)-3-(tetrahydropyran-2-yloxy)propanamide (95.1 mg).

Melting point: 135°–141° C.

IR vmax cm$^{-1}$ (KBr): 3251, 1684, 1325, 1161, 1026, 835, 804, 569

$^1$H-NMR δ ppm (CDCl$_3$): 1.3–1.9 (6H, m), 3.4–3.6 (2H, m), 3.599 (2H, s), 3.7–4.0 (3H, m), 3.819 (3/2H, s), 3.838 (3/2H, s), 4.3–4.5 (1H, m), 6.9–7.0 (2H, m), 7.16–7.24 (2H, m), 7.36–7.48 (2H, m), 7.813 (2H, d, J=8.78 Hz)

$^{13}$C-NMR δ ppm (CDCl$_3$): 20.38, 20.45, 24.93, 25.00, 30.57, 30.68, 40.29, 55.62, 56.57, 56.87, 64.28, 64.35, 68.05, 68.31, 100.98, 114.37, 114.48, 120.09, 129.22, 129.44, 129.59, 129.66, 129.73, 129.88, 130.17, 130.39, 136.37, 163.33, 167.10, 167.32, 176.20

Fab-MS m/z: 493 (MH$^+$), 492 (M$^+$), 409

Example 58

Preparation of (RS)-N-(4-(carboxymethyl) phenyl)-2-(4-chloro-3-nitrobenzenesulfonylamino)-3-(tetrahydropyran-2-yloxy)propanamide The procedure described in Example 39 was repeated, except that (RS)-2-(4-chloro-3-nitrobenzenesulfonylamino)-N-(4-(ethoxycarbonylmethyl)phenyl)-3-(tetrahydropyran-2-yloxy)propanamide (102.1 mg) was hydrolyzed to obtain (RS)-N-( 4-(carboxymethyl)phenyl)-2-(4-chloro-3-nitrobenzenesulfonylamino)-3-(tetrahydropyran-2-yloxy) propanamide (100.3 mg).

Melting point: 131°–140° C.

IR vmax cm⁻¹ (KBr): 3442, 1684, 1539, 1352, 1173, 1032

¹H-NMR δ ppm (DMSO-d₆): 1.3–1.9 (6H, m), 3.483 (2H, s), 3.4–3.6 (2H, m), 3.6–3.8 (2H, m), 4.1–4.3 (1H, m), 4.4–4.6 (1H, m), 7.148 (2H, d, J=8.55 Hz), 7.26–7.36 (2H, m), 7.849 (1H, d, J=8.54 Hz), 8.0–8.1 (1H, m), 8.40–8.46 (1H, m)

¹³C-NMR δ ppm (DMSO-d₆): 18.34, 18.52, 29.64, 56.81, 60.95, 61.21, 66.64, 97.63, 97.77, 119.15, 123.74, 129.16, 130.19, 131.18, 132.46, 136.39, 141.23, 146.88, 166.60, 172.14

Fab-MS m/z: 542 (MH⁺), 541 (M⁺), 458

Example 60

Preparation of (RS)-N-(4-(carboxymethyl) phenyl)-N-(4-(carboxymethyl)phenyl)-2-(2-naphthalenesulfonylamino)-3-(tetrahydropyran-2-yloxy)propanamide The procedure described in Example 39 was repeated, except that (RS)-N-(4-(ethoxycarbonylmethyl)phenyl)-2-(2-naphthalenesulfonylamino)-3-(tetrahydropyran-2-yloxy) propanamide (82.6 mg) was hydrolyzed to obtain (RS)-N-(4-(carboxymethyl)phenyl)-N-(4-(carboxymethyl)phenyl)-2-(2-naphthalenesulfonylamino)-3-(tetrahydropyran-2-yloxy) propanamide (78.8 mg).

Melting point: 130°–140° C.

IR vmax cm⁻¹ (KBr): 1709, 1684, 1327, 1161, 1132, 1074, 1032, 661

¹H-NMR δ ppm (CDCl₃-CD₃OD): 1.2–1.8 (6H, m), 3.3–3.6 (2H, m), 3.6–4.2 (3H, m), 4.3–4.5 (1H, m), 7.0–7.3 (4H, m), 7.5–7.7 (2H, m), 7.8–8.0 (4H, m), 8.452 (1H, s)

¹³C-NMR δ ppm (CDCl₃-CD₃OD): 19.69, 19.91, 25.82, 30.88, 41.26, 58.02, 58.20, 63.04, 63.30, 68.21, 99.97, 100.04, 120.91, 123.00, 128.20, 128.53, 129.12, 129.52, 129.82, 130.19, 131.54, 132.97, 135.80, 136.93, 137.63, 168.91, 169.02, 175.03

Fab-MS m/z: 513 (MH⁺), 512 (M⁺), 429

Example 61

Preparation of (S)-N-(4-carboxyphenyl)-2-(4-chlorobenzenesulfonylamino)-3-hydroxypropanamide The procedure described in Example 39 was repeated, except that (S)-2-(4-chlorobenzenesulfonylamino)-N-(4-ethoxycarbonylphenyl)-3-hydroxypropanamide (120 mg) was hydrolyzed to obtain (S)-N-(4-carboxyphenyl)-2-(4-chlorobenzenesulfonylamino)-3-hydroxypropanamide (111 mg).

Melting point: 231°–234° C.

IR vmax cm⁻¹ (KBr): 3440, 3273, 1678, 1319, 1169

¹H-NMR δ ppm (CD₃OD): 3.71 (2H, m), 4.01 (1H, t, J=6 Hz), 7.41 (2H, d, J=8.8 Hz), 7.46 (2H, d, J=9.0 Hz), 7.82 (2H, d, J=8.8 Hz), 7.92 (2H, d, J=9.0 Hz)

¹³C-NMR δ ppm (CD₃OD): 60.49, 63.74, 120.19, 127.30, 129.95, 130.23, 131.65, 140.06, 140.49, 143.37, 169.37, 170.12

Fab-MS m/z: 399 (MH⁺)

Example 62

Preparation of (S)-N-(3-carboxyphenyl)-2-(4-chlorobenzenesulfonylamino)-3-hydroxypropanamide The procedure described in Example 39 was repeated, except that (S)-2-(4-chlorobenzenesulfonylamino)-N-(3-ethoxycarbonylphenyl)-3-hydroxypropanamide (100 mg) was hydrolyzed to obtain (S)-N-(3-carboxyphenyl)-2-(4-chlorobenzenesulfonylamino)-3-hydroxypropanamide (93 mg).

Melting point: 220°–224° C.

IR vmax cm⁻¹ (KBr): 3454, 3249, 1697, 1326, 1164

¹H-NMR δ ppm (CDCl₃): 3.72 (2H, m), 3.998 (1H, t, J=6 Hz), 7.356 (1H, t, J=7.5 Hz), 7.413 (2H, d, J=8.8 Hz), 7.577 (1H, m), 7.727 (1H, dt, J=7.5 Hz, J=1.5 Hz), 7.831 (2H, d, J=8.8 Hz), 7.991 (1H, t, J=1.5 Hz)

¹³C-NMR δ ppm (CDCl₃): 60.49, 63.77, 122.37, 125.46, 126.58, 129.78, 129.98, 130.26, 139.28, 140.55, 169.43, 170.00

Fab-MS m/z: 399 (MH⁺)

Example 63

Preparation of (RS)-N-(3-carboxyphenyl)-2-(4-chlorobenzenesulfonylamino)-3-hydroxypropanamide The procedure described in Example 39 was repeated, except that (RS)-2-(4-chlorobenzenesulfonylamino)-N-(3-ethoxycarbonylphenyl)-3-hydroxypropanamide (983 mg) was hydrolyzed to obtain (RS)-N-(3-carboxyphenyl)-2-(4-chlorobenzenesulfonylamino)-3-hydroxypropanamide (633 mg).

IR vmax cm⁻¹ (KBr): 3454, 3249, 1697, 1326, 1164

¹H-NMR δ ppm (CDCl₃): 3.72 (2H, m), 3.998 (1H, t, J=6 Hz), 7.356 (1H, t, J=7.5 Hz), 7.413 (2H, d, J=8.8 Hz), 7.577 (1H, m), 7.727 (1H, dt, J=7.5 Hz, J=1.5 Hz), 7.831 (2H, d, J=8.8 Hz), 7.991 (1H, t, J=1.5 Hz)

¹³C-NMR δ ppm (CDCl₃): 60.49, 63.77, 122.37, 125.46, 126.58, 129.78, 129.98, 130.26, 139.28, 140.55, 169.43, 170.00

Fab-MS m/z: 399 (MH⁺)

Example 64

Preparation of (RS)-N-(5-carboxypentyl)-2-(4-chlorobenzenesulfonylamino)-3-hydroxypropanamide The procedure described in Example 39 was repeated, except that (RS)-2-(4-chlorobenzenesulfonylamino)-N-(5-methoxycarbonylpentyl)-3-hydroxypropanamide (28 mg) was hydrolyzed to obtain (RS)-N-(5-carboxypentyl)-2-(4-chlorobenzenesulfonylamino)-3-hydroxypropanamide (24 mg).

IR vmax cm⁻¹ (KBr): 3700–2400 (br), 3131, 3190, 1706, 1635, 1340, 1164, 1093, 756

¹H-NMR δ ppm (DMSO-d₆): 1.15–1.35 (4H, m), 1.479 (2H, qu, J=7.3 Hz), 2.162 (2H, t, J=7.3 Hz), 2.889 (2H, dd, J=12.5 Hz, J=6.4 Hz), 3.456 (2H, d, J=5.9 Hz), 3.715 (1H, t, J=5.9 Hz), 7.556 (1H, m), 7.572 (2H, d, J=8.6 Hz), 7.790 (2H, d, J=8.6 Hz)

¹³C-NMR δ ppm (DMSO-d₆): 23.77, 25.46, 28.06, 33.30, 38.11, 58.35, 61.98, 128.17, 128.47, 168.25, 173.68

Fab-MS m/z: 393 (MH⁺)

Example 65

Preparation of (S)-2-(4-chlorobenzenesulfonylamino)-N-(4-ethoxycarbonylphenyl-3-methanesulfonyloxypropanamide Methanesulfonyl chloride (hereinafter referred to as mesyl chloride) (96 µl) was added to a solution of (S)-2-(4-chlorobenzenesulfonylamino)-N-(4-ethoxycarbonylphenyl)-3-hydroxypropanamide (132 mg) in pyridine (2.5 ml) and the mixture was stirred for 2 hours at room temperature. The reaction mixture was poured into a saturated saline solution and extracted with ethyl acetate. The combined ethyl acetate layers were washed with saturated saline solution, 1N HCl, and a saturated saline solution, and dried over Na₂SO₄. Then, the solvent was evaporated under reduced pressure to obtain (S)-2-(4-chlorobenzenesulfonylamino)-N-(4-ethoxycarbonylphenyl)-3-methanesulfonyloxypropanamide (133 mg).

IR vmax cm$^{-1}$ (KBr): 3363, 3259, 1710, 1679, 1348, 1274, 1168, 1114, 1091

$^1$H-NMR δ ppm (CDCl$_3$): 1.40 (3H, t, J=7.1 Hz), 3.02 (3H, s), 4.34 (3H, m), 4.37 (2H, q, J=7.1 Hz), 7.43 (2H, d, J=8.8 Hz), 7.51 (2H, d, J=8.8 Hz), 7.83 (2H, d, J=8.8 Hz), 7.98 (2H, d, J=8.8 Hz)

$^{13}$C-NMR δ ppm (CDCl$_3$-CD$_3$OD): 13.76, 36.76, 55.91, 60.81, 68.18, 118.95, 126.06, 128.22, 129.14, 130.27, 138.04, 139.34, 141.09, 165.80, 166.20

Fab-MS m/z: 505 (MH$^+$)

Example 66

Preparation of (RS)-2-(4-chlorobenzenesulfonylamino)-N-(4-ethoxycarbonylphenyl)-3-methanesulfonyloxypropanamide The procedure described in Example 65 was repeated, except that (RS)-2-(4-chlorobenzenesulfonylamino)-N-(4-ethoxycarbonylphenyl)-3-hydroxypropanamide (1 g) was reacted with mesyl chloride to obtain (RS)-2-(4-chlorobenzenesulfonylamino)-N-(4-ethoxycarbonylphenyl)-3-methanesulfonyloxypropanamide (943 mg). CHCl$_3$ was used for recrystallization.

Melting point: 153°–158° C.

IR vmax cm$^{-1}$ (KBr): 3346, 3240, 1709, 1689, 1355, 1176

$^1$H-NMR δ ppm (CDCl$_3$-CD$_3$OD): 1.407 (3H, t, J=7.2 Hz), 3.029 (3H, s), 4.3–4.5 (3H, m), 4.370 (2H, q, J=7.2 Hz), 7.433 (2H, d, J=8.5 Hz), 7.504 (2H, d, J=8.8 Hz), 7.836 (2H, d, J=8.5 Hz), 7.976 (2H, d, J=8.8 Hz)

$^{13}$C-NMR δ ppm (CDCl$_3$-CD$_3$OD): 14.47, 37.48, 56.86, 61.67, 69.10, 119.87, 126.87, 129.17, 129.95, 131.10, 139.25, 140.08, 142.24, 166.89, 167.18

Fab-MS m/z: 505 (MH$^+$)

Example 67

Preparation of (RS)-2-(4-chlorobenzenesulfonylamino)-N-(4-(ethoxycarbonylmethyl)phenyl)-3-methanesulfonyloxypropanamide The procedure described in Example 65 was repeated, except that (RS)-2-(4-chlorobenzenesulfonylamino)-N-(4-(ethoxycarbonylmethyl)phenyl)-3-hydroxypropanamide (1.32 g) was reacted with mesyl chloride to obtain (RS)-2-(4-chlorobenzenesulfonylamino)-N-(4-(ethoxycarbonylmethyl)phenyl)-3-methanesulfonyloxypropanamide (1.04 g).

Melting point: 142°–143° C.

IR vmax cm$^{-1}$ (KBr): 3332, 1732, 1676, 1348, 1180

$^1$H-NMR δ ppm (CDCl$_3$-DMSO-d$_6$): 1.251 (3H, t, J=7.1 Hz), 2.992 (3H, s), 3.560 (2H, s), 4.132 (2H, q, J=7.1 Hz), 4.36 (2H, m), 4.45 (1H, m), 7.192 (2H, d, J=8.5 Hz), 7.346 (2H, d, J=8.5 Hz), 7.392 (2H, d, J=8.8 Hz), 7.827 (2H, d, J=8.8 Hz)

$^{13}$C-NMR δ ppm (CDCl$_3$-DMSO-d$_6$): 13.76, 37.05, 40.35, 56.15, 60.37, 68.90, 119.59, 128.12, 128.87, 129.24, 130.01, 135.97, 138.39, 138.74, 164.96, 170.99

Fab-MS m/z: 519 (MH$^+$)

Example 68

Preparation of (RS)-2-(4-chlorobenzenesulfonylamino)-3-methanesulfonyloxy-N-(4-(2-methoxycarbonylethyl)phenyl)propanamide The procedure described in Example 65 was repeated, except that (RS)-2-(4-chlorobenzenesulfonylamino)-N-(4-(2-methoxycarbonylethyl)phenyl)-3-hydroxypropanamide (882 mg) was reacted with mesyl chloride to obtain (RS)-2-(4-chlorobenzenesulfonylamino)-3-methanesulfonyloxy-N-(4-(2-methoxycarbonylethyl)phenyl)propanamide (246 mg).

IR vmax cm$^{-1}$ (KBr): 3307, 3242, 1736, 1664, 1356, 1167

$^1$H-NMR δ ppm (CDCl$_3$-DMSO-d$_6$): 2.596 (2H, t, J=7.5 Hz), 2.898 (2H, t, J=7.5 Hz), 2.990 (3H, s), 3.663 (3H, s), 4.36 (2H, m), 4.45 (1H, m), 7.108 (2H, d, J=8.4 Hz), 7.295 (2H, d, J=8.4 Hz), 7.387 (2H, d, J=8.8 Hz), 7.827 (2H, d, J=8.8 Hz), 7.933 (1H, d, J=8.5 Hz), 9.328 (1H, s)

$^{13}$C-NMR δ ppm (CDCl$_3$-DMSO-d$_6$): 29.93, 30.52, 35.23, 51.17, 56.19, 68.95, 119.59, 128.16, 128.27, 128.89, 135.24, 136.52, 138.89, 138.79, 164.88, 172.73

Fab-MS m/z: 519 (MH$^+$)

Example 69

Preparation of (S)-2-(4-chlorobenzenesulfonylamino)-N-(3-ethoxycarbonylphenyl)-3-methanesulfonyloxypropanamide The procedure described in Example 65 was repeated, except that (S)-2-(4-chlorobenzenesulfonylamino)-N-(3-ethoxycarbonylphenyl)-3-hydroxypropanamide (1.38 g) was reacted with mesyl chloride to obtain (S)-2-(4-chlorobenzenesulfonylamino)-N-(3-ethoxycarbonylphenyl)-3-methanesulfonyloxypropanamide (915 mg).

IR vmax cm$^{-1}$ (KBr): 3342, 3260, 1708, 1680, 1355, 1290, 1172

$^1$H-NMR δ ppm (CDCl$_3$-CD$_3$OD): 1.41 (3H, t, J=7.1 Hz), 3.00 (3H, s), 4.28 (2H, m), 4.39 (2H, q, J=7.1 Hz), 4.48 (1H, dd, J=12.2 Hz, J=7.1 Hz), 7.39 (1H, m), 7.45 (2H, d, J=8.8 Hz), 7.7–7.8 (2H, m), 7.84 (2H, d, J=8.8 Hz), 7.97 (1H, t, J=1 Hz)

$^{13}$C-NMR δ ppm (CDCl$_3$-CD$_3$OD): 14.07, 37.14, 56.03, 61.27, 68.33, 120.88, 124.42, 125.92, 128.45, 129.00, 129.46, 131.04, 137.06, 137.98, 139.71, 165.69, 166.29

Fab-MS m/z: 505 (MH$^+$)

Example 70

Preparation of (RS)-2-(4-chlorobenzenesulfonylamino)-N-(3-ethoxycarbonylphenyl)-3-methanesulfonyloxypropanamide The procedure described in Example 65 was repeated, except that (RS)-2-(4-chlorobenzenesulfonylamino)-N-(3-ethoxycarbonylphenyl)-3-hydroxypropanamide (1 g) was reacted with mesyl chloride to obtain (RS)-2-(4-chlorobenzenesulfonylamino)-N-(3-ethoxycarbonylphenyl)-3-methanesulfonyloxypropanamide (763 mg). Recrystallization from CHCl$_3$ was carried out.

Melting point: 170°–173° C.

IR vmax cm$^{-1}$ (KBr): 3466, 3346, 1720, 1689, 1356, 1176

$^1$H-NMR δ ppm (CDCl$_3$-CD$_3$OD): 1.49 (3H, t, J=7.1 Hz), 3.035 (3H, s), 4.33 (2H, m), 4.392 (2H, q, J=7.1 Hz), 4.45 (1H, m), 7.398 (1H, t, J=7.8 Hz), 7.433 (2H, d, J=8.8 Hz), 7.664 (1H, ddd, J=7.8 Hz, J=2 Hz, J=1 Hz), 7.797 (1H, dt, J=7.8 Hz, J=1 Hz), 7.884 (2H, d, J=8.8 Hz), 7.99 (1H, t, J=2 Hz)

$^{13}$C-NMR δ ppm (CDCl$_3$-CD$_3$OD): 14.59, 37.45, 57.38, 62.19, 69.59, 121.97, 125.46, 126.52, 129.75, 129.89, 130.24, 130.30, 132.14, 140.20, 167.41

Fab-MS m/z: 505 (MH$^+$)

Example 71

Preparation of (RS)-2-(4-chlorobenzenesulfonylamino)-3-methanesulfonyloxy-N-(3-methoxycarbonylpropyl) propanamide The procedure described in Example 65 was repeated, except that (RS)-2-(4-chlorobenzenesulfonylamino)-3-hydroxy-N-(3-methoxycarbonylpropyl)propanamide (504 mg) was reacted with mesyl chloride to obtain (RS)-2-(4-chlorobenzenesulfonylamino)-3-methanesulfonyloxy-N-(3-methoxycarbonylpropyl)propanamide (497.8 mg).

Melting point: 95°–99° C.

IR νmax cm$^{-1}$ (KBr): 3371, 3251, 3039, 1736, 1670, 1348, 1325, 1167, 1095

$^1$H-NMR δ ppm (CDCl$_3$): 1.794 (2H, qw, J=7.0 Hz), 2.347 (2H, q, J=7.0 Hz), 2.999 (3H, s), 3.269 (2H, q, J=6.3 Hz), 3.681 (3H, s), 4.0–4.2 (2H, m), 4.503 (1H, dd, J=10.5 Hz, J=4.4 Hz), 6.386 (1H, d, J=8.1 Hz), 7.065 (1H, t, J=5.6 Hz), 7.517 (2H, d, J=8.7 Hz), 7.841 (2H, d, J=8.7 Hz)

$^{13}$C-NMR δ ppm (CDCl$_3$): 24.19, 31.16, 37.32, 39.38, 51.81, 55.66, 68.49, 128.71, 129.70, 137.66, 140.00, 167.03, 173.70

Fab-MS m/z: 457 (MH$^+$)

Example 72

Preparation of (RS)-2-(4-chlorobenzenesulfonylamino)-3-methanesulfonyloxy-N-(4-methoxycarbonylbutyl) propanamide The procedure described in Example 65 was repeated, except that (RS)-2-(4-chlorobenzenesulfonylamino)-3-hydroxy-N-(4-methoxycarbonylbutyl)propanamide (507 mg) was reacted with mesyl chloride to obtain (RS)-2-(4-chlorobenzenesulfonylamino)-3-methanesulfonyloxy-N-(4-methoxycarbonylbutyl)propanamide (409.7 mg).

Melting point: 95°–97° C.

IR νmax cm$^{-1}$ (KBr): 3375, 3250, 2951, 1736, 1672, 1350, 1327, 1171, 1092

$^1$H-NMR δ ppm (CDCl$_3$): 1.4–1.7 (4H, m), 2.328 (2H, t, J=7.0 Hz), 3.007 (3H, s), 3.232 (2H, q, J=6.4 Hz), 3.674 (3H, s), 4.0–4.2 (2H, m), 4.518 (1H, dd, J=10.5 Hz, J=4.2 Hz), 6.160 (1H, d, J=8.1 Hz), 6.7–6.9 (1H, m), 7.523 (2H, d, J=8.8 Hz), 7.788 (2H, d, J=8.8 Hz)

$^{13}$C-NMR δ ppm (CDCl$_3$): 21.77, 28.52, 33.29, 37.36, 39.49, 51.62, 55.55, 68.35, 128.74, 129.73, 137.58, 140.08, 166.74, 173.92

Fab-MS m/z: 471 (MH$^+$)

Example 73

Preparation of (RS)-2-(4-chlorobenzenesulfonylamino)-3-methanesulfonyloxy-N-(5-methoxycarbonylpentyl) propanamide The procedure described in Example 65 was repeated, except that (RS)-2-(4-chlorobenzenesulfonylamino)-3-hydroxy-N-(5-methoxycarbonylpentyl)propanamide (507 mg) was reacted with mesyl chloride to obtain (RS)-2-(4-chlorobenzenesulfonylamino)-3-methanesulfonyloxy-N-(5-methoxycarbonylpentyl)propanamide (483.5 mg).

Melting point: 81°–84° C.

IR νmax cm$^{-1}$ (KBr): 3273, 3234, 2941, 1734, 1660, 1354, 1331, 1182, 1099

$^1$H-NMR δ ppm (CDCl$_3$): 1.3–1.7 (6H, m), 2.318 (2H, t, J=7.2 Hz), 2.992 (3H, s), 3.235 (2H, q, J=6.6 Hz), 3.679 (3H, s), 4.0–4.2 (2H, m), 4.521 (1H, dd, J=10.9 Hz, J=4.3 Hz), 6.020 (1H, d, J=8.1 Hz), 7.525 (2H, d, J=8.3 Hz), 7.831 (2H, d, J=8.3 Hz)

$^{13}$C-NMR δ ppm (CDCl$_3$): 24.16, 25.95, 28.56, 33.69, 37.43, 39.63, 51.62, 55.58, 68.31, 128.74, 129.81, 137.58, 140.15, 166.59, 174.18

Fab-MS m/z: 485 (MH$^+$)

Example 74

Preparation of (RS)-2-(4-chlorobenzenesulfonylamino)-3-methanesulfonyloxy-N-(6-methoxycarbonylhexyl) propanamide The procedure described in Example 65 was repeated, except that (RS)-2-(4-chlorobenzenesulfonylamino)-3-hydroxy-N-(6-methoxycarbonylhexyl)propanamide (502 mg) was reacted with mesyl chloride to obtain (RS)-2-(4-chlorobenzenesulfonylamino)-3-methanesulfonyloxy-N-(6-methoxycarbonylhexyl)propanamide (453.1 mg).

Melting point: 77°–82° C.

IR νmax cm$^{-1}$ (KBr): 3273, 3223, 2937, 1734, 1660, 1354, 1331, 1184, 1097

$^1$H-NMR δ ppm (CDCl$_3$): 1.2–1.4 (4H, m), 1.4–1.5 (2H, m), 1.5–1.7 (2H, m), 2.312 (2H, t, J=7.3 Hz), 2.995 (3H, s), 3.202 (2H, dd, J=12.9 Hz, J=6.8 Hz), 3.673 (3H, s), 4.0–4.2 (2H, m), 4.512 (1H, dd, J=10.5 Hz, J=4.4 Hz), 6.207 (1H, d, J=8.1 Hz), 6.7–6.8 (1H, m), 7.523 (2H, d, J=8.8 Hz), 7.837 (2H, d, J=8.8 Hz)

$^{13}$C-NMR δ ppm (CDCl$_3$): 24.60, 26.21, 28.48, 28.81, 33.80, 37.36, 39.89, 51.51, 55.55, 68.38, 128.71, 129.73, 137.62, 140.04, 166.63, 174.25

Fab-MS m/z: 499 (MH$^+$)

Example 75

Preparation of (RS)-2-(4-chlorobenzenesulfonylamino)-3-methanesulfonyloxy-N-(7-methoxycarbonylheptyl) propanamide The procedure described in Example 65 was repeated, except that (RS)-2-(4-chlorobenzenesulfonylamino)-3-hydroxy-N-(7-methoxycarbonylheptyl)propanamide (504 mg) was reacted with mesyl chloride to obtain (RS)-2-(4-chlorobenzenesulfonylamino)-3-methanesulfonyloxy-N-(7-methoxycarbonylheptyl)propanamide (503.2 mg).

Melting point: 90°–95° C.

IR νmax cm$^{-1}$ (KBr): 3275, 3224, 2935, 1740, 1660, 1354, 1331, 1184, 1099

$^1$H-NMR δ ppm (CDCl$_3$): 1.2–1.3 (6H, m), 1.4–1.5 (2H, m), 1.6–1.7 (2H, m), 2.307 (2H, t, J=7.5 Hz), 2.991 (3H, s), 3.205 (2H, q, J=6.6 Hz), 3.671 (3H, s), 4.101 (2H, dd, J=10.5 Hz, J=4.6 Hz), 4.514 (1H, dd, J=10.5 Hz, J=4.4 Hz), 6.107 (1H, d, J=8.1 Hz), 6.7–6.7 (1H, m), 7.524 (2H, d, J=8.8 Hz), 7.836 (2H, d, J=8.8 Hz)

$^{13}$C-NMR δ ppm (CDCl$_3$): 24.63, 26.28, 28.89, 28.74, 29.00, 33.91, 37.36, 39.96, 51.48, 55.55, 68.31, 128.71, 129.77, 137.55, 140.11, 166.59, 174.36

Fab-MS m/z: 513 (MH$^+$)

Example 76

Preparation of (RS)-N-(4-(ethoxycarbonylmethyl) phenyl)-2-(4-fluorobenzenesulfonylamino)-3-methanesulfonyloxypropanamide The procedure described in Example 65 was repeated, except that (RS)-N-(4-(ethoxycarbonylmethyl)phenyl)-2-(4-fluorobenzenesulfonylamino)-3-hydroxypropanamide (1.88 g) was reacted with mesyl chloride to obtain (RS)-N-(4-(ethoxycarbonylmethyl)phenyl)-2-(4-fluorobenzenesulfonylamino)-3-methanesulfonyloxypropanamide (1.70 g).

Melting point: 81°–82° C.

IR νmax cm$^{-1}$ (KBr): 3342, 3261, 1732, 1655, 1355, 1178

$^1$H-NMR δ ppm (CDCl$_3$): 1.250 (3H, t, J=7.08 Hz), 2.969 (3H, s), 3.569 (2H, s), 4.144 (2H, q, J=7.08 Hz), 4.15–4.30 (2H, m), 4.557 (1H, dd, J=10.50 Hz, J=4.20 Hz), 6.331 (1H, d, J=8.06 Hz), 7.20 (4H, m), 7.364 (2H, d, J=8.30 Hz), 7.926 (2H, dd, J=8.79 Hz, J=4.88 Hz)

$^{13}$C-NMR δ ppm (CDCl$_3$): 14.11, 37.40, 40.70, 56.10, 60.97, 68.13, 116.64, 116.97, 120.38, 129.92, 130.06, 130.21, 131.16, 135.57, 165.16, 171.61

Fab-MS m/z: 503 (MH$^+$)

Example 77

Preparation of (RS)-2-(4-bromobenzenesulfonylamino)-N-(4-(ethoxycarbonylmethyl)phenyl)-3-methanesulfonyloxypropanamide The procedure described in Example 65 was repeated, except that (RS)-2-(4-bromobenzenesulfonylamino)-N-(4-(ethoxycarbonylmethyl)phenyl)-3-hydroxypropanamide (674.0 mg) was reacted with mesyl chloride to obtain (RS)-2-(4-bromobenzenesulfonylamino)-N-(4-(ethoxycarbonylmethyl)phenyl)-3-methanesulfonyloxypropanamide (582.16 mg).

Melting point: 155°–156° C.

IR νmax cm$^{-1}$ (KBr): 3332, 1732, 1676, 1348, 1180, 769

$^1$H-NMR δ ppm (DMSO-d$_6$): 1.180 (3H, t, J=7.1 Hz), 3.110 (3H, s), 3.575 (2H, s), 4.075 (2H, q, J=7.1 Hz), 4.2–4.5 (3H, m), 7.172 (2H, d, J=8.6 Hz), 7.302 (2H, d, J=8.6 Hz), 7.661 (2H, d, J=8.8 Hz), 7.736 (2H, d, J=8.8 Hz)

$^{13}$C-NMR δ ppm (DMSO-d$_6$); 13.76, 36.75, 39.68, 55.67, 59.89, 68.54, 119.52, 126.08, 128.28, 129.13, 129.86, 131.73, 136.31, 139.87, 165.06, 170.67

Fab-MS m/z: 566, 565, 564, 53 (MH$^+$), 562 (M$^+$)

Example 78

Preparation of (RS)-N-(4-(ethoxycarbonylmethyl) phenyl)-2-(4-iodo-benzenesulfonylamino)-3-methanesulfonyloxypropanamide The procedure described in Example 65 was repeated, except that (RS)-N-(4-(ethoxycarbonylmethyl)phenyl)-3-hydroxy-2-(4-iodobenzenesulfonylamino)propanamide (2.60 g) was reacted with mesyl chloride to obtain (RS)-N-(4-(ethoxycarbonylmethyl)phenyl)-2-(4-iodobenzenesulfonylamino)-3-methanesulfonyloxypropanamide (2.69 g).

Melting point: 160°–162° C.

IR νmax cm$^{-1}$ (KBr): 3334, 1728, 1676, 1348, 1180, 737

$^1$H-NMR δ ppm (CDCl$_3$-DMSO-d$_6$): 1.233 (3H, t, J=7.1 Hz), 3.010 (3H, s), 3.546 (2H, s), 4.113 (2H, q, J=7.1 Hz), 4.3–4.5 (3H, m), 7.171 (2H, d, J=8.3 Hz), 7.330 (2H, d, J=8.3 Hz), 7.593 (2H, d, J=8.6 Hz), 7.763 (2H, d, J=8.6 Hz)

$^{13}$C-NMR δ ppm (CDCl$_3$-DMSO-d$_6$): 13.54, 36.82, 39.98, 55.82, 59.85, 68.47, 99.17, 119.44, 127.84, 128.87, 129.64, 136.02, 137.41, 139.98, 164.81, 170.42

Fab-MS m/z: 611 (MH$^+$)

Example 79

Preparation of (S)-2-(4-chlorobenzenesulfonylamino)-N-(4-ethoxycarbonylphenyl)-3-(1H-imidazol-1-yl) propanamide Sodium hydride (60% dispersion in mineral oil, 15.84 mg) was washed with hexane, and suspended in DMF (500 μl) under argon and cooled to 0° C. After imidazole (33.7 mg) was added, the whole was stirred for 15 minutes. Then, a solution of (S)-2-(4-chlorobenzenesulfonylamino)-N-(4-ethoxycarbonylphenyl)-3-methanesulfonyloxypropanamide (100 mg) in DMF (500 μl) was added and the whole was stirred for 4 hours. The reaction mixture was poured into a saturated saline solution and extracted with ethyl acetate. The combined ethyl acetate layers were washed with a saturated saline solution, and dried over Na$_2$SO$_4$. Then, the solvent was evaporated and the residue was purified by column chromatography (silica gel=25 g, ethyl acetate/ethanol=20/1) to obtain the desired (S)-2-(4-chlorobenzenesulfonylamino)-N-(4-ethoxycarbonylphenyl)-3-(1H-imidazol-1-yl)propanamide (4 mg) together with a less polar by-product. The by-product was not investigated further.

IR νmax cm$^{-1}$ (neat): 3249, 1716, 1278, 1164, 1106

$^1$H-NMR δ ppm (DMSO-d$_6$): 1.38 (3H, t, J=7.2 Hz), 4.17 (1H, m), 4.36 (2H, q, J=7 Hz), 4.48 (2H, m), 6.80 (1H, m), 6.85 (1H, m), 7.37 (2H, d, J=6.8 Hz), 7.40 (2H, d, J=6.8 Hz), 7.55 (1H, m), 7.72 (1H, m), 7.80 (2H, d, J=8.8 Hz), 7.96 (2H, d, J=8.8 Hz), 9.64 (1H, m)

Fab-MS m/z: 477 (MH$^+$)

Example 80

Preparation of (RS)-2-(4-chlorobenzenesulfonylamino)-N-(4-ethoxycarbonylphenyl)-3-(1H-imidazol-1-yl) propanamide The procedure described in Example 79 was repeated, except that (RS)-2-(4-chlorobenzenesulfonylamino)-N-(4-ethoxycarbonylphenyl)-3-methanesulfonyloxypropanamide (600 mg) was reacted with imidazole to obtain the desired (RS)-2-(4-chlorobenzenesulfonylamino)-N-(4-ethoxycarbonylphenyl)-3-(1H-imidazol-1-yl)propanamide (115.5 mg) together with a by-product having lower polarity. The by-product was not investigated further.

IR νmax cm$^{-1}$ (KBr): 3251, 1705, 1680, 1354, 1280, 1167

$^1$H-NMR δ ppm (CDCl$_3$-CD$_3$OD): 1.398 (3H, t, J=7.1 Hz), 4.3–4.4 (3H, m), 4.361 (2H, q, J=7.1 Hz), 6.924 (1H, s), 7.024 (1H, s), 7.340 (2H, d, J=8.8 Hz), 7.423 (2H, d, J=8.8 Hz), 7.621 (1H, s), 7.701 (2H, d, J=8.8 Hz), 7.945 (2H, d, J=8.8 Hz)

$^{13}$C-NMR δ ppm (CDCl$_3$-CD$_3$OD): 14.50, 58.62, 61.70, 119.81, 120.59, 126.90, 128.62, 129.06, 129.89, 131.13, 138.24, 139.34, 139.91, 142.30, 167.21, 167.84

Fab-MS m/z: 477 (MH$^+$)

Example 81

Preparation of (RS)-2-(4-chlorobenzenesulfonylamino)-N-(4-(ethoxycarbonylmethyl)phenyl)-3-(1H-imidazol-1-yl) propanamide The procedure described in Example 79 was repeated, except that (RS)-2-(4-chlorobenzenesulfonylamino)-N-(4-(ethoxycarbonylmethyl)phenyl)-3-methanesulfonyloxypropanamide (311 mg) was reacted with imidazole to obtain the desired (RS)-2-(4-chlorobenzenesulfonylamino)-N-(4-(ethoxycarbonylmethyl)phenyl)-3-(1H-imidazol-1-yl)propanamide (86 mg) together with a less polar by-product. The by-product was not investigated further.

Melting point: 164°–165° C.

IR νmax cm$^{-1}$ (neat): 3250, 1732, 1695, 1335, 1163

$^1$H-NMR δ ppm (CDCl$_3$-DMSO-d$_6$): 1.252 (3H, t, J=7.1 Hz), 3.555 (3H, s), 4.122 (3H, t, J=7.1 Hz), 4.15–4.4 (3H, m), 6.877 (1H, s), 6.941 (1H, s), 7.137 (2H, d, J=8.3 Hz), 7.314 (2H, d, J=8.3 Hz), 7.317 (2H, d, J=8.5 Hz), 7.643 (2H, d, J=8.5 Hz), 7.660 (1H, s)

$^{13}$C-NMR δ ppm (CDCl$_3$): 13.25, 39.72, 47.44, 57.20, 59.69, 118.60, 119.03, 127.28, 128.08, 128.62, 129.20, 135.69, 136.87, 137.56, 138.24, 165.73, 170.33

Fab-MS m/z: 491 (MH$^+$)

Example 82

Preparation of (RS)-2-(4-chlorobenzenesulfonylamino)-3-(1H-imidazol-1-yl)-N-(4-(2-methoxycarbonylethyl)phenyl)propanamide The procedure described in Example 79 was repeated, except that (RS)-2-(4-chlorobenzenesulfonylamino)-3-methanesulfonyloxy-N-(4-(2-methoxycarbonylethyl)phenyl)propanamide (208 mg) was reacted with imidazole to obtain the desired (RS)-2-(4-chlorobenzenesulfonylamino)-3-(1H-imidazol-1-yl)-N-(4-(2-methoxycarbonylethyl)phenyl)propanamide (111 mg) together with a less polar by-product. The by-product was not investigated further.

Melting point: 79°–82° C.

IR νmax cm$^{-1}$ (KBr): 3280, 1734, 1691, 1330, 1162

$^1$H-NMR δ ppm (CDCl$_3$): 2.569 (2H, t, J=7.3 Hz), 2.874 (2H, t, J=7.3 Hz), 3.654 (3H, s), 4.20 (1H, m), 4.42 (2H, m), 6.7–7.9 (12H, m), 9.256 (1H, s)

$^{13}$C-NMR δ ppm (CDCl$_3$): 30.28, 35.49, 48.87, 51.62, 57.97, 118.11, 120.24, 128.27, 128.78, 129.55, 134.98, 135.60, 137.33, 137.44, 138.21, 139.38, 166.15, 173.23

Fab-MS m/z: 491 (MH$^+$)

Example 83

Preparation of (S)-2-(4-chlorobenzenesulfonylamino)-N-(3-ethoxycarbonylphenyl)-3-(1H-imidazol-1-yl)propanamide The procedure described in Example 79 was repeated, except that (S)-2-(4-chlorobenzenesulfonylamino)-N-(3-ethoxycarbonylphenyl)-3-methanesulfonyloxypropanamide (100 mg) was reacted with imidazole to obtain the desired (S)-2-(4-chlorobenzenesulfonylamino)-N-(3-ethoxycarbonylphenyl)-3-(1H-imidazol-1-yl)propanamide (19.9 mg) together with a less polar by-product. The by-product was not investigated further.

IR νmax cm$^{-1}$ (neat): 3471, 1716, 1690, 1288, 1165

$^1$H-NMR δ ppm (CDCl$_3$-CD$_3$OD): 1.414 (3H, t, J=7.1 Hz), 4.2–4.4 (3H, m), 4.388 (2H, q, J=7.1 Hz), 6.955 (1H, s), 7.022 (1H, s), 7.3–7.9 (3H, m), 7.350 (2H, d, J=8.8 Hz), 7.706 (2H, d, J=8.8 Hz), 7.924 (1H, t, J=2 Hz)

$^{13}$C-NMR δ ppm (CDCl$_3$-CD$_3$OD): 14.34, 58.05, 61.63, 119.49, 120.40, 121.15, 124.72, 126.19, 127.63, 128.64, 129.30, 129.61, 131.34, 137.50, 138.48, 139.75, 166.21, 166.40

Fab-MS m/z: 479 (M$^+$+2), 477 (MH$^+$)

Example 84

Preparation of (RS)-2-(4-chlorobenzenesulfonylamino)-N-(3-ethoxycarbonylphenyl)-3-(1H-imidazol-1-yl)propanamide The procedure described in Example 79 was repeated, except that (RS)-2-(4-chlorobenzenesulfonylamino)-N-(3-ethoxycarbonylphenyl)-3-methanesulfonyloxypropanamide (163.3 mg) was reacted with imidazole to obtain the desired (RS)-2-(4-chlorobenzenesulfonylamino)-N-(3-ethoxycarbonylphenyl)-3-(1H-imidazol-1-yl)propanamide (63.5 mg) together with a less polar by-product. The by-product was not investigated further.

IR νmax cm$^{-1}$ (neat): 3471, 1716, 1690, 1288, 1165

$^1$H-NMR δ ppm (CDCl$_3$-CD$_3$OD): 1.414 (3H, t, J=7.1 Hz), 4.2–4.4 (3H, m), 4.388 (2H, q, J=7.1 Hz), 6.955 (1H, s), 7.022 (1H, s), 7.3–7.9 (3H, m), 7.350 (2H, d, J=8.8 Hz), 7.706 (2H, d, J=8.8 Hz), 7.924 (1H, t, J=2 Hz)

$^{13}$C-NMR δ ppm (CDCl$_3$-CD$_3$OD): 14.34, 58.05, 61.63, 119.49, 120.40, 121.15, 124.72, 126.19, 127.63, 128.64, 129.30, 129.61, 131.34, 137.50, 138.48, 139.75, 166.21, 166.40

Fab-MS m/z: 479 (M$^+$+2), 477 (MH$^+$)

Example 85

Preparation of (RS)-2-(4-chlorobenzenesulfonylamino)-3-(1H-imidazol-1-yl)-N-(3-methoxycarbonylpropyl)propanamide The procedure described in Example 79 was repeated, except that (RS)-2-(4-chlorobenzenesulfonylamino)-3-methanesulfonyloxy-N-(3-methoxycarbonylpropyl)propanamide (107.6 mg) was reacted with imidazole to obtain the desired (RS)-2-(4-chlorobenzenesulfonylamino)-3-(1H-imidazol-1-yl)-N-(3-methoxycarbonylpropyl)propanamide (16.3 mg) together with a less polar by-product. The by-product was not investigated further.

IR νmax cm$^{-1}$ (neat): 3234, 3091, 2929, 1734, 1670, 1394, 1330, 1165, 1086

$^1$H-NMR δ ppm (CD$_3$OD): 1.616 (2H, t, J=7.1 Hz), 2.196 (2H, t, J=7.4 Hz), 2.968 (2H, t, J=6.8 Hz), 3.661 (3H, s), 4.1–4.3 (3H, m), 7.4–7.6 (4H, m), 7.706 (2H, d, J=8.8 Hz), 7.799 (1H, d, J=8.8 Hz)

$^{13}$C-NMR δ ppm (CD$_3$OD): 25.38, 31.84, 39.65, 45.59, 52.08, 58.68, 122.53, 129.68, 130.38, 130.52, 139.47, 140.02, 140.61, 167.45, 170.27

Fab-MS m/z: 429 (MH$^+$)

Example 86

Preparation of (RS)-2-(4-chlorobenzenesulfonylamino)-3-(1H-imidazol-1-yl)-N-(4-methoxycarbonylbutyl)propanamide The procedure described in Example 79 was repeated, except that (RS)-2-(4-chlorobenzenesulfonylamino)-3-methanesulfonyloxy-N-(4-methoxy carbonylbutyl)propanamide (152.5 mg) was reacted with imidazole to obtain the desired (RS)-2-(4-chlorobenzenesulfonylamino)-3-(1H-imidazol-1-yl)-N-(4-methoxycarbonylbutyl)propanamide (32.4 mg) together with a less polar by-product. The by-product was not investigated further.

IR νmax cm$^{-1}$ (neat): 3219, 3118, 2949, 1730, 1666, 1331, 1165, 1086

$^1$H-NMR δ ppm (CDCl$_3$): 1.3–1.6 (4H, m), 2.2–2.3 (2H, m), 3.0–3.1 (2H, m), 3.661 (3H, s), 4.242 (2H, t, J=4.6 Hz), 4.3–4.4 (1H, m), 6.836 (1H, s), 7.106 (1H, s), 7.441 (2H, dd, J=6.8 Hz, J=2.0 Hz), 7.7–7.8 (2H, m), 8.0–8.1 (1H, m)

$^{13}$C-NMR δ ppm (CDCl$_3$): 21.88, 28.45, 33.29, 39.34, 48.80, 51.59, 57.60, 119.91, 121.63, 128.30, 129.55, 135.05, 138.68, 139.38, 168.02, 173.85

Fab-MS m/z: 443 (MH$^+$)

Example 87

Preparation of (RS)-2-(4-chlorobenzenesulfonylamino)-N-(5-methoxycarbonylpentyl)-3-(1H-imidazol-1-yl)propanamide The procedure described in Example 79 was repeated, except that (RS)-2-(4-chlorobenzenesulfonylamino)-3- methanesulfonyloxy-N-(5-methoxycarbonylpentyl) propanamide (150.3 mg) was reacted with imidazole to obtain the desired (RS)-2-(4-chlorobenzenesulfonylamino)-N-(5-methoxycarbonylpentyl)-3-(1H-imidazol-1-yl) propanamide (46.8 mg) together with a less polar by-product. The by-product was not investigated further.

IR vmax cm$^{-1}$ (neat): 3367, 3232, 2942, 1734, 1668, 1396, 1335, 1165, 1093

$^1$H-NMR δ ppm (CDCl$_3$): 1.2–1.4 (4H, m), 1.567 (2H, qw, J=7.4 Hz), 2.271 (2H, t, J=7.3 Hz), 3.075 (2H, dd, J=12.9 Hz, J=6.8 Hz), 3.660 (3H, s), 4.135 (1H, dd, J=13.8 Hz, J=5.3 Hz), 4.250 (1H, t, J=4.9 Hz), 4.488 (1H, dd, J=13.9 Hz, J=4.6 Hz), 6.800 (2H, d, J=9.8Hz), 7.2–7.3 (1H, m), 7.479 (2H, d, J=8.5 Hz), 7.789 (2H, d, J=8.5 Hz)

$^{13}$C-NMR δ ppm (CDCl$_3$): 24.23, 26.10, 28.67, 33.69, 39.78, 48.84, 51.70, 57.56, 119.91, 119.98, 128.38, 129.59, 137.55, 138.87, 139.49, 167.84, 174.00

Fab-MS m/z: 457 (MH$^+$)

Example 88

Preparation of (RS)-2-(4-chlorobenzenesulfonylamino)-3-(1H-imidazol-1-yl)-N-(6-methoxycarbonylhexyl) propanamide The procedure described in Example 79 was repeated, except that (RS)-2-(4-chlorobenzenesulfonylamino)-3-methanesulfonyloxy-N-(6-methoxycarbonylhexyl) propanamide (144.6 mg) was reacted with imidazole to obtain the desired (RS)-2-(4-chlorobenzenesulfonylamino)-3-(1H-imidazol-1-yl)-N-(6-methoxycarbonylhexyl) propanamide (50.6 mg) together with a less polar by-product. The by-product was not investigated further.

IR vmax cm$^{-1}$ (KBr): 3219, 2935, 1734, 1670, 1331, 1232, 1163, 1086

$^1$H-NMR δ ppm (CDCl$_3$): 1.2–1.4 (6H, m), 1.5–1.6 (2H, m), 2.294 (2H, t, J=7.3 Hz), 3.0–3.1 (1H, m), 3.672 (3H, s), 4.1–4.2 (2H, m), 4.4–4.5 (1H, m), 7.0–7.1 (1H, m), 7.463 (2H, d, J=8.6 Hz), 7.750 (2H, d, J=8.3 Hz), 8.0–8.1 (1H, m)

$^{13}$C-NMR δ ppm (CDCl$_3$): 24.60, 26.28, 28.48, 28.78, 33.80, 36.48, 48.65, 51.51, 57.42, 119.72, 121.85, 128.27, 129.59, 135.05, 138.72, 162.56, 167.87, 174.25

Fab-MS m/z: 471 (MH$^+$)

Example 89

Preparation of (RS)-2-(4-chlorobenzenesulfonylamino)-3-(1H-imidazol-1-yl)-N-(7-methoxycarbonylheptyl) propanamide The procedure described in Example 79 was repeated, except that (RS)-2-(4-chlorobenzenesulfonylamino)-3-methanesulfonyloxy-N-(7-methoxycarbonylheptyl) propanamide (152.2 mg) was reacted with imidazole to obtain the desired (RS)-2-(4-chlorobenzenesulfonylamino)-3-(1H-imidazol-1yl)-N-(7-methoxycarbonylheptyl) propanamide (53.4 ml) together with a less polar by-product. The by-product was not investigated further.

IR vmax cm$^{-1}$ (neat): 3221, 2926, 1738, 1682, 1338, 1232, 1165, 1086

$^1$H-NMR δ ppm (CDCl$_3$): 1.1–1.4 (8H, m), 1.5–1.7 (2H, m), 2.298 (2H, t, J=7.4 Hz), 3.062 (2H, t, J=6.0 Hz), 3.667 (3H, s), 4.1–4.3 (2H, m), 4.3–4.5 (1H, m), 6.8–6.9 (1H, m), 7.0–7.1 (1H, m), 7.453 (2H, d, J=8.8 Hz), 7.749 (2H, d, J=8.5 Hz), 8.006 (2H, s)

$^{13}$C-NMR δ ppm (CDCl$_3$): 24.71, 26.39, 28.81, 31.42, 33.91, 36.44, 39.78, 48.73, 51.44, 57.53, 119.61, 123.32, 128.30, 129.55, 138.61, 139.45, 162.56, 167.84, 174.25

Fab-MS m/z: 485 (MH$^+$)

Example 90

Preparation of (RS)-N-(4-(ethoxycarbonylmethyl)phenyl-2-(4-fluorobenzenesulfonylamino)-3-(1H-imidazol-1-yl) propanamide The procedure described in Example 79 was repeated, except that (RS)-N-(4-(ethoxycarbonylmethyl)phenyl)-2-(4-fluorobenzenesulfonylamino)-3-methanesulfonyloxypropanamide (560 mg) was reacted with imidazole to obtain the desired (RS)-N-(4-(ethoxycarbonylmethyl)phenyl)-2-(4-fluorobenzenesulfonylamino)-3-(1H-imidazol-1-yl) propanamide (152.3 mg) together with a less polar by-product. The by-product was not investigated further.

Melting point: 155°–157° C.

IR vmax cm$^{-1}$ (KBr): 1732, 1693, 1338, 1294, 1236, 1171, 1155, 1092

$^1$H-NMR δ ppm (CDCl$_3$-CD$_3$OD): 1.247 (3H, t, J=7.08 Hz), 3.562 (2H, s), 4.138 (2H, q, J=7.08 Hz), 4.2–4.4 (3H, m), 6.85 (2H, m), 7.07 (2H, m), 7.183 (2H, d, J=8.55 Hz), 7.275 (2H, d, J=8.55 Hz), 7.351 (1H, s), 7.795 (2H, dd, J=8.79 Hz, J=4.88 Hz)

$^{13}$C-NMR δ ppm (CDCl$_3$-CD$_3$OD): 14.00, 40.66, 48.62, 57.71, 60.90, 116.24, 116.57, 119.87, 120.09, 120.20, 128.41, 129.48, 129.62, 129.73, 130.83, 135.75, 137.51, 166.37, 171.61

Fab-MS m/z: 475 (MH$^+$)

Example 91

Preparation of (RS)-2-(4-bromobenzenesulfonylamino)-N-(4-(ethoxycarbonylmethyl)phenyl)-3-(1H-imidazol-1-yl) propanamide The procedure described in Example 79 was repeated, except that (RS)-2-(4-bromobenzenesulfonylamino)-N-(4-(ethoxycarbonylmethyl)phenyl)-3-methanesulfonyloxypropanamide (500 mg) was reacted with imidazole to obtain the desired (RS)-2-(4-bromobenzenesulfonylamino)-N-(4-(ethoxycarbonylmethyl)phenyl)-3-(1H-imidazol-1-yl) propanamide (85.0 mg) together with a less polar by-product. The by-product was not investigated further.

Melting point: 201°–202° C.

IR vmax cm$^{-1}$ (KBr): 3253, 1730, 1691, 1335, 1165, 1032, 741, 609

$^1$H-NMR δ ppm (DMSO-d$_6$): 1.242 (3H, t, J=7.08 Hz), 3.577 (2H, s), 4.130 (2H, q, J=7.08 Hz), 4.2–4.4 (3H, m), 6.894 (1H, s), 7.038 (1H, s), 7.527 (2H, d, J=8.79 Hz), 7.645 (2H, d, J=8.79 Hz), 7.824 (1H, s)

$^{13}$C-NMR δ ppm (DMSO-d$_6$): 13.65, 47.31, 57.54, 59.74, 119.11, 119.41, 125.86, 127.92, 128.03, 128.94, 129.57, 131.40, 136.28, 137.27, 139.76, 166.24, 170.45

Fab-MS m/z: 537 (MH$^+$+2), 535 (MH$^+$)

Example 92

Preparation of (S)-N-(4-carboxyphenyl)-2-(4-chlorobenzenesulfonylamino)-3-(1H-imidazol-1-yl) propanamide hydrochloride 2N NaOH (2.6 ml) was added to solution of (S)-2-(4-chlorobenzenesulfonylamino)-N-(4-ethoxycarbonylphenyl)

-3-(1H-imidazol-1-yl)propanamide (120 mg) in ethanol (10 ml) and the whole was stirred at room temperature overnight. The reaction mixture was concentrated under reduced pressure. A small amount of water was added to the residue, and the whole was concentrated under reduced pressure. The above procedure was repeated 3 times to remove ethanol. The residue was dissolved in 1N HCl (20 ml), and diluted with water (20 ml). Then, the solution was washed 3 times with ethyl acetate (10 ml). The aqueous layer was concentrated under reduced pressure. A small amount of water was added, and the whole was concentrated under reduced pressure. The concentrating steps were repeated 3 times to evaporate excess HCl. The residue was dried under reduced pressure in a desiccator. After ethanol was added, the insoluble materials were removed by filtration. The combined filtrates were concentrated under reduced pressure and dried to obtain (S)-N-(4-carboxyphenyl)-2-(4-chlorobenzenesulfonylamino)-3-(1H-imidazol-1-yl)propanamide hydrochloride (84 mg).

IR νmax cm$^{-1}$ (KBr): 1695, 1357, 1173

$^1$H-NMR δ ppm (CD$_3$OD): 4.4–4.6 (3H, m), 6.926 (1H, d, J=8.5 Hz), 7.365 (2H, d, J=9.1 Hz), 7.399 (2H, d, J=9.1 Hz), 7.767 (2H, d, J=8.8 Hz), 7.857 (1H, J=8.5 Hz), 7.933 (2H, d, J=8.8 Hz), 8.909 (1H, s)

Fab-MS m/z: 449 (MH$^+$–HCl)

Example 93

Preparation of (RS)-N-(4-carboxyphenyl)-2-(4-chlorobenzenesulfonylamino)-3-(1H-imidazol-1-yl)propanamide hydrochloride The procedure described in Example 92 was repeated, except that (RS)-2-(4-chlorobenzenesulfonylamino)-N-(4-ethoxycarbonylphenyl)-3-(1H-imidazol-1-yl)propanamide (61.9 mg) was hydrolyzed, and then reacted with HCl to obtain (RS)-N-(4-carboxyphenyl)-2-(4-chlorobenzenesulfonylamino)-3-(1H-imidazol-1-yl)propanamide hydrochloride (44.4 mg).

IR νmax cm$^{-1}$ (KBr): 1695, 1357, 1173

$^1$H-NMR δ ppm (CD$_3$OD): 4.4–4.6 (3H, m), 6.926 (1H, d, J=8.5 Hz), 7.365 (2H, d, J=9.1 Hz), 7.399 (2H, d, J=9.1 Hz), 7.767 (2H, d, J=8.8 Hz), 7.857 (1H, J=8.5 Hz), 7.933 (2H, d, J=8.8 Hz), 8.909 (1H, s)

Fab-MS m/z: 449 (MH$^+$–HCl)

Example 94

Preparation of (RS)-N-(4-(carboxymethyl)phenyl)-2-(4-chlorobenzenesulfonylamino)-3-(1H-imidazol-1-yl)propanamide hydrochloride The procedure described in Example 92 was repeated, except that (RS)-2-(4-chlorobenzenesulfonylamino)-N-(4-(ethoxycarbonylmethyl)phenyl)-3-(pyridin-3-yloxy)propanamide (50 mg) was hydrolyzed, and then reacted with HCl to obtain (RS)-N-(4-(carboxymethyl)phenyl)-2-(4-chlorobenzenesulfonylamino)-3-(1H-imidazol-1-yl)propanamide hydrochloride (37 mg).

Fab-MS m/z: 463 (MH$^+$–HCl)

Example 95

Preparation of (RS)-N-(4-(2-carboxyethyl)phenyl)-2-(4-chlorobenzenesulfonylamino)-3-(1H-imidazol-1-yl)propanamide hydrochloride The procedure described in Example 92 was repeated, except that (RS)-2-(4-chlorobenzenesulfonylamino)-3-(1H-imidazol-1-yl)-N-(4-(2-methoxycarbonylethyl)phenyl) propanamide (74 mg) was hydrolyzed, and then reacted with HCl to obtain (RS)-N-(4-(2-carboxyethyl)phenyl)-2-(4-chlorobenzenesulfonylamino)-3-(1H-imidazol-1-yl)propanamide hydrochloride (74 mg).

Melting point: 131°–134° C.

IR νmax cm$^{-1}$ (KBr): 3700–2200 (br), 3257, 1689, 1330, 1163

$^1$H-NMR δ ppm (DMSO-d$_6$): 2.485 (2H, t, J=7.4 Hz), 2.787 (2H, t, J=7.4 Hz), 4.15 (1H, m), 4.30 (2H, m), 6.7–7.9 (12H, m), 10.075 (1H, s)

$^{13}$C-NMR δ ppm (DMSO-d$_6$): 29.49, 34.92, 47.24, 57.76, 108.85, 117.72, 119.41, 119.52, 127.81, 127.92, 128.43, 128.80, 135.65, 136.31, 137.01, 165.14

Fab-MS m/z: 477 (MH$^+$–HCl)

Example 96

Preparation of (S)-N-(3-carboxyphenyl)-2-(4-chlorobenzenesulfonylamino)-3-(1H-imidazol-1-yl)propanamide hydrochloride The procedure described in Example 92 was repeated, except that (S)-2-(4-chlorobenzenesulfonylamino)-N-(3-ethoxycarbonylphenyl)-3-(1H-imidazol-1-yl)propanamide (53.1 mg) was hydrolyzed, and then reacted with HCl to obtain (S)-N-(3-carboxyphenyl)-2-(4-chlorobenzenesulfonylamino)-3-(1H-imidazol-1-yl)propanamide hydrochloride (18.03 mg).

IR νmax cm$^{-1}$ (KBr): 3427, 3145, 1701, 1167

$^1$H-NMR δ ppm (CD$_3$OD): 4.50 (3H, m), 7.3–7.8 (5H, m), 7.41 (2H, d, J=8.6 Hz), 7.797 (2H, d, J=8.6 Hz), 8.031 (1H, s), 9.009 (1H, s)

Fab-MS m/z: 451 (MH$^+$+2–HCl), 449 (MH$^+$–HCl)

Example 97

Preparation of (RS)-N-(3-carboxyphenyl)-2-(4-chlorobenzenesulfonylamino)-3-(1H-imidazol-1-yl)propanamide hydrochloride The procedure described in Example 92 was repeated, except that (RS)-2-(4-chlorobenzenesulfonylamino)-N-(3-ethoxycarbonylphenyl)-3-(1H-imidazol-1-yl)propanamide (35.3 mg) was hydrolyzed, and then reacted with HCl to obtain (RS)-N-(3-carboxyphenyl)-2-(4-chlorobenzenesulfonylamino)-3-(1H-imidazol-1-yl)propanamide hydrochloride (25.9 mg).

IR νmax cm$^{-1}$ (KBr): 3427, 3145, 1701, 1167

$^1$H-NMR δ ppm (CD$_3$OD): 4.50 (3H, m), 7.3–7.8 (5H, m), 7.41 (2H, d, J=8.6 Hz), 7.797 (2H, d, J=8.6 Hz), 8.031 (1H, s), 9.009 (1H, s)

Fab-MS m/z: 451 (MH$^+$+2–HCl), 449 (MH$^+$–HCl)

Example 98

Preparation of (RS)-N-(3-carboxypropyl)-2-(4-chlorobenzenesulfonylamino)-3-(1H-imidazol-1-yl)propanamide hydrochloride The procedure described in Example 92 was repeated, except that (RS)-2-(4-chlorobenzenesulfonylamino)-3-(1H-imidazol-1-yl)-N-(3-methoxycarbonylpropyl)propanamide (15.8 mg) was hydrolyzed, and then reacted with HCl to obtain (RS)-N-(3-carboxypropyl)-2-(4-chlorobenzenesulfonylamino)-3-(1H-imidazol-1-yl)propanamide hydrochloride (16.2 mg).

IR νmax cm$^{-1}$ (neat): 3223, 3084, 1728, 1680, 1335, 1165, $^1$H-NMR δ ppm (CD$_3$OD): 1.615 (2H, qw, J=7.1 Hz), 2.217 (2H, t, J=7.5 Hz), 3.0–3.1 (2H, m), 4.3–4.4 (2H, m), 4.609 (1H, t, J=4.8 Hz), 7.5–7.7 (5H, m), 7.7–7.9 (2H, m)

$^{13}$C-NMR δ ppm (CD$_3$OD): 25.46, 31.91, 39.76, 52.08, 57.91, 120.47, 120.91, 124.07, 129.82, 130.52, 130.63, 140.31, 168.73, 172.00

Fab-MS m/z: 416 (M+2–HCl)

Example 99

Preparation of (RS)-N-(4-carboxybutyl)-2-(4-chlorobenzenesulfonylamino)-3-(1H-imidazol-1-yl)propanamide hydrochloride The procedure described in Example 92 was repeated, except that (RS)-2-(4-chlorobenzenesulfonylamino)-3-(1H-imidazol-1-yl)-N-(4-methoxycarbonylbutyl)propanamide (16.8 mg) was hydrolyzed, and then reacted with HCl to obtain (RS)-N-(4-carboxybutyl)-2-(4-chlorobenzenesulfonylamino)-3-(1H-imidazol-1-yl)propanamide hydrochloride (17.2 mg).

IR νmax cm$^{-1}$ (neat): 3412, 3149, 2968, 1670, 1331, 1165, 1095

$^1$H-NMR δ ppm (D$_2$O): 1.2–1.6 (4H, m), 2.462 (2H, t, J=7.1 Hz), 3.0–3.1 (2H, m), 4.3–4.7 (3H, m), 7.5–7.6 (2H, m), 7.7–7.8 (2H, m), 7.8–7.9 (2H, m), 8.806 (1H, s), 8.886 (1H, t, J=1.5 Hz)

$^{13}$C-NMR δ ppm (D$_2$O): 24.27, 30.32, 36.04, 41.91, 52.99, 59.26, 122.88, 125.16, 131.21, 132.64, 138.25, 139.60, 142.61, 170.81, 181.19

Fab-MS m/z: 429 (MH$^+$–HCl)

Example 100

Preparation of (RS)-N-(5-carboxypentyl)-2-(4-chlorobenzenesulfonylamino)-3-(1H-imidazol-1-yl)propanamide hydrochloride The procedure described in Example 92 was repeated, except that (RS)-2-(4-chlorobenzenesulfonylamino)-N-(5-methoxycarbonylpentyl)-3-(1H-imidazol-1-yl)propanamide (23.9 mg) was hydrolyzed, and then reacted with HCl to obtain (RS)-N-(5-carboxypentyl)-2-(4-chlorobenzenesulfonylamino)-3-(1H-imidazol-1-yl)propanamide hydrochloride (24.8 mg).

IR νmax cm$^{-1}$ (neat): 3223, 3142, 2943, 1718, 1672, 1342, 1165, 1093

$^1$H-NMR δ ppm (D$_2$O): 1.0–1.2 (4H, m), 1.3–1.5 (2H, m), 2.1–2.2 (2H, m), 2.7–2.8 (2H, m), 3.9–4.0 (1H, m), 4.1–4.3 (2H, m), 7.2–7.3 (2H, m), 7.4–7.5 (2H, m), 7.5–7.6 (3H, m), 8.6–8.7 (1H, m)

$^{13}$C-NMR δ ppm (D$_2$O): 26.52, 28.05, 30.32, 36.49, 41.96, 52.84, 59.12, 122.73, 125.01, 131.05, 132.49, 138.11, 139.52, 142.43, 170.56, 179.69

Fab-MS m/z: 444 (M+2–HCl)

Example 101

Preparation of (RS)-N-(6-carboxyhexyl)-2-(4-chlorobenzenesulfonylamino)-3-(1H-imidazol-1-yl)propanamide hydrochloride The procedure described in Example 92 was repeated, except that (RS)-2-(4-chlorobenzenesulfonylamino)-3-(1H-imidazol- 1-yl)-N-(6-methoxycarbonylhexyl)propanamide (36.3 mg) was hydrolyzed, and then reacted with HCl to obtain (RS)-N-(6-carboxyhexyl)-2-(4-chlorobenzenesulfonylamino)-3-(1H-imidazol-1-yl)propanamide hydrochloride (29.3 mg).

IR νmax cm$^{-1}$ (neat): 2929, 2860, 1711, 1674, 1333, 1165, 1093

$^1$H-NMR δ ppm (D$_2$O): 1.2–1.5 (6H, m), 1.684 (2H, qw, J=7.4 Hz), 2.502 (2H, t, J=7.3 Hz), 3.0–3.1 (2H, m), 4.4–4.6 (2H, m), 4.707 (1H, dd, J=14.0 Hz, J=4.8 Hz), 7.5–7.7 (3H, m), 7.725 (2H, d, J=8.8 Hz), 7.874 (2H, d, J=8.8 Hz), 8.905 (1H, s)

$^{13}$C-NMR δ ppm (D$_2$O): 26.95, 28.38, 30.58, 30.65, 36.59, 42.28, 53.06, 59.29, 121.78, 122.92, 125.19, 131.24, 132.67, 138.28, 142.65, 170.70, 181.92

Fab-MS m/z: 457 (MH$^+$–HCl)

Example 102

Preparation of (RS)-N-(7-carboxyheptyl)-2-(4-chlorobenzenesulfonylamino)-3-(1H-imidazol-1-yl)propanamide hydrochloride The procedure described in Example 92 was repeated, except that (RS)-2-(4-chlorobenzenesulfonylamino)-3-(1H-imidazol-1-yl)-N-(7-methoxycarbonylheptyl)propanamide (25.6 mg) was hydrolyzed, and then reacted with HCl to obtain (RS)-N-(7-carboxyheptyl)-2-(4-chlorobenzenesulfonylamino)-3-(1H-imidazol-1-yl)propanamide hydrochloride (24.9 mg).

IR νmax cm$^{-1}$ (neat): 3402, 2943, 1664, 1659, 1331, 1165, 1093

$^1$H-NMR δ ppm (D$_2$O): 1.2–1.5 (8H, m), 1.6–1.8 (2H, m), 2.507 (2H, t, J=7.3 Hz), 3.0–3.1 (2H, m), 3.769 (1H, q, J=7.1 Hz), 4.274 (1H, q, J=7.1 Hz), 4.4–4.5 (1H, m), 7.600 (2H, d, J=9.0 Hz), 7.727 (2H, d, J=8.8 Hz), 7.876 (2H, d, J=8.5 Hz), 8.898 (1H, s)

$^{13}$C-NMR δ ppm (D$_2$O): 27.04, 28.48, 30.64, 30.70, 30.84, 36.63, 42.30, 53.04, 59.29, 122.88, 125.15, 131.20, 132.67, 138.28, 139.66, 142.63, 168.84, 170.68

Fab-MS m/z: 471 (MH$^+$–HCl)

Example 103

Preparation of (RS)-N-(4-(carboxymethyl)phenyl)-2-(4-fluorobenzenesulfonylamino)-3-(1H-imidazol-1-yl)propanamide 2N NaOH (1.085 ml) was added to a solution of (RS)-N-(4-(ethoxycarbonylmethyl)phenyl)-2-(4-fluorobenzenesulfonyl-amino)-3-(1H-imidazol-1-yl)propanamide (103 mg) in ethanol (5 ml) and the whole was stirred for 5 hours. The reaction mixture was concentrated under reduced pressure. The residue was dissolved in water, washed with ethyl acetate 3 times, neutralized by 2N HCl (1.085 ml), and then extracted with ethyl acetate. The combined ethyl acetate layers were washed with a saturated saline solution and dried over Na$_2$SO$_4$. The solvent was evaporated under reduced pressure to obtain (RS)-N-(4-(carboxymethyl)phenyl)-2-(4-fluorobenzenesulfonylamino)-3-(1H-imidazol-1-yl)propanamide (34.3 mg).

Melting point: 162.5°–165° C.

IR νmax cm$^{-1}$ (KBr): 3442, 3234, 1689, 1170, 1155, 1092, 841

$^1$H-NMR δ ppm (CD$_3$OD): 3.558 (2H, s), 4.2–4.6 (3H, m), 7.198 (2H, d, J=8.54 Hz), 7.292 (2H, d, J=8.54 Hz), 7.829 (2H, dd, J=8.79 Hz, J=5.13 Hz)

$^{13}$C-NMR δ ppm (CD$_3$OD): 41.30, 50.80, 58.80, 116.92, 117.25, 121.06, 130.60, 130.71, 130.82, 132.39, 137.09, 137.31, 167.08

Fab-MS m/z: 447 (MH$^+$)

Example 104

Preparation of (RS)-2-(4-bromobenzenesulfonylamino)-N-(4-(carboxymethyl)phenyl)-3-(1H-imidazol-1-yl)propanamide The procedure described in Example 103 was repeated, except that (RS)-2-(4-bromobenzenesulfonylamino)-N-(4-(ethoxycarbonylmethyl)phenyl)-3-(1H-imidazol-1-yl)propanamide (36.8 mg) was hydrolyzed to obtain (RS)-2-(4-bromobenzenesulfonylamino)-N-(4-(carboxymethyl)phenyl)-3-(1H-imidazol-1-yl)propanamide (30.0 mg).

Melting point: 131°–140° C.

IR νmax cm$^{-1}$ (KBr): 1687, 1545, 1331, 1165, 1070, 742, 613

$^1$H-NMR δ ppm (DMSO-d$_6$): 3.492 (2H, s), 4.1–4.5 (3H, m), 7.166 (2H, d, J=8.30 Hz), 7.315 (2H, d, J=8.30 Hz), 7.555 (2H, d, J=8.54 Hz), 7.593 (2H, d, J=8.54 Hz), 10.067 (1H, s)

$^{13}$C-NMR δ ppm (DMSO-d$_6$): 24.91, 57.43, 66.82, 119.41, 126.08, 127.99, 129.13, 130.34, 131.55, 136.17, 139.65, 165.94, 172.18

Fab-MS m/z: 509 (MH$^+$+2), 507 (MH$^+$)

Example 105

Preparation of (RS)-2-(4-chlorobenzenesulfonylamino)-N-(4-ethoxycarbonylphenyl)-3-(pyridin-3-yloxy)propanamide Sodium hydride (60 % dispersion in mineral oil, 15.84 mg) was washed with hexane, suspended in DMF (1 ml) under argon and cooled to 0° C. 3-Hydroxypyridine (37.67 mg) was added and the whole was stirred for 15 minutes. Then, a solution of (RS)-2-(4-chlorobenzenesulfonylamino)-N-(4-ethoxycarbonylphenyl)-3-methanesulfonyloxypropanamide (100 mg) in DMF (500 μl) was added and the whole was stirred for 2 hours. The reaction mixture was poured into a saturated saline solution and extracted with ethyl acetate. The combined ethyl acetate layers were washed with a saturated saline solution and dried over Na$_2$SO$_4$, and the solvent was evaporated to obtain the desired (RS)-2-(4-chlorobenzenesulfonylamino)-N-(4-ethoxycarbonylphenyl)-3-(pyridin-3-yloxy)propanamide (94.9 mg).

Melting point: 119°–124° C.

IR νmax cm$^{-1}$ (neat): 3261, 1700, 1668, 1338, 1161

$^1$H-NMR δ ppm (CDCl$_3$-CD$_3$OD): 1.405 (3H, t, J=7.1 Hz), 4.15–4.5 (3H, m), 4.369 (2H, q, J=7.1 Hz), 7.2–8.2 (4H, m), 7.406 (2H, d, J=8.3 Hz), 7.551 (2H, d, J=8.6 Hz), 7.842 (2H, d, J=8.3 Hz), 7.986 (2H, d, J=8.6 Hz)

$^{13}$C-NMR δ ppm (CDCl$_3$-CD$_3$OD): 14.16, 56.58, 61.01, 67.78, 119.09, 121.66, 123.27, 127.65, 128.48, 129.14, 129.37, 130.58, 137.26, 137.35, 140.00, 142.27, 154.17, 166.29, 166.87

Fab-MS m/z: 504 (MH$^+$)

Example 106

Preparation of (RS)-2-(4-chlorobenzenesulfonylamino)-N-(4-(ethoxycarbonylmethyl)phenyl)-3-(pyridin-3-yloxy)propanamide The procedure described in Example 105 was repeated, except that (RS)-2-(4-chlorobenzenesulfonylamino)-N-(4-(ethoxycarbonylmethyl)phenyl)-3-methanesulfonyloxypropanamide (101.7 mg) was reacted with 3-hydroxypyridine to obtain (RS)-2-(4-chlorobenzenesulfonylamino)-N-(4-(ethoxycarbonylmethyl)phenyl)-3-(pyridin-3-yloxy)propanamide (62.5 mg).

Melting point: 136°–139° C.

IR νmax cm$^{-1}$ (KBr): 3335, 3269, 1734, 1678, 1338, 1162

$^1$H-NMR δ ppm (CDCl$_3$-CD$_3$OD): 1.261 (3H, q, J=7.1 Hz), 3.591 (2H, s), 4.148 (2H, q, J=7.7 Hz), 4.2–4.4 (3H, m), 7.1–7.3 (1H, m), 7.233 (2H, d, J=8.5 Hz), 7.392 (2H, d, J=8.5 Hz), 7.418 (2H, d, J=8.8 Hz), 7.836 (2H, d, J=8.8 Hz), 8.0–8.3 (3H, m)

$^{13}$C-NMR δ ppm (CDCl$_3$-CD$_3$OD): 14.21, 41.07, 56.93, 61.37, 68.45, 120.63, 122.21, 124.68, 128.86, 129.67, 130.04, 130.96, 136.47, 137.70, 138.86, 139.79, 142.38, 154.87, 167.13, 172.43

Fab-MS m/z: 518 (MH$^+$)

Example 107

Preparation of (RS)-2-(4-chlorobenzenesulfonylamino)-N-(3-ethoxycarbonylphenyl)-3-methanesulfonyloxypropanamide The procedure described in Example 105 was repeated, except that (RS)-2-(4-chlorobenzenesulfonylamino)-N-(3-ethoxycarbonylphenyl)-3-(pyridin-3-yloxy)propanamide (100 mg) was reacted with 3-hydroxypyridine to obtain (RS)-2-(4-chlorobenzenesulfonylamino)-N-(3-ethoxycarbonylphenyl)-3-methanesulfonyloxypropanamide (93.0 mg).

Melting point: 125°–129° C.

IR νmax cm$^{-1}$ (neat): 3257, 1712, 1680 (sh), 1363, 1165

$^1$H-NMR δ ppm (CDCl$_3$): 1.369 (3H, t, J=7.1 Hz), 4.10 (1H, m), 4.351 (2H, q, J=7.1 Hz), 4.3–4.5 (2H, m), 7.402 (2H, d, J=8.5 Hz), 7.826 (2H, d, J=8.5 Hz)

$^{13}$C-NMR δ ppm (CDCl$_3$): 14.30, 56.60, 61.33, 67.63, 121.05, 121.43, 124.22, 124.48, 126.06, 128.71, 129.17, 129.66, 131.30, 137.12, 137.70, 140.03, 142.68, 153.97, 166.12, 166.49

Fab-MS m/z: 504 (MH$^+$)

Example 108

Preparation of (RS)-2-(4chlorobenzenesulfonylamino)-N-(3-methoxycarbonylpropyl)-3-(pyridin-3-yloxy)propanamide The procedure described in Example 105 was repeated, except that (RS)-2-(4-chlorobenzenesulfonylamino)-3-methanesulfonyloxy-N-(3-methoxycarbonylpropyl)propanamide (102.2 mg) was reacted with 3-hydroxypyridine to obtain (RS)-2-(4-chlorobenzenesulfonylamino)-N-(3-methoxycarbonylpropyl)-3-(pyridin-3-yloxy)propanamide (92.8 mg).

IR νmax cm$^{-1}$ (neat): 3271, 3089, 2931, 1734, 1668, 1389, 1338, 1167, 1095

$^1$H-NMR δ ppm (CDCl$_3$): 1.785 (2H, t, J=7.0 Hz), 2.319 (2H, t, J=7.2 Hz), 3.261 (2H, q, J=6.5 Hz), 3.662 (3H, s), 4.0–4.3 (2H, m), 7.0–7.1 (1H, m), 7.1–7.3 (2H, m), 7.448 (2H, d, J=8.8 Hz), 7.819 (2H, d, J=8.8 Hz), 8.1–8.2 (2H, m)

$^{13}$C-NMR δ ppm (CDCl$_3$): 24.30, 31.38, 36.40, 39.05, 51.62, 56.10, 120.90, 122.91, 123.87, 128.60, 129.33, 137.95, 138.17, 142.61, 153.97, 162.52, 173.48

Fab-MS m/z: 456 (MH$^+$)

Example 109

Preparation of (RS)-2-(4-chlorobenzenesulfonylamino)-N-(4-methoxycarbonylbutyl)-3-(pyridin-3-yloxy)propanamide The procedure described in Example 105 was repeated, except that (RS)-2-(4-chlorobenzenesulfonylamino)-3-methanesulfonyloxy-N-(4-methoxycarbonylbutyl)propanamide (65.7 mg) was reacted with 3-hydroxypyridine to obtain (RS)-2-(4-chlorobenzenesulfonylamino)-N-(4-methoxycarbonylbutyl)-3-(pyridin-3-yloxy)propanamide (64.3 mg).

IR vmax cm⁻¹ (neat): 3248, 3089, 2953, 1732, 1668, 1338, 1165, 1095

¹H-NMR δ ppm (CDCl₃): 1.4–1.7 (4H, m), 2.2–2.4 (2H, m), 3.2–3.3 (2H, m), 3.664 (3H, s), 4.059 (2H, t, J=4.2 Hz), 4.3–4.4 (1H, m), 7.463 (2H, d, J=8.6 Hz), 7.818 (2H, d, J=8.8 Hz), 8.0–8.3 (3H, m)

¹³C-NMR δ ppm (CDCl₃): 21.74, 28.89, 33.29, 36.51, 39.38, 51.66, 55.80, 121.01, 123.21, 124.01, 128.67, 129.55, 137.80, 138.98, 142.86, 153.86, 162.59, 173.74

Fab-MS m/z: 470 (MH⁺)

Example 110

Preparation of (RS)-2-(4-chlorobenzenesulfonylamino)-N-(5-methoxycarbonylpentyl)-3-pyridin-3-yloxy) propanamide The procedure described in Example 105 was repeated, except that (RS)-2-(4-chlorobenzenesulfonylamino)-3-methanesulfonyloxy-N-(5-methoxycarbonylpentyl) propanamide (95.4 mg) was reacted with 3-hydroxypyridine to obtain (RS)-2-(4-chlorobenzenesulfonylamino)-N-(5-methoxycarbonylpentyl)-3-(pyridin-3-yloxy)propanamide (91.3 mg).

IR vmax cm⁻¹ (neat): 3307, 3089, 1726, 1662, 1441, 1279, 1159, 1093

¹H-NMR δ ppm (CDCl₃): 1.2–1.7 (6H, m), 2.2–2.4 (2H, m), 3.1–3.3 (2H, m), 3.666 (3H, s), 4.0–4.4 (3H, m), 7.0–7.1 (1H, m), 7.1–7.2 (2H, m), 7.3–7.5 (2H, m), 7.692 (1H, d, J=8.5 Hz), 7.814 (1H, d, J=8.6 Hz), 8.0–8.1 (1H, m), 8.271 (1H, d, J=2.2 Hz)

¹³C-NMR δ ppm (CDCl₃): 24.23, 28.74, 31.49, 33.73, 36.48, 36.55, 51.51, 56.50, 123.46, 124.38, 128.63, 128.89, 129.44, 137.77, 138.50, 140.00, 154.38, 162.63, 176.86

Fab-MS m/z: 484 (MH⁺)

Example 111

Preparation of (RS)-2-(4-chlorobenzenesulfonylamino)-N-(6-methoxycarbonylhexyl)-9-(pyridin-3-yloxy) propanamide The procedure described in Example 105 was repeated, except that (RS)-2-(4-chlorobenzenesulfonylamino)-3-methanesulfonyloxy-N-(6-methoxycarbonylhexyl) propanamide (70.0 mg) was reacted with 3-hydroxypyridine to obtain (RS)-2-(4-chlorobenzenesulfonylamino)-N-(6-methoxycarbonylhexyl)-3-(pyridin-3-yloxy)propanamide (30.3 mg).

IR vmax cm⁻¹ (neat): 2929, 2858, 1730, 1664, 1477, 1277, 1165, 1095

¹H-NMR δ ppm (CDCl₃): 1.2–1.7 (8H, m), 2.2–2.4 (2H, m), 3.1–3.3 (2H, m), 3.665 (3H, s), 3.9–4.4 (3H, m), 7.2–7.3 (2H, m), 7.4–7.5 (2H, m), 7.7–7.9 (1H, m), 8.0–8.1 (2H, m), 8.1–8.2 (1H, m)

¹³C-NMR δ ppm (CDCl₃): 24.63, 26.25, 28.48, 28.92, 31.49, 33.84, 36.51, 51.44, 55.80, 124.20, 124.67, 127.90, 128.63, 129.29, 129.55, 137.07, 139.60, 142.72, 162.63, 173.85

Fab-MS m/z: 498 (MH⁺)

Example 112

Preparation of (RS)-2-(4-chlorobenzenesulfonylamino)-N-(7-methoxycarbonylheptyl)-3-(pyridin-3-yloxy) propanamide The procedure described in Example 105 was repeated, except that (RS)-2-(4-chlorobenzenesulfonylamino)-3-methanesulfonyloxy-N-(7-methoxycarbonylheptyl) propanamide (69.0 mg) was reacted with 3-hydroxypyridine to obtain (RS)-2-(4-chlorobenzenesulfonylamino)-N-(7-methoxycarbonylheptyl)-3-(pyridin-3-yloxy)propanamide (36.7 mg).

IR vmax cm⁻¹ (KBr): 3244, 2933, 1733, 1662, 1477, 1277, 1165, 1101

¹H-NMR δ ppm (CDCl₃): 1.2–1.6 (10H, m), 2.292 (2H, t, J=7.4 Hz), 3.202 (2H, q, J=6.6 Hz), 3.662 (3H, s), 4.0–4.1 (2H, m), 4.3–4.4 (1H, m), 7.453 (2H, d, J=8.8 Hz), 7.811 (2H, d, J=8.8 Hz), 8.0–8.3 (4H, m)

¹³C-NMR δ ppm (CDCl₃): 24.67, 28.63, 28.78, 29.07, 31.45, 33.91, 36.51, 39.82, 51.44, 55.88, 121.08, 123.35, 128.60, 129.48, 137.88, 139.67, 140.26, 142.72, 162.63, 167.80, 172.93

Fab-MS m/z: 512 (MH⁺)

Example 113

Preparation of (RS)-N-(4-(ethoxycarbonylmethyl)phenyl)-2-(4-fluorobenzenesulfonylamino)-3-(pyridin-3-yloxy) propanamide The procedure described in Example 105 was repeated, except that (RS)-N-(4-(ethoxycarbonylmethyl)phenyl)-2-(4-fluorobenzenesulfonylamino)-3-methanesulfonyloxypropanamide (250 mg) was reacted with 3-hydroxypyridine to obtain (RS)-N-(4-(ethoxycarbonylmethyl)phenyl)-2-(4-fluorobenzenesulfonylamino)-3-(pyridin-3-yloxy) propanamide (112.6 mg).

Melting point: 149.5°–151.5° C.

IR vmax cm⁻¹ (KBr): 3496, 3265, 1734, 1687, 1662, 1338, 1167, 1157, 1092, 571, 550

¹H-NMR δ ppm (CDCl₃-DMSO-d₆): 1.223 (3H, t, J=7.08 Hz), 3.541 (2H, s), 4.103 (2H, q, J=7.08 Hz), 4.223 (2H, d, J=5.86 Hz), 4.482 (1H, t, J=5.86 Hz), 7.0–7.2 (6H, m), 7.402 (2H, d, J=8.32 Hz), 7.911 (2H, dd, J=9.03 Hz, J=5.13 Hz), 8.1–8.2 (2H, m)

¹³C-NMR δ ppm (CDCl₃-DMSO-d₆): 13.50, 56.30, 59.74, 68.18, 115.08, 115.41, 119.33, 120.80, 123.22, 128.80, 129.20, 129.20, 136.42, 137.71, 141.85, 153.84, 166.05, 170.38

Fab-MS m/z: 502 (MH⁺)

Example 114

Preparation of (RS)-2-(4-bromobenzenesulfonylamino)-N-(4-(ethoxycarbonylmethyl)phenyl)-3-(pyridin-3-yloxy) propanamide The procedure described in Example 105 was repeated, except that (RS)-2-(4-bromobenzenesulfonylamino)-N-(4-(ethoxycarbonylmethyl)phenyl)-3-methanesulfonyloxypropanamide (307 mg) was reacted with 3-hydroxypyridine to obtain (RS)-2-(4-bromobenzenesulfonylamino)-N-(4-(ethoxycarbonylmethyl)phenyl)-3-(pyridin-3-yloxy) propanamide (90.4 mg).

Melting point: 168.5°–171° C.

IR vmax cm⁻¹ (KBr): 1730, 1689, 1338, 1277, 1165, 740, 611, 565

¹H-NMR δ ppm (CD₃OD-DMSO-d₆): 1.224 (3H, t, J=7.08 Hz), 3.579 (2H, s), 4.115 (2H, q, J=7.08 Hz), 4.244 (2H, d, J=5.86 Hz), 4.402 (1H, t, J=5.86 Hz), 7.200 (2H, d, J=8.5 Hz), 7.29 (2H, m), 7.359 (2H, d, J=8.5 Hz), 7.608 (2H, d, J=8.79 Hz), 7.786 (2H, d, J=8.79 Hz), 8.13 (2H, m)

¹³C-NMR δ ppm (CD₃OD-DMSO-d₆): 14.75, 41.37, 57.95, 61.73, 69.57, 121.24, 123.15, 125.53, 128.21, 129.93, 130.71, 130.82, 131.81, 133.31, 137.89, 138.85, 141.30, 143.25, 155.97, 168.07, 172.84

Fab-MS m/z: 562 (MH$^+$), 564 (MH$^+$2)

Example 115

Preparation of (RS)-N-(4-carboxyphenyl)-2-(4-chlorobenzenesulfonylamino)-3-(pyridin-3-yloxy) propanamide hydrochloride 2N NaOH (143 μl) was added to a solution of (RS)-2-(4-chlorobenzenesulfonylamino)-N-(4-ethoxycarbonylphenyl)-3-(pyridin-3-yloxy)propanamide (48.1 mg) in ethanol (5 ml), and the whole was stirred at room temperature overnight. The reaction mixture was concentrated under reduced pressure. A small amount of purified water was added to the residue, and the mixture was concentrated under reduced pressured. The concentration step was repeated 3 times to remove ethanol. The residue was dissolved in 1N HCl (20 ml), diluted with water (20 ml), and then washed 3 times with ethyl acetate (10 ml). The aqueous layer was concentrated under reduced pressure. A small amount of purified water was added, and the mixture was concentrated under reduced pressure. The concentrating step was repeated 3 times to evaporate excess HCl. The residue was dried under reduced pressure in a desiccator, and ethanol was added. The insoluble materials were removed by filtration. The combined filtrates were concentrated and dried under reduced pressure to obtain (RS)-N-(4-carboxyphenyl)- 2-(4-chlorobenzenesulfonylamino)-3-(pyridin-3-yloxy) propanamide hydrochloride (21.8 mg).

Melting point: 150°–155° C.

$^1$H-NMR δ ppm (CD$_3$OD): 4.4–4.9 (3H, m), 7.41 (1H, m), 7.8–8.4 (11H, m)

Fab-MS m/z: 476 (MH$^+$–HCl)

Example 116

Preparation of (RS)-N-(4-(carboxymethyl) phenyl)-2-(4-chlorobenzenesulfonylamino)-3-pyridin-3-yloxy) propanamide hydrochloride The procedure described in Example 115 was repeated, except that (RS)-2-(4-chlorobenzenesulfonylamino)-N-(4-(ethoxycarbonylmethyl)phenyl)-3-(pyridin-3-yloxy) propanamide (38.1 mg) was hydrolyzed, and then reacted with HCl to obtain (RS)-N-(4-(carboxymethyl)phenyl)-2-(4-chlorobenzenesulfonylamino)-3-(pyridin-3-yloxy) propanamide hydrochloride (29.7 mg).

Melting point: 162°–165° C.

$^1$H-NMR δ ppm (CDCl$_3$-CD$_3$OD): 3.569 (2H, s), 3.5–3.7 (2H, m), 4.15 (1H, m), 7.217 (2H, d, J=8 Hz), 7.383 (2H, d, J=8 Hz), 7.432 (2H, d, J=8 Hz), 7.872 (2H, d, J=8 Hz), 7.9–8.7 (4H, m)

$^{13}$C-NMR δ ppm (CDCl$_3$-CD$_3$OD): 41.04, 56.88, 70.64, 120.77, 128.83, 129.20, 129.93, 130.23, 139.91, 157.73, 166.72, 174.60

Fab-MS m/z: 490 (MH$^+$–HCl)

Example 117

Preparation of (RS)-N-(3-carboxyphenyl)-2-(4-chlorobenzenesulfonylamino)-3-(pyridin-3-yloxy) propanamide hydrochloride The procedure described in Example 115 was repeated, except that (RS)-2-(4-chlorobenzenesulfonylamino)-N-(3-ethoxycarbonylphenyl)-3-(pyridin-3-yloxy)propanamide (41.7 mg) was hydrolyzed, and then reacted with HCl to obtain (RS)-N-(3-carboxyphenyl)-2-(4-chlorobenzenesulfonylamino)-3-(pyridin-3-yloxy) propanamide hydrochloride (23.3 mg).

Melting point: 165°–167° C.

$^1$H-NMR δ ppm (CD$_3$OD): 4.50 (1H, m), 4.6–4.9 (2H, m), 7.42 (1H, m), 7.8–8.4 (11H, m)

Fab-MS m/z: 476 (MH$^+$–HCl)

Example 118

Preparation of (RS)-N-(3-carboxypropyl)-2-(4-chlorobenzenesulfonylamino)-3-(pyridin-3-yloxy) propanamide hydrochloride The procedure described in Example 115 was repeated, except that (RS)-2-(4-chlorobenzenesulfonylamino)-N-(3-methoxycarbonylpropyl)-3-(pyridin-3-yloxy)propanamide (39.6 mg) was hydrolyzed, and then reacted with HCl to obtain (RS)-N-(3-carboxypropyl)-2-(4-chlorobenzenesulfonylamino)-3-(pyridin-3-yloxy) propanamide hydrochloride (31.4 mg).

IR νmax cm$^{-1}$ (neat): 3700–2400 (br), 1734, 1684, 1394, 1344, 1163, 1086

$^1$H-NMR δ ppm (CD$_3$OD): 1.698 (2H, t, J=7.2 Hz), 2.292 (2H, dd, J=7.3 Hz, J=2.4 Hz), 3.126 (2H, t, J=6.8 Hz), 4.101 (1H, t, J=7.1 Hz), 4.2–4.4 (2H, m), 7.554 (2H, d, J=8.8 Hz), 7.876 (2H, d, J=8.5 Hz), 8.1–8.6 (4H, m)

$^{13}$C-NMR δ ppm (CD$_3$OD): 25.57, 31.91, 39.80, 57.18, 71.00, 129.46, 129.97, 130.49, 130.93, 133.71, 135.77, 140.13, 140.72, 159.20, 165.73, 169.87

Fab-MS m/z: 442 (MH$^+$–HCl)

Example 119

Preparation of (RS)-N-(4-carboxybutyl)-2-(4-chlorobenzenesulfonylamino)-3-(pyridin-3-yloxy) propanamide hydrochloride The procedure described in Example 115 was repeated, except that (RS)-2-(4-chlorobenzenesulfonylamino)-N-(4-methoxycarbonylbutyl)-3-(pyridin-3-yloxy)propanamide (41.4 mg) was hydrolyzed, and then reacted with HCl to obtain (RS)-N-(4-carboxybutyl)-2-(4-chlorobenzenesulfonylamino)-3-(pyridin-3-yloxy) propanamide hydrochloride (29.6 mg).

IR νmax cm$^{-1}$ (neat): 3394, 3080, 2953, 1713, 1666, 1396, 1335, 1165, 1093

$^1$H-NMR δ ppm (D$_2$O): 1.3–1.6 (4H, m), 2.370 (2H, t, J=7.1 Hz), 3.0–3.1 (2H, m), 4.3–4.5 (3H, m), 7.576 (2H, d, J=8.8 Hz), 7.6–7.7 (1H, m), 7.843 (2H, d, J=8.5 Hz), 8.050 (1H, d, J=7.3 Hz), 8.2–8.4 (2H, m)

$^{13}$C-NMR δ ppm DD$_2$O): 24.25, 30.44, 36.08, 41.90, 58.34, 71.50, 130.85, 131.00, 131.37, 132.55, 132.70, 135.00, 136.18, 139.90, 142.43, 163.11, 172.12

Fab-MS m/z: 456 (MH$^+$–HCl)

Example 120

Preparation of (RS)-N-(5-carboxypentyl)-2-(4-chlorobenzenesulfonylamino)-3-(pyridin-3-3-yloxy) propanamide hydrochloride The procedure described in Example 115 was repeated, except that (RS)-2-(4-chlorobenzenesulfonylamino)-N-(5-methoxycarbonylpentyl)-3-(pyridin-3-yloxy)propanamide (46.6 mg) was hydrolyzed, and then reacted with HCl to obtain (RS)-N-(5-carboxypentyl)-2-(4-chlorobenzenesulfonylamino)-3-(pyridin-3-yloxy) propanamide hydrochloride (30.7 mg).

IR νmax cm$^{-1}$ (neat): 3369, 3234, 2933, 1709, 1664, 1558, 1396, 1315, 1164, 1093

¹H-NMR δ ppm (CD₃OD): 1.2–1.7 (6H, m), 2.302 (2H, t, J=7.3 Hz), 3.064 (2H, t, J=6.8 Hz), 3.622 (1H, t, J=7.1 Hz), 4.2–4.5 (2H, m), 7.569 (1H, t, J=8.3 Hz), 7.8–8.1 (4H, m), 8.3–8.4 (2H, m)

¹³C-NMR δ ppm (CD₃OD): 25.53, 27.26, 29.79, 34.63, 40.79, 57.18, 71.09, 129.46, 130.01, 130.47, 130.61, 133.61, 134.18, 135.74, 140.08, 158.72, 164.88, 175.76

Fab-MS m/z: 470 (MH⁺–HCl)

Example 121

Preparation of (RS)-N-(6-carboxyhexyl)-3-(4-chlorobenzenesulfonylamino)-3-(pyridin-3-yloxy)propanamide hydrochloride The procedure described in Example 115 was repeated, except that (RS)-2-(4-chlorobenzenesulfonylamino)-N-(6-methoxycarbonylhexyl)-3-(pyridin-3-yloxy)propanamide (12.3 mg) was hydrolyzed, and then reacted with HCl to obtain (RS)-N-(6-carboxyhexyl)-2-(4-chlorobenzenesulfonylamino)-3-(pyridin-3-yloxy)propanamide hydrochloride (12.5 mg).

IR νmax cm⁻¹ (neat): 3369, 3080, 2931, 1722, 1664, 1552, 1392, 1282, 1165, 1088

¹H-NMR δ ppm (D₂O): 1.2–1.8 (8H, m), 2.3–2.5 (2H, m), 3.0–3.4 (2H, m), 3.645 (1H, t, J=4.4 Hz), 3.7–3.8 (1H, m), 4.1–4.4 (1H, m), 7.878 (2H, d, J=8.8 Hz), 8.047 (2H, d, J=8.8 Hz), 8.2–8.5 (3H, m)

Fab-MS m/z: 485 (M⁺2–HCl)

Example 122

Preparation of (RS)-N-(7-carboxyheptyl)-2-(4-chlorobenzenesulfonylamino)-3-(pyridin-3-yloxy)propanamide hydrochloride The procedure described in Example 115 was repeated, except that (RS)-2-(4-chlorobenzenesulfonylamino)-N-(7-methoxycarbonylheptyl)-3-(pyridin-3-yloxy)propanamide (16.5 mg) was hydrolyzed, and then reacted with HCl to obtain (RS)-N-(7-carboxyheptyl)-2-(4-chlorobenzenesulfonylamino)-3-(pyridin-3-yloxy)propanamide hydrochloride (17.0 mg).

Melting point: 73°–74° C.

IR νmax cm⁻¹ (KBr): 3427, 3078, 2929, 1720, 1664, 1554, 1396, 1305, 1165, 1093

¹H-NMR δ ppm (D₂O): 1.2–1.7 (10H, m), 2.360 (2H, t, J=7.4 Hz), 3.060 (2H, t, J=6.6 Hz), 4.3–4.4 (2H, m), 4.444 (1H, d, J=7.3 Hz), 7.585 (2H, d, J=8.5 Hz), 7.846 (2H, d, J=8.5 Hz), 8.0–8.1 (2H, m), 8.3–8.4 (2H, m)

Fab-MS m/z: 498 (MH⁺–HCl)

Example 123

Preparation of (RS)-N-(4-(carboxymethyl) phenyl)-2-(4-fluorobenzenesulfonylamino)-3-(pyridin-3-yloxy)propanamide The procedure described in Example 103 was repeated, except that (RS)-N-(4-(ethoxycarbonylmethyl)phenyl)-2-(4-fluorobenzenesulfonylamino)-3-(pyridin-3-yloxy)propanamide (160.0 mg) was hydrolyzed to obtain (RS)-N-(4-(carboxymethyl)phenyl)-2-(4-fluorobenzenesulfonylamino)-3-(pyridin-3-yloxy)propanamide (138.9 mg).

Melting point: 152°–153° C.

IR νmax cm⁻¹ (KBr): 3269, 1691 (br), 1332, 1155

¹H-NMR δ ppm (CDCl₃-DMSO-d₆): 3.489 (2H, s), 4.217 (2H, d, J=5.86 Hz), 4.408 (1H, t, J=5.86 Hz), 7.0–7.2 (6H, m), 7.388 (2H, d, J=8.55 Hz), 7.8–8.0 (2H, m), 7.913 (2H, dd, J=8.79 Hz, J=5.13 Hz)

Fab-MS m/z: 474 (MH⁺)

Example 124

Preparation of (RS)-2-(4-bromobenzenesulfonylamino)-N-(4-(carboxymethyl)phenyl)-3-(pyridin-3-yloxy)propanamide The procedure described in Example 103 was repeated, except that (RS)-2-(4-bromobenzenesulfonylamino)-N-(4-(ethoxycarbonylmethyl)phenyl)-3-(pyridin-3-yloxy) propanamide (65.0 mg) was hydrolyzed to obtain (RS)-2-(4-bromobenzenesulfonylamino)-N-(4-(carboxymethyl)phenyl)-3-(pyridin-3-yloxy)propanamide (43.0 mg).

Melting point: 205°–207° C.

IR νmax cm⁻¹ (KBr): 1687 (br), 1333, 1277, 1238, 1092, 741, 609

¹H-NMR δ ppm (CD₃OD-DMSO-d₆): 3.563 (2H, s), 4.269 (2H, d, J=5.9 Hz), 4.452 (1H, t, J=5.9 Hz), 7.238 (2H, d, J=8.54 Hz), 7.31 (2H, m), 7.405 (2H, d, J=8.54 Hz), 7.676 (2H, d, J=7.9 Hz), 7.826 (2H, d, J=7.9 Hz), 8.188 (2H, m)

¹³C-NMR δ ppm (CD₃OD-DMSO-d₆): 56.92, 68.69, 120.10, 121.90, 124.32, 128.03, 128.91, 129.71, 131.07, 132.13, 132.21, 136.83, 138.15, 140.57, 142.51, 166.79, 166.79, 172.91

Fab-MS m/z: 534 (MH⁺), 536 (MH⁺+2)

Example 125

Preparation of (RS)-2-(4-chlorobenzenesulfonylamino)-N-(4-(ethoxycarbonylmethyl)phenyl)-3-phenoxypropanamide Sodium hydride (60%dispersion in mineral oil, 73.6 mg) was washed with hexane, then suspended in DMF (0.5 ml) under argon and cooled to 0° C. A solution of phenol (138.5 mg) in DMF (1 ml) was added and the mixture was stirred for 15 minutes. Then, a solution of (RS)-2-(4-chlorobenzenesulfonylamino)-N-(4-(ethoxycarbonylmethyl)phenyl)-3-methanesulfonyloxypropanamide (382 mg) in DMF (1.5 ml) was added and the mixture was stirred for 1.5 hours. The reaction mixture was poured into a saturated saline solution and extracted with ethyl acetate. The combined ethyl acetate layers were washed with a saturated saline solution and dried over Na₂SO₄. The solvent was evaporated, and then, the residue was recrystallized from a mixture of hexane/ethyl acetate to obtain (RS)-2-(4-chlorobenzenesulfonylamino)-N-(4-(ethoxycarbonylmethyl) phenyl)-3-phenoxypropanamide (309 mg).

Melting point: 145°–146.5° C.

IR νmax cm⁻¹ (KBr): 3365, 1732, 1670, 1331, 1244, 1167, 831, 756

¹H-NMR δ ppm (CDCl₃-DMSO-d₆): 1.236 (3H, t, J=7.08 Hz), 3.543 (2H, s), 4.1–4.2 (2H, m), 4.1–4.2 (2H, m), 4.2 (1H, m), 6.761 (2H, d, J=7.5 Hz), 6.920 (1H, t, J=7.5 Hz), 7.218 (2H, t, J=7.5 Hz), 7.177 (2H, d, J=8.5 Hz), 7.364 (2H, d, J=8.55 Hz), 7.393 (2H, d, J=8.5 Hz), 7.837 (2H, d, J=8.55 Hz)

¹³C-NMR δ ppm (CDCl₃-DMSO-d₆): 13.38, 56.46, 59.87, 67.47, 77.48, 113.93, 119.32, 120.64, 127.87, 128.30, 128.67, 128.74, 128.96, 129.37, 136.01, 137.95, 138.50, 157.24, 166.19, 170.59

Fab-MS m/z: 517 (MH⁺)

Example 126

Preparation of (RS)-2-(4-chlorobenzenesulfonylamino)-N-(4-(ethoxycarbonylmethyl)phenyl)-3-(4-chlorophenoxy)propanamide The procedure described in Example 125 was repeated, except that (RS)-2-(4-chlorobenzenesulfonylamino)-N-(4-(ethoxycarbonylmethyl)phenyl)-3-methanesulfonyloxypropanamide (360 mg) was reacted with 4-chlorophenol (178.3 mg) to obtain (RS)-2-(4-chlorobenzenesulfonylamino)-N-(4-(ethoxycarbonylmethyl)phenyl)-3-(4-chlorophenoxy) propanamide (248 mg).

Melting point: 136°–137.5° C.

IR vmax cm$^{-1}$ (KBr): 3429, 1734, 1649, 1340, 1244, 1169, 827, 758

$^1$H-NMR δ ppm (CDCl$_3$-DMSO-d$_6$): 1.235 (3H, t, J=7.08 Hz), 3.541 (2H, s), 4.144 (2H, q, J=7.08 Hz), 4.15 (2H, m), 4.361 (1H, t, J=5.62 Hz), 6.726 (1H, d, J=9.040 Hz), 7.14–7.2 (4H, m), 7.366 (2H, d, J=8.8 Hz), 7.384 (2H, d, J=8.55 Hz), 7.612 (1H, d, J=9.3 Hz), 7.828 (1H, d, J=8.8 Hz), 7.943 (1H, d, J=9.3 Hz)

$^{13}$C-NMR δ ppm (CDCl$_3$-DMSO-d$_6$): 13.50, 26.70, 56.37, 68.14, 82.11, 115.74, 119.33, 127.92, 128.32, 128.58, 128.76, 129.02, 129.38, 129.79, 137.63, 156.23, 166.09, 170.38

Fab-MS m/z: 551 (MH$^+$)

Example 127

Preparation of (RS)-2-(4-chlorobenzenesulfonylamino)-3-(3-chlorophenoxy)-N-(4-(ethoxycarbonylmethyl)phenyl) propanamide The procedure described in Example 125 was repeated, except that (RS)-2-(4-chlorobenzenesulfonylamino)-N-(4-(ethoxycarbonylmethyl)phenyl)-3-methanesulfonyloxypropanamide (401 mg) was reacted with 3-chlorophenol (198.7 mg) and was recrystallized from hexane-ethyl acetate to obtain (RS)-2-(4-chlorobenzenesulfonyl-amino)-3-(3-chlorophenoxy)-N-(4-(ethoxycarbonylmethyl)phenyl) propanamide (363.2 mg).

Melting point: 173°–174° C.

IR vmax cm$^{-1}$ (KBr): 3356, 1728, 1670, 1331, 1230, 1165, 756

$^1$H-NMR δ ppm (CDCl$_3$-DMSO-d$_6$): 1.246 (3H, t, J=7.2 Hz), 3.560 (2H, s), 4.126 (2H, q, J=7.2 Hz), 4.16–4.24 (2H, m), 4.359 (1H, t, J=5.4 Hz), 6.649 (1H, dd, J=8.3 Hz, J=2.3 Hz), 6.739 (1H, t, J=2.3 Hz), 6.912 (1H, bd, J=8.1 Hz), 7.160 (1H, dd, J=8.3 Hz, J=8.1 Hz), 7.194 (2H, d, J=8.5 Hz), 7.373 (2H, d, J=8.8 Hz), 7.403 (2H, d, J=8.5 Hz), 7.836 (2H, d, J=8.8 Hz)

$^{13}$C-NMR δ ppm (CDCl$_3$-DMSO-d$_6$): 13.60, 40.22, 56.54, 60.13, 67.98, 112.50, 114.81, 119.54, 121.01, 128.05, 128.60, 129.04, 129.77, 134.17, 136.08, 138.35, 138.61, 158.23, 166.08, 170.77

Fab-MS m/z: 551 (MH$^+$)

Example 128

Preparation of (RS)-2-(4-chlorobenzenesulfonylamino)-3-(2-chlorophenoxy)-N-(4-(ethoxycarbonylmethyl)phenyl) propanamide The procedure described in Example 125 was repeated, except that (RS)-2-(4-chlorobenzenesulfonylamino)-N-(4-(ethoxycarbonylmethyl)phenyl)-3-methanesulfonyloxypropanamide (403 mg) was reacted with 2-chlorophenol (390.2 mg) to obtain (RS)-2-(4-chlorobenzenesulfonylamino)-3-(2-chlorophenoxy)-N-(4-(ethoxycarbonylmethyl)phenyl) propanamide (390.2 mg).

Melting point: 141°–142.5° C. (recrystallized from hexane/ethyl acetate)

IR vmax cm$^{-1}$ (KBr): 3334, 3244, 1734, 1657, 1340, 1250, 1169, 829

$^1$H-NMR δ ppm (CDCl$_3$-DMSO-d$_6$): 1.242 (3H, t, J=7.2 Hz), 3.562 (2H, s), 4.09–4.18 (1H, m), 4.133 (2H, q, J=7.2 Hz), 4.239 (1H, m), 4.441 (1H, dd, J=9.2 Hz, J=4.5 Hz), 6.86–6.98 (2H, m), 7.15–7.45 (8H, m), 7.848 (2H, d, J=8.8 Hz), 8.886 (1H, s)

$^{13}$C-NMR δ ppm (CDCl$_3$-DMSO-d$_6$): 13.65, 40.28, 56.47, 60.18, 69.00, 113.66, 119.73, 121.89, 122.41, 127.42, 128.11, 128.72, 129.06, 129.78, 136.12, 138.31, 138.51, 152.97, 166.13, 170.85

Fab-MS m/z: 551 (MH$^+$)

Example 129

Preparation of (RS)-N-(4-(carboxymethyl) phenyl)-2-(4-chlorobenzenesulfonylamino)-3-phenoxypropanamide The procedure described in Example 39 was repeated, except that (RS)-2-(4-chlorobenzenesulfonylamino)-N-(4-(ethoxycarbonylmethyl)phenyl)-3-phenoxypropanamide (178.9 mg) was hydrolyzed to obtain (RS)-N-(4-(carboxymethyl)phenyl)-2-(4-chlorobenzenesulfonylamino)-3-phenoxypropanamide (106.5 mg).

Melting point: 190.5°–192.5° C. (recrystallized from ethyl acetate)

IR vmax cm$^{-1}$ (KBr): 3358, 1695, 1670, 1331, 1242, 1165, 829, 756

$^1$H-NMR δ ppm (CDCl$_3$-DMSO-d$_6$): 3.515 (2H, s), 4.2 (1H, m), 4.3 (1H, m), 6.754 (2H, d, J=7.5 Hz), 6.919 (1H, t, J=7.5 Hz), 7.212 (2H, t, J=7.5 Hz), 7.918 (2H, d, J=8.5 Hz), 7.364 (2H, d, J=8.79 Hz), 7.378 (2H, d, J=8.5 Hz), 7.833 (2H, d, J=8.79 Hz)

$^{13}$C-NMR δ ppm (CDCl$_3$-DMSO-d$_6$): 40.17, 56.67, 67.84, 114.23, 119.50, 120.86, 128.00, 128.83, 129.04, 130.25, 135.98, 138.22, 138.77, 157.49, 166.21, 172.52

Fab-MS m/z: 489 (MH$^+$)

Example 130

Preparation of (RS)-N-(4-(carboxymethyl) phenyl)-2-(4-chlorobenzenesulfonylamino)-3-(4-chlorophenoxy) propanamide The procedure described in Example 39 was repeated, except that (RS)-2-(4-chlorobenzenesulfonylamino)-N-(4-(ethoxycarbonylmethyl)phenyl)-3-(4-chlorophenoxy) propanamide (180 mg) was hydrolyzed and recrystallized from hexane/ethyl acetate to obtain (RS)-N-(4-(carboxymethyl)phenyl)-2-(4-chlorobenzenesulfonylamino)-3-(4-chlorophenoxy)propanamide (49.7 mg).

Melting point: 205°–207° C.

IR vmax cm$^{-1}$ (KBr): 3400, 1670, 1606, 1329, 1242, 1165, 825, 756

$^1$H-NMR δ ppm (CDCl$_3$-DMSO-d$_6$): 4.1–4.2 (2H, m), 4.33 (1H, m), 6.692 (2H, d, J=9.0 Hz), 7.171 (2H, d, J=9.0 Hz), 7.202 (2H, d, J=8.6 Hz), 7.367 (2H, d, J=8.6 Hz), 7.380 (2H, d, J=8.5 Hz), 7.826 (2H, d, J=8.5 Hz)

$^{13}$C-NMR δ ppm (CDCl$_3$-DMSO-d$_6$): 40.18, 56.50, 68.02, 115.40, 115.51, 119.47, 128.01, 128.86, 128.71, 129.15, 130.21, 135.86, 138.39, 138.54, 156.06, 166.08, 172.86

Fab-MS m/z: 523 (MH$^+$)

Example 131

Preparation of (RS)-N-(4-(carboxymethyl) phenyl)-2-(4-chlorobenzenesulfonylamino)-3-(3-chlorophenoxy) propanamide The procedure described in Example 39 was repeated, except that (RS)-2-(4-chlorobenzenesulfonylamino)-3-(3-chlorophenoxy)-N-(4-(ethoxycarbonylmethyl)phenyl) propanamide (200 mg) was hydrolyzed and recrystallized from ethyl acetate to obtain (RS)-N-(4-(carboxymethyl) phenyl)-2-(4-chlorobenzenesulfonylamino)-3-(3-chlorophenoxy)propanamide (38.11 mg).

Melting point: 219.5°–221° C.

IR νmax cm$^{-1}$ (KBr): 3400 (br), 3323, 1716, 1655, 1344, 1230, 1167, 756

$^1$H-NMR δ ppm (CDCl$_3$-DMSO-d$_6$): 3.494 (2H, s), 4.083 (1H, dd, J=9.9 Hz, J=7.2 Hz), 4.152 (1H, dd, J=9.9 Hz, J=5.5 Hz), 4.31–4.44 (1H, m), 6.738 (1H, dd, J=8.3 Hz, J=1.7 Hz), 6.786 (1H, t, J=2.2 Hz), 6.949 (1H, dd, J=8.0 Hz, J=2.0 Hz), 7.169 (2H, d, J=8.5 Hz), 7.233 (1H, t, J=8.1 Hz), 7.381 (2H, d, J=8.5 Hz), 7.494 (2H, d, J=8.5 Hz), 7.837 (2H, d, J=8.5 Hz)

$^{13}$C-NMR δ ppm (CDCl$_3$-DMSO-d$_6$): 39.98, 56.22, 68.07, 113.14, 114.68, 119.30, 120.73, 128.06, 128.50, 128.69, 129.02, 130.15, 133.56, 136.39, 137.19, 139.72, 158.46, 166.05, 172.03, Fab-MS m/z: 523 (MH$^+$)

Example 132

Preparation of (RS)-N-(4-(carboxymethyl) phenyl)-2-(4-chlorobenzenesulfonylamino)-3-(2-chlorophenoxy) propanamide The procedure described in Example 39 was repeated, except that (RS)-2-(4-chlorobenzenesulfonylamino)-3-(2-chlorophenoxy)-N-(4-(ethoxycarbonylmethyl)phenyl) propanamide (200 mg) was hydrolyzed and recrystallized from hexane/ethyl acetate to obtain (RS)-N-(4-(carboxymethyl)phenyl)-2-(4-chlorobenzenesulfonylamino)-3-(2-chlorophenoxy)propanamide (62.5 mg).

Melting point: 190°–191° C.

IR νmax cm$^{-1}$ (KBr): 3435, 3329, 3259, 1705, 1660, 1336, 1248, 1167, 756

$^1$H-NMR δ ppm (CDCl$_3$-DMSO-d$_6$): 3.484 (2H, s), 4.189 (2H, d, J=6.3 Hz), 4.429 (1H, t, J=6.3 Hz), 6.932 (1H, td, J=7.9 Hz, J=1.3 Hz), 7.040 (1H, dd, J=7.9 Hz, J=1.3 Hz), 7.158 (2H, d, J=8.5 Hz), 7.228 (1H, td, J=7.9 Hz, J=1.6 Hz), 7.321 (1H, dd, J=7.9 Hz, J=1.6 Hz), 7.357 (2H, d, J=8.5 Hz), 7.454 (2H, d, J=8.4 Hz), 7.846 (2H, d, J=8.4 Hz), 9.895 (1H, s)

$^{13}$C-NMR δ ppm (CDCl$_3$-DMSO-d$_6$): 40.01, 56.19, 68.73, 114.13, 119.41, 121.79, 127.70, 128.10, 128.54, 128.98, 129.60, 130.12, 136.42, 137.23, 139.58, 153.15, 166.20, 172.07

Fab-MS m/z: 523 (MH$^+$)

Example 133

Preparation of (RS)-N-(4-(ethoxycarbonylmethyl)phenyl)-2-(4-fluorobenzenesulfonylamino)-3-phenoxypropanamide The procedure described in Example 125 was repeated, except that (RS)-N-(4-(ethoxycarbonylmethyl)phenyl)-2-(4-fluorobenzene-sulfonylamino)-3-methanesulfonyloxypropanamide (500 mg) was reacted with phenol (187 mg) to obtain (RS)-N-(4-(ethoxycarbonylmethyl)phenyl)-2-(4-fluorobenzenesulfonylamino)-3-phenoxypropanamide (400.58 mg).

Melting point: 122.2°–123.5° C. (recrystallized from ethyl acetate)

IR νmax cm$^{-1}$ (KBr): 3367, 1732, 1670, 1331, 1244, 1167, 565

$^1$H-NMR δ ppm (CDCl$_3$-DMSO-d$_6$): 1.239 (3H, t, J=7.08 Hz), 3.551 (2H, s), 4.126 (2H, q, J=7.08 Hz), 4.2–4.4 (3H, m), 6.758 (2H, d, J=7.81 Hz), 6.928 (1H, t, J=7.4 Hz), 7.076 (2H, t, J=8.5 Hz), 7.14–7.28 (4H, m), 7.409 (1H, d, J=8.5 Hz), 7.917 (2H, dd, J=8.5 Hz, J=5.0 Hz), 9.267 (1H, s)

$^{13}$C-NMR δ ppm (CDCl$_3$-DMSO-d$_6$): 13.67, 40.29, 56.72, 60.24, 67.76, 114.19, 115.43, 115.76, 119.61, 120.97, 129.00, 129.11, 129.48, 129.77, 136.01, 136.15, 157.46, 162.59, 166.33, 166.44, 170.95

Fab-MS m/z: 501 (MH$^+$)

Example 194

Preparation of (RS)-3-(4-chlorophenoxy)-N-(4-(ethoxycarbonylmethyl)phenyl)-2-(4-fluorobenzenesulfonylamino)propanamide The procedure described in Example 125 was repeated, except that (RS)-N-(4-(ethoxycarbonylmethyl)phenyl)-2-(4-fluorobenzenesulfonylamino)-3-methanesulfonyloxypropanamide (300 mg) was reacted with 4-chlorophenol (153 mg) to obtain (RS)-3-(4-chlorophenoxy)-N-(4-(ethoxycarbonylmethyl)phenyl)-2-(4-fluorobenzenesulfonylamino)propanamide (236.25 mg).

Melting point: 132°–134.5° C. (recrystallized from hexane/ethyl acetate)

IR νmax cm$^{-1}$ (KBr): 3350, 3223, 1732, 1666, 1333, 1295, 1241, 1155

$^1$H-NMR δ ppm (CDCl$_3$-DMSO-d$_6$): 1.246 (3H, t, J=7.08 Hz), 4.133 (2H, q, J=7.08 Hz), 4.2–4.35 (3H, m), 6.698 (2H, d, J=9.1 Hz), 7.096 (2H, t, J=8.8 Hz), 7.180 (2H, d, J=9.1 Hz), 7.202 (2H, d, J=8.1 Hz), 7.406 (2H, d, J=8.1 Hz), 7.914 (2H, dd, J=8.8 Hz, J=5.13 Hz), 9.156 (1H, s)

$^{13}$C-NMR δ ppm (CDCl$_3$-DMSO-d$_6$): 13.52, 40.40, 56.46, 60.09, 68.09, 115.29, 115.58, 119.50, 125.63, 128.67, 128.96, 129.18, 129.33, 129.62, 136.08, 156.10, 162.41, 166.19, 170.77

Fab-MS m/z: 535 (MH$^+$)

Example 135

Preparation of (RS)-3-(3-chlorophenoxy)-N-(4-(ethoxycarbonylmethyl)phenyl)-2-(4-fluorobenzenesulfonylamino)propanamide The procedure described in Example 125 was repeated, except that (RS)-N-(4-(ethoxycarbonylmethyl)phenyl)-2-(4-fluorobenzenesulfonylamino)-3-methanesulfonyloxypropanamide (310 mg) was reacted with 3-chlorophenol (125 μl) to obtain (RS)-3-(3-chlorophenoxy)-N-(4-(ethoxycarbonylmethyl)phenyl)-2-(4-fluorobenzenesulfonylamino)propanamide (257.24 mg).

Melting point: 164°–165.3° C. (recrystallized from hexane/ethyl acetate)

IR νmax cm$^{-1}$ (KBr): 3321, 1738, 1652, 1340, 1176, 1090

$^1$H-NMR δ ppm (CDCl$_3$-DMSO-d$_6$): 1.233 (3H, t, J=7.1 Hz), 3.542 (2H, s), 4.118 (2H, q, J=7.1 Hz), 4.18 (2H, m), 4.369 (1H, t, J=5.5 Hz), 6.699 (1H, dd, J=8.3 Hz, J=2.2 Hz), 6.778 (1H, t, J=2.2 Hz), 6.903 (1H, d, J=8.3 Hz), 7.101 (2H, t, J=8.5 Hz), 7.164 (1H, t, J=8.3 Hz), 7.169 (2H, d, J=8.8 Hz), 7.406 (2H, 8.8 Hz), 7.914 (2H, dd, J=8.5 Hz, J=5.1 Hz)

$^{13}$C-NMR δ ppm (CDCl$_3$-DMSO-d$_6$): 13.19, 39.71, 56.01, 59.69, 67.58, 112.25, 114.38, 114.90, 115.24, 119.13, 120.48, 128.88, 128.81, 128.95, 129.21, 129.44, 133.59, 135.86, 135.98, 157.89, 161.98, 165.87, 170.42

Fab-MS m/z: 535 (MH$^+$)

Example 136

Preparation of (RS)-N-(4-(carboxymethyl) phenyl)-2-(4-fluorobenzenesulfonylamino)-3-phenoxypropanamide The procedure described in Example 39 was repeated, except that (RS)-N-(4-(ethoxycarbonylmethyl)phenyl)-2-(4-fluorobenzenesulfonylamino)-3-phenoxypropanamide (180.9 mg) was hydrolyzed to obtain -(RS)-N-(4-carboxymethyl)-phenyl)-2-(4-fluorobenzenesulfonylamino)-3-phenoxypropanamide (115.69 mg).

Melting point: 173.4°–175° C. (recrystallized from hexane/ethyl acetate)

IR vmax cm$^{-1}$ (KBr): 3340, 1700, 1670, 1331, 1294, 1240, 1155, 1092

$^1$H-NMR δ ppm (CDCl$_3$-DMSO-d$_6$): 3.495 (2H, s), 4.168 (2H, m), 4.368 (2H, t, J=5.74 Hz), 6.775 (2H, d, J=7.8 Hz), 6.910 (1H, t, J=7.3 Hz), 7.111 (2H, t, J=8.8 Hz), 7.187 (4H, m), 7.393 (2H, d, J=8.5 Hz), 7.917 (2H, dd, J=9.03 Hz, J=5.13 Hz), 9.555 (1H, s)

$^{13}$C-NMR δ ppm (CDCl$_3$-DMSO-d$_6$): 40.12, 56.52, 67.88, 114.27, 115.15, 115.48, 119.41, 120.76, 128.94, 129.27, 130.12, 136.24, 136.68, 157.58, 162.24, 166.38, 172.29

Fab-MS m/z: 473 (MH$^+$)

Example 137

Preparation of (RS)-N-(4-(carboxymethyl) phenyl)-3-(4-chlorophenoxy)-2-(4-fluorobenzenesulfonylamino) propanamide The procedure described in Example 39 was repeated, except that (RS)-3-(4-chlorophenoxy)-N-(4-(ethoxycarbonylmethyl)phenyl)-2-(4-fluorobenzenesulfonylamino)propanamide (160 mg) was hydrolyzed to obtain (RS)-N-(4-(carboxymethyl)phenyl)-3-(4-chlorophenoxy)-2-(4-fluorobenzenesulfonylamino) propanamide (47.25 mg).

Melting point: 183.5°–186° C. (recrystallized from hexane/ethyl acetate)

IR vmax cm$^{-1}$ (KBr): 3338, 1697, 1315, 1241, 1171, 1155

$^1$H-NMR δ ppm (CDCl$_3$-DMSO-d$_6$): 3.527 (2H, s), 4.1–4.4 (3H, m), 6.720 (2H, d, J=9.3 Hz), 7.097 (2H, t, J=9.1 Hz), 7.1–7.3 (4H, m), 7.419 (2H, d, J=8.6 Hz), 7.913 (2H, dd, J=9.1 Hz, J=5.1 Hz), 9.362 (1H, s)

$^{13}$C-NMR δ ppm (CDCl$_3$-DMSO-d$_6$): 39.71, 56.43, 68.09, 115.58, 119.47, 119.58, 119.87, 127.09, 128.67, 129.18, 129.29, 129.36, 135.90, 156.10, 166.15, 172.35

Fab-MS m/z: 507 (MH$^+$)

Example 138

Preparation of (RS)-N-(4-(carboxymethyl) phenyl)-3-(3-chlorophenoxy)-3-(4-fluorobenzenesulfonylamino) propanamide The procedure described in Example 39 was repeated, except that (RS)-3-(3-chlorophenoxy)-N-(4-(ethoxycarbonylmethyl)phenyl)-2-(4-fluorobenzenesulfonylamino)propanamide (184.9 mg) was hydrolyzed to obtain (RS)-N-(4-(carboxymethyl)phenyl)-3-(3-chlorophenoxy)-2-(4-fluorobenzenesulfonylamino) propanamide (104.94 mg).

Melting point: 195°–197° C. (recrystallized from ethyl acetate)

IR vmax cm$^{-1}$ (KBr): 3300 (br), 1710, 1684, 1333, 1240, 1155, 839

$^1$H-NMR δ ppm (CDCl$_3$-DMSO-d$_6$): 3.536 (2H, s), 4.1–4.4 (3H, m), 6.660 (1H, ddd, J=8.3 Hz, J=2.5 Hz, J=1.0 Hz), 6.755 (1H, t, J=2.5 Hz), 6.913 (1H, ddd, J=8.1 Hz, J=1.8 Hz, J=0.7 Hz), 7.0–7.3 (3H, m), 7.210 (2H, d, J=8.5 Hz), 7.40 (2H, d, J=8.5 Hz), 7.913 (2H, dd, J=8.8 Hz, J=5.1 Hz), 9.228 (1H, s)

$^{13}$C-NMR δ ppm (CDCl$_3$-DMSO-d$_6$): 40.40, 56.65, 68.13, 112.68, 115.07, 115.62, 115.95, 119.80, 121.26, 127.39, 129.37, 129.59, 129.95, 130.58, 134.39, 136.04, 136.15, 158.37, 162.78, 166.33, 173.12

Fab-MS m/z: 507 (MH$^+$)

Example 139

Preparation of (RS)-2-(4-bromobenzenesulfonylamino)-N-(4-(ethoxycarbonylmethyl)phenyl)-3-phenoxypropanamide The procedure described in Example 125 was repeated, except that ((RS)-2-(4-bromobenzenesulfonylamino)-N-(4-(ethoxycarbonylmethyl)phenyl)-3-methanesulfonyloxypropanamide (500 mg) was reacted with phenol (167 mg) to obtain (RS)-2-(4-bromobenzenesulfonylamino)-N-(4-(ethoxycarbonylmethyl)phenyl)-3-phenoxypropanamide (425.22 mg).

Melting point: 150.5°–153° (recrystallized from ethyl acetate)

IR vmax cm$^{-1}$ (KBr): 3369, 3161, 1734, 1670, 1331, 1244, 1167, 557

$^1$H-NMR δ ppm (CDCl$_3$-DMSO-d$_6$): 1.244 (3H, t, J=7.1 Hz), 3.555 (2H, s), 4.125 (2H, q, J=7.1 Hz), 4.20 (2H, m), 4.345 (1H, t, J=5.2 Hz), 6.744 (2H, d, J=8.0 Hz), 6.930 (1H, t, J=7.3 Hz), 7.1–7.3 (4H, m), 7.390 (2H, d, J=8.0 Hz), 7.524 (2H, d, J=8.6 Hz), 7.762 (2H, d, J=8.6 Hz), 9.332 (1H, s)

$^{13}$C-NMR δ ppm (CDCl$_3$-DMSO-d$_6$): 13.63, 40.22, 56.65, 60.17, 67.65, 114.11, 119.43, 119.54, 120.86, 126.87, 128.16, 128.93, 129.04, 129.62, 131.57, 139.01, 157.38, 166.30, 170.84

Fab-MS m/z: 563 (MH$^+$+2), 561 (MH$^+$)

Example 140

Preparation of (RS)-2-(4-bromobenzenesulfonylamino)-3-(4-chlorophenoxy)-N-(4-(ethoxycarbonylmethyl)phenyl) propanamide The procedure described in Example 125 was repeated, except that ((RS)-2-(4-bromobenzenesulfonylamino)-N-(4-(ethoxycarbonylmethyl)phenyl)-3-methanesulfonyloxypropanamide (420 mg) was reacted with 4-chlorophenol (191.6 µl) to obtain (RS)-2-(4-bromobenzenesulfonylamino)-3-(4-chlorophenoxy)-N-(4-(ethoxycarbonylmethyl)phenyl) propanamide (242.12 mg).

Melting point: 154.5°–156° C. (recrystallized from hexane/ethyl acetate)

IR vmax cm$^{-1}$ (KBr): 3342, 3250, 1732, 1672, 1333, 1242, 1165, 823, 742

$^1$H-NMR δ ppm (CDCl$_3$-DMSO-d$_6$): 1.243 (3H, t, J=7.1 Hz), 3.553 (2H, s), 4.118 (2H, q, J=7.1 Hz), 4.14 (2H, m), 4.368 (1H, t, J=5.7 Hz), 6.713 (2H, d, J=9.0 Hz), 7.179 (2H, d, 8.6 Hz), 7.181 (2H, d, J=9.0 Hz), 7.388 (2H, d, J=8.6 Hz), 7.526 (2H, d, J=8.6 Hz), 7.759 (2H, d, J=8.6 Hz), 9.578 (1H, s)

$^{13}$C-NMR δ ppm (CDCl$_3$-DMSO-d$_6$): 13.19, 39.63, 55.91, 59.62, 67.50, 115.10, 118.95, 124.89, 126.10, 127.64, 128.23, 128.82, 129.00, 130.98, 135.79, 138.90, 155.62, 165.67, 170.29

Fab-MS m/z: 595 (MH$^+$)

Example 141

Preparation of (RS)-2-(4-bromobenzenesulfonylamino)-3-(3-chlorophenoxy)-N-(4-(ethoxycarbonylmethyl) phenyl) propanamide The procedure described in Example 125 was repeated, except that ((RS)-2-(4-bromobenzenesulfonylamino)-N-(4-(ethoxycarbonylmethyl)phenyl)-3-methanesulfonyloxypropanamide (315 mg) was reacted with 3-chlorophenol (113.2 μl) to obtain (RS)-2-(4-bromobenzenesulfonylamino)-3-(3-chlorophenoxy)-N-(4-(ethoxycarbonylmethyl)phenyl) propanamide (214.48 mg).

Melting point: 59.5°–161° C. (recrystallized from chloroform/hexane)

IR νmax cm$^{-1}$ (KBr): 3323, 1740, 1653, 1342, 1232, 1167, 746

$^1$H-NMR δ ppm (CDCl$_3$-DMSO-d$_6$): 1.244 (3H, t, J=7.1 Hz), 3.557 (2H, s), 4.128 (2H, q, J=7.1 Hz), 4.15–4.25 (2H, m), 4.348 (1H, t, J=5.2 Hz), 6.647 (1H, dd, J=8.1 Hz, J=2.4 Hz), 6.748 (1H, t, J=2.2 Hz), 6.915 (1H, dd, J=8.1 Hz, J=1.0 Hz), 7.156 (1H, t, J=8.1 Hz), 7.199 (2H, d, J=8.5 Hz), 7.396 (2H, d, J=8.5 Hz), 7.539 (2H, d, J=8.8 Hz), 7.759 (2H, d, J=8.8 Hz)

$^{13}$C-NMR δ ppm (CDCl$_3$-DMSO-d$_6$): 13.60, 40.18, 56.46, 60.17, 67.80, 112.39, 114.66, 119.50, 120.93, 126.87, 128.08, 129.04, 129.62, 129.77, 131.57, 134.10, 136.10, 138.98, 158.08, 166.04, 170.88

Fab-MS m/z: 595 (MH$^+$)

Example 142

Preparation of (RS)-2-(4-bromobenzenesulfonylamino)-N-(4-(carboxymethyl)phenyl)-3-phenoxypropanamide The procedure described in Example 39 was repeated, except that (RS)-2-(4-bromobenzenesulfonylamino)-N-(4-(ethoxycarbonylmethyl)phenyl)-3-phenoxypropanamide (200 mg) was hydrolyzed to obtain (RS)-2-(4-bromobenzenesulfonylamino)-N-(4-(carboxymethyl)phenyl)-3-phenoxypropanamide (147.9 mg).

Melting point: 201°–204° C. (recrystallized from ethyl acetate)

IR νmax cm$^{-1}$ (KBr): 3475, 3352, 3259, 1695, 1670, 1329, 1242, 1165, 752

$^1$H-NMR δ ppm (CDCl$_3$-DMSO-d$_6$): 3.526 (2H, s), 4.175 (2H, m), 4.361 (1H, m), 6.745 (2H, d, J=8.6 Hz), 6.928 (1H, t, J=7.5 Hz), 7.1–7.3 (4H, m), 7.387 (2H, d, J=8.6 Hz), 7.528 (2H, d, J=8.5 Hz), 7.767 (2H, d, J=8.5 Hz), 9.496 (1H, s)

$^{13}$C-NMR δ ppm (CDCl$_3$-DMSO-d$_6$): 39.96, 56.35, 67.36, 113.78, 114.92, 119.17, 120.53, 126.43, 127.86, 128.63, 128.85, 129.84, 131.24, 135.79, 138.94, 157.13, 166.00, 172.57

Fab-MS m/z: 535 (MH$^+$+2), 533 (MH$^+$)

Example 143

Preparation of (RS)-2-(4-bromobenzenesulfonylamino)-N-(4-(carboxymethyl)phenyl)-3-(4-chlorophenoxy) propanamide The procedure described in Example 39 was repeated, except that (RS)-2-(4-bromobenzenesulfonylamino)-3-(4-chlorophenoxy)-N-(4-(ethoxycarbonylmethyl)phenyl) propanamide (164 mg) was hydrolyzed to obtain (RS)-2-(4-bromobenzenesulfonylamino)-N-(4-(carboxymethyl) phenyl)-3-(4-chlorophenoxy)propanamide (86.85 mg).

Melting point: 217.5°–219.5° C. (recrystallized from hexane/ethyl acetate)

IR νmax cm$^{-1}$ (KBr): 3300 (br), 1666, 1325, 1244, 1165, 822

$^1$H-NMR δ ppm (CDCl$_3$-DMSO-d$_6$): 3.513 (2H, s), 4.165 (2H, m), 4.357 (1H, t, J=5.5 Hz), 6.716 (2H, d, J=9.0 Hz), 7.175 (2H, d, J=9.0 Hz), 7.193 (2H, d, J=8.5 Hz), 7.373 (2H, d, J=8.5 Hz), 7.534 (2H, d, J=8.7 Hz), 7.755 (2H, d, J=8.7 Hz), 9.395 (1H, s)

$^{13}$C-NMR δ ppm (CDCl$_3$-DMSO-d$_6$): 39.93, 56.28, 67.94, 115.47, 119.25, 125.26, 126.32, 127.83, 128.41, 128.74, 129.99, 131.20, 135.75, 139.23, 155.95, 165.82, 172.16

Fab-MS m/z: 569 (MH$^+$+2), 567 (MH$^+$)

Example 144

Preparation of (RS)-2-(4-bromobenzenesulfonylamino)-N-(4-(carboxymethyl)phenyl)-3-(3-chlorophenoxy) propanamide The procedure described in Example 39 was repeated, except that (RS)-2-(4-bromobenzenesulfonylamino)-3-(3-chlorophenoxy)-N-(4-(ethoxycarbonylmethyl)phenyl) propanamide (154 mg) was hydrolyzed to obtain (RS)-2-(4-bromobenzenesulfonylamino)-N-(4-(carboxymethyl) phenyl)-3-(3-chlorophenoxy)propanamide (81.02 mg).

Melting point: 225°–227.5° C. (recrystallized from ethyl acetate)

IR νmax cm$^{-1}$ (KBr): 3300 (br), 1664, 1327, 1232, 1165, 742

$^1$H-NMR δ ppm (CDCl$_3$-DMSO-d$_6$): 3.508 (2H, s), 4.182 (2H, m), 4.372 (1H, t, J=5.6 Hz), 6.677 (1H, dd, J=8.3 Hz, J=2.5 Hz), 6.764 (1H, t, J=2.5 Hz), 6.908 (1H, ddd, J=7.8 Hz, J=2.0 Hz, J=0.7 Hz), 7.166 (1H, t, J=8.3 Hz), 7.190 (2H, d, J=8.5 Hz), 7.380 (2H, d, J=8.5 Hz), 7.545 (2H, d, J=8.8 Hz), 7.762 (2H, d, J=8.8 Hz), 9.483 (1H, s)

$^{13}$C-NMR δ ppm (CDCl$_3$-DMSO-d$_6$): 39.82, 56.13, 67.72, 112.35, 14.48, 119.14, 120.53, 126.18, 127.72, 128.63, 129.40, 129.88, 131.09, 133.66, 135.71, 139.23, 157.97, 165.67, 172.02

Fab-MS m/z: 569 (MH$^+$+2), 567 (MH$^+$)

Example 145

Preparation of (RS)-N-(4-(ethoxycarbonylmethyl)phenyl)-2-(4-iodobenzenesulfonylamino)-3-phenoxypropanamide The procedure described in Example 125 was repeated, except that (RS)-N-(4-(carbethoxymethyl)phenyl)-2-(4-iodobenzenesulfonylamino)-3-methanesulfonyloxypropanamide (400 mg) was reacted with phenol (123 mg) to obtain (RS)-N-(4-(ethoxycarbonylmethyl)phenyl)-2-(4-iodobenzenesulfonylamino)-3-phenoxypropanamide (252.62 mg).

Melting point: 177.5°–180.5° C. (recrystallized from ethyl acetate)

IR νmax cm$^{-1}$ (KBr): 3358, 3271, 1732, 1670, 1331, 1242, 1165, 756, 735

$^1$H-NMR δ ppm (CDCl$_3$-DMSO-d$_6$): 1.235 (3H, t, J=7.1 Hz), 3.546 (2H, s), 4.116 (2H, q, J=7.1 Hz), 4.16 (2H, m), 4.363 (1H, t, J=5.7 Hz), 6.752 (2H, d, J=8.3 Hz), 6.85–7.30 (5H, m), 7.379 (2H, d, J=8.3 Hz), 7.603 (2H, d, J=8.6 Hz), 7.742 (2H, d, J=8.6 Hz), 9.473 (1H, s)

$^{13}$C-NMR δ ppm (CDCl$_3$-DMSO-d$_6$): 13.50, 44.27, 56.59, 59.85, 67.74, 98.98, 114.20, 115.26, 119.44, 119.77, 120.73, 121.57, 127.66, 127.88, 128.83, 128.94, 129.42, 136.24, 137.34, 140.13, 157.47, 166.20, 170.45

Fab-MS m/z: 609 (MH$^+$)

Example 146

Preparation of (RS)-3-(4-chlorophenoxy)-N-(4-(ethoxycarbonylmethyl)phenyl)-2-(4-iodobenzenesulfonylamino)propanamide The procedure described in Example 125 was repeated, except that (RS)-N-(4-(carbethoxymethyl)phenyl)-2-(4-iodobenzenesulfonylamino)-3-methanesulfonyloxypropanamide (380 mg) was reacted with 4-chlorophenol (160 µl) to obtain (RS)-3-(4-chlorophenoxy)-N-(4-(ethoxycarbonylmethyl) phenyl)-2-(4-iodobenzenesulfonylamino)propanamide (297.11 mg).

Melting point: 161.5°–163° C. (recrystallized from hexane/ethyl acetate)

IR vmax cm⁻¹ (KBr): 3346, 1732, 1670, 1333, 1244, 1165, 822, 733

¹H-NMR δ ppm (CDCl₃-DMSO-d₆): 1.240 (3H, t, J=7.1 Hz), 3.551 (2H, s), 4.125 (2H, q, J=7.1 Hz), 4.15 (2H, m), 4.347 (1H, t, J=5.5 Hz), 6.702 (2H, d, J=9.0 Hz), 7.177 (2H, d, J=9.0 Hz), 7.186 (2H, d, J=8.5 Hz), 7.376 (2H, d, J=8.5 Hz), 7.594 (2H, d, J=8.8 Hz), 7.744 (2H, d, J=8.8 Hz), 9.325 (1H, s)

¹³C-NMR δ ppm (CDCl₃-DMSO-d₆): 14.00, 40.59, 56.90, 60.53, 68.38, 99.74, 115.91, 119.91, 125.92, 128.34, 129.11, 129.44, 129.99, 136.45, 137.88, 140.15, 156.47, 166.52, 171.17

Fab-MS m/z: 643 (MH⁺)

Example 147

Preparation of (RS)-3-(3chlorophenoxy)-N-(4-(ethoxycarbonylmethyl)phenyl)-2-(4-iodobenzenesulfonylamino)propanamide The procedure described in Example 125 was repeated, except that (RS)-N-(4-(carbethoxymethyl)phenyl)-2-(4-iodobenzenesulfonylamino)-3-methanesulfonyloxypropanamide (380 mg) was reacted with 3-chlorophenol (160 mg) to obtain (RS)-3-(3-chlorophenoxy)-N-(4-(ethoxycarbonylmethyl)phenyl)-2-(4-iodobenzenesulfonylamino)propanamide (267.88 mg).

Melting point: 168.8°–170° C. (recrystallized from hexane/ethyl acetate)

IR vmax cm⁻¹ (KBr): 3323, 1736, 1653, 1342, 1232, 1167, 737

¹H-NMR δ ppm (CDCl₃-DMSO-d₆): 1.245 (3H, t, J=7.1 Hz), 3.560 (2H, s), 4.128 (2H, q, J=7.1 Hz), 4.15–4.25 (2H, m), 4.348 (1H, t, J=5.4 Hz), 6.641 (1H, ddd, J=8.1 Hz, J=2.4 Hz, J=1.0 Hz), 6.748 (1H, t, J=2.1 Hz), 6.918 (1H, ddd, J=8.1 Hz, J=2.0 Hz, J=0.9 Hz), 7.162 (1H, t, J=8.1 Hz), 7.200 (2H, d, J=8.8 Hz), 7.388 (2H, d, J=8.8 Hz), 7.601 (2H, d, J=8.8 Hz), 8.755 (2H, d, J=8.8 Hz)

¹³C-NMR δ ppm (CDCl₃-DMSO-d₆): 13.63, 40.22, 56.46, 60.17, 67.80, 99.41, 112.43, 114.66, 119.50, 120.97, 127.94, 129.07, 129.62, 129.77, 136.01, 137.51, 139.60, 158.08, 166.04, 170.88

Fab-MS m/z: 643 (MH⁺)

Example 148

Preparation of (RS)-3-(2-chlorophenoxy)-N-(4-(ethoxycarbonylmethyl)phenyl)-2-(4-iodobenzenesulfonylamino)propanamide The procedure described in Example 125 was repeated, except that (RS)-N-(4-(carbethoxymethyl)phenyl)-2-(4-iodobenzenesulfonylamino)-3-methanesulfonyloxypropanamide (430 mg) was reacted with 2-chlorophenol (163 mg) to obtain (RS)-3-(2-chlorophenoxy)-N-(4-(ethoxycarbonylmethyl)phenyl)-2-(4-iodobenzenesulfonylamino)propanamide (285.8 mg).

Melting point: 140.5°–142° C. (recrystallized from hexane/ethyl acetate)

IR vmax cm⁻¹ (KBr): 3498, 3348, 3259, 1734, 1670, 1338, 1250, 1167, 818

¹H-NMR δ ppm (CDCl₃-DMSO-d₆): 1.237 (3H, t, J=7.1 Hz), 3.544 (2H, s), 4.123 (2H, q, J=7.1 Hz), 4.15–4.34 (2H, m), 4.387 (1H, t, J=5.4 Hz), 6.86–6.95 (2H, m), 7.162 (1H, dd, J=8.1 Hz, J=1.7 Hz), 7.180 (2H, d, J=8.6 Hz), 7.298 (1H, dd, J=8.1 Hz, J=1.7 Hz), 7.375 (2H, d, J=8.6 Hz), 7.607 (2H, d, J=8.5 Hz), 7.730 (2H, d, J=8.5 Hz), 9.299 (1H, s)

¹³C-NMR δ ppm (CDCl₃-DMSO-d₆): 13.49, 40.11, 56.43, 59.91, 69.01, 99.15, 113.82, 119.61, 121.74, 122.40, 127.24, 127.86, 128.85, 129.55, 129.62, 136.12, 137.47, 139.71, 152.98, 165.97, 170.51

Fab-MS m/z: 643 (MH⁺)

Example 149

Preparation of (RS)-N-(4-(carboxymethyl) phenyl)-2-(4-iodobenzenesulfonylamino)-3-phenoxypropanamide The procedure described in Example 39 was repeated, except that (RS)-N-(4-(ethoxycarbonylmethyl)phenyl)-2-(4-iodobenzenesulfonylamino)-3-phenoxypropanamide (153 mg) was hydrolyzed to obtain (RS)-N-(4-(carboxymethyl)phenyl)-2-(4-iodobenzenesulfonylamino)-3-phenoxypropanamide (73.99 mg).

Melting point: 223.5°–225° C. (recrystallized from hexane/ethyl acetate)

IR vmax cm⁻¹ (KBr): 3300 (br), 1695, 1670, 1331, 1242, 1165, 756, 733

¹H-NMR δ ppm (CDCl₃-DMSO-d₆): 3.515 (2H, s), 4.153 (2H, d, J=5.9 Hz), 4.364 (1H, t, J=5.9 Hz), 6.743 (2H, d, J=8.2 Hz), 6.924 (1H, t, J=8.2 Hz), 7.191 (2H, d, J=8.6 Hz), 7.226 (2H, d, J=8.2 Hz), 7.375 (2H, d, J=8.6 Hz), 7.607 (2H, d, J=8.3 Hz), 7.742 (2H, d, J=8.3 Hz), 9.589 (1H, s)

¹³C-NMR δ ppm (CDCl₃-DMSO-d₆): 39.71, 56.02, 67.10, 98.75, 113.56, 118.88, 120.24, 127.42, 128.38, 128.56, 129.51, 135.60, 136.85, 139.45, 156.87, 165.75, 172.09

Fab-MS m/z: 581 (MH⁺)

Example 150

Preparation of (RS)-N-(4-(carboxymethyl) phenyl)-3-(4-chlorophenoxy)-2-(4-iodobenzenesulfonylamino) propanamide The procedure described in Example 39 was repeated, except that (RS)-3-(4-chlorophenoxy)-N-(4-(ethoxycarbonylmethyl)phenyl)-2-(4-iodobenzenesulfonylamino)propanamide (170 mg) was hydrolyzed to obtain (RS)-N-(4-(carboxymethyl)phenyl)-3-(4-chlorophenoxy)-2-(4-iodobenzenesulfonylamino) propanamide (47.57 mg).

Melting point: 196°–198° C. (recrystallized from hexane/ethyl acetate)

IR vmax cm⁻¹ (KBr): 3400 (br), 3354, 3251, 1701, 1670, 1327, 1242, 1163, 820, 733

¹H-NMR δ ppm (CDCl₃-DMSO-d₆): 3.523 (2H, s), 4.149 (2H, m), 4.353 (1H, t, J=5.5 Hz), 6.701 (2H, d, J=9.0 Hz), 7.182 (2H, d, J=9.0 Hz), 7.202 (2H, d, J=8.6 Hz), 7.373 (2H, d, J=8.6 Hz), 7.598 (2H, d, J=8.8 Hz), 7.744 (2H, d, J=8.8 Hz), 9.471 (1H, s)

¹³C-NMR δ ppm (CDCl₃-DMSO-d₆): 39.93, 56.17, 67.72, 98.97, 115.29, 119.14, 125.15, 127.61, 128.38, 128.78, 129.84, 135.71, 137.14, 139.64, 155.81, 165.78, 172.35

Fab-MS m/z: 615 (MH⁺)

Example 151

Preparation of (RS)-N-(4-(carboxymethyl) phenyl)-3-(3-chlorophenoxy)-2-(4-iodobenzenesulfonylamino) propanamide The procedure described in Example 39 was repeated, except that (RS)-3-(3-chlorophenoxy)-N-(4-(ethoxycarbonyl-methyl)phenyl)-2-(4-iodobenzenesulfonylamino)propanamide (183 mg) was hydrolyzed and recrystallized from hexane/ethyl acetate to obtain (RS)-N-(4-(carboxymethyl)phenyl)-3-(3-chlorophenoxy)-2-(4-iodobenzenesulfonylamino) propanamide (109.37 mg).

Melting point: 225°–226° C.

IR vmax cm$^{-1}$ (KBr): 3321, 3300 (br), 1713, 1655, 1340, 1230, 1165, 735

$^1$H NMR δ ppm (CDCl$_3$-DMSO-d$_6$): 3.521 (2H, s), 4.1–4.2 (2H, m), 4.362 (1H, t, J=5.5 Hz), 6.658 (1H, dd, J=8.0 Hz, J=2.44 Hz), 6.751 (1H, t, J=2.2 Hz), 6.911 (1H, d, J=8.0 Hz), 7.173 (1H, t, J=8.2 Hz), 7.202 (2H, t, J=8.4 Hz), 7.378 (2H, d, J=8.4 Hz), 7.603 (2H, d, J=8.5 Hz), 7.755 (2H, d, J=8.5 Hz)

$^{13}$C-NMR δ ppm (CDCl$_3$-DMSO-d$_6$): 39.93, 56.13, 67.61, 98.97, 112.28, 114.41, 119.17, 119.65, 120.60, 127.61, 128.78, 128.96, 129.51, 129.84, 133.69, 135.71, 137.14, 139.64, 157.93, 165.75, 172.35

Fab-MS m/z: 615 (MH$^+$)

Example 152

Preparation of (RS)-N-(4-(carboxymethyl) phenyl)-3-(2chlorophenoxy)-2-(4-iodobenzenesulfonylamino) propanamide The procedure described in Example 39 was repeated, except that (RS)-3-(2-chlorophenoxy)-N-(4-(ethoxycarbonylmethyl)phenyl)-2-(4-iodobenzenesulfonylamino)propanamide (165 mg) was hydrolyzed and recrystallized from hexane/ethyl acetate to obtain (RS)-N-(4-(carboxymethyl) phenyl)-3-(2-chlorophenoxy)-2-(4-iodobenzenesulfonylamino) propanamide (55.95 mg).

Melting point: 198.5°–200.5° C.

IR vmax cm$^{-1}$ (KBr): 3344, 3280, 3200 (br), 1697 (br), 1338, 1246, 1165

$^1$H NMR δ ppm (CDCl$_3$-DMSO-d$_6$): 3.520 (2H, s), 4.15–4.45 (3H, m), 6.87–6.95 (2H, m), 7.163 (1H, dd, J=8.1 Hz, J=1.7 Hz), 7.203 (2H, d, J=8.6 Hz), 7.301 (1H, dd, J=8.1 Hz, J=1.7 Hz), 7.367 (2H, d, J=8.6 Hz), 7.606 (2H, d, J=8.6 Hz), 7.735 (2H, d, J=8.6 Hz), 9.238 (1H, s)

$^{13}$C-NMR δ ppm (CDCl$_3$-DMSO-d$_6$): 39.97, 56.09, 68.65, 98.80, 113.57, 119.22, 119.59, 121.40, 126.53, 126.96, 127.54, 128.60, 128.69, 128.83, 129.27, 129.76, 135.75, 137.10, 139.58, 152.71, 165.69, 171.97

Fab-MS m/z: 615 (MH$^+$)

Example 153

Preparation of (RS)-2-(4-chlorobenzenesulfonylaminomethyl)-N-(4-ethoxycarbonylphenyl)-3-(tetrahydropyran-2-yloxy) propanamide 60% NaH (2.4 g) was suspended in THF (100 ml), and dimethyl malonate (6.9 ml) was added dropwise at 0° C. The mixture was stirred at room temperature for 30 minutes, and then benzylchloromethylether (8.3 ml) in THF (20 ml) was added dropwise. The mixture was stirred at room temperature for further 1 hour. Then, the reaction mixture was cooled to 0° C. and a suspension of 60% NaH (3.36 g) in THF (20 ml) was added dropwise. The whole was stirred for 30 minutes, and then THF (20 ml) and benzylchloromethylether (11.7 ml) were added dropwise. The mixture was stirred at room temperature for 1.5 hours. An excess NaH was decomposed with methanol, and the product was diluted with ethyl acetate, rinsed, dried over Na$_2$SO$_4$, and concentrated. The resulting residue was recrystallized from isopropyl alcohol to give dimethyl (RS)-2,2-bis-(benzyloxymethyl)-1,3-propanedioic acid (11.8 g).

Dimethyl (RS)-2,2-bis-(benzyloxymethyl)-1,3-propanedioic acid (1.05 g) was dissolved in ethanol and 10% KOH, and the mixture was stirred at room temperature for 6 hours, and then at 50° C. for 17 hours. The mixture was acidified to pH1 with 2N HCl and was extracted with ethyl acetate. The organic layer was washed with a saline solution, dried over Na$_2$SO$_4$ and concentrated. Toluene (30 ml) was added to the resulting residue, and the mixture was heated under reflux for 17 hours. The reaction mixture was concentrated under reduced pressure to give crude (RS)-3-benzyloxy-2-benzyloxy-methylpropanoic acid (850 mg) as a colorless syrup. The syrup (850 mg) was dissolved in methylene chloride, and then ethyl 4-aminobenzoate (650 mg) and triethylamine (0.92 ml) were added thereto. The mixture was added to a suspension of 2-chloro-1-methylpyridinium iodide (1.7 g) in methylene chloride (15 ml), and the mixture was heated under reflux under argon for 15 hours. The reaction mixture was washed with 2N HCl, saturated NaHCO$_3$, and saturated NaCl, dried over Na$_2$SO$_4$, and concentrated. The resulting residue was purified by silica gel column chromatography (Wakogel C-200, ethyl acetate/toluene=1/15) to give (RS)-3-benzyloxy-2-benzyloxymethyl-N-(4-ethoxycarbonylphenyl)propanamide (930 mg). The resulting (RS)-3-benzyloxy-2-benzyloxymethyl-N-(4-ethoxycarbonyl-phenyl) propanamide (930 mg) was suspended in methanol (20ml) and 10%Pd-C (200 mg) was added thereto. The mixture was stirred under hydrogen for 20 hours. The reaction mixture was filtered through Cellite, and the filtrate was concentrated. The resulting residue was recrystallized from toluene to obtain (RS)-N-(4-ethoxycarbonylphenyl)- 3-hydroxy-2-hydroxymethylpropanamide (354 mg).

(RS)-N-(4-ethoxycarbonylphenyl)-3-hydroxy-2-hydroxymethylpropanamide (261 mg) and PPTS (74 mg) were dissolved in THF (10 ml), and dihydropyrane (134 µl) was added thereto under argon. The mixture was stirred at room temperature for 24 hours. The reaction mixture was diluted with ethyl acetate, washed with saturated NaHCO$_3$and saturated NaCl, dried over Na$_2$SO$_4$ and concentrated. The resulting residue was purified by silica gel column chromatography (Wakogel C-200, methylethylketone/toluene=1/2) to give (RS)-N-(4-ethoxycarbonylphenyl)-2-hydroxymethyl-3-(tetrahydropyran-2-yloxy)propanamide (201 mg).

(RS)-N-(4-ethoxycarbonylphenyl)-2-hydroxymethyl-3-(tetrahydropyran-2-yloxy)propanamide (30.5 mg) was dissolved in pyridine, and tosyl chloride (33 mg) was added thereto. The whole was stirred at room temperature overnight. Methanol was added to the reaction mixture to decompose the excess reagents. Then, the mixture was concentrated under reduced pressure. The residue was dissolved with ethyl acetate, washed with water, 2N HCl, saturated NaHCO$_3$and saturated NaCl, dried over Na$_2$SO$_4$ and concentrated. The resulting residue and sodium azide (28 mg) were dissolved in a mixture (DMSO-d$_6$:H$_2$O=4:1) (1 ml) and the solution was stirred at 100° C. for 2 hours. The reaction mixture was poured in ice water and extracted with ethyl acetate. The ethyl acetate layer was washed with water, dried over Na$_2$SO$_4$ and concentrated. The resulting residue was dissolved in ethanol (1 ml), and 10% Pd—C (5 mg) was added. The whole was stirred under a hydrogen atmosphere for 30 minutes. The reaction mixture was filtered through Cellite. The filtrate was concentrated, and the residue was dissolved in pyridine (0.5 ml). After 4-chlorobenzenesulfonyl chloride (27 mg) was added, and the whole was stirred at room temperature for 3 hours. Methanol was added to the reaction mixture to decompose the excess reagents. Then, the mixture was concentrated under reduced pressure, and the residue was purified by silica gel column chromatography (Wakogel C-300, ethyl acetate/hexane=1/3) to obtain (RS)-2-(4-chlorobenzenesulfonylaminomethyl)-N-(4-ethoxycarbonylphenyl)-3-(tetrahydropyran-2-yloxy) propanamide (13.1 mg).

$^1$H NMR δ ppm (CDCl$_3$): 1.390 (3H, t, J=7.08 Hz), 1.48–1.92 (6H, m), 2.78–3.04 (1H, m), 3.10–3.35 (2H, m), 3.46–3.63 (1H, m), 3.68–4.17 (3H, m), 4.362 (2H, q, J=7.08 Hz), 4.53–4.67 (1H, m), 5.48–5.60 (1H, m), 7.46–7.58 (4H, m), 7.797 (2H, d, J=8.7 Hz), 8.006 (2H, d, J=8.7 Hz), 8.73 (0.5H, br.s), 8.78 (0.5H, br.s)

Fab-MS m/z: 524 (M$^+$), 441

Example 154

Preparation of (RS)-N-(4-carboxyphenyl)-2-(4-chlorobenzenesulfonylaminomethyl)-3-(tetrahydropyran-2-yloxy)propanamide The procedure described in Example 39 was repeated, except that (RS)-2-(4-chlorobenzenesulfonylaminomethyl)-N-(4-ethoxycarbonylphenyl)-3-(tetrahydropyran-2-yloxy) propanamide (7.7 mg) was hydrolyzed to obtain (RS)-N-(4-carboxyphenyl)-2-(4-chlorobenzenesulfonylaminomethyl)-3-(tetrahydropyran-2-yloxy)propanamide (7.2 mg).

Fab-MS m/z: 497 (MH$^+$)

Example 155

Preparation of (RS)-2-(4-chlorobenzenesulfonylaminomethyl)-N-(4-ethoxycarbonylphenyl)-3-hydroxypropanamide After (RS)-2-(4-chlorobenzenesulfonylaminomethyl)-N-(4-ethoxycarbonylphenyl)-3-(tetrahydropyran-2-yloxy) propanamide (10.8 mg) was dissolved in methanol (5 ml), the mixture was acidified with p-toluenesulfonic acid to pH less than 4, and the whole was stirred for 2 hours. The reaction mixture was concentrated under reduced pressure, and the residue was dissolved in ethyl acetate. The resulting solution was washed with saturated NaHCO$_3$ and saturated NaCl and dried over Na$_2$SO$_4$ and concentrated to give (RS)-2-(4-chlorobenzenesulfonylaminomethyl)-N-(4-ethoxycarbonylphenyl)-3-hydroxypropanamide (8.1 mg).

$^1$H NMR δ ppm (CD$_3$OD): 1.387 (3H, t, J=7.08 Hz), 2.80–2.90 (1H, m), 3.123 (1H, dd, J=5.61 Hz, J=13.55 Hz), 3.221 (1H, dd, J=8.30 Hz, J=13.55 Hz), 3.678 (1H, dd, J=5.86 Hz, J=10.99 Hz), 3.762 (1H, dd, J=6.84 Hz, J=10.99 Hz), 4.344 (2H, q, J=7.08 Hz), 7.10–7.24 (1H, m), 7.513 (2H, d, J=8.79 Hz), 7.670 (2H, d, J=9.03 Hz), 7.815 (2H, d, J=8.79 Hz), 7.880 (1H, s), 7.954 (2H, d, J=9.03 Hz)

Fab-MS m/z: 441 (MH$^+$)

Example 156

Preparation of (RS)-N-(4-carboxyphenyl)-2-(4-chlorobenzenesulfonylaminomethyl)-3-hydroxypropanamide The procedure described in Example 39 was repeated, except that (RS)-2-(4-chlorobenzenesulfonylaminomethyl)-N-(4-ethoxycarbonylphenyl)-3-hydroxypropanamide (8.1 mg) was hydrolyzed to obtain (RS)-N-(4-carboxyphenyl)-2-(4-chlorobenzenesulfonylaminomethyl)-3-hydroxypropanamide (7.5 mg).

Fab-MS m/z: 413 (MH$^+$)

Example 157

Preparation of (RS)-2-(4-chlorobenzenesulfonylaminomethyl)-N-(4-(ethoxycarbonylmethyl)phenyl)-3-(tetrahydropyran-2-yloxy)propanamide The crude (RS)-3-benzyloxy-2-benzyloxymethylpropanoic acid (1.56 g) obtained by the same manner as the method described in Example 153 was dissolved in methylene chloride, and then ethyl 4-aminophenylacetate (2.24 g) and triethylamine (2.2 ml) were added. The mixture was added under argon to a suspension of 2-chloro-1-methylpyridinium iodide (2.65 g) suspended in methylene chloride (20 ml) and the whole was heated under reflux for 24 hours. The reaction mixture was washed with 2N HCl, saturated NaHCO$_3$ and saturated NaCl, dried over Na$_2$SO$_4$ and concentrated. The resulting residue was purified by silica gel column chromatography (Wakogel C-200, ethyl acetate/hexane=1/4) to give (RS)-3-benzyloxy-2-benzyloxymethyl-N-(4-(ethoxycarbonylmethyl)-phenyl)propanamide (655 mg). The functional group in the resulting (RS)-3-benzyloxy-2-benzyloxymethyl-N-(4-(ethoxycarbonylmethyl)phenyl) propanamide (520 mg) was converted in the same manner as in Example 153 to obtain (RS)-2-(4-chlorobenzenesulfonylaminomethyl)-N-(4-(ethoxycarbonylmethyl)phenyl)-3-(tetrahydropyran-2-yloxy)propanamide (140 mg).

IR νmax cm$^{-1}$ (KBr): 3512, 3305, 2943, 1732, 1666, 1604, 1415, 1333, 1161, 1030, 754, 619

$^1$H NMR δ ppm (CDCl$_3$): 1.246 (3H, t, J=7.18 Hz), 1.43–1.93 (6H, m), 2.88–2.92 (1H, m), 3.16–3.27 (2H, m), 3.572 (2H, s), 3.51–4.07 (4H, m), 4.141 (2H, q, J=7.18 Hz), 4.584 (1H, bs), 5.710 (1H, t, J=6.45 Hz), 7.20–7.24 (2H, m), 7.38–7.48 (4H, m), 7.76–7.82 (2H, m), 8.509 (1H, d, 10.50 Hz)

$^{13}$C-NMR δ ppm (CDCl$_3$): 14.15, 20.01, 20.34, 25.11, 30.61, 30.90, 40.81, 42.20, 42.35, 46.31, 46.38, 60.86, 63.40, 64.06, 66.51, 67.47, 99.74, 100.91, 119.94, 120.09, 128.45, 129.44, 129.84, 130.25, 136.56, 138.32, 139.12, 170.44, 171.54

Fab-MS m/z: 538 (M$^+$), 455 (M$^+$)

Example 158

Preparation of (RS)-N-(4-(carboxymethyl) phenyl)-2-(4-chlorobenzenesulfonylaminomethyl)-3-(tetrahydropyran-2-yloxy)propanamide The procedure described in Example 39 was repeated, except that (RS)-2-(4-chlorobenzenesulfonylaminomethyl)-N-(4-(ethoxycarbonylmethyl)phenyl)-3-(tetrahydropyran-2-yloxy)propanamide (32 mg) was hydrolyzed to obtain (RS)-N-(4-(carboxymethyl)phenyl)-2-(4-chlorobenzenesulfonylaminomethyl)-3-(tetrahydropyran-2-yloxy)propanamide (30 mg).

IR νmax cm$^{-1}$ (KBr): 3466, 2945, 1713, 1662, 1533, 1329, 1159, 1093, 1028, 482

$^1$H NMR δ ppm (CD$_3$OD): 1.30–2.02 (6H, m), 2.95–4.10 (9H, m), 4.674 (1H, bd, J=11.72 Hz), 7.20–7.42 (2H, m), 7.46–7.73 (4H, m), 7.78–8.01 (2H, m)

¹³C-NMR δ ppm (CD₃OD): 19.99, 20.40, 26.37, 31.43, 31.54, 41.52, 42.95, 62.90, 63.45, 67.41, 67.74, 99.72, 100.56, 121.35, 121.87, 129.60, 130.38, 130.63, 130.82, 131.99, 138.30, 139.80, 140.42, 172.44, 172.58, 175.66

Fab-MS m/z: 511 (MH⁺)

Example 159

Preparation of (RS)-2-(4-chlorobenzenesulfonylaminomethyl)-N-(3-ethoxycarbonylphenyl)-3-(tetrahydropyran-2-yloxy)propanamide The crude (RS)-3-benzyloxy-2-benzyloxymethylpropanoic acid (1.52 g) obtained in the same manner as the method described in Example 153 was dissolved in methylene chloride, and then, ethyl 3-aminobenzoate (1.51 g) and triethylamine (1.4 ml) were added. The reaction mixture was added to a suspension of 2-chloro-1-methylpyridinium iodide (2.59 g) suspended in methylene chloride (20 ml) under argon and heated under reflux for 24 hours. The reaction mixture was washed with 2N HCl, saturated NaHCO₃ and saturated NaCl, dried over Na₂SO₄ and concentrated. The resulting residue was purified by silica gel column chromatography (Wakogel C-200, ethyl acetate/toluene=1/15) to obtain (RS)-3-benzyloxy-2-benzyloxymethyl-N-(3-ethoxycarbonylphenyl)-propanamide (1.31 g). The functional group of (RS)-3-benzyloxy-2-benzyloxymethyl-N-(3-ethoxycarbonylphenyl)propanamide (1.17 g) was converted in the same manner as Example 153 to obtain (RS)-2-(4-chlorobenzenesulfonylaminomethyl)-N-(3-ethoxycarbonylphenyl)-3-(tetrahydropyran-2-yloxy)propanamide (267 mg).

IR vmax cm⁻¹ (KBr): 3325, 2943, 1718, 1552, 1288, 1162, 1028, 754

1H-NMR δ ppm (CDCl₃): 1.390 (3H, t, J=7.18 Hz), 1.46–1.91 (6H, m), 2.83–3.01 (1H, m), 3.12–3.35 (2H, m), 3.05–3.45 (1H, m), 3.69–4.07 (3H, m), 4.373 (2H, q, J=7.18 Hz), 4.603 (1H, bs), 5.693 (1H, bs), 7.35–7.48 (3H, m), 7.77–7.85 (4H, m), 8.014 (1H, s), 8.735 (1H, d, J=4.39 Hz)

¹³C-NMR δ ppm (CDCl₃): 14.29, 20.16, 20.49, 25.07, 30.68, 30.98, 42.16, 42.31, 46.27, 46.49, 61.12, 63.69, 64.31, 66.51, 67.39, 99.92, 101.17, 120.57, 120.71, 124.05, 124.23, 125.41, 128.45, 129.07, 129.44, 131.27, 137.84, 138.32, 139.16, 161.11, 170.66, 170.73

Fab-MS m/z: 524 (M⁺), 441

Example 160

Preparation of (RS)-N-(3-carboxyphenyl)-3-(4-chlorobenzenesulfonylaminomethyl)-3-(tetrahydropyran-2-yloxy)propanamide The procedure described in Example 39 was repeated, except that (RS)-2-(4-chlorobenzenesulfonylaminomethyl)-N-(3-ethoxycarbonylphenyl)-3-(tetrahydropyran-2-yloxy)propanamide (46 mg) was hydrolyzed to obtain (RS)-N-(3-carboxyphenyl)-2-(4-chlorobenzenesulfonylaminomethyl)-3-(tetrahydropyran-2-yloxy)propanamide (44 mg).

IR vmax cm⁻¹ (KBr): 3278, 2945, 1695, 1593, 1552, 1325, 1161, 1093, 1086, 1026, 754, 482

¹H-NMR δ ppm (CD₃OD): 1.32–1.88 (6H, m), 2.94–3.02 (1H, m), 3.08–3.31 (2H, m), 3.37–3.65 (2H, m), 3.69–3.92 (2H, m), 4.587 (1H, bd, J=13.42 Hz) 7.37–7.55 (3H, m), 7.74–7.85 (4H, m), 8.19–8.23 (1H, m)

¹³C-NMR δ ppm (CD₃OD): 19.99, 20.40, 26.37, 31.43, 31.54, 42.88, 45.11, 62.90, 63.49, 67.37, 67.70, 99.72, 100.56, 122.09, 122.45, 122.93, 125.53, 126.08, 126.34, 126.52, 129.60, 129.79, 130.38, 132.54, 139.80, 140.50, 169.47, 172.73, 172.84

Fab-MS m/z: 497 (MH⁺)

Example 161

Preparation of (RS)-2-(4-chlorobenzenesulfonylaminomethyl)-N-(4-methoxycarbonylbutyl)-3-(tetrahydropyran-2-yloxy)propanamide The crude (RS)-3-benzyloxy-2-benzyloxymethylpropanoic acid (948 mg) obtained in the same manner as the method described in Example 153 was dissolved in methylene chloride, and then, methyl 5-aminopentanoate (1.06 g) and triethylamine (2.2 ml) were added. The reaction mixture was added to a suspension of 2-chloro-1-methylpyridinium iodide (1.61 g) suspended in methylene chloride (20 ml) under argon, and the whole was heated under reflux for 15 hours. The reaction mixture was washed with 2N HCl, saturated NaHCO₃ and saturated NaCl, dried over Na₂SO₄ and concentrated. The resulting residue was purified by silica gel column chromatography (Wakogel C-200, ethyl acetate/hexane=1/4) to obtain (RS)-3-benzyloxy-2-benzyloxymethyl-N-(4-methoxycarbonylbutyl)propanamide (935 mg). The functional group of the resulting (RS)-3-benzyloxy-2-benzyloxymethyl-N-(4-methoxycarbonylbutyl)propanamide (914 mg) was converted in the same manner as Example 153 to obtain (RS)-2-(4-chlorobenzenesulfonylaminomethyl)-N-(4-methoxycarbonyl-butyl)-3-(tetrahydropyran -2-yloxy)propanamide (127 mg).

IR vmax cm⁻¹ (KBr): 3377, 2937, 1736, 1651, 1335, 1165, 1095, 754, 619, 484

¹H-NMR δ ppm (CDCl₃): 1.52–1.74 (10H, m), 2.331 (2H, t, J=7.20 Hz), 2.70–2.76 (1H, m), 3.10–3.27 (4H, m), 3.47–3.64 (2H, m), 3.662 (3H, s), 3.79–3.92 (2H, m), 4.523 (1H, d, J=5.61 Hz), 6.074 (1H, t, J=6.35 Hz), 6.636 (1H, bs), 7.479 (2H, d, J=8.67 Hz), 7.800 (2H, d, J=8.67 Hz)

¹³C-NMR δ ppm (CDCl₃): 19.65, 19.87, 21.85, 25.04, 28.59, 28.85, 30.35, 30.50, 33.25, 38.75, 42.27, 45.72, 45.83, 51.37, 62.81, 63.21, 66.29, 66.88, 99.26, 99.96, 128.34, 128.67, 129.18, 129.62, 138.32, 138.79, 171.94, 173.67

Fab-MS m/z: 491 (MH⁺)

Example 162

Preparation of (RS)-N-(4-carboxybutyl)-2-(4-chlorobenzenesulfonylaminomethyl)-3-(tetrahydropyran-2-yloxy)propanamide The procedure described in Example 39 was repeated, except that (RS)-2-(4-chlorobenzenesulfonylaminomethyl)-N-(4-methoxycarbonylbutyl)-3-(tetrahydropyran-2-yloxy)propanamide (12 mg) was hydrolyzed to obtain (RS)-N-(4-carboxybutyl)-2-(4-chlorobenzenesulfonylaminomethyl)-3-(tetrahydropyran-2-yloxy)propanamide (10 mg).

IR vmax cm⁻¹ (KBr): 3305, 2943, 1711, 1651, 1556, 1333, 1163, 1095, 1028, 754, 619, 482

¹H-NMR δ ppm (CDCl₃): 1.49–1.73 (10H, m), 2.359 (2H, t, J=6.96 Hz), 2.72–2.81 (1H, m), 3.133 (2H, q, J=6.43 Hz), 3.22–3.28 (2H, m), 3.47–3.64 (2H, m), 3.77–3.93 (2H, m), 4.536 (1H, bs), 6.123 (1H, bs), 6.750 (1H, bs), 7.472 (2H, d, J=8.66 Hz), 7.794 (2H, d, J=8.66 Hz)

¹³C-NMR δ ppm (CDCl₃): 14.11, 19.72, 19.90, 20.93, 21.77, 25.11, 28.56, 30.46, 30.57, 33.29, 38.97, 42.20, 46.09, 46.20, 60.35, 63.03, 63.32, 66.40, 66.88, 99.44, 99.99, 128.45, 129.29, 138.39, 138.94, 172.38, 172.46, 177.37

Fab-MS m/z: 477 (MH$^+$), 393 (MH$^+$)

Example 163

Preparation of (RS)-2-(4-chlorobenzenesulfonylaminomethyl)-N-(4-ethoxycarbonylphenyl)-3-(1H-imidazol-1-yl)propanamide (RS)-2-(4-chlorobenzenesulfonylaminomethyl)-N-(4-ethoxycarbonylphenyl)-3-hydroxypropanamide (13.0 mg) obtained in the same manner as the method described in Example 153 was dissolved in pyridine, and tosyl chloride (10 mg) was added. The whole was stirred at room temperature overnight. Methanol was added to the reaction mixture to decompose the excess reagents. The product was concentrated under reduced pressure. The residue was diluted with ethyl acetate, washed with water, 2N HCl, saturated NaHCO$_3$ and saturated NaCl, dried over Na$_2$SO$_4$ and concentrated. The resulting residue was purified by silica gel column chromatography (Wakogel C-200, ethyl acetate/toluene=1/2) to obtain (RS)-2-(4-chlorobenzenesulfonylaminomethyl)-N-(4-ethoxycarbonylphenyl)-3-toluenesulfonyloxypropanamide (12 mg).

A solution of imidazole (6.9 mg) in DMF (0.5 ml) was added to a 60% NaH (4.0 mg) suspension in anhydrous DMF (0.5 ml) prepared at 0° C., under argon. After stirring for 20 minutes, a DMF solution of (RS)-2-(4-chlorobenzenesulfonylaminomethyl)-N-(4-ethoxycarbonylphenyl)-3-toluenesulfonyloxypropanamide (12 mg) was added. The whole was stirred at 0° C. to room temperature overnight. The reaction mixture was poured into a saturated saline solution and extracted with ethyl acetate. The combined ethyl acetate layers were washed with a saturated saline solution and dried over Na$_2$SO$_4$. The solvent was evaporated, and the residue was purified by column chromatography (6% water-containing silica gel, chloroform/methanol=5/1) to obtain the desired (RS)-2-(4-chlorobenzenesulfonylaminomethyl)-N-(4-ethoxycarbonylphenyl)-3-(1H-imidazol-1-yl)propanamide (7 mg).

IR vmax cm$^{-1}$ (KBr): 3151, 2927, 1699, 1605, 1279, 1176, 1095, 771, 691

$^1$H-NMR δ ppm (CD$_3$OD): 1.351 (3H, t, J=7.08 Hz), 2.645 (1H, m), 3.05–3.28 (3H, m), 3.413 (1H, dd, J=6.47 Hz, J=13.55 Hz), 4.281 (2H, q, J=7.08 Hz), 6.554 (2H, d, J=8.67 Hz), 7.143 (2H, bs), 7.446 (2H, d, J=8.67 Hz), 7.743 (2H, d, J=4.89 Hz), 7.775 (2H, d, J=4.89 Hz), 7.879 (1H, bs)

$^{13}$C-NMR δ ppm (CD$_3$OD):

Fab-MS m/z: 491 (MH$^+$)

Example 164

Preparation of (RS)-2-(4-chlorobenzenesulfonylamino)-4-butanolide (RS)-2-amino-4-hydroxybutanoic acid (2.0438 g) was dissolved in water (20 ml). The solution was cooled to 0° C., and potassium carbonate (5.217 g) and ethyl acetate (20 ml) were added. Then, p-chlorobenzenesulfonyl chloride (9.0536 g) and THF (2 ml) were added, and the whole was stirred overnight. After the reaction was completed, the ethyl acetate layer was separated. The aqueous layer was acidified with 2N HCl and extracted with ethyl acetate. The combined ethyl acetate layers were concentrated to give a crude product. The crude product was purified by silica gel column chromatography (silica gel 50 g, hexane/ethyl acetate=2/1) to obtain (RS)-2-(4-chlorobenzenesulfonylamino)-4-butanolide (2.8674 g).

Melting point: 113°–115° C.

IR vmax cm$^{-1}$ (KBr): 3255, 1776, 1407, 1336, 1188, 1169, 1091, 756

$^1$H-NMR δ ppm (CD$_3$OD): 2.0–2.2 (1H, m), 2.4–2.5 (2H, m), 4.1–4.3 (1H, m), 4.2–4.4 (2H, m), 7.561 (2H, d, J=8.8 Hz), 7.897 (2H, d, J=8.8 Hz)

$^{13}$C-NMR δ ppm (CD$_3$OD): 31.73, 53.22, 67.12, 130.05, 130.60, 140.24, 141.52, 176.58

Fab-MS m/z: 276 (MH$^+$)

Example 165

Preparation of methyl (RS)-2-(4-chlorobenzenesulfonylamino)-4-hydroxybutanoate (RS)-2-(4-chlorobenzenesulfonylamino)-4-butanolide (1.0084 g) was dissolved in methanol (50 ml). To the resulting solution, triethylamine hydrochloride (1.007 g) and triethylamine (0.370 g) were added, and the whole was stirred at room temperature overnight. The reaction mixture was concentrated. Ethyl acetate and saturated saline solution were added to the residue. After the mixture was shaken, 2 layers were separated. The ethyl acetate layer was washed with 2N HCl and then water, then dried over Na$_2$SO$_4$ and concentrated to give a crude product. The crude product was purified by column chromatography (silica gel 50 g, hexane/ethyl acetate=1/1) to obtain methyl (RS)-2-(4-chlorobenzenesulfonylamino)-4-hydroxybutanoate (787.3 mg).

Melting point: 91°–92° C.

IR vmax cm$^{-1}$ (neat): 3275, 3093, 2954, 1740, 1587, 1477, 1340, 1162, 1088, 756

$^1$H-NMR δ ppm (CDCl$_3$): 1.8–1.9 (1H, m), 2.0–2.1 (1H, m), 3.538 (3H, s), 3.7–3.8 (2H, m), 4.127 (1H, dt, J=8.5 Hz, J=4.6 Hz), 6.215 (1H, d, J=9.0 Hz), 7.478 (2H, d, J=8.3 Hz), 7.807 (2H, d, J=8.5 Hz)

$^{13}$C-NMR δ ppm (CDCl$_3$): 35.08, 52.50, 53.13, 57.97, 128.86, 129.22, 138.10, 139.23, 172.09

Fab-MS m/z: 308 (MH$^+$)

Example 166

Preparation of methyl (RS)-2-(4-chlorobenzenesulfonylamino)-4-(tetrahydropyran-2-yloxy)butanoate Methyl (RS)-2-(4-chlorobenzenesulfonylamino)-4-hydroxybutanoate (743.3 mg) was dissolved in dichloromethane (4.4 ml). Further, dihydropyrane (4.06 g) and PPTS (52.8 mg) were added under argon and the whole was stirred at room temperature overnight. The reaction solution was poured into a saturated saline solution, and extracted with dichloromethane. The dichloromethane layer was washed with water, dried over Na$_2$SO$_4$ and concentrated to give methyl (RS)-2-(4-chlorobenzenesulfonylamino)-4-(tetrahydropyran-2-yloxy) butanoate (933.5 mg).

Melting point: 93°–94° C.

IR vmax cm$^{-1}$ (KBr): 3161, 2954, 1743, 1479, 1344, 1167, 1086, 1016, 754

$^1$H-NMR δ ppm (CDCl$_3$): 1.5–1.9 (6H, m), 2.0–2.1 (2H, m), 3.4–3.5 (2H, m), 3.560 (3H, s), 3.7–3.9 (2H, m), 4.4–4.6 (1H, m), 5.767 (1H, d, J=8.6 Hz), 7.474 (2H, d, J=8.6 Hz), 7.798 (2H, d, J=8.8 Hz)

$^{13}$C-NMR δ ppm (CDCl$_3$): 19.54, 19.65, 25.26 and 25.37, 30.61, 30.87, 32.48 and 32.74, 52.36, 62.77, 98.34, 128.60, 129.15, 138.50, 139.12, 171.65 and 171.83

Fab-MS m/z: 392 (MH$^+$), 308 (MH$^+$–THP)

Example 167

Preparation of (RS)-2-(4chlorobenzenesulfonylamino)-4-(tetrahydropyran-2-yloxy)butanoic acid The procedure described in Example 39 was repeated, except that methyl (RS)-2-(4-chlorobenzenesulfonylamino)-4-(tetrahydropyran-2-yloxy)butanoate (552.8 mg) was hydrolyzed to give (RS)-2-(4-chlorobenzenesulfonylamino)-(RS)-2-(4-chlorobenzenesulfonylamino)-4-(tetrahydropyran-2-yloxy)butanoic acid (519.8 mg).

Melting point: 110°–111° C.

IR vmax cm$^{-1}$ (neat): 3271, 2945, 1732, 1477, 1340, 1165, 1093, 1024, 756

$^1$H-NMR δ ppm (CDCl$_3$): 1.4–1.8 (6H, m), 2.0–2.1 (2H, m), 3.4–3.5 (2H, m), 3.7–3.9 (2H, m), 4.509 (1H, d, J=25.9 Hz), 5.918 (1H, d, J=8.3 Hz), 7.466 (2H, d, J=8.3 Hz), 7.809 (2H, d, J=8.8 Hz)

$^{13}$C-NMR δ ppm (CDCl$_3$): 14.11, 20.97, 25.18, 30.21 and 30.39, 32.59, 53.60, 60.46, 99.44, 128.63, 129.26, 138.50, 139.23, 174.51, 174.73

Fab-MS m/z: 378 (MH$^+$), 294 (MH$^+$–THP)

Example 168

Preparation of (RS)-2-(4-chlorobenzenesulfonylamino)-N-(4-(ethoxycarbonylmethyl)phenyl)-4-(tetrahydropyran-2-yloxy)butanamide (RS)-2-(4-chlorobenzenesulfonylamino)-(RS)-2-(4-chlorobenzenesulfonylamino)-4-(tetrahydropyran-2-yloxy) butanoic acid (1.8464 g) was dissolved in 30 ml of THF, and triethylamine (642.8 mg) and pivaloyl chloride (648.1 mg) were added under argon. The whole was stirred at room temperature. After 2 hours, triethylamine (642.8 mg) and pivaloyl chloride (294.6 mg) were added, and the whole was stirred for 1.5 hours. To the resulting solution, ethyl p-aminophenylacetate hydrochloride (1.265 g) and triethylamine (642.8 mg) were added, and then the whole was stirred at room temperature overnight. The reaction solution was poured into a saturated saline solution, extracted 3 times with ethyl acetate, washed with a saline solution, dried over Na$_2$SO$_4$, and then concentrated to give a crude product. The crude was purified by column chromatography (silica gel 180g, hexane/ethyl acetate=2/1) to obtain (RS)-2-(4-chlorobenzenesulfonylamino)-N-(4-(ethoxycarbonylmethyl)phenyl)-4-(tetrahydropyran-2-yloxy) butanamide (1.0727 g).

IR vmax cm$^{-1}$ (KBr): 3275, 2939, 1734, 1684, 1539, 1416, 1340, 1165, 1040, 1093, 1034, 756

$^1$H-NMR δ ppm (CDCl$_3$): 1.247 (3H, t, J=7.1 Hz), 1.5–1.9 (8H, m), 2.1–2.2 (1H, m), 3.4–3.6 (2H, m), 3.575 (2H, s), 3.7–4.0 (2H, m), 4.142 (2H, q, J=7.1 Hz), 4.4–4.5 (1H, m), 7.2–7.3 (2H, m), 7.407 (2H, t, J=8.7 Hz), 7.484 (2H, dd, J=8.7 Hz, J=5.7 Hz), 7.831 (2H, dd, J=8.8 Hz, J=2.0 Hz)

$^{13}$C-NMR δ ppm (CDCl$_3$): 14.18, 20.09, 20.53, 25.11, 30.79, 40.88, 43.52, 56.02, 60.90, 63.51, 100.73, 120.13, 128.82, 129.59, 129.84, 130.65, 136.08, 138.43, 141.07, 168.28, 171.47

Fab-MS m/z: 539 (MH$^+$)

Example 169

Preparation of (RS)-N-(4-(carboxymethyl) phenyl)-2-(4-chlorobenzenesulfonylamino)-4-(tetrahydropyran-2-yloxy) butanamide The procedure described in Example 39 was repeated, except that (RS)-2-(4-chlorobenzenesulfonylamino)-N-(4-(ethoxycarbonylmethyl)phenyl)- 4-(tetrahydropyran-2-yloxy) butanamide (23.2 mg) was hydrolyzed to give (RS)-N-(4-(carboxymethyl)phenyl)-2-(4-chlorobenzenesulfonylamino)-4-(tetrahydropyran-2-yloxy) butanamide (20.1 mg).

Melting point: 158°–162° C.

IR vmax cm$^{-1}$ (KBr): 3278, 2937, 1684, 1608, 1541, 1416, 1325, 1165, 1093, 1024, 756

$^1$H-NMR δ ppm (CDCl$_3$): 1.4–1.6 (6H, m), 1.7–1.9 (2H, m), 2.0–2.2 (1H, m), 3.4–3.6 (2H, m), 3.618 (2H, s), 3.7–3.9 (2H, m), 3.9–4.1 (1H, m), 4.4–4.5 (1H, m), 7.219 (2H, dd, J=8.5 Hz, J=2.4 Hz), 7.3–7.5 (4H, m), 7.813 (2H, dd, J=8.8 Hz, J=1.2 Hz)

$^{13}$C-NMR δ ppm (CDCl$_3$): 20.49, 25.11, 29.22, 30.90, 40.22, 42.64, 63.54, 64.94, 99.99, 120.27, 120.35, 128.78, 129.51, 129.92, 134.10, 137.80, 139.75, 175.50, 179.42

Fab-MS m/z: 511 (MH$^+$), 509 (MH$^+$–2)

Example 170

Preparation of (RS)-2-(4-chlorobenzenesulfonylamino)-N-(4-(ethoxycarbonylmethyl)phenyl)-4-hydroxybutanamide The procedure described in Example 25 was repeated, except that the THP was removed from (RS)-2-(4-chlorobenzenesulfonylamino)-N-(4-(ethoxycarbonylmethyl)phenyl)-4-(tetrahydropyran-2-yloxy)butanamide (981.2 mg) to obtain (RS)-2-(4-chlorobenzenesulfonylamino)-N-(4-(ethoxycarbonylmethyl)phenyl)-4-hydroxybutanamide (745.7 mg).

Melting point: 164°–167° C.

IR vmax cm$^{-1}$ (KBr): 3527, 3277, 2895, 1716, 1664, 1603, 1547, 1414, 1325, 1171, 1082, 1024, 754

$^1$H-NMR δ ppm (CD$_3$OD): 1.234 (3H, t, J=7.2 Hz), 1.8–1.9 (2H, m), 3.572 (2H, s), 3.6–3.7 (2H, m), 4.0–4.1 (1H, m), 4.125 (2H, q, J=7.2 Hz), 7.172 (2H, d, J=8.8 Hz), 7.243 (2H, d, J=8.8 Hz), 7.392 (2H, d, J=8.8 Hz), 7.806 (2H, d, J=8.5 Hz)

$^{13}$C-NMR δ ppm (CD$_3$OD): 14.46, 36.94, 41.48, 55.97, 58.94, 61.91, 121.32, 129.90, 130.16, 130.56, 137.82, 139.91, 140.50, 171.12, 173.43

Fab-MS m/z: 455 (MH$^+$)

Example 171

Preparation of (RS)-2-(4-chlorobenzenesulfonylamino)-N-(4-(ethoxycarbonylmethyl)phenyl)-4-phenylbutanamide The procedure described in Example 179 was repeated, except that (RS)-2-(4-chlorobenzenesulfonylamino)-4-phenylbutanoic acid (252.0 mg) and ethyl 4-aminophenylacetate hydrochloride (184.3 mg) were condensed in THF (4 ml) in the presence of triethylamine (384.9 µl) and pivaloyl chloride (140.4 µl), and then the resulting crude product was purified by column chromatography (silica gel 50 g, hexane/ethyl acetate=3/1) to obtain (RS)-2-(4-chlorobenzenesulfonylamino)-N-(4-(ethoxycarbonylmethyl)phenyl)-4-phenylbutanamide (170.5 mg).

Melting point: 114°–115° C.

IR vmax cm$^{-1}$ (KBr): 3201, 2970, 1733, 1637, 1539, 1516, 1416, 1327, 1163, 1093, 1032, 829, 754, 700

$^1$H-NMR δ ppm (CDCl$_3$): 1.234 (3H, t, J=7.1 Hz), 1.8–2.0 (1H, m), 2.1–2.3 (1H, m), 2.5–2.7 (2H, m), 3.556 (2H, s), 4.130 (2H, q, J=7.1 Hz), 4.7–4.8 (1H, m), 6.595 (1H, d, J=8.3 Hz), 7.012 (1H, d, J=6.4 Hz), 7.1–7.2 (4H, m), 7.223 (2H, dd, J=9.8 Hz, J=8.3 Hz), 7.319 (2H, d, J=8.8 Hz), 7.509 (2H, d, J=8.5 Hz), 7.735 (2H, d, J=8.5 Hz)

$^{13}$C-NMR δ ppm (CDCl$_3$): 14.11, 27.38, 33.84, 40.73, 53.38, 60.83, 120.09, 120.24, 126.14, 126.29, 128.27, 128.52, 128.71, 129.40, 129.73, 130.14, 136.74, 140.08, 170.00, 179.20

Fab-MS m/z: 515 (MH$^+$)

Example 172

Preparation of (RS)-N-(4-(carboxymethyl) phenyl)-2-(4-chlorobenzenesulfonylamino)-4-phenylbutanamide The procedure described in Example 39 was repeated, except that (RS)-2-(4-chlorobenzenesulfonylamino)-N-(4-(ethoxycarbonylmethyl)phenyl)-4-phenylbutanamide (118.7 mg) was hydrolyzed to obtain (RS)-N-(4-(carboxymethyl)phenyl)-2-(4-chlorobenzenesulfonylamino)-4-phenylbutanamide (109.2 mg).

Melting point: 163°–167° C.

IR νmax cm$^{-1}$ (KBr): 3327, 2933, 1710, 1674, 1606, 1516, 1416, 1321, 1163, 1093, 830, 756, 700

$^1$H-NMR δ ppm (CD$_3$OD): 2.0–2.2 (2H, m), 2.6–2.8 (2H, m), 3.559 (2H, s), 4.5–4.6 (1H, m), 7.1–7.2 (4H, m), 7.209 (2H, d, J=8.1 Hz), 7.226 (2H, d, J=8.8 Hz), 7.370 (1H, d, J=8.8 Hz), 7.504 (2H, d, J=8.8 Hz), 7.797 (2H, d, J=8.8 Hz)

$^{13}$C-NMR δ ppm (CD$_3$OD): 27.76, 33.12, 34.99, 55.12, 121.35, 127.07, 129.42, 129.49, 129.86, 130.19, 130.63, 130.74, 132.02, 132.13, 138.14, 142.32, 172.54, 175.47

Fab-MS m/z: 487 (MH$^+$)

Example 173

Preparation of (RS)-2-(4-chlorobenzenesulfonylamino)-N-(4-(2-methoxycarbonylethyl)phenyl)-4-phenylbutanamide The procedure described in Example 177 was repeated, except that (RS)-2-(4-chlorobenzenesulfonylamino)-4-phenylbutanoic acid (270.3 mg) and methyl 4-aminophenylpropionate hydrochloride (167.8 mg) were condensed in chloroform (10 ml) in the presence of triethylamine (360 μl) and 1-methyl-2-chloropyridinium iodide (243.2 mg), and then the resulting crude product was purified by column chromatography (silica gel 50 g, hexane/ethyl acetate=2/1) to obtain (RS)-2-(4-chlorobenzenesulfonylamino)-N-(4-(2-methoxycarbonylethyl)phenyl)-4-phenylbutanamide (43.2 mg) as a colorless oil.

IR νmax cm$^{-1}$ (KBr): 3267, 2929, 1736, 1713, 1604, 1518, 1352, 1165, 1093, 827, 756, 700

$^1$H-NMR δ ppm (CDCl$_3$): 1.9–2.1 (2H, m), 2.5–2.7 (4H, m), 2.879 (2H, dd, J=15.6 Hz, J=7.6 Hz), 3.658 (3H, s), 4.1–4.2 (1H, m), 7.0–7.3 (7H, m), 7.348 (2H, d, J=8.5 Hz), 7.732 (2H, d, J=8.5 Hz), 7.844 (1H, d, J=8.8 Hz), 8.060 (1H, d, J=9.0 Hz)

$^{13}$C-NMR δ ppm (CDCl$_3$): 30.32, 31.27, 34.50, 35.60, 51.62, 57.01, 120.31, 126.43, 128.27, 128.34, 128.60, 128.82, 129.15, 129.22, 129.37, 129.48, 134.98, 137.95, 168.57, 173.19

Fab-MS m/z: 515 (MH$^+$)

Example 174

Preparation of (RS)-N-(4-(2-carboxyethyl) phenyl)-2-(4-chlorobenzenesulfonylamino)-4-phenylbutanamide The procedure described in Example 39 was repeated, except that (RS)-2-(4-chlorobenzenesulfonylamino)-N-(4-(2-methoxycarbonylethyl)phenyl)-4-phenylbutanamide (41.5 mg) was hydrolyzed to obtain (RS)-N-(4-(2-carboxyethyl)phenyl)-2-(4-chlorobenzenesulfonylamino)-4-phenylbutaneamide (27.7 mg) as a colorless oil.

IR νmax cm$^{-1}$ (KBr): 3388, 2926, 1711, 1666, 1539, 1414, 1325, 1163, 1093, 827, 756, 700

$^1$H-NMR δ ppm (CD$_3$OD): 1.8–2.0 (2H, m), 2.5–2.7 (4H, m), 2.863 (2H, t, J=7.6 Hz), 3.8–3.9 (1H, m), 7.0–7.3 (7H, m), 7.382 (2H, d, J=8.8 Hz), 7.515 (2H, d, J=8.8 Hz), 7.796 (2H, d, J=8.8 Hz)

$^{13}$C-NMR δ ppm (CD$_3$OD): 20.73, 31.36, 32.72, 56.52, 58.24, 121.43, 127.04, 129.42, 129.53, 129.86, 130.16, 130.38, 130.52, 136.90, 139.91, 140.50, 142.04, 171.04, 175.11

Fab-MS m/z: 501 (MH$^+$)

Example 175

Preparation of (RS)-2-(4-bromobenzenesulfonylamino)-N-(4-(ethoxycarbonylmethyl)phenyl)-4-phenylbutanamide The procedure described in Example 179 was repeated, except that (RS)-2-(4-bromobenzenesulfonylamino)-4-phenylbutanoic acid (310.3 mg) and ethyl 4-aminophenylacetate hydrochloride (201.6 mg) were condensed in THF (5 ml) in the presence of triethylamine (421.2 μl) and pivaloyl chloride (153.6 μl), and then the resulting crude product was purified by column chromatography (silica gel 50 g, hexane/ethyl acetate=3/1) to obtain (RS)-2-(4-bromobenzenesulfonylamino)-N-(4-(ethoxycarbonylmethyl)phenyl)-4-phenylbutanamide (117.6 mg).

Melting point: 130°–131° C.

IR νmax cm$^{-1}$ (KBr): 3350, 3255, 2974, 1740, 1664, 1637, 1551, 1520, 1419, 1221, 1169, 1030, 835, 700

$^1$H-NMR δ ppm (CDCl$_3$): 1.237 (3H, t, J=7.1 Hz), 2.0–2.1 (1H, m), 2.1–2.3 (1H, m), 2.6–2.7 (2H, m), 3.561 (2H, s), 4.133 (2H, q, J=7.1 Hz), 4.7–4.8 (1H, m), 6.5–6.6 (1H, m), 7.0–7.2 (5H, m), 7.211 (2H, d, J=7.3 Hz), 7.244 (2H, d, J=6.6 Hz), 7.502 (2H, dd, J=12.0 Hz, J=8.6 Hz), 7.651 (1H, d, J=8.6 Hz)

$^{13}$C-NMR δ ppm (CDCl$_3$): 14.15, 31.67, 33.91, 53.38, 60.83, 115.25, 120.13, 120.24, 126.14, 126.32, 128.30, 128.52, 129.73, 130.10, 132.41, 136.85, 140.81, 170.04, 179.13

Fab-MS m/z: 561 (MH$^+$+2), 559 (MH$^+$)

Example 176

Preparation of (RS)-2-(4-bromobenzenesulfonylamino)-N-(4-(carboxymethyl)phenyl)-4-phenylbutanamide The procedure described in Example 39 was repeated, except that (RS)-2-(4-bromobenzenesulfonylamino)-N-(4-(ethoxycarbonylmethyl)phenyl)-4-phenylbutanamide (56.3 mg) was hydrolyzed to obtain (RS)-2-(4-bromobenzenesulfonylamino)-N-(4-(carboxymethyl) phenyl)-4-phenylbutanamide (54.7 mg).

Melting point: 155°–160° C.

IR νmax cm$^{-1}$ (KBr): 3317, 2964, 1713, 1639, 1516, 1417, 1254, 1163, 1068, 812, 741, 700

$^1$H-NMR δ ppm (CD$_3$OD): 2.0–2.2 (2H, m), 2.6–2.8 (2H, m), 3.559 (2H, s), 4.5–4.6 (1H, m), 7.1–7.2 (6H, m), 7.214 (2H, d, J=8.1 Hz), 7.229 (2H, d, J=8.5 Hz), 7.519 (2H, t, J=8.5 Hz), 7.718 (1H, d, J=8.8 Hz)

$^{13}$C-NMR δ ppm (CD$_3$OD): 27.73, 33.12, 34.99, 55.09, 121.32, 127.07, 129.38, 129.46, 129.93, 130.63, 130.74, 132.03, 132.10, 133.24, 138.15, 142.33, 172.55, 175.44

Fab-MS m/z: 533 (MH$^+$+2), 531 (MH$^+$)

Example 177

Preparation of (RS)-2-(4-chlorobenzenesulfonylamino)-N-(4-(ethoxycarbonylmethyl)phenyl)butanamide Triethylamine (1.99 ml), ethyl 4-aminophenylacetate hydrochloride (699 mg), and 1-methyl-2-chloropyridinium iodide (1.1 g) were added to a solution of (RS)-2-(4-chlorobenzenesulfonylamino)butanoic acid (1 g) in chloroform (30 ml), and the whole was heated under reflux for 2 hours under argon. The reaction mixture was concentrated under reduced pressure. After adding 1N HCl, the residue was extracted with ethyl acetate. The combined ethyl acetate layers were washed with a saturated saline solution, and dried over Na$_2$SO$_4$. The solvent was evaporated under reduced pressure. The residue was purified by column chromatography (silica gel 70 g, hexane/ethyl acetate=2/1) to give (RS)-2-(4-chlorobenzenesulfonylamino)-N-(4-(ethoxycarbonylmethyl) phenyl)butanamide (237 mg).

Melting point: 150°–152° C.

IR vmax cm$^{-1}$ (KBr): 3367, 1734, 1676, 1331, 1171, 831, 754

$^1$H-NMR δ ppm (CDCl$_3$-CD$_3$OD): 0.928 (3H, t, J=7.3 Hz), 1.260 (3H, t, J=7.1 Hz), 1.71 (2H, m), 3.57 (2H, s), 3.801 (1H, t, J=7.0 Hz), 4.146 (2H, q, J=7.1 Hz), 7.195 (2H, d, J=8.5 Hz), 7.281 (2H, d, J=8.5 Hz), 7.378 (2H, d, J=8.8 Hz), 7.789 (2H, d, J=8.8 Hz)

$^{13}$C-NMR δ ppm (CDCl$_3$-CD$_3$OD): 10.13, 14.27, 27.00, 41.19, 59.31, 61.50, 120.69, 129.02, 129.64, 130.04, 130.74, 136.83, 139.14, 139.58, 170.42, 172.73

Fab-MS m/z: 439 (MH$^+$)

Example 178

Preparation of (RS)-2-(4-chlorobenzenesulfonylamino)-N-(4-(ethoxycarbonylmethyl)phenyl)pentanamide The procedure described in Example 177 was repeated, except that (RS)-2-(4-chlorobenzenesulfonylamino) pentanoic acid (1 g) and ethyl 4-aminophenylacetate hydrochloride (665 mg) were condensed in chloroform (30 ml) in the presence of triethylamine (1.9 ml) and 1-methyl-2-chloropyridinium iodide (1.05 g) to obtain (RS)-2-(4-chlorobenzenesulfonylamino)-N-(4-(ethoxycarbonylmethyl)phenyl)pentanamide (387 mg).

Melting point: 93°–95° C.

IR vmax cm$^{-1}$ (KBr): 3327, 3257, 1732, 1660, 1340, 1167, 829, 756

$^1$H-NMR δ ppm (CDCl$_3$): 0.798 (3H, t, J=7.33 Hz), 1.2 (2H, m), 1.252 (3H, t, J=7.08 Hz), 1.5–1.7 (2H, m), 3.56 (2H, s), 3.88 (1H, m), 4.14 (2H, q, J=7.08 Hz), 7.16 (2H, d, J=8.55 Hz), 7.259 (2H, d, J=8.55 Hz), 7.37 (2H, d, J=8.79 Hz), 7.79 (2H, d, J=8.79 Hz)

$^{13}$C-NMR δ ppm (CDCl$_3$): 13.41, 14.11, 18.47, 35.12, 57.49, 60.97, 120.31, 127.83, 128.56, 129.37, 129.73, 130.03, 130.54, 135.90, 137.99, 139.56, 169.27, 171.72

Fab-MS m/z: 453 (MH$^+$)

Example 179

Preparation of (RS)-2-(4-chlorobenzenesulfonylamino)-N-(4-(ethoxycarbonylmethyl)phenyl)hexanamide Triethylamine (2.28 ml) and pivaloyl chloride (443 μl) were added to a solution of (RS)-2-(4-chlorobenzenesulfonylamino)hexanoic acid (1 g) in THF (20 ml), and the whole was stirred for 2 hours under argon. Then, ethyl 4-aminophenylacetate hydrochloride (829 mg) was added, and the whole was stirred at room temperature overnight. The reaction mixture was poured into a saturated saline solution, and extracted with ethyl acetate. The combined ethyl acetate layers were washed with a saturated saline solution and dried over Na$_2$SO$_4$. The solvent was evaporated under reduced pressure, and 1.31 g of a yellow oil was obtained. The product was purified by column chromatography (silica gel 60 g, hexane/ethyl acetate=3/1) to obtain (RS)-2-(4-chlorobenzenesulfonylamino)-N-(4-(ethoxycarbonylmethyl)phenyl)hexanamide (395 mg).

Melting point: 100°–103° C.

IR vmax cm$^{-1}$ (KBr): 3354, 3251, 1736, 1676, 1329, 1167, 831, 756

$^1$H-NMR δ ppm (CDCl$_3$): 0.786 (3H, t, J=7.08 Hz), 0.9 (2H, m), 1.2 (2H, m), 1.252 (3H, t, J=7.1 Hz), 1.6–1.7 (2H, m), 3.56 (2H, s), 4.15 (2H, q, J=7.1 Hz), 7.17 (2H, d, J=8.6 Hz), 7.27 (2H, d, J=8.6 Hz), 7.38 (2H, d, J=8.6 Hz), 7.79 (2H, d, 8.6 Hz)

$^{13}$C-NMR δ ppm (CDCl$_3$): 13.71, 14.15, 22.10, 27.27, 32.85, 40.77, 57.71, 60.94, 117.38, 120.27, 128.60, 128.85, 129.40, 129.77, 130.58, 130.83, 135.93, 138.10, 139.60, 169.16, 171.65

Fab-MS m/z: 467 (MH$^+$)

Example 180

Preparation of (S)-2-(4-chlorobenzenesulfonylamino)-N-(4-(ethoxycarbonylmethyl)phenyl)hexanamide (S)-2-(4-chlorobenzenesulfonylamino)hexanoic acid (3 g) and ethyl 4-aminophenylacetate (2.116 g) were dissolved in dichloromethane (50 ml). To the solution, N,N'-dicyclohexylcarbodiimide (2.43 g) was added, and then the whole was stirred at room temperature overnight under argon. The reaction mixture was concentrated, poured in a saturated saline solution and extracted with ethyl acetate. The combined ethyl acetate layers were washed with a saturated saline solution and dried over Na$_2$SO$_4$. The solvent was evaporated under reduced pressure, and the resulting crude product was recrystallized from ethanol to obtain (S)-2-(4-chlorobenzenesulfonylamino)-N-(4-(ethoxycarbonylmethyl)phenyl)hexanamide (1.493 g).

$[\alpha]_D^{24}$ –52.5° (c 0.85, CHCl$_3$)

Melting point: 157°–158° C.

The various spectra (IR, $^1$H-NMR, $^{13}$C-NMR, Fab-MS) were found to be identical to those of the racemate of Example 179.

Example 181

Preparation of (R)-2-(4-chlorobenzenesulfonylamino)-N-(4-(ethoxycarbonylmethyl)phenyl)hexanamide The procedure described in Example 177 was repeated, except that (R)-2-(4-chlorobenzenesulfonylamino)hexanoic acid (3 g) and ethyl 4-aminophenylacetate hydrochloride (1.9 g) were condensed in chloroform (100 ml) in the presence of triethylamine (5.4 ml) and 1-methyl-2-chloropyridinium iodide (3.01 g) to obtain as a colorless oily substance (R)-2-(4-chlorobenzenesulfonylamino)-N-(4-(ethoxycarbonylmethyl)phenyl)hexanamide (3.58 g).

$[\alpha]_D^{24}$ +52.3° (c 0.70, CHCl$_3$)

Melting point: 157°–158° C.

The various spectra (IR, $^1$H-NMR, $^{13}$C-NMR, Fab-MS) were found to be identical to those of the racemate of Example 179.

Example 182

Preparation of (S)-2-(4-chlorobenzenesulfonylamino)-N-(4-(2-methoxycarbonylethyl)phenyl)hexanamide The procedure described in Example 180 was repeated, except that (S)-2-(4-chlorobenzenesulfonylamino)hexanoic acid (3.024 g) and methyl 4-aminophenylpropionate (1.86 g) were condensed in dichloromethane (70 ml) in the presence of N,N'-dicyclohexylcarbodiimide (2.44 g). The reaction mixture was filtered, and the filtrate was concentrated. The resulting crude product was recrystallized from toluene to obtain (S)-2-(4-chlorobenzenesulfonylamino)-N-(4-(2-methoxycarbonylethyl)phenyl)hexanamide (3.28 g).

$[\alpha]_D^{27}$–45.3° (c 0.950, CHCl$_3$)

Melting point: 106°–108° C.

The various spectra (IR, $^1$H-NMR, $^{13}$C-NMR, Fab-MS) were found to be identical to those of the racemate of Example 179.

Example 183

Preparation of (RS)-2-(4-bromobenzenesulfonylamino)-N-(4-(ethoxycarbonylmethyl)phenyl)hexanamide The procedure described in Example 177 was repeated, except that (RS)-2-(4-bromobenzenesulfonylamino) hexanoic acid (1 g) and ethyl 4-aminophenylacetate hydrochloride (554.2 mg) were condensed in chloroform (30 ml) in the presence of triethylamine (1.6 ml) and 1-methyl-2-chloropyridinium iodide (875.4 mg) to obtain (RS)-2-(4-bromobenzenesulfonylamino)-N-(4-(ethoxycarbonylmethyl)phenyl)hexanamide (123.8 mg).

$^1$H-NMR δ ppm (CDCl$_3$): 0.810 (3H, t, J=6.8 Hz), 1.20–1.70 (4H, m), 1.254 (3H, t, J=7.2 Hz), 1.52–1.85 (2H, m), 3.571 (2H, s), 3.838 (1H, bd, J=5.4 Hz), 4.149 (2H, q, J=7.2 Hz), 5.669 (1H, bd, J=7.8 Hz), 7.189 (2H, d, J=8.7 Hz), 7.273 (2H, d, J=8.7 Hz), 7.561 (2H, d, J=8.8 Hz), 7.721 (2H, d, J=8.8 Hz), 8.020 (1H, s)

$^{13}$C-NMR δ ppm (CDCl$_3$): 13.74, 14.45, 22.14, 27.27, 32.88, 40.81, 57.71, 60.94, 120.24, 128.16, 128.71, 129.81, 130.61, 132.45, 135.86, 168.94, 171.61

Fab-MS m/z: 511

Example 184

Preparation of (S)-2-(4-bromobenzenesulfonylamino)-N-(4-(ethoxycarbonylmethyl)phenyl)hexanamide The procedure described in Example 180 was repeated, except that (S)-2-(4-bromobenzenesulfonylamino)hexanoic acid (3.50 g) and ethyl 4-aminophenylacetate (1.61 g) were condensed in dichloromethane (40 ml) in the presence of N,N'-dicyclohexylcarbodiimide (2.47 g). The reaction mixture was filtered, and the filtrate was concentrated. The resulting crude product was recrystallized from isopropyl alcohol to obtain (S)-2-(4-bromobenzenesulfonylamino)-N-(4-(ethoxycarbonylmethyl)phenyl)hexanamide (3.36 g).

$[\alpha]_D^{28}$–42.9° (c 1.08, CHCl$_3$)

Melting point: 157°–159° C.

The various spectra (IR, $^1$H-NMR, $^{13}$C-NMR, Fab-MS) were found to be identical to those of the racemate of Example 183.

Example 185

Preparation of (S)-2-(4-bromobenzenesulfonylamino)-N-(4-(2-methoxycarbonylethyl)phenyl)hexanamide The procedure described in Example 180 was repeated, except that (S)-2-(4-bromobenzenesulfonylamino)hexanoic acid (3.50 g) and methyl 4-aminophenylpropionate (1.61 g) were condensed in dichloromethane (40 ml) in the presence of N,N'-dicyclohexylcarbodiimide (2.47 g). The reaction mixture was filtered, and the filtrate was concentrated. The resulting crude product was recrystallized from isopropyl alcohol to obtain (S)-2-(4-bromobenzenesulfonylamino)-N-(4-(2-methoxycarbonylethyl)phenyl)hexaneamide (3.47 g).

$[\alpha]_D^{28}$–28.1° (c 1.02, CHCl$_3$)

Melting point: 112°–116° C.

IR νmax cm$^{-1}$ (KBr): 3263, 1738, 1662, 1535, 1329, 1167, 1092, 741, 613, 567

$^1$H-NMR δ ppm (CDCl$_3$): 0.796 (3H, t, J=7.0 Hz), 1.03–1.97 (6H, m), 2.594 (2H, t, J=7.7 Hz), 2.900 (2H, t, J=7.7 Hz), 3.666 (3H, s), 3.81–3.95 (1H, m), 5.95 (1H, bs), 7.092 (2H, d, J=8.6 Hz), 7.231 (2H, d, J=8.6 Hz), 7.528 (2H, d, J=8.7 Hz), 7.722 (2H, d, J=8.7 Hz), 8.202 (1H, s)

$^{13}$C-NMR δ ppm (CDCl$_3$): 13.74, 22.14, 27.31, 30.32, 32.92, 35.63, 51.66, 57.78, 120.13, 120.38, 128.05, 128.71, 132.37, 135.20, 137.11, 138.61, 169.12, 173.26

Fab-MS m/z: 511 (MH$^+$)

Example 186

Preparation of (S)-2-(4-bromobenzenesulfonylamino)-N-(3-ethoxycarbonylphenyl)hexanamide The procedure described in Example 180 was repeated, except that (S)-2-(4-bromobenzenesulfonylamino) hexanoic acid (3.64 g) and ethyl 3-aminobenzoate (1.47 ml) were condensed in dichloromethane (40 ml) in the presence of N,N'-dicyclohexylcarbodiimide (2.57 g). The reaction mixture was filtered, and the filtrate was concentrated. The resulting crude product was recrystallized from toluene to obtain (S)-2-(4-bromobenzenesulfonylamino)-N-(3-ethoxycarbonylphenyl)hexanamide (1.85 g).

$[\alpha]_D^{28}$–36.9° (c 0.271, CHCl$_3$)

Melting point: 122°–125° C.

IR νmax cm$^{-1}$ (KBr): 3329, 1724, 1657, 1311, 1245, 1090, 640

$^1$H-NMR δ ppm (CDCl$_3$-CD$_3$OD): 0.851 (3H, t, J=7.3 Hz), 1.413 (3H, t, J=7.1 Hz), 1.0–1.95 (6H, m), 3.852 (1H, dd, J=8.0 Hz, J=5.9 Hz), 7.368 (1H, t, J=8.1 Hz), 7.513 (2H, d, J=8.8 Hz), 7.68 (1H, m), 7.707 (2H, d, J=8.8 Hz), 7.768 (1H, dt, J=7.6 Hz, J=1.5 Hz), 7.855 (1H, t, J=1.5 Hz)

$^{13}$C-NMR δ ppm (CDCl$_3$-CD$_3$OD): 13.60, 14.11, 22.03, 27.35, 32.81, 57.56, 61.23, 120.60, 124.31, 125.41, 127.72, 128.60, 130.87, 132.12, 137.55, 138.83, 157.60, 166.52, 169.85

Fab-MS m/z: 499 (MH$^+$+2), 497 (MH$^+$)

Example 187

Preparation of (RS)-2-(4-chlorobenzenesulfonylamino)-N-(4-(ethoxycarbonylmethyl)phenyl)octanamide The procedure described in Example 177 was repeated, except that (RS)-2-(4-chlorobenzenesulfonylamino) octanoic acid (1 g) and ethyl 4-aminophenylacetate hydrochloride (581 mg) were condensed in chloroform (30 ml) in the presence of triethylamine (1.66 ml) and 1-methyl-2-chloropyridinium iodide (918 mg) to obtain (RS)-2-(4-chlorobenzenesulfonylamino)-N-(4-(ethoxycarbonylmethyl)phenyl)octanamide (350 mg).

Melting point: 110°–112° C.

IR νmax cm$^{-1}$ (KBr): 3304, 3228, 1740, 1662, 1331, 1163, 833, 758

$^1$H-NMR δ ppm (CDCl$_3$): 0.825 (3H, t, J=6.8 Hz), 1.1–1.3 (8H, m), 1.25 (3H, t, J=7.1 Hz), 3.56 (2H, s), 3.8 (1H, m), 4.15 (2H, q, J=7.1 Hz), 7.16 (2H, d, J=8.4 Hz), 7.27 (2H, d, J=8.4 Hz), 7.38 (2H, d, J=8.6 Hz), 7.8 (2H, d, J=8.6 Hz)

$^{13}$C-NMR δ ppm (CDCl$_3$): 13.97, 14.19, 22.48, 25.23, 28.75, 31.54, 33.19, 40.82, 57.80, 61.02, 120.36, 128.68, 129.45, 129.82, 130.00, 130.59, 136.02, 138.11, 139.65, 169.31, 171.81, Fab-MS m/z: 495 (MH$^+$)

Example 188

Preparation of (RS)-2-(4-chlorobenzenesulfonylamino)-N-(4-(ethoxycarbonylmethyl)phenyl)-3-methylbutanamide The procedure described in Example 177 was repeated, except that (RS)-2-(4-chlorobenzenesulfonylamino)-3-methylbutanoic acid (1 g) and ethyl 4-aminophenylacetate hydrochloride (665 mg) were condensed in chloroform (30 ml) in the presence of triethylamine (1.9 ml) and 1-methyl-2-chloropyridinium iodide (1.05 g) to obtain (RS)-2-(4-chlorobenzenesulfonylamino)-N-(4-(ethoxycarbonylmethyl) phenyl)-3-methylbutanamide (542 mg).

Melting point: 100°–102° C.

IR vmax cm$^{-1}$ (KBr): 3319, 3265, 1732, 1655, 1335, 1167, 829, 756

$^1$H-NMR δ ppm (CDCl$_3$): 0.887 (3H, d, J=6.6 Hz), 0.911 (3H, d, J=6.4 Hz), 1.25 (3H, t, J=7.1 Hz), 2.1 (1H, m), 3.5 (2H, s), 3.6 (1H, m), 4.15 (2H, q, J=7.1 Hz) 7.17 (2H, d, J=8.6 Hz), 7.23 (2H, d, J=8.6 Hz), 7.36 (2H, d, J=8.79 Hz), 7.47 (2H, d, J=8.79 Hz), 7.79 (2H, d, J=8.6 Hz), 7.86 (2H, d, J=8.6 Hz)

$^{13}$C-NMR δ ppm (CDCl$_3$): 14.19, 17.60, 19.14, 31.54, 40.81, 61.02, 63.08, 120.43, 127.95, 128.72, 129.19, 129.41, 129.63, 129.82, 130.04, 130.77, 135.76, 138.00, 139.65, 168.65, 171.70

Fab-MS m/z: 453 (MH$^+$)

Example 189

Preparation of (RS)-2-(4-chlorobenzenesulfonylamino)-N-(4-(ethoxycarbonylmethyl)phenyl)-4-methylpentanamide The procedure described in Example 177 was repeated, except that (RS)-2-(4-chlorobenzenesulfonylamino)-4-methylpentanoic acid (1 g) and ethyl 4-aminophenylacetate hydrochloride (635 mg) were condensed in chloroform (30 ml) in the presence of triethylamine (1.82 ml) and 1-methyl-2-chloropyridinium iodide (1 g) to obtain (RS)-2-(4-chlorobenzenesulfonylamino)-N-(4-(ethoxycarbonylmethyl) phenyl)-4-methylpentanamide (455 mg).

Melting point: 117°–120° C.

IR vmax cm$^{-1}$ (KBr): 3365, 3273, 1728, 1672, 1342, 1165, 829, 754

$^1$H-NMR δ ppm (CDCl$_3$): 0.73 (3H, d, J=6.0 Hz), 0.85 (3H, d, J=6.0 Hz), 1.25 (3H, t, J=7.1 Hz), 1.5–1.6 (2H, m), 3.56 (2H, s), 3.9 (1H, m), 4.15 (2H, q, J=7.1 Hz), 7.15 (2H, d, J=8.5 Hz), 7.23 (2H, d, J=8.5 Hz), 7.35 (2H, d, J=8.5 Hz), 7.79 (2H, d, J=8.5 Hz)

$^{13}$C-NMR δ ppm (CDCl$_3$): 14.19, 21.42, 22.85, 24.42, 40.82, 42.06, 56.36, 61.02, 115.37, 120.40, 128.72, 128.94, 129.41, 128.59, 129.78, 130.11, 130.59, 135.98, 138.11, 139.61, 169.72, 171.81

Fab-MS m/z: 467 (MH$^+$)

Example 190

Preparation of (RS)-2-(4-chlorobenzenesulfonylamino)-N-(4-(ethoxycarbonylmethyl)phenyl)-4-methylthiobutanamide The procedure described in Example 177 was repeated, except that (RS)-2-(4-chlorobenzenesulfonylamino)-4-methylthiobutanoic acid (1 g) and ethyl 4-aminophenylacetate hydrochloride (599 mg) were condensed in chloroform (30 ml) in the presence of triethylamine (1.72 ml) and 1-methyl-2-chloropyridinium iodide (946.8 mg) to obtain (RS)-2-(4-chlorobenzenesulfonylamino)-N-(4-(ethoxycarbonylmethyl)phenyl)-4-methylthiobutanamide (306.3 mg).

Melting point: 121°–123° C.

IR vmax cm$^{-1}$ (KBr): 3336, 3271, 1736, 1726, 1664, 1336, 1165, 758, 561

$^1$H-NMR δ ppm (CDCl$_3$): 1.253 (3H, t, J=7.08 Hz), 1.94–2.05 (2H, m), 2.036 (3H, s), 2.40–2.57 (2H, m), 3.574 (2H, s), 4.03–4.13 (1H, m), 4.149 (2H, q, J=7.08 Hz), 6.071 (1H, bs), 7.207 (2H, d, J=8.55 Hz), 7.30 (2H, d, J=8.55 Hz), 7.429 (2H, d, J=8.54 Hz), 7.818 (2H, d, J=8.54 Hz), 8.160 (1H, s)

$^{13}$C-NMR δ ppm (CDCl$_3$): 14.19, 15.22, 30.11, 31.50, 40.82, 56.55, 60.99, 120.25, 128.72, 129.60, 129.93, 130.88, 135.80, 137.92, 139.83, 168.32, 171.62

Fab-MS m/z: 485 (MH$^+$)

Example 191

Preparation of (S)-2-(4-chlorobenzenesulfonylamino)-N-(4-(ethoxycarbonylmethyl)phenyl)-4-methylthiobutanamide The procedure described in Example 180 was repeated, except that (S)-2-(4-chlorobenzenesulfonylamino)-4-methylthiobutanoic acid (8 g) and ethyl 4-aminophenyl acetate (4.43 g) were condensed in dichloromethane (60 ml) in the presence of N,N'-dicyclohexylcarbodiimide (6.12 g). The reaction mixture was filtered, and the filtrate was concentrated. The resulting crude product was recrystallized from ethanol to obtain (S)-2-(4-chlorobenzenesulfonylamino)-N-(4-(ethoxycarbonylmethyl)phenyl)-4-methylthiobutanamide (4.14 g).

Melting point: 144°–145.5° C.

$[\alpha]_D^{26}$ –42.2° (c 1.00, CHCl$_3$)

The various spectra (IR, $^1$H-NMR, $^{13}$C-NMR, Fab-MS) were found to be identical to those of the racemate of Example 190.

Example 192

Preparation of (R)-2-(4-chlorobenzenesulfonylamino)-N-(4-(ethoxycarbonylmethyl)phenyl)-4-methylthiobutanamide The procedure described in Example 180 was repeated, except that (R)-2-(4-chlorobenzenesulfonylamino)-4-methylthiobutanoic acid (715 mg) and ethyl 4-aminophenylacetate (430 mg) were condensed in dichloromethane (15 ml) in the presence of N,N'-dicyclohexylcarbodiimide (546 mg). The reaction mixture was filtered, and the filtrate was concentrated. The resulting crude product was recrystallized from hexanechloroform to obtain (R)-2-(4-chlorobenzenesulfonylamino)-N-(4-(ethoxycarbonylmethyl)phenyl)-4-methylthiobutanamide (22.9 mg).

Melting point: 138°–140° C.

The various spectra (IR, $^1$H-NMR, $^{13}$C-NMR, Fab-MS) were found to be identical to those of the racemate of Example 190.

Example 193

Preparation of (RS)-2-(4-chlorobenzenesulfonylamino)-N-(4-(2-methoxycarbonylethyl)phenyl)-4-methylthiobutanamide The procedure described in Example 177 was repeated, except that (RS)-2-(4-chlorobenzenesulfonylamino)-4-methylthiobutanoic acid (1.03 g) and methyl 4-aminophenylpropionate hydrochloride (617.4 mg) were condensed in chloroform (30 ml) in the presence of triethylamine (1.76 ml) and 1-methyl-2-chloropyridinium iodide (975.2 mg) to obtain as a colorless oil (RS)-2-(4-chlorobenzenesulfonylamino)-N-(4-(2-methoxycarbonylethyl)phenyl)-4-methylthiobutanamide (177.1 mg).

Melting point: 115.5°–117.5° C.

The various spectra (IR, $^1$H-NMR, Fab-MS) were found to be identical to those of the S-form of Example 194.

Example 194

Preparation of (S)-2-(4-chlorobenzenesulfonylamino)-N-(4-(2-methoxycarbonylethyl)phenyl)-4-methylthiobutanamide The procedure described in Example 180 was repeated, except that (S)-2-(4-chlorobenzenesulfonylamino)-4-methylthiobutanoic acid (14.79 g) and methyl 4-aminophenylpropionate (7.98 g) were condensed in dichloromethane (150 ml) in the presence of N,N'-dicyclohexylcarbodiimide (11.3 g)-The reaction mixture was filtered, and the filtrate was concentrated. The resulting crude product was recrystallized from methanolethyl acetate to obtain (S)-2-(4-chlorobenzenesulfonylamino)-N-(4-(2-methoxycarbonylethyl)phenyl)-4-methylthiobutanamide (5.66 g).

$[\alpha]_D^{27}$ –39.5° (c 1.00, CHCl$_3$)

Melting point: 116.5°–117.5° C.

IR vmax cm$^{-1}$ (KBr): 3350, 3250, 1736, 1664, 1327, 1165, 758.

$^1$H-NMR δ ppm (CDCl$_3$): 1.95–2.01 (2H, m), 2.036 (3H, s), 2.437 (1H, dd, J=13.8 Hz, J=6.3 Hz), 2.539 (1H, dd, J=13.8 Hz, J=6.8 Hz), 2.600 (2H, t, J=7.7 Hz), 2.910 (2H, t, J=7.7 Hz), 3.666 (3H, s), 4.077 (1H, q, J=7.2 Hz), 6.059 (1H, d, J=8.5 Hz), 7.123 (2H, d, J=8.3 Hz), 7.263 (2H, d, J=8.3 Hz), 7.424 (2H, d, J=8.8 Hz), 7.822 (2H, d, J=8.8 Hz), 8.085 (1H, s)

$^{13}$C-NMR δ ppm (CDCl$_3$): 15.17, 30.06, 30.32, 31.42, 35.60, 51.62, 56.50, 120.27, 128.67, 128.85, 129.55, 134.94, 137.36, 137.88, 139.78, 168.17, 173.19

Fab-MS m/z: 485 (MH$^+$)

Example 195

Preparation of (S)-2-(4chlorobenzenesulfonylamino)-N-(3-ethoxycarbonylphenyl)-4-methylthiobutanamide The procedure described in Example 180 was repeated, except that (S)-2-(4-chlorobenzenesulfonylamino)-4-methylthiobutanoic acid (10 g) and ethyl 3-aminobenzoate (4.1 g) were condensed in dichloromethane (80 ml) in the presence of N,N'-dicyclohexylcarbodiimide (7.65 g). The reaction mixture was filtered, and the filtrate was concentrated. The resulting crude product was recrystallized from methanol-ethyl acetate to obtain (S)-2-(4-chlorobenzenesulfonylamino)-N-(3-ethoxycarbonylphenyl)-4-methylthiobutanamide (2.13 g).

$[\alpha]_D^{28}$ –52.34° (c 1.01, CHCl$_3$)

Melting point: 150.5°–151° C.

IR vmax cm$^{-1}$ (KBr): 3273, 1724, 1660, 1545, 1439, 1292, 1163, 756, 565

$^1$H-NMR δ ppm (CDCl$_3$): 1.406 (3H, t, J=7.1 Hz), 1.84–2.13 (2H, m), 2.051 (3H, s), 2.42–2.64 (2H, m), 4.088 (1H, d, J=5.1 Hz, J=8.9 Hz), 4.380 (2H, q, J=7.1 Hz), 7.023 (1H, d, J=9.0 Hz), 7.30–7.38 (4H, m), 7.73–7.88 (4H, m), 9.307 (1H, s)

$^{13}$C-NMR δ ppm (CDCl$_3$): 13.79, 14.71, 29.40, 32.11, 56.27, 60.38, 119.91, 123.42, 124.40, 128.00, 128.23, 128.43, 130.27, 137.56, 138.22, 138.37, 165.49, 168.60

Fab-MS m/z: 471 (MH$^+$)

Example 196

Preparation of (S)-2-(4-bromobenzenesulfonylamino)-N-(4-(ethoxycarbonylmethyl)phenyl)-4-methylthiobutanamide The procedure described in Example 180 was repeated, except that (S)-2-(4-bromobenzenesulfonylamino)-4-methylthiobutanoic acid (7.86 g) and ethyl 4-aminophenylacetate (3.64 g) were condensed in dichloromethane (80 ml) in the presence of N,N'-dicyclohexylcarbodiimide (5.28 g). The reaction mixture was filtered, and the filtrate was concentrated. The resulting crude product was recrystallized from ethanol to obtain (S)-2-(4-bromobenzenesulfonylamino)-N-(4-(ethoxycarbonylmethyl)phenyl)-4-methylthiobutanamide (1.67 g).

$[\alpha]_D^{29}$ –34.3° (c 0.93, CHCl$_3$)

Melting point: 160°–161° C.

IR vmax cm$^{-1}$ (KCl-Solid): 3250, 1734, 1662, 1331, 1165, 742, 565

$^1$H-NMR δ ppm (CDCl$_3$): 1.255 (3H, t, J=7.1 Hz), 1.90–2.08 (2H, m), 2.031 (3H, s), 2.21–2.54 (2H, m), 3.576 (2H, s), 4.076 (1H, dd, J=8.7 Hz, J=5.5 Hz), 4.151 (2H, q, J=7.1 Hz), 6.150 (1H, d, J=8.5 Hz), 7.197 (2H, d, J=8.3 Hz), 7.282 (2H, d, J=8.3 Hz), 7.577 (2H, d, J=8.8 Hz), 7.740 (2H, d, J=8.8 Hz), 8.215 (1H, s)

$^{13}$C-NMR δ ppm (CDCl$_3$): 14.15, 15.21, 30.02, 31.60, 40.77, 56.50, 60.97, 120.24, 128.23, 128.74, 129.88, 130.76, 132.52, 135.75, 138.46, 168.31, 171.61

Fab-MS m/z: 529 (MH$^+$)

Example 197

Preparation of (S)-2-(4-bromobenzenesulfonylamino)-N-(4-(2-methoxycarbonylethyl)phenyl)-4-methylthiobutanamide The procedure described in Example 180 was repeated, except that (S)-2-(4-bromobenzenesulfonylamino)-4-methylthiobutanoic acid (10.72 g) and methyl 4-aminophenylpropionate (4.96 g) were condensed in dichloromethane (100 ml) in the presence of N,N'-dicyclohexylcarbodiimide (7.21 g). The reaction mixture was filtered, and the filtrate was concentrated. The resulting crude product was recrystallized from ethanol to obtain (S)-2-(4-bromobenzenesulfonylamino)-N-(4-(2-methoxycarbonylethyl)phenyl)-4-methylthiobutanamide (2.6 g).

$[\alpha]_D^{28}$ –28.8° (c 1.01, CHCl$_3$)

Melting point: 124°–125.5° C.

IR vmax cm$^{-1}$ (KBr): 3244, 1736, 1662, 1327, 1165, 823, 742, 611, 611, 567

$^1$H-NMR δ ppm (CDCl$_3$): 1.92–2.09 (2H, m), 2.009 (3H, s), 2.475 (2H, t, J=6.8 Hz), 2.596 (2H, t, J=7.7 Hz), 2.902 (2H, t, J=7.8 Hz), 3.665 (3H, s), 4.090 (1H, m), 6.411 (1H, bs), 7.100 (2H, d, J=8.3 Hz), 7.235 (2H, d, J=8.3 Hz), 7.537 (2H, d, J=8.5 Hz), 7.732 (2H, d, J=8.5 Hz), 8.400 (1H, s)

$^{13}$C-NMR δ ppm (CDCl$_3$): 15.17, 29.99, 30.28, 33.76, 35.60, 51.59, 56.57, 120.35, 128.08, 128.74, 129.37, 132.41, 135.05, 137.18, 138.54, 168.50, 173.23

Fab-MS m/z: 531 (MH$^+$+2)

Example 198

Preparation of (S)-2-(4-bromobenzenesulfonylamino)-N-(3-ethoxycarbonylphenyl)-4-methylthiobutanamide The procedure described in Example 180 was repeated, except that (S)-2-(4-bromobenzenesulfonylamino)-4-methylthiobutanoic acid (2.99 g) and ethyl 3-aminobenzoate (1.34 g) were condensed in dichloromethane (100 ml) in the presence of N,N'-dicyclohexylcarbodiimide (2.01 g). The reaction mixture was filtered, and the filtrate was concentrated. The resulting crude product was recrystallized from ethanol to obtain (S)-2-(4-bromobenzenesulfonylamino)-N-(3-ethoxycarbonylphenyl)-4-methylthiobutanamide (2.018 g).

$[\alpha]_D^{27}$ −36.3° (c 1.00, CHCl$_3$)

Melting point: 157°–158° C.

IR vmax cm$^{-1}$ (KBr): 3327, 3269, 2927, 2850, 1724, 1659, 1628, 1576, 1338, 1290, 1163, 1088, 829, 750

$^1$H-NMR δ ppm (CDCl$_3$): 1.406 (3H, t, J=7.1 Hz), 1.9–2.0 (2H, m), 2.050 (3H, s), 2.4–2.6 (2H, m), 4.0–4.1 (1H, m), 4.378 (2H, q, J=7.1 Hz), 7.345 (1H, t, J=8.1 Hz), 7.494 (2H, d, J=8.5 Hz), 7.730 (4H, d, J=8.5 Hz), 7.889 (1H, s), 9.448 (1H, s)

$^{13}$C-NMR δ ppm (CDCl$_3$): 14.05, 24.59, 29.72, 33.63, 56.64, 60.70, 120.22, 123.77, 124.83, 127.22, 128.40, 128.58, 130.65, 131.80, 137.70, 138.94, 165.84, 168.86

Fab-MS m/z: 517 (MH$^+$+2), 515(MH$^+$)

Example 199

Preparation of (RS)-2-(4-chlorobenzenesulfonylamino)-N-(4-(ethoxycarbonylmethyl)phenyl)-4-ethylthiobutanamide The procedure described in Example 177 was repeated, except that (RS)-2-(4-chlorobenzenesulfonylamino)-4-ethylthiobutanoic acid (1 g) and ethyl 4-aminophenylacetate hydrochloride (574.6 mg) were condensed in chloroform (30 ml) in the presence of triethylamine (1.64 ml) and 1-methyl-2-chloropyridinium iodide (907.5 mg) to obtain (RS)-2-(4-chlorobenzenesulfonylamino)-N-(4-(ethoxycarbonylmethyl)phenyl)-4-ethylthiobutanamide (113 mg).

Melting point: 70°–73° C.

IR vmax cm$^{-1}$ (KBr): 3331, 3250, 1734, 1664, 1340, 1165, 756, 625

$^1$H-NMR δ ppm (CDCl$_3$): 1.194 (3H, t, J=7.32 Hz), 1.249 (3H, t, J=7.08 Hz), 1.91–2.00 (2H, m), 2.40–2.53 (2H, m), 2.452 (2H, q, J=7.32 Hz), 3.567 (2H, s), 4.08–4.17 (1H, m), 4.141 (2H, q, J=7.08 Hz), 6.189 (1H, m), 7.186 (2H, d, J=8.54 Hz), 7.288 (2H, d, J=8.54 Hz), 7.404 (2H, d, J=8.79 Hz), 7.810 (2H, d, J=8.79 Hz), 8.272 (1H, s)

$^{13}$C-NMR δ ppm (CDCl$_3$): 14.19, 14.56, 25.82, 27.47, 32.16, 40.82, 56.62, 61.02, 120.32, 128.72, 129.38, 129.52, 129.89, 130.81, 135.83, 137.96, 139.76, 168.58, 171.70

Fab-MS m/z: 499 (MH$^+$)

Example 200

Preparation of (S)-2-(4-chlorobenzenesulfonylamino)-N-(4-(ethoxycarbonylmethyl)phenyl)-4-ethylthiobutanamide The procedure described in Example 180 was repeated, except that (S)-2-(4-chlorobenzenesulfonylamino)-4-ethylthiobutanoic acid (695.2 mg) and ethyl 4-aminophenylacetate (380 mg) were condensed in dichloromethane (30 ml) in the presence of N,N'-dicyclohexylcarbodiimide (509.5 mg). The reaction mixture was filtered, and the filtrate was concentrated. The resulting crude product was recrystallized from ethanol to obtain (S)-2-(4-chlorobenzenesulfonylamino)-N-(4-(ethoxycarbonylmethyl)phenyl)-4-ethylthiobutanamide (321.5 mg).

$[\alpha]_D^{23}$ −34.8° (c 0.76, CHCl$_3$)

Melting point: 143.5°–144° C.

The various spectra (IR, $^1$H-NMR, $^{13}$C-NMR, Fab-MS) were found to be identical to those of the racemate of Example 199.

Example 201

Preparation of (RS)-2-(4-chlorobenzenesulfonylamino)-N-(4-(2-methoxycarbonylethyl)phenyl)-4-ethylthiobutanamide The procedure described in Example 177 was repeated, except that (RS)-2-(4-chlorobenzenesulfonylamino)-4-ethylthiobutanoic acid (1.0 g) and methyl 4-aminophenylpropionate hydrochloride (638.4 mg) were condensed in chloroform (30 ml) in the presence of triethylamine (1.4 ml) and 1-methyl-2-chloropyridinium iodide (907.5 mg) to obtain (RS)-2-(4-chlorobenzenesulfonylamino)-N-(4-(2-methoxycarbonylethyl)phenyl)-4-ethylthiobutanamide (374 mg).

Melting point: 87°–89° C.

IR vmax cm$^{-1}$ (KBr): 3354, 3234, 1738, 1672, 1327, 1165, 829, 756

$^1$H-NMR δ ppm (CDCl$_3$): 1.183 (3H, t, J=7.3 Hz), 1.94–2.00 (2H, m), 2.39–2.50 (4H, m), 2.594 (2H, t, J=7.7 Hz), 2.899 (2H, t, J=7.8 Hz), 3.663 (3H, s), 4.02–4.17 (1H, m), 6.366 (1H, d, J=8.3 Hz), 7.100 (2H, d, J=8.4 Hz), 7.258 (2H, d, J=8.4 Hz), 7.390 (2H, d, J=8.7 Hz), 7.819 (2H, d, J=8.7 Hz), 8.298 (1H, s)

$^{13}$C-NMR δ ppm (CDCl$_3$): 14.48, 25.71, 27.41, 30.26, 32.14, 35.56, 51.57, 56.58, 120.34, 128.63, 128.75, 129.44, 135.03, 137.24, 137.99, 139.60, 168.52, 173.21

Fab-MS m/z: 499 (MH$^+$)

Example 202

Preparation of (S)-2-(4-bromobenzenesulfonylamino)-N-(4-(ethoxycarbonylmethyl)phenyl)-4-ethylthiobutanamide The procedure described in Example 180 was repeated, except that (S)-2-(4-bromobenzenesulfonylamino)-4-ethylthiobutanoic acid (199 mg) and ethyl 4-aminophenylacetate (95.7 mg) were condensed in dichloromethane (2 ml) in the presence of N,N'-dicyclohexylcarbodiimide (139.1 mg). The reaction mixture was filtered, and the filtrate was concentrated. The resulting crude product was recrystallized from ethanol to obtain (S)-2-(4-bromobenzenesulfonylamino)-N-(4-(ethoxycarbonylmethyl)phenyl)-4-ethylthiobutanamide (117.3 mg).

$[\alpha]_D^{30}$ −29.699° (c 1.00, CHCl$_3$)

Melting point: 154°–155° C.

IR vmax cm$^{-1}$ (KBr): 3253, 1732, 1656, 1338, 1157, 742, 563

$^1$H-NMR δ ppm (CD$_3$OD): 1.203 (3H, t, J=7.4 Hz), 1.234 (3H, t, J=7.1 Hz), 1.82–1.97 (2H, m), 2.41–2.66 (2H, m), 2.486 (2H, q, J=7.4 Hz), 3.577 (2H, s), 4.027 (1H, dd, J=8.5 Hz, J=5.6 Hz), 4.125 (2H, q, J=7.1 Hz), 7.179 (2H, d, J=8.7 Hz), 7.251 (2H, d, J=8.7 Hz), 7.561 (2H, d, J=8.8 Hz), 7.736 (2H, d, J=8.8 Hz)

$^{13}$C-NMR δ ppm (CD$_3$OD): 14.46, 15.04, 26.52, 28.24, 34.33, 41.48, 57.80, 61.91, 121.39, 128.36, 129.97, 130.63, 131.81, 133.27, 137.75, 141.05, 170.82, 173.43

Fab-MS m/z: 545 (MH$^+$+2)

Example 203

Preparation of (S)-2-(4-bromobenzenesulfonylamino)-4-ethylthio-N-(4-(2-methoxycarbonylethyl)phenyl)butanamide The procedure described in Example 180 was repeated, except that (S)-2-(4-bromobenzenesulfonylamino)-4-ethylthiobutanoic acid (224 mg) and methyl 4-aminophenylpropionate (102 mg) were condensed in dichloromethane (20 ml) in the presence of N,N'-dicyclohexylcarbodiimide (157 mg). The reaction mixture was filtered, and the filtrate was concentrated. The resulting crude product was recrystallized from ethanol to obtain (S)-2-(4-bromobenzenesulfonylamino)-4-ethylthio-N-(4-(2-methoxycarbonylethyl)phenyl)butanamide (105 mg).

$[\alpha]_D^{29}$ −24.4° (c 0.97, CHCl$_3$)

Melting point: 113.5°–115° C.

IR vmax cm$^{-1}$ (KBr): 3350, 3250, 1736, 1660, 1329, 1167, 1090, 1070, 825, 746, 567

$^1$H-NMR δ ppm (CDCl$_3$): 1.224 (3H, t, J=7.3 Hz), 1.981 (2H, q, J=7.3 Hz), 2.4–2.5 (4H, m), 2.603 (2H, t, J=7.7 Hz), 2.914 (2H, t, J=7.7 Hz), 3.668 (3H, s), 4.060 (1H, dd, J=14.9 Hz, J=6.6 Hz), 6.041 (1H, d, J=8.3 Hz), 7.134 (2H, d, J=8.5 Hz), 7.257 (2H, d, J=8.5 Hz), 7.594 (2H, d, J=8.8 Hz), 7.743 (2H, d, J=8.8 Hz), 8.055 (1H, s)

$^{13}$C-NMR δ ppm (CDCl$_3$): 14.51, 25.81, 27.49, 30.32, 31.86, 35.60, 51.62, 56.61, 120.27, 128.27, 128.78, 128.89, 132.52, 134.94, 137.36, 138.39, 168.09, 173.19

Fab-MS m/z: 545 (MH$^+$+2), 543 (MH$^+$)

Example 204

Preparation of (RS)-2-(4-chlorobenzenesulfonylamino)-N-(4-(ethoxycarbonylmethyl)phenyl)-3-phenylpropanamide The procedure described in Example 177 was repeated, except that (RS)-2-(4-chlorobenzenesulfonylamino)-3-phenylpropanoic acid (1 g) and ethyl 4-aminophenylacetate hydrochloride (571 mg) were condensed in chloroform (35 ml) in the presence of triethylamine (1.64 ml) and 1-methyl-2-chloropyridinium iodide (902 mg) to obtain (RS)-2-(4-chlorobenzenesulfonylamino)-N-(4-(ethoxycarbonylmethyl) phenyl)-3-phenylpropanamide (442.3 mg).

Melting point: 148°–150° C.

IR vmax cm$^{-1}$ (KBr): 3342, 1736, 1678, 1319, 1163, 829, 756

$^1$H-NMR δ ppm (CDCl$_3$): 1.25 (3H, t, J=7.2 Hz), 2.953 (1H, dd, J=13.9 Hz, J=8.0 Hz), 3.095 (1H, dd, J=13.9 Hz, J=6.1 Hz), 3.57 (2H, s), 4.14 (2H, q, J=7.08 Hz), 6.6–7.4 (5H, m), 6.97 (2H, d, J=8.3 Hz), 7.06 (2H, d, J=8.3 Hz), 7.31 (2H, d, J=8.8 Hz), 7.55 (2H, d, J=8.8 Hz)

$^{13}$C-NMR δ ppm (CDCl$_3$): 14.19, 38.69, 40.85, 58.82, 60.95, 115.30, 120.39, 127.47, 127.99, 128.39, 128.53, 128.75, 129.52, 129.85, 130.11, 130.84, 135.76, 137.04, 139.72, 168.07, 171.55

Fab-MS m/z: 501 (MH$^+$)

Example 205

Preparation of (S)-2-(4chlorobenzenesulfonylamino)-N-(4-(ethoxycarbonylmethyl)phenyl)-3-phenylpropanamide The procedure described in Example 180 was repeated, except that (S)-2-(4-chlorobenzenesulfonylamino)-3-phenylpropanoic acid (2.92 g) and ethyl 4-aminophenylacetate (1.54 mg) were condensed in dichloromethane (40 ml) in the presence of N,N'-dicyclohexylcarbodiimide (1.0 g). The reaction mixture was filtered, and the filtrate was concentrated. The resulting crude product was recrystallized from ethanol to obtain (S)-2-(4-chlorobenzenesulfonylamino)-N-(4-(ethoxycarbonylmethyl)phenyl)-3-phenylpropanamide (722.3 mg).

$[\alpha]_D^{26}$ −80.9° (c 1.05, CHCl$_3$)

Melting point: 165°–165.5° C.

The various spectra (IR, $^1$H-NMR, $^{13}$C-NMR, Fab-MS) were found to be identical to those of the racemate of Example 204.

Example 206

Preparation of (RS)-2-(4-chlorobenzenesulfonylamino)-N-(4-(2-methoxycarbonylethyl)phenyl)-3-phenylpropanamide Triethylamine (480 μl) and pivaloyl chloride (175 μl) were added to a solution of (RS)-2-(4-chlorobenzenesulfonylamino)-3-phenylpropanoic acid (301.7 mg) in THF (5 ml), and the whole was stirred for 2 hours. After methyl 4-aminophenylpropionate hydrochloride (229.8 mg) was added, the whole was stirred at room temperature overnight. The reaction mixture was poured into a saturated saline solution and extracted with ethyl acetate. The combined ethyl acetate layers were washed with a saturated saline solution, and dried over Na$_2$SO$_4$. The solvent was evaporated under reduced pressure to obtain a yellow oil. The product was purified by column chromatography (silica gel 50 g, hexane/ethyl acetate=3/1) to obtain (RS)-2-(4-chlorobenzenesulfonylamino)-N-(4-(2-methoxycarbonylethyl) phenyl)-3-phenylpropanamide (40.4 mg).

IR vmax cm$^{-1}$ (KBr): 3329, 1734, 1676, 1362, 1160, 1088, 754, 627

$^1$H-NMR δ ppm (CDCl$_3$): 2.596 (2H, t, J=7.8 Hz), 2.906 (2H, t, J=7.8 Hz), 3.104 (2H, dd, J=14.0 Hz, J=6.8 Hz), 3.662 (3H, s), 4.346 (1H, t, J=6.8 Hz), 6.980 (2H, d, J=7.3 Hz), 7.1–7.3 (5H, m), 7.305 (2H, d, J=8.6 Hz), 7.467 (1H, d, J=8.6 Hz), 7.553 (2H, d, J=8.6 Hz), 7.856 (1H, d, J=8.6 Hz)

$^{13}$C-NMR δ ppm (CDCl$_3$): 30.35, 35.60, 38.68, 51.62, 58.81, 120.39, 127.46, 128.49, 128.78, 129.07, 129.44, 134.98, 135.27, 137.07, 139.06, 168.60, 173.19

Fab-MS m/z: 501 (MH$^+$)

Example 207

Preparation of (S)-2-(4-chlorobenzenesulfonylamino)-N-(4-(2-methoxycarbonylethyl)phenyl)-3-phenylpropanamide The procedure described in Example 180 was repeated, except that (S)-2-(4-chlorobenzenesulfonylamino)-3-phenylpropanoic acid (3.10 g) and methyl 4-aminophenylpropionate (1.90 g) were condensed in dichloromethane (40 ml) in the presence of N,N'-dicyclohexylcarbodiimide (2.19 g). The reaction mixture was filtered, and the filtrate was concentrated. The resulting crude product was recrystallized from ethanol to obtain (S)-(RS)-2-(4-chlorobenzenesulfonylamino)-N-(4-(2-methoxycarbonylethyl)phenyl)-3-phenylpropanamide (2.65 g).

$[\alpha]_D^{29}$ −49.5° (c 0.786, CHCl$_3$)

Melting point: 145°–145.5° C.

The various spectra (IR, $^1$H-NMR, $^{13}$C-NMR, Fab-MS) were found to be identical to those of the racemate of Example 206.

Example 208

Preparation of (RS)-2-(4-bromobenzenesulfonylamino)-N-(4-(ethoxycarbonylmethyl)phenyl)-3-phenylpropanamide The procedure described in Example 179 was repeated, except that (RS)-2-(4-bromobenzenesulfonylamino)-3-phenylpropanoic acid (300.2 mg) and ethyl 4-aminophenylacetate hydrochloride (202.2 mg) were condensed in THF (5 ml) in the presence of triethylamine (422.4 μl) and pivaloyl chloride (153.9 μl), and then the resulting crude product was recrystallized from ethanol to obtain (RS)-2-(4-bromobenzenesulfonylamino)-N-(4-(ethoxycarbonylmethyl)phenyl)-3-phenylpropanamide (35.1 mg).

IR vmax cm$^{-1}$ (KBr): 3263, 1730, 1655, 1531, 1338, 1165, 744, 555

$^1$H-NMR δ ppm (CDCl$_3$): 1.249 (3H, t, J=7.2 Hz), 2.939 (1H, dd, J=14.0 Hz, J=8.2 Hz), 3.107 (1H, dd, J=14.0 Hz, J=6.0 Hz), 3.567 (2H, s), 3.987 (1H, m), 4.141 (2H, q, J=7.1 Hz), 5.399 (1H, d, J=7.1 Hz), 6.969 (2H, dd, J=7.7 Hz, J=1.6 Hz), 7.11–7.32 (7H, m), 7.466 (4H, s), 8.002 (1H, s)

$^{13}$C-NMR δ ppm (CDCl$_3$): 14.19, 38.69, 40.85, 58.86, 60.99, 120.43, 127.47, 128.24, 128.57, 129.12, 129.85, 130.81, 132.50, 135.25, 135.76, 137.56, 168.10, 171.59

Fab-MS m/z: 547

Example 209

Preparation of (S)-2-(4-bromobenzenesulfonylamino)-N-(4-(ethoxycarbonylmethyl)phenyl)-3-phenylpropanamide The procedure described in Example 180 was repeated, except that (S)-2-(4-bromobenzenesulfonylamino)-3-phenylpropanoic acid (5.83 g) and ethyl 4-aminophenylacetate (2.58 g) were condensed in dichloromethane (70 ml) in the presence of N,N'-dicyclohexylcarbodiimide (3.76 g). The reaction mixture was filtered, and the filtrate was concentrated. The resulting crude product was recrystallized from ethanol to obtain (S)-2-(4-bromobenzenesulfonylamino)-N-(4-(ethoxycarbonylmethyl)phenyl)-3-phenylpropanamide (3.20 g).

[α]$_D^{29}$ −71.6° (c 1.03, CHCl$_3$)

Melting point: 170.5°–171° C.

The various spectra (IR, $^1$H-NMR, $^{13}$C-NMR, Fab-MS) were found to be identical to those of the racemate of Example 208.

Example 210

Preparation of (R)-2-(4-bromobenzenesulfonylamino)-N-(4-(ethoxycarbonylmethyl)phenyl)-3-phenylpropanamide The procedure described in Example 180 was repeated, except that (R)-2-(4-bromobenzenesulfonylamino)-3-phenylpropanoic acid (3.0 g) and ethyl 4-aminophenylacetate (1.40 g) were condensed in dichloromethane (30 ml) in the presence of N,N'-dicyclohexylcarbodiimide (1.93 g). The reaction mixture was filtered, and the filtrate was concentrated. The resulting crude product was recrystallized from ethanol to obtain (R)-2-(4-bromobenzenesulfonylamino)-N-(4-(ethoxycarbonylmethyl)phenyl)-3-phenylpropanamide (3.34 g).

[α]$_D^{29}$ +71.2° (c 1.01, CHCl$_3$)

Melting point: 171°–171.5° C.

The various spectra (IR, $^1$H-NMR, $^{13}$C-NMR, Fab-MS) were found to be identical to those of the racemate of Example 208.

Example 211

Preparation of (S)-2-(4-bromobenzenesulfonylamino)-N-(4-(2-methoxycarbonylethyl)phenyl)-3-phenylpropanamide The procedure described in Example 180 was repeated, except that (S)-2-(4-bromobenzenesulfonylamino)-3-phenylpropanoic acid (5.17 g) and methyl 4-aminophenylpropionate (2.29 g) were condensed in dichloromethane (60 ml) in the presence of N,N'-dicyclohexylcarbodiimide (3.33 g). The reaction mixture was filtered, and the filtrate was concentrated. The resulting crude product was recrystallized from ethanol to obtain (S)-2-(4-bromobenzenesulfonylamino)-N-(4-(2-methoxycarbonylethyl)phenyl)-3-phenylpropanamide (3.73 g).

[α]$_D^{27}$ −68.5° (c 0.97, CHCl$_3$)

Melting point: 142°–143° C.

IR vmax cm$^{-1}$ (KBr): 3159, 1738, 1670, 1545, 1317, 1155, 744, 613

$^1$H-NMR δ ppm (CDCl$_3$): 2.584 (2H, t, J=7.7 Hz), 2.894 (2H, t, J=7.7 Hz), 2.83–2.96 (1H, m), 3.116 (1H, dd, J=13.9 Hz, J=5.9 Hz), 3.656 (3H, s), 4.031 (1H, bq, J=7.1 Hz), 5.647 (1H, d, J=6.6 Hz), 6.969 (2H, d, J=6.6 Hz), 7.10–7.21 (7H, m), 7.409 (2H, d, J=9.0 Hz), 7.466 (2H, d, J=9.0 Hz), 8.099 (1H, s)

$^{13}$C-NMR δ ppm (CDCl$_3$): 30.28, 35.56, 38.68, 51.62, 58.88, 120.53, 127.24, 128.05, 128.45, 128.74, 128.89, 129.04, 132.37, 134.94, 135.27, 137.22, 137.66, 168.31, 173.23

Fab-MS m/z: 547 (MH$^+$+2)

Example 212

Preparation of (R)-2-(4-bromobenzenesulfonylamino)-N-(4-(2-methoxycarbonylethyl)phenyl)-3-phenylpropanamide The procedure described in Example 180 was repeated, except that (R)-2-(4-bromobenzenesulfonylamino)-3-phenylpropanoic acid (3 g) and methyl 4-aminophenylpropionate (2.58 g) were condensed in dichloromethane (30 ml) in the presence of N,N'-dicyclohexylcarbodiimide (1.93 g). The reaction mixture was filtered, and the filtrate was concentrated. The resulting crude product was recrystallized from ethanol to obtain (R)-2-(4-bromobenzenesulfonylamino)-N-(4-(2-methoxycarbonylethyl)phenyl)-3-phenylpropanamide (3.09 g).

[α]$_D^{29}$ +70.2° (c 1.04, CHCl$_3$)

Melting point: 143°–144° C.

The various spectra (IR, $^1$H-NMR, $^{13}$C-NMR, Fab-MS) were found to be identical to those of the R form of Example 211.

Example 213

Preparation of (S)-2-(4-bromobenzenesulfonylamino)-N-(4-ethoxycarbonylphenyl)-3-phenylpropanamide The procedure described in Example 180 was repeated, except that (S)-2-(4-bromobenzenesulfonylamino)-3-phenylpropanoic acid (2 g) and ethyl 4-aminobenzoate were condensed in dichloromethane (100 ml) in the presence of N,N'-dicyclohexylcarbodiimide (1.29 g). The reaction mixture was filtered, and the filtrate was concentrated. The resulting crude product was recrystallized from a mixture of carbon tetrachloride and ethanol to obtain (S)-2-(4-bromobenzenesulfonylamino)-N-(4-ethoxycarbonylphenyl)-3-phenylpropanamide (623 mg).

[α]$_D^{28}$ 49.7° (c 0.90, THF)

Melting point: 176°–177° C.

IR vmax cm$^{-1}$ (KBr): 3356, 1687, 1601, 1535, 1410, 1313, 1279, 1167, 1109, 741

$^1$H-NMR δ ppm (CD$_3$OD): 1.374 (3H, t, J=7.1 Hz), 2.878 (1H, dd, J=13.6 Hz, J=8.3 Hz), 3.038 (1H, dd, J=13.6 Hz, J=7.0 Hz), 4.133 (1H, t, J=7.6 Hz), 4.339 (2H, q, J=7.1 Hz), 7.13–7.18 (5H, m), 7.377 (2H, d, J=8.8 Hz), 7.452 (2H, d, J=8.8 Hz), 7.572 (2H, d, J=8.8 Hz), 7.906 (2H, d, J=8.8 Hz)

$^{13}$C-NMR δ ppm (CD$_3$OD): 14.60, 40.16, 60.30, 61.98, 120.29, 127.04, 127.88, 128.17, 129.46, 129.79, 130.41, 131.37, 133.13, 137.53, 141.01, 143.39, 167.63, 171.26

Fab-MS m/z: 531 (MH$^+$)

Example 214

Preparation of (S)-2-(4-bromobenzenesulfonylamino)-N-(3-ethoxycarbonylphenyl)-3-phenylpropanamide The procedure described in Example 180 was repeated, except that (S)-2-(4-bromobenzenesulfonylamino)-3-phenylpropanoic acid (2 g) and ethyl 3-aminobenzoate were condensed in dichloromethane (100 ml) in the presence of N,N'-dicyclohexylcarbodiimide (1.29 g). The reaction mixture was filtered, and the filtrate was concentrated. The resulting crude product was recrystallized from ethanol to obtain (S)-2-(4-bromobenzenesulfonylamino)-N-(3-ethoxycarbonylphenyl)-3-phenylpropanamide (812 mg).

$[\alpha]_D^{28}$ –74.4° (c 0.84, CHCl$_3$)

Melting point: 173°–173.5° C.

IR vmax cm$^{-1}$ (KBr): 3257, 1724, 1695, 1552, 1165, 746, 619

$^1$H-NMR δ ppm (CDCl$_3$): 1.486 (3H, t, J=7.1 Hz), 3.034 (1H, dd, J=13.9 Hz, J=8.3 Hz), 3.238 (1H, dd, J=13.9 Hz, J=5.9 Hz), 4.11–4.20 (1H, m), 4.458 (2H, q, J=7.1 Hz), 5.646 (1H, d, J=7.3 Hz), 7.065 (2H, d, J=6.3 Hz), 7.21–7.37 (3H, m), 7.468 (1H, t, J=7.9 Hz), 7.534 (2H, d, J=9.0 Hz), 7.587 (2H, d, J=9.0 Hz), 7.839 (1H, d, J=9.3 Hz), 7.897 (1H, d, J=7.8 Hz), 8.014 (1H, s), 8.438 (1H, s)

$^{13}$C-NMR δ ppm (CDCl$_3$): 14.29, 38.16, 58.99, 61.27, 121.04, 124.60, 125.88, 127.35, 128.19, 128.52, 129.00, 129.11, 131.20, 132.45, 135.09, 137.11, 137.47, 166.15, 168.57

Fab-MS m/z: 533 (MH+2), 531 (MH$^+$)

Example 215

Preparation of (S)-2-(4chlorobenzenesulfonylamino)-N-(4-(ethoxycarbonylmethyl)phenyl)-3-(3-indolyl) propanamide The procedure described in Example 180 was repeated, except that (S)-2-(4-chlorobenzenesulfonylamino)-3-(3-indolyl) propanoic acid (5 g) and ethyl 4-aminophenylacetate (2.36 g) were condensed in a mixed solvent of dichloromethane (100 ml) and acetonitrile (10 ml) in the presence of N,N'-dicyclohexylcarbodiimide (3.27 g). The reaction mixture was filtered, and the filtrate was concentrated. The resulting crude product was recrystallized from ethanol/acetonitrile (10/1) to obtain (S)-2-(4-chlorobenzenesulfonylamino)-N-(4-(ethoxycarbonylmethyl)phenyl)-3-(3-indolyl)propanamide (4.86 g).

$[\alpha]_D^{29}$ –12.4° (c 0.99, MeCN)

Melting point: 182°–183.5° C.

IR vmax cm$^{-1}$ (KBr): 3251, 1720, 1648, 1533, 1340, 1165, 750

$^1$H-NMR δ ppm (DMSO-d$_6$): 1.202 (3H, t, J=7.1 Hz), 2.953 (1H, dd, J=14.5 Hz, J=8.2 Hz), 3.545 (2H, s), 4.086 (2H, q, J=7.1 Hz), 4.14–4.20 (1H, m), 6.89–7.57 (13H, m), 9.689 (1H, s), 10.538 (1H, s)

$^{13}$C-NMR δ ppm (DMSO-d$_6$): 13.67, 28.39, 39.79, 57.58, 59.77, 108.79, 110.94, 117.88, 119.41, 120.48, 123.64, 126.84, 127.68, 128.05, 128.86, 129.07, 135.83, 136.75, 136.83, 139.37, 169.03, 170.55

Fab-MS m/z: 540 (MH$^+$)

Example 216

Preparation of (S)-2-(4-chlorobenzenesulfonylamino)-3-(3-indolyl)-N-(4-(2-methoxycarbonylethyl)phenyl) propanamide The procedure described in Example 180 was repeated, except that (S)-2-(4-chlorobenzenesulfonylamino)-3-(3-indolyl) propanoic acid (4.80 g) and methyl 4-aminophenylpropionate (2.73 g) were condensed in a mixture of dichloromethane (80 ml) and acetonitrile (13 ml) in the presence of N,N'-dicyclohexylcarbodiimide (3.14 g). The reaction mixture was filtered, and the filtrate was concentrated. The resulting crude product was recrystallized from hexane/ethyl acetate (13/16) to obtain (S)-2-(4-chlorobenzenesulfonylamino)-3-(3-indolyl)-N-(4-(2-methoxycarbonylethyl)phenyl)propanamide (3.60 g).

$[\alpha]_D^{28}$ –13.3° (c 0.99, MeCN)

Melting point: 182°–183.5° C.

IR vmax cm$^{-1}$ (KBr): 3404, 1732, 1670, 1531, 1414, 1338, 1165, 754

$^1$H-NMR δ ppm (CDCl$_3$-DMSO-d$_6$): 2.577 (2H, t, J=7.5 Hz), 2.834 (2H, t, J=7.5 Hz), 2.952 (1H, dd, J=14.5 Hz, J=8.4 Hz), 3.130 (1H, dd, J=14.5 Hz, J=6.0 Hz), 3.612 (3H, s), 4.10–4.22 (1H, m), 6.938 (1H, t, J=7.0 Hz), 6.99–7.09 (4H, m), 7.136 (2H, d, J=8.7 Hz), 7.305 (3H, t, J=9.0 Hz), 7.481 (1H, d, J=8.9 Hz), 7.514 (2H, d, J=8.7 Hz), 8.126 (1H, d, J=9.2 Hz), 9.742 (1H, s), 10.545 (1H, s)

$^{13}$C-NMR δ ppm (CDCl$_3$-DMSO-d$_6$): 28.43, 29.67, 34.99, 50.94, 57.58, 108.81, 111.05, 117.98, 119.41, 120.58, 123.70, 126.82, 127.92, 127.99, 135.32, 135.84, 136.24, 136.94, 139.14, 169.06, 172.25

Fab-MS m/z: 540 (MH$^+$)

Example 217

Preparation of (RS)-2-(4-chlorobenzenesulfonylamino)-3-cyclohexylpropanoic acid (RS)-phenylalanine (500.2 mg) was dissolved in H$_2$O (50 ml) and 2N NaOH (1.5 ml). Rh/Al$_2$O$_3$ catalyst (500.5 mg) was added, and the whole was stirred overnight under a hydrogen atmosphere at atmospheric pressure. After the reaction was completed, Rh/Al$_2$O$_3$ was separated by filtration. The filtrate was concentrated to give crude (RS)-2-amino-3-cyclohexylpropanoic acid. Then, the crude (RS)-2-amino-3-cyclohexylpropanoic acid was dissolved in 2N NaOH (15.08 ml). THF (15 ml) and then 4-chlorobenzenesulfonyl chloride (3.196 g) were added, and the whole was stirred at room temperature overnight under argon. The reaction mixture was diluted with water, washed with ethyl acetate, acidified with 2N HCl and extracted 3 times with ethyl acetate. The combined ethyl acetate layers were washed with a saturated saline solution, and dried over Na$_2$SO$_4$. The solvent was evaporated under reduced pressure. The residue was purified by column chromatography (silica gel 80 g, ethyl acetate) and then by preparative TLC to obtain (RS)-2-(4-chlorobenzenesulfonylamino)-3-cyclohexylpropanoic acid (200.9 mg).

Melting point: 127°–129° C.

IR vmax cm$^{-1}$ (KBr): 3309, 2922, 2850, 1718, 1693, 1450, 1344, 1169, 1095, 825, 754

¹H-NMR δ ppm (CD₃OD): 0.8–1.0 (2H, m), 1.1–1.4 (2H, m), 1.4–1.5 (2H, m), 1.6–1.7 (5H, m), 3.315 (2H, dd, J=3.2 Hz, J=1.7 Hz), 3.8–3.9 (1H, m), 7.534 (2H, d, J=8.8 Hz), 7.819 (2H, d, J=8.8 Hz)

¹³C-NMR δ ppm (CD₃OD): 27.00, 27.25, 27.40, 32.94, 34.63, 34.77, 41.34, 54.83, 129.79, 130.12, 139.69, 141.01, 175.41

Fab-MS m/z: 346 (MH⁺)

Example 218

Preparation of (RS)-2-(4-chlorobenzenesulfonylamino)-3-cyclohexyl-N-(4-(ethoxycarbonylmethyl)phenyl)propanamide The procedure described in Example 179 was repeated, except that (RS)-2-(4-chlorobenzenesulfonylamino)-3-cyclohexylpropanoic acid (118.9 mg) and ethyl 4-aminophenylacetate hydrochloride (88.98 mg) were condensed in THF (3 ml) in the presence of triethylamine (135.67 mg) and pivaloyl chloride (66.33 mg), and then the resulting crude product was purified by column chromatography (silica gel 20 g, hexane/ethyl acetate=3/1) to obtain as a colorless oil (RS)-2-(4-chlorobenzenesulfonylamino)-3-cyclohexyl-N-(4-(ethoxycarbonylmethyl)phenyl)propanamide (66.2 mg).

IR vmax cm⁻¹ (neat): 3369, 2981, 2927, 2852, 1730, 1628, 1518, 1416, 1369, 1163, 1093, 1032, 829, 754

¹H-NMR δ ppm (CDCl₃): 0.7–1.1 (4H, m), 1.1–1.4 (2H, m), 1.238 (3H, t, J=7.1 Hz), 1.3–1.7 (5H, m), 3.4–3.5 (2H, m), 3.562 (2H, s), 3.8–3.9 (1H, m), 4.128 (2H, q, J=7.1 Hz), 6.628 (2H, d, J=8.3 Hz), 7.055 (2H, d, J=8.3 Hz), 7.178 (1H, d, J=8.3 Hz), 7.268 (1H, d, J=8.5 Hz), 7.370 (1H, d, J=8.5 Hz), 7.771 (1H, d, J=8.5 Hz)

¹³C-NMR δ ppm (CDCl₃): 14.11, 25.77, 26.06, 26.17, 32.00, 33.51, 40.51, 40.77, 55.47, 60.64, 60.86, 115.21, 120.24, 123.98, 128.63, 129.37, 129.70, 130.03, 145.32, 169.60, 171.58

Fab-MS m/z: 507 (MH⁺)

Example 219

Preparation of (RS)-2-(4-chlorobenzenesulfonylamino)-3-cyclohexyl-N-(4-(2-methoxycarbonylethyl)phenyl)propanamide The procedure described in Example 180 was repeated, except that (RS)-2-(4-chlorobenzenesulfonylamino)-3-cyclohexylpropanoic acid (200 mg) and methyl 4-aminophenylpropionate (103.64 mg) were condensed in dichloromethane (5 ml) in the presence of N,N'-dicyclohexylcarbodiimide (143.18 mg). The reaction mixture was filtered, and the filtrate was concentrated. The resulting crude product was purified by column chromatography (silica gel 20 g, hexane/ethyl acetate=3/1) to obtain (RS)-2-(4-chlorobenzenesulfonylamino)-3-cyclohexyl-N-(4-(2-methoxycarbonylethyl)phenyl)propanamide (165.2 mg).

Melting point: 64°–65° C.

IR vmax cm⁻¹ (neat): 3271, 2926, 2852, 1738, 1666, 1605, 1535, 1414, 1323, 1163, 1093, 825, 754

¹H-NMR δ ppm (CDCl₃): 0.7–1.0 (2H, m), 1.0–1.4 (4H, m), 1.4–1.7 (5H, m), 2.598 (2H, t, J=7.7 Hz), 2.905 (2H, t, J=7.7 Hz), 3.4–3.6 (2H, m), 3.670 (3H, s), 3.8–3.9 (1H, m), 5.783 (1H, d, J=7.8 Hz), 7.106 (2H, d, J=8.3 Hz), 7.263 (2H, d, J=8.5 Hz), 7.399 (2H, d, J=8.5 Hz), 7.814 (2H, d, J=8.5 Hz), 8.138 (1H, s)

¹³C-NMR δ ppm (CDCl₃): 24.82, 25.81, 26.06, 30.32, 32.11, 33.58, 33.84, 35.63, 40.59, 51.62, 55.62, 120.35, 128.74, 128.93, 129.44, 135.24, 137.11, 137.88, 139.67, 169.52, 173.26

Fab-MS m/z: 507 (MH⁺)

Example 220

Preparation of (RS)-N-(4-(carboxymethyl) phenyl)-3-(4-chlorobenzenesulfonylamino)butanamide A mixture of (RS)-2-(4-chlorobenzenesulfonylamino)-N-(4-(ethoxycarbonylmethyl)phenyl)butanamide (114.2 mg), ethanol (8 ml), and 2N NaOH (650 ml) was stirred at room temperature overnight under argon. The reaction mixture was concentrated under reduced pressure. It was repeated 3 times in order to remove ethanol completely that a small amount of purified water was added to the residue, and then the product was concentrated under reduced pressure. The residue was dissolved in purified water and washed with ethyl acetate. The aqueous layer was acidified with 1N HCl and then extracted with ethyl acetate. The combined ethyl acetate layers were washed with a saturated saline solution and dried over Na₂SO₄. Then, the solvent was evaporated under reduced pressure to obtain (RS)-N-(4-(carboxymethyl) phenyl)-2-(4-chlorobenzenesulfonylamino) butanamide (91.1 mg).

Melting point: 185°–186° C.

IR vmax cm⁻¹ (KBr): 3250, 1710, 1325, 1165, 829, 756

¹H-NMR δ ppm (CDCl₃-CD₃OD-DMSO-d₆): 0.915 (3H, t, J=7.45 Hz), 1.5–1.8 (2H, m), 3.54 (2H, s), 3.822 (1H, t, J=7.0 Hz), 7.18 (2H, d, J=8.4 Hz), 7.28 (2H, d, J=8.4 Hz), 7.425 (2H, d, J=8.5 Hz), 7.815 (2H, d, J=8.5 Hz)

¹³C-NMR δ ppm (CDCl₃-CD₃OD-DMSO-d₆): 10.64, 27.55, 41.31, 59.97, 121.14, 129.80, 130.12, 130.64, 131.91, 137.81, 139.54, 140.75, 170.95, 174.61

Fab-MS m/z: 411 (MH⁺)

Example 221

Preparation of (RS)-N-(4-(carboxymethyl)phenyl)-2-(4-chlorobenzenesulfonylamino)pentanamide The procedure described in Example 39 was repeated, except that (RS)-2-(4-chlorobenzenesulfonylamino)-N-(4-(ethoxycarbonylmethyl)phenyl)pentanamide (122.4 mg) was hydrolyzed to obtain (RS)-N-(4-(carboxymethyl) phenyl)-2-(4-chlorobenzenesulfonylamino)pentanamide (103.6 mg).

Melting point: 202°–204° C.

IR vmax cm⁻¹ (KBr): 3331, 3263, 1705, 1660, 1333, 1165, 829, 756

¹H-NMR δ ppm (CDCl₃-CD₃OD-DMSO-d₆): 0.833 (3H, t, J=7.32 Hz), 1.2–1.5 (2H, m), 1.5 (2H, m), 3.49 (2H, s), 3.6–3.8 (1H, m), 7.15 (2H, d, J=8.54 Hz), 7.29 (2H, d, J=8.54 Hz), 7.48 (2H, d, J=8.7 Hz), 7.79 (2H, d, J=8.7 Hz)

¹³C-NMR δ ppm (CDCl₃-CD₃OD-DMSO-d₆): 13.17, 18.23, 34.77, 39.50, 56.77, 119.52, 119.59, 127.59, 128.43, 128.80, 129.27, 130.23, 136.68, 136.79, 137.34, 139.87, 169.32, 172.51

Fab-MS m/z: 425 (MH⁺)

Example 222

Preparation of (RS)-N-(4-(carboxymethyl)phenyl)-2-(4-chlorobenzenesulfonylamino)hexanamide The procedure described in Example 39 was repeated, except that (RS)-2-(4-chlorobenzenesulfonylamino)-N-(4-(ethoxycarbonylmethyl)phenyl)hexanamide (113.3 mg) was hydrolyzed to obtain (RS)-N-(4-(carboxymethyl)phenyl)-2-(4-chlorobenzenesulfonylamino)hexanamide (96.1 mg).

Melting point: 192°–194° C.

IR vmax cm$^{-1}$ (KBr): 3259, 1709, 1666, 1327, 1165, 829, 756

$^1$H-NMR δ ppm (CDCl$_3$-CD$_3$OD): 0.87 (3H, t, J=7.0 Hz), 1.2 (2H, m), 1.3 (2H, m), 1.6 (2H, m), 3.3 (2H, s), 3.5–3.6 (1H, m), 7.22 (2H, d, J=8.3 Hz), 7.40 (2H, d, J=8.3 Hz), 7.52 (2H, d, J=8.8 Hz), 7.80 (2H, d, J=8.8 Hz)

$^{13}$C-NMR δ ppm (CDCl$_3$-CD$_3$OD): 14.13, 23.03, 28.64, 33.91, 41.34, 58.89, 121.28, 129.75, 130.09, 130.55, 131.99, 137.55, 139.88, 140.37, 171.44, 175.27

Fab-MS m/z: 439 (MH$^+$)

Example 223

Preparation of (S)-N-(4-(carboxymethyl)phenyl)-2-(4-chlorobenzenesulfonylamino)hexanamide The procedure described in Example 39 was repeated, except that (S)-2-(4-chlorobenzenesulfonylamino)-N-(4-(ethoxycarbonylmethyl)phenyl)hexanamide (1.88 g) was hydrolyzed to obtain (S)-N-(4-(carboxymethyl)phenyl)-2-(4-chlorobenzenesulfonylamino)hexanamide (1.552 g).

$[α]_D^{28}$ –11.3° (c 0.92, THF)

Melting point: 212°–214° C.

The various spectra (IR, $^1$H-NMR, $^{13}$C-NMR, Fab-MS) were found to be identical to those of the racemate of Example 222.

Example 224

Preparation of (R)-N-(4-(carboxymethyl)phenyl)-2-(4-chlorobenzenesulfonylamino)hexanamide The procedure described in Example 39 was repeated, except that (R)-2-(4-chlorobenzenesulfonylamino)-N-(4-(ethoxycarbonylmethyl)phenyl)hexanamide (126.4 mg) was hydrolyzed to obtain (R)-N-(4-(carboxymethyl)phenyl)-2-(4-chlorobenzenesulfonylamino)hexanamide (87.0 mg).

Melting point: 165°–167° C.

The various spectra (IR, $^1$H-NMR, $^{13}$C-NMR, Fab-MS) were found to be identical to those of the racemate of Example 222.

Example 225

Preparation of (S)-N-(4-(2-carboxyethyl)phenyl)-2-(4-chlorobenzenesulfonylamino)hexanamide (S)-2-(4-chlorobenzenesulfonylamino)-N-(4-(ethoxycarbonylmethyl)phenyl)hexanamide (2.717 g) was dissolved in methanol (50 ml). 2N NaOH (8.72 ml) was added and the whole was stirred at room temperature overnight under argon. The reaction mixture was concentrated under reduced pressure to remove methanol. The concentrate was poured in 6N HCl while cooling with ice. The precipitated crystals were filtered and recrystallized from acetonitrile to obtain (S)-N-(4-(2-carboxyethyl)phenyl)-2-(4-chlorobenzenesulfonylamino)hexanamide (1.629 g).

$[α]_D^{28}$ –11.4° (c 0.901, THF)

Melting point: 178°–179° C.

The various spectra (IR, $^1$H-NMR, $^{13}$C-NMR, Fab-MS) were found to be identical to those of the racemate of Example 222.

Example 226

Preparation of (RS)-2-(4-bromobenzenesulfonylamino)-N-(4-(carboxymethyl)phenyl)hexanamide The procedure described in Example 39 was repeated, except that (RS)-2-(4-bromobenzenesulfonylamino)-N-(4-(ethoxycarbonylmethyl)phenyl)hexanamide (123.8 mg) was hydrolyzed to obtain (RS)-2-(4-bromobenzenesulfonylamino)-N-(4-(carboxymethyl)phenyl)hexanamide (50.4 mg).

Melting point: 180°–182° C.

IR vmax cm$^{-1}$ (KBr): 3332, 3253, 1707, 1670, 1329, 1165, 742

$^1$H-NMR δ ppm (CDCl$_3$-DMSO-d$_6$): 0.820 (3H, t, J=7.0 Hz), 1.15–1.33 (4H, m), 1.52–1.63 (2H, m), 3.473 (2H, s), 3.873 (1H, bd, J=6.8 Hz), 7.137 (2H, d, J=8.5 Hz), 7.295 (2H, d, J=8.5 Hz), 7.589 (2H, d, J=8.8 Hz), 7.713 (2H, d, J=8.8 Hz), 7.870 (1H, d, J=8.5 Hz), 9.616 (1H, s)

$^{13}$C-NMR δ ppm (CDCl$_3$-DMSO-d$_6$): 13.61, 15.37, 21.67, 27.21, 32.53, 57.17, 119.62, 126.11, 128.53, 129.30, 130.15, 131.73, 136.93, 140.56, 169.24, 172.43

Fab-MS m/z: 485 (MH$^+$+2)

Example 227

Preparation of (S)-2-(4-bromobenzenesulfonylamino)-N-(4-(carboxymethyl)phenyl)hexanamide The procedure described in Example 225 was repeated, except that (S)-2-(4-bromobenzenesulfonylamino)-N-(4-(ethoxycarbonylmethyl)phenyl)hexanamide (3.0 g) was hydrolyzed and recrystallized from acetonitrile to obtain (S)-2-(4-bromobenzenesulfonylamino)-N-(4-(carboxymethyl) phenyl)hexanamide (2.23 g).

$[α]_D^{29}$ –22.5° (c 0.99, MeOH)

Melting point: 199.5°–201° C.

The various spectra (IR, $^1$H-NMR, $^{13}$C-NMR, Fab -MS) were found to be identical to those of the racemate of Example 225.

Example 228

Preparation of (S)-2-(4-bromobenzenesulfonylamino)-N-(4-(2-carboxyethyl)phenyl)hexanamide The procedure described in Example 225 was repeated, except that (S)-2-(4-bromobenzenesulfonylamino)-N-(4-(2-methoxycarbonylethyl)phenyl)hexanamide (3.0 g) was hydrolyzed and recrystallized from acetonitrile to obtain (S)-2-(4-bromobenzenesulfonylamino)-N-(4-(2-carboxyethyl)phenyl)hexanamide (1.36 g).

$[α]_D^{29}$ –20.1° (c 1.02, MeOH)

Melting point: 183°–185° C.

IR vmax cm$^{-1}$ (KBr): 3255, 1707, 1657, 1539, 1336, 1165, 741, 611

$^1$H-NMR δ ppm (DMSO-d$_6$): 0.798 (3H, t, J=6.8 Hz), 1.12–1.30 (4H, m), 1.47–1.65 (2H, m), 2.488 (2H, t, J=7.4 Hz), 2.775 (2H, t, J=7.6 Hz), 3.81–3.90 (1H, m), 7.098 (2H, d, J=8.5 Hz), 7.251 (2H, d, J=8.5 Hz), 7.628 (2H, d, J=8.9 Hz), 7.703 (2H, d, J=8.9 Hz), 7.983 (2H, d, J=9.0 Hz), 9.648 (1H, s), 11.873 (1H, s)

$^{13}$C-NMR δ ppm (DMSO-d$_6$): 13.32, 21.27, 26.89, 29.60, 32.09, 35.06, 38.58, 56.74, 119.37, 125.75, 127.95, 128.28, 131.55, 135.84, 136.06, 168.80, 173.24

Fab-MS m/z: 497 (MH$^+$)

Example 229

Preparation of (S)-3-(4-bromobenzenesulfonylamino)-N-(3-carboxyphenyl)hexanamide The procedure described in Example 225 was repeated, except that (S)-2-(4-bromobenzenesulfonylamino)-N-(3- ethoxycarbonylphenyl)hexanamide (1.85 g) was hydrolyzed and recrystallized from acetonitrile to obtain (S)-2-(4-bromobenzenesulfonylamino)-N-(3-carboxyphenyl) hexanamide (1.21 g).

$[\alpha]_D^{29}$ -9.36° (c 0.94, THF)

Melting point: 235°–236° C.

IR vmax cm$^{-1}$ (KBr): 3248, 1699, 1552, 1327, 1165, 742, 617

$^1$H-NMR δ ppm (DMSO-d$_6$): 0.808 (3H, t, J=7.0 Hz), 1.14–1.34 (4H, m), 1.50–1.68 (2H, m), 3.82–3.92 (1H, m), 7.369 (1H, t, J=7.8 Hz), 7.59–7.69 (2H, m), 7.619 (2H, d, J=8.5 Hz), 7.711 (2H, d, J=8.5 Hz), 8.001 (1H, t, J=1.7 Hz), 8.024 (1H, d, J=8.8 Hz), 9.908 (1H, s), 12.668 (1H, s)

$^{13}$C-NMR δ ppm (DMSO-d$_6$): 13.27, 21.21, 26.86, 31.90, 56.78, 119.99, 123.15, 124.02, 125.78, 128.25, 128.40, 131.07, 131.48, 138.22, 140.12, 166.67, 169.20

Fab-MS m/z: 469 (MH$^+$)

Example 230

Preparation of (RS)-N-(4-(carboxymethyl)phenyl)-2-(4-chlorobenzenesulfonylamino)octanamide The procedure described in Example 39 was repeated, except that (RS)-2-(4-chlorobenzenesulfonylamino)-N-(4-(ethoxycarbonylmethyl)phenyl)octanamide (123.6 mg) was hydrolyzed to obtain (RS)-N-(4-(carboxymethyl)phenyl)-2-(4-chlorobenzenesulfonylamino)octanamide (112.5 mg).

Melting point: 192°–193° C.

IR vmax cm$^{-1}$ (KBr): 3452, 3263, 1701, 1655, 1335, 1165, 829, 756

$^1$H-NMR δ ppm (CDCl$_3$-DMSO-d$_6$): 0.84 (3H, t, J=6.7 Hz), 1.1–1.3 (6H, m), 1.5 (4H, m), 3.0–3.8 (4H, m), 7.15 (2H, d, J=8.54 Hz), 7.30 (2H, d, J=8.54 Hz), 7.48 (2H, d, J=8.55 Hz), 7.79 (2H, d, J=8.55 Hz)

$^{13}$C-NMR δ ppm (CDCl$_3$-DMSO-d$_6$): 13.57, 21.71, 24.76, 27.91, 30.88, 32.53, 40.12, 56.92, 119.44, 128.28, 128.65, 129.13, 130.04, 136.68, 137.19, 139.83, 139.17, 172.33

Fab-MS m/z: 467 (MH$^+$)

Example 231

Preparation of (RS)-N-(4-(carboxymethyl) phenyl)-2-(4-chlorobenzenesulfonylamino)-3-methylbutanamide The procedure described in Example 39 was repeated, except that (RS)-2-(4-chlorobenzenesulfonylamino)-N-(4-(ethoxycarbonylmethyl)phenyl)-3-methylbutanamide (121.7 mg) was hydrolyzed to obtain (RS)-N-(4-(carboxymethyl)phenyl)-2-(4-chlorobenzenesulfonylamino)-3-methylbutanamide (93.4 mg).

Melting point: 228°–230° C.

IR vmax cm$^{-1}$ (KBr): 3280, 1705, 1660, 1329, 1165, 829, 756

$^1$H-NMR δ ppm (CDCl$_3$-DMSO-d$_6$): 0.895 (3H, d, J=6.4 Hz), 0.872 (3H, d, J=6.4 Hz), 1.9 (1H, m), 3.47 (2H, s), 3.6–3.7 (1H, m), 7.13 (2H, d, J=8.3 Hz), 7.25 (2H, d, J=8.3 Hz), 7.45 (2H, d, J=8.55 Hz), 7.59 (2H, d, J=8.55 Hz), 7.77 (2H, d, J=8.55 Hz), 7.83 (2H, d, J=8.55 Hz)

$^{13}$C-NMR δ ppm (CDCl$_3$-DMSO-d$_6$): 18.08, 18.62, 30.66, 40.13, 62.42, 119.34, 127.33, 128.19, 128.48, 129.03, 129.92, 136.46, 136.92, 139.77, 168.37, 172.17

Fab-MS m/z: 425 (MH$^+$)

Example 232

Preparation of (RS)-N-(4-(carboxymethyl) phenyl)-2-(4-chlorobenzenesulfonylamino)-4-methylpentanamide The procedure described in Example 39 was repeated, except that (RS)-2-(4-chlorobenzenesulfonylamino)-N-(4-(ethoxycarbonylmethyl)phenyl)-4-methylpentanamide (111.4 mg) was hydrolyzed to obtain (RS)-N-(4-(carboxymethyl) phenyl)-2-(4-chlorobenzenesulfonylamino)-4-methylpentanamide (99.0 mg).

Melting point: 208°–209° C.

IR vmax cm$^{-1}$ (KBr): 3273, 1711, 1674, 1325, 1165, 827, 754

$^1$H-NMR δ ppm (CDCl$_3$-DMSO-d$_6$): 0.818 (3H, d, J=6.6 Hz), 0.882 (3H, d, J=6.6 Hz), 1.2 (1H, m), 1.4–1.5 (2H, m), 3.5 (2H, s), 3.7–3.9 (1H, m), 7.14 (2H, d, J=8.5 Hz), 7.28 (2H, d, J=8.5 Hz), 7.45 (2H, d, J=8.1 Hz), 7.79 (2H, d, J=8.1 Hz)

$^{13}$C-NMR δ ppm (CDCl$_3$-DMSO-d$_6$): 22.52, 23.87, 40.12, 41.48, 55.60, 119.48, 128.28, 128.61, 129.09, 130.01, 136.68, 137.19, 139.76, 169.35, 172.29

Fab-MS m/z: 439 (MH$^+$)

Example 233

Preparation of (RS)-N-(4-(carboxymethyl) phenyl)-2-(4-chlorobenzenesulfonylamino)-4-methylthiobutanamide The procedure described in Example 39 was repeated, except that (RS)-2-(4-chlorobenzenesulfonylamino)-N-(4-(ethoxycarbonylmethyl)phenyl)-4-methylthiobutanamide (119.4 mg) was hydrolyzed to obtain (RS)-N-(4-(carboxymethyl)phenyl)-2-(4-chlorobenzenesulfonylamino)-4-methylthiobutanamide (109.4 mg).

Melting point: 169.5°–177° C.

IR vmax cm$^{-1}$ (KBr): 3261, 1705, 1659, 1335, 1163, 1093, 1086, 756, 625

$^1$H-NMR δ ppm (CDCl$_3$): 1.79–1.91 (2H, m), 1.994 (3H, s), 2.30–2.52 (4H, m), 3.477 (2H, s), 3.89–4.07 (1H, m), 7.144 (2H, d, J=8.54 Hz), 7.311 (2H, d, J=8.54 Hz), 7.475 (2H, d, J=8.55 Hz), 7.792 (2H, d, J=8.54 Hz), 8.024 (1H, bs), 9.708 (1H, s), $^{13}$C-NMR δ ppm (CDCl$_3$): 14.38, 29.16, 32.24, 39.98, 55.97, 119.30, 128.06, 128.47, 128.91, 129.90, 136.46, 137.12, 139.58, 168.29, 172.03

Fab-MS m/z: 457 (MH$^+$)

Example 234

Preparation of (S)-N-(4-(carboxymethyl) phenyl)-2-(4chlorobenzenesulfonylamino)-4-methylthiobutanamide A solution of K$_2$CO$_3$ (3.2 g) in water (40 ml) was added to a solution of (S)-2-(4-chlorobenzenesulfonylamino)-N-(4-(ethoxycarbonylmethyl)phenyl)-4-methylthiobutanamide (3.75 g) in methanol (80 ml), and the whole was stirred at room temperature overnight under argon. The reaction mixture was concentrated under reduced pressure. It was repeated 3 times in order to remove methanol completely that a small amount of purified water was added to the residue, and then the product was concentrated under reduced pressure. The residue was dissolved in purified water and washed with ethyl acetate. The aqueous layer was acidified with 1N HCl, and then extracted with ethyl acetate. The combined ethyl acetate layers were washed with a saturated saline solution, and dried over Na$_2$SO$_4$. Then, the solvent was evaporated under reduced pressure, and the resulting crude product was recrystallized from acetonitrile to obtain (S)-N-(4-(carboxymethyl)phenyl)-2-(4-chlorobenzenesulfonylamino)-4-methylthiobutanamide (2.84 g).

Melting point: 192.5°–193.5° C.

[α]$_D^{27}$ –26.8° (c 1.17, THF)

The various spectra (IR, $^1$H-NMR, $^{13}$C-NMR, Fab-MS) were found to be identical to those of the racemate of Example 233.

Example 235

Preparation of (R)-N-(4-(carboxymethyl) phenyl)-2-4-chlorobenzenesulfonylamino)-4-methylthiobutanamide The procedure described in Example 39 was repeated, except that (R)-2-(4-chlorobenzenesulfonylamino)-N-(4-(ethoxycarbonylmethyl)phenyl)-4-methylthiobutanamide (19.5 mg) was hydrolyzed to obtain (R)-N-(4-(carboxymethyl) phenyl)-2-(4-chlorobenzenesulfonylamino)-4-methylthiobutanamide (12.0 mg).

Melting point: 169°–170° C.

The various spectra (IR, $^1$H-NMR, $^{13}$C-NMR, Fab-MS) were found to be identical to those of the racemate of Example 233.

Example 236

Preparation of (RS)-N-(4-(2-carboxyethyl) phenyl)-2-(4-chlorobenzenesulfonylamino)-4-methylthiobutanamide The procedure described in Example 39 was repeated, except that (RS)-2-(4-chlorobenzenesulfonylamino)-N-(4-(2-methoxycarbonylethyl)phenyl)-4-methylthiobutanamide (82.3 mg) was hydrolyzed to obtain (RS)-N-(4-(2-carboxyethyl) phenyl)-2-(4-chlorobenzenesulfonylamino)-4-methylthiobutanamide (58.7 mg).

Melting point: 143°–145° C.

The various spectra (IR, $^1$H-NMR, $^{13}$C-NMR, Fab-MS) were found to be identical to those of the S-form of Example 237.

Example 237

Preparation of (S)-N-(4-(2-carboxyethyl) phenyl)-2-(4-chlorobenzenesulfonylamino)-4-methylthiobutanamide The procedure described in Example 234 was repeated, except that (S)-2-(4-chlorobenzenesulfonylamino)-N-(4-(2-methoxycarbonylethyl)phenyl)-4-methylthiobutanamide (4.29 g) was hydrolyzed and recrystallized from acetonitrile to obtain (S)-N-(4-(2-carboxyethyl)phenyl)-2-(4-chlorobenzenesulfonylamino)-4-methylthiobutanamide (3.48 g).

[α]$_D^{27}$ –25.6° (c 0.91, MeOH)

Melting point: 167.5°–169° C.

IR νmax cm$^{-1}$ (KBr): 3400 (br), 3338, 3259, 1701, 1662, 1335, 1163, 758

$^1$H-NMR δ ppm (CDCl$_3$-DMSO-d$_6$): 1.81–2.02 (2H, m), 2.034 (3H, s), 2.40–2.57 (2H, m), 2.564 (2H, t, J=7.8 Hz), 2.891 (2H, t, J=7.8 Hz), 4.02–4.08 (1H, m), 7.112 (2H, d, J=8.5 Hz), 7.256 (2H, d, J=8.5 Hz), 7.351 (2H, d, J=8.8 Hz), 7.797 (2H, d, J=8.8 Hz), 9.098 (1H, s)

$^{13}$C-NMR δ ppm (CDCl$_3$-DMSO-d$_6$): 14.95, 29.69, 30.06, 32.33, 35.45, 56.43, 119.72, 128.27, 128.67, 128.85, 135.42, 136.63, 138.43, 138.68, 168.46, 174.58

Fab-MS m/z: 471 (MH$^+$)

Example 238

Preparation of (S)-N-(3-carboxyphenyl)-2-(4-chlorobenzenesulfonylamino)-4-methylthiobutanamide The procedure described in Example 39 was repeated, except that (S)-2-(4-chlorobenzenesulfonylamino)-N-(3-ethoxycarbonylphenyl)-4-methylthiobutanamide (2 g) was hydrolyzed and recrystallized from acetonitrile to obtain (S)-N-(3-carboxyphenyl)-2-(4-chlorobenzenesulfonylamino)-4-methylthiobutanamide (1.60 g).

[α]$_D^{27}$ –15.75° (c 1.003, THF)

Melting point: 225°–225.5° C.

IR νmax cm$^{-1}$ (KBr): 3246, 2920, 1699, 1593, 1437, 1327, 1163, 1093, 829, 756

$^1$H-NMR δ ppm (DMSO-d$_6$): 1.8–2.0 (2H, m), 2.002 (3H, s), 2.3–2.5 (2H, m), 4.0–4.1 (1H, m), 7.370 (1H, t, J=8.3 Hz), 7.480 (2H, d, J=8.8 Hz), 7.628 (2H, d, J=8.3 Hz), 7.794 (2H, d, J=8.8 Hz), 8.014 (1H, s)

$^{13}$C-NMR δ ppm (DMSO-d$_6$): 18.16, 29.16, 32.09, 56.04, 120.18, 123.30, 124.14, 128.17, 128.36, 128.61, 131.11, 137.08, 138.18, 139.58, 166.68, 168.69

Fab-MS m/z: 443 (MH$^+$)

Example 239

Preparation of (S)-2-(4-bromobenzenesulfonylamino)-N-(4-(carboxymethyl)phenyl)-4-methylthiobutanamide A solution of K$_2$CO$_3$ (962 mg) in water (15 ml) was added to a solution of (S)-2-(4-bromobenzenesulfonylamino)-N-(4-(ethoxycarbonylmethyl)phenyl)-4-methylthiobutanamide (1.23 g) in ethanol (50 ml). The whole was stirred at room temperature overnight under argon. The reaction mixture was concentrated under reduced pressure. It was repeated 3 times in order to remove ethanol completely that a small amount of purified water was added to the residue, and then the mixture was concentrated under reduced pressure. The residue was dissolved in purified water and washed with ethyl acetate. The aqueous layer was acidified with 1N HCl, and then extracted with ethyl acetate. The combined ethyl acetate layers were washed with a saturated saline solution and dried over Na$_2$SO$_4$. Then, the solvent was evaporated under reduced pressure and the crude product was recrystallized from acetonitrile to obtain (S)-2-(4-bromobenzenesulfonylamino)-N-(4-(carboxymethyl)phenyl)-4-methylthiobutanamide (800 mg).

[α]$_D^{29}$ –22.71° (c 1.048, MeOH)

Melting point: 188.5°–189.5° C.

IR νmax cm$^{-1}$ (KBr): 3086 (br), 1709, 1665, 1338, 1161, 823, 742, 613, 565

$^1$H-NMR δ ppm (CD$_3$OD): 1.82–2.04 (2H, m), 2.043 (3H, s), 2.39–2.63 (2H, m), 3.552 (2H, s), 4.036 (1H, dd, J=8.7 Hz, J=5.5 Hz), 7.192 (2H, d, J=8.7 Hz), 7.251 (2H, d, J=8.7 Hz), 7.566 (2H, d, J=8.8 Hz), 7.735 (2H, d, J=8.8 Hz)

$^{13}$C-NMR δ ppm (CD$_3$OD): 15.26, 30.92, 33.86, 41.37, 57.73, 121.39, 128.39, 130.01, 130.71, 132.25, 133.31, 137.67, 141.05, 170.90, 175.44

Fab-MS m/z: 501 (MH$^+$)

Example 240

Preparation of (S)-2-(4-bromobenzenesulfonylamino)-N-(4-(2-carboxyethyl)phenyl)-4-methylthiobutanamide The procedure described in Example 234 was repeated, except that (S)-2-(4-bromobenzenesulfonylamino)-N-(4-(2-methoxycarbonylethyl)phenyl)-4-methylthiobutanamide (2.6 g) was hydrolyzed and recrystallized from acetonitrile to obtain (S)-2-(4-bromobenzenesulfonylamino)-N-(4-(2-carboxyethyl)phenyl)-4-methylthiobutanamide (1.7 g).

[α]$_D^{26}$ –20.3° (c 1.09, MeOH)

Melting point: 183°–184.5° C.

IR vmax cm$^{-1}$ (KBr): 3259, 1701, 1662, 1335, 1161, 742, 609

$^1$H-NMR δ ppm (CD$_3$OD): 1.80–2.02 (2H, m), 2.045 (3H, s), 2.39–2.65 (2H, m), 2.574 (2H, t, J=7.3 Hz), 2.868 (2H, t, J=7.6 Hz), 4.025 (1H, dd, J=8.5 Hz, J=5.6 Hz), 7.129 (2H, d, J=8.8 Hz), 7.195 (2H, d, J=8.8 Hz), 7.555 (2H, d, J=8.7 Hz), 7.731 (2H, d, J=8.7 Hz)

$^{13}$C-NMR δ ppm (CD$_3$OD): 15.26, 30.88, 31.40, 33.82, 36.64, 57.66, 121.50, 128.39, 129.60, 129.97, 133.24, 136.90, 138.48, 140.97, 170.75, 176.58

Fab-MS m/z: 514 (M$^+$)

Example 241

Preparation of (S)-2-(4-bromobenzenesulfonylamino)-N-(3-carboxyphenyl)-4-methylthiobutanamide The procedure described in Example 225 was repeated, except that (S)-2-(4-bromobenzenesulfonylamino)-N-(3-(ethoxycarbonylmethyl)phenyl)-4-methylthiobutanamide (1.946 g) was hydrolyzed and recrystallized from acetonitrile to obtain (S)-2-(4-bromobenzene-sulfonylamino)-N-(3-carboxyphenyl)-4-methylthiobutanamide (895 mg).

$[α]_D^{30}$–12.5° (c 0.80, THF)

Melting point: 229°–229.5° C.

IR vmax cm$^{-1}$ (KBr): 3246, 2920, 1697, 1616, 1595, 1554, 1437, 1327, 1161, 1090, 823, 742

$^1$H-NMR δ ppm (CD$_3$OD): 1.8–2.0 (2H, m), 2.048 (3H, s), 2.4–2.6 (2H, m), 4.0–4.1 (1H, m), 7.363 (1H, t, J=7.9 Hz), 7.543 (2H, d, J=8.5 Hz), 7.55–7.6 (1H, m), 7.7–7.75 (1H, m), 7.741 (2H, d, J=8.5 Hz), 8.003 (1H, t, J=2.0 Hz)

$^{13}$C-NMR δ ppm (CD$_3$OD): 16.52, 30.51, 33.36, 58.33, 120.50, 122.95, 126.03, 128.31, 130.78, 131.56, 132.11, 134.07, 140.43, 140.55, 168.56, 170.23

Fab-MS m/z: 489 (MH$^+$+2), 487 (MH$^+$)

Example 242

Preparation of (RS)-N-(4-(carboxymethyl) phenyl)-2-(4-chlorobenzenesulfonylamino)-4-ethylthiobutanamide The procedure described in Example 39 was repeated, except that (RS)-2-(4-chlorobenzenesulfonylamino)-N-(4-(ethoxycarbonylmethyl)phenyl)-4-ethylthiobutanamide (47.5 mg) was hydrolyzed to obtain (RS)-N-(4-(carboxymethyl) phenyl)-2-(4-chlorobenzenesulfonylamino)-4-ethylthiobutanamide (36.4 mg).

Melting point: 152°–154° C.

IR vmax cm$^{-1}$ (KBr): 3423, 1709, 1606, 1537, 1325, 1163, 1093, 756, 624

$^1$H-NMR δ ppm (CDCl$_3$-CD$_3$OD): 1.159 (3H, t, J=7.32 Hz), 1.77–1.95 (2H, m), 2.34–2.58 (2H, m), 2.448 (2H, q, J=7.32 Hz), 3.502 (2H, s), 7.165 (2H, d, J=8.30 Hz), 7.317 (2H, d, J=8.30 Hz), 7.474 (2H, d, J=8.55 Hz), 7.811 (2H, d, J=8.55 Hz)

$^{13}$C-NMR δ ppm (CDCl$_3$): 14.49, 25.24, 27.07, 33.27, 56.55, 119.85, 128.65, 129.02, 129.49, 130.59, 137.85, 139.98, 168.88, 172.69

Fab-MS m/z: 471 (MH$^+$)

Example 243

Preparation of (S)-N-(4-(carboxymethyl) phenyl)-2-(4-chlorobenzenesulfonylamino)-4-ethylthiobutanamide The procedure described in Example 234 was repeated, except that (S)-2-(4-chlorobenzenesulfonylamino)-N-(4-(ethoxycarbonylmethyl)phenyl)-4-ethylthiobutanamide (105.6 mg) was hydrolyzed to obtain (S)-N-(4-(carboxymethyl)phenyl)-2-(4-chlorobenzenesulfonylamino)-4-ethylthiobutanamide (95.1 mg).

$[α]_D^{30}$–8.00° (c 0.250, THF)

Melting point: 199°–200.5° C.

The various spectra (IR, $^1$H-NMR, $^{13}$C-NMR, Fab-MS) were found to be identical to those of the racemate of Example 242.

Example 244

Preparation of (RS)-N-(4-(2-carboxyethyl) phenyl)-2-(4-chlorobenzenesulfonylamino)-4-ethylthiobutanamide The procedure described in Example 39 was repeated, except that (RS)-2-(4-chlorobenzenesulfonylamino)-N-(4-(2-methoxycarbonylethyl)phenyl)-4-ethylthiobutanamide (370 mg) was hydrolyzed to obtain (RS)-N-(4-(2-carboxyethyl)phenyl)-2-(4-chlorobenzenesulfonylamino)-4-ethylthiobutanamide (297.6 mg).

Melting point: 145°–146° C.

IR vmax cm$^{-1}$ (KBr): 3338, 3259, 1707, 1660, 1335, 1163, 756

$^1$H-NMR δ ppm (DMSO-d$_6$): 1.134 (3H, t, J=7.3 Hz), 1.820 (2H, qw, J=7.2 Hz), 2.30–2.52 (6H, m), 2.781 (2H, t, J=7.6 Hz), 3.988 (1H, bq, J=7.6 Hz), 7.105 (2H, d, J=8.5 Hz), 7.275 (2H, d, J=8.5 Hz), 7.501 (2H, d, J=8.7 Hz), 7.789 (2H, d, J=8.7 Hz), 8.088 (1H, d, J=9.0 Hz), 9.688 (1H, s)

$^{13}$C-NMR δ ppm (DMSO-d$_6$): 14.38, 24.80, 26.63, 29.67, 32.86, 35.14, 38.91, 56.19, 119.37, 119.52, 127.99, 128.50, 128.69, 136.02, 137.16, 139.72, 168.33, 173.32

Fab-MS m/z: 485 (MH$^+$)

Example 245

Preparation of (S)-2-(4-bromobenzenesulfonylamino)-N-(4-(carboxymethyl)phenyl)-4-ethylthiobutanamide The procedure described in Example 234 was repeated, except that (S)-2-(4-bromobenzenesulfonylamino)-N-(4-(ethoxycarbonylmethyl)phenyl)-4-ethylthiobutanamide (30.8 mg) was hydrolyzed to obtain (S)-2-(4-bromobenzenesulfonylamino)-N-(4-(carboxymethyl) phenyl)-4-ethylthiobutanamide (26.7 mg).

Melting point: 193.5°–195° C.

$[α]_D^{29}$–19.04° (c 0.961, MeOH)

IR vmax cm$^{-1}$ (KBr): 3265 (br), 1705, 1657, 1538, 1335, 1163, 741, 613

$^1$H-NMR δ ppm (CD$_3$OD): 1.205 (3H, t, J=7.4 Hz), 1.82–2.05 (2H, m), 2.42–2.66 (2H, m), 2.489 (2H, q, J=7.4 Hz), 3.552 (2H, s), 4.028 (1H, dd, J=8.5 Hz, J=5.6 Hz), 7.193 (2H, d, J=8.9 Hz), 7.254 (2H, d, J=8.9 Hz), 7.568 (2H, d, J=8.8 Hz), 7.737 (2H, d, J=8.8 Hz)

$^{13}$C-NMR δ ppm (CD$_3$OD): 15.05, 26.51, 28.21, 34.34, 41.40, 57.78, 121.37, 128.36, 129.95, 130.67, 132.19, 133.26, 137.61, 141.01, 170.81, 175.42

Fab-MS m/z: 516 (MH$^+$+1)

Example 246

Preparation of (S)-2-(4-bromobenzenesulfonylamino)-N-(4-(2-carboxyethyl)phenyl)-4-ethylthio-butanamide The procedure described in Example 225 was repeated, except that (S)-2-(4-bromobenzenesulfonylamino)-N-(4-(2-methoxycarbonylethyl)phenyl)-4-ethylthiobutanamide (7.8 mg) was hydrolyzed and recrystallized from acetonitrile to obtain (S)-2-(4-bromobenzenesulfonylamino)-N-(4-(2-carboxyethyl)phenyl)-4-ethylthiobutanamide (7 mg).

Melting point: 174.5°–175.5° C.

IR νmax cm$^{-1}$ (KBr): 3253, 1703, 1657, 1336, 1164, 1089, 1070, 825, 742

$^1$H-NMR δ ppm (CD$_3$OD): 1.196 (3H, t, J=7.3 Hz), 1.8–2.0 (2H, m), 2.477 (2H, q, J=7.3 Hz), 2.576 (2H, t, J=7.6 Hz), 2.867 (2H, t, J=7.6 Hz), 4.023 (1H, m), 7.132 (2H, d, J=8.8 Hz), 7.197 (2H, d, J=8.8 Hz), 7.555 (2H, d, J=8.8 Hz), 7.735 (2H, d, J=8.8 Hz)

$^{13}$C-NMR δ ppm (CD$_3$OD): 15.08, 26.52, 28.24, 31.40, 34.37, 36.64, 57.80, 121.54, 128.43, 129.60, 129.97, 133.27, 136.90, 138.48, 140.97, 170.75, 176.58

Fab-MS m/z: 531 (MH$^+$+2), 529 (MH$^+$)

Example 247

Preparation of (RS)-N-(4-(carboxymethyl) phenyl)-2-(4-chlorobenzenesulfonylamino)-3-phenylpropanamide The procedure described in Example 39 was repeated, except that (RS)-2-(4-chlorobenzenesulfonylamino)-N-(4-(ethoxycarbonylmethyl)phenyl)-3-phenylpropanamide (122.5 mg) was hydrolyzed to obtain (RS)-N-(4-(carboxymethyl) phenyl)-2-(4-chlorobenzenesulfonylamino)-3-phenylpropanamide (99.9 mg).

Melting point: 204°–206° C.

IR νmax cm$^{-1}$ (KBr): 3342, 1709, 1676, 1321, 1163, 829, 754

$^1$H-NMR δ ppm (CDCl$_3$-DMSO-d$_6$): 2.795 (1H, dd, J=13.7 Hz, J=7.3 Hz), 2.966 (1H, dd, J=13.7 Hz, J=7.3 Hz), 8.49 (2H, s), 4.1 (1H, m), 7.1–7.3 (5H, m), 7.15 (2H, d, J=8.4 Hz), 7.27 (2H, d, J=8.4 Hz), 7.37 (2H, d, J=8.55 Hz), 7.61 (2H, d, J=8.55 Hz)

$^{13}$C-NMR δ ppm (CDCl$_3$-DMSO-d$_6$): 30.37, 40.12, 58.31, 111.41, 119.52, 119.77, 126.23, 126.52, 127.40, 127.84, 128.06, 128.25, 128.58, 129.09, 129.16, 129.38, 129.68, 130.15, 136.61, 136.97, 139.69, 168.62, 172.32

Fab-MS m/z: 473 (MH$^+$)

Example 248

Preparation of (S)-N-(4-(carboxymethyl) phenyl)-2-(4-chlorobenzenesulfonylamino)-3-phenylpropanamide The procedure described in Example 234 was repeated, except that (S)-2-(4-chlorobenzenesulfonylamino)-N-(4-(ethoxycarbonylmethyl)phenyl)-3-phenylpropanamide (2.52 g) was hydrolyzed and recrystallized from acetonitrile to obtain (S)-N-(4-(carboxymethyl)phenyl)-2-(4-chlorobenzenesulfonylamino)-3-phenylpropanamide (2.22 g).

$[α]_D^{28}$+49.37° (c 1.03, THF)

Melting point: 218°–218.8° C.

The various spectra (IR, $^1$H-NMR, $^{13}$C-NMR, Fab-MS) were found to be identical to those of the racemate of Example 247.

Example 249

Preparation of (RS)-N-(4-(2-carboxyethyl) phenyl)-2-(4chlorobenzenesulfonylamino)-3-phenylpropanamide The procedure described in Example 39 was repeated, except that (RS)-2-(4-chlorobenzenesulfonylamino)-N-(4-(2-methoxycarbonylethyl)phenyl)-3-phenylpropanamide (36.7 mg) was hydrolyzed and recrystallized from acetonitrile to obtain (RS)-N-(4-(2-carboxyethyl)phenyl)-2-(4-chlorobenzenesulfonylamino)-3-phenylpropanamide (28.0 mg).

Melting point: 214°–215° C.

IR νmax cm$^{-1}$ (KBr): 3325, 1709, 1674, 1321, 1161, 1089, 754, 628

$^1$H-NMR δ ppm (CDCl$_3$): 2.563 (2H, t, J=7.6 Hz), 2.855 (2H, t, J=7.6 Hz), 3.025 (2H, dd, J=13.6 Hz, J=7.0 Hz), 4.108 (1H, t, J=7.6 Hz), 7.1–7.2 (7H, m), 7.305 (2H, d, J=8.8 Hz), 7.542 (1H, d, J=8.8 Hz), 7.653 (2H, d, J=8.8 Hz), 7.872 (1H, d, J=8.8 Hz)

$^{13}$C-NMR δ ppm (CDCl$_3$): 31.40, 36.68, 40.27, 60.22, 121.65, 127.84, 128.87, 129.46, 129.53, 129.71, 130.12, 130.41, 136.87, 137.64, 138.52, 140.53, 170.82, 176.58

Fab-MS m/z: 487 (MH$^+$)

Example 250

Preparation of (S)-N-(4-(2-carboxyethyl) phenyl)-3-(4chlorobenzenesulfonylamino)-3-phenylpropanamide The procedure described in Example 234 was repeated, except that (S)-2-(4-chlorobenzenesulfonylamino)-N-(4-(2-methoxycarbonylethyl)phenyl)-3-phenylpropanamide (2.50 g) was hydrolyzed and recrystallized from acetonitrile to obtain (S)-N-(4-(2-carboxyethyl)phenyl)-2-(4-chlorobenzenesulfonylamino)-3-phenylpropanamide (2.09 g).

$[α]_D^{29}$+52.47° (c 0.97, THF)

Melting point: 194°–194.5° C.

The various spectra (IR, $^1$H-NMR, $^{13}$C-NMR, Fab-MS) were found to be identical to those of the racemate of Example 249.

Example 251

Preparation of (RS)-2-(4-bromobenzenesulfonylamino)-N-(4-(carboxymethyl)phenyl)-3-phenylpropanamide The procedure described in Example 39 was repeated, except that (RS)-2-(4-bromobenzenesulfonylamino)-N-(4-(ethoxycarbonylmethyl)phenyl)-3-phenylpropanamide (33.7 mg) was hydrolyzed and recrystallized from acetonitrile to obtain (RS)-2-(4-bromobenzenesulfonylamino)-N-(4-(carboxymethyl)phenyl)-3-phenylpropanamide (29.8 mg).

Melting point: 184°–185° C.

The various spectra (IR, $^1$H-NMR, $^{13}$C-NMR, Fab-MS) were found to be identical to those of the S-form of Example 252.

Example 252

Preparation of (S)-2-(4-bromobenzenesulfonylamino)-N-(4-(carboxymethyl)phenyl)-3-phenylpropanamide (S)-2-(4-bromobenzenesulfonylamino)-N-(4-(ethoxycarbonylmethyl)phenyl)-3-phenylpropanamide (17.0 g) was dissolved in methanol (200 ml) and cooled to 0° C. After 2N NaOH (46.8 ml) was added, the whole was stirred at room temperature overnight under argon. The reaction mixture was concentrated under reduced pressure to remove methanol. The concentrate was poured to 6N HCl while cooling with ice. The precipitated crystal was filtered and recrystallized from acetonitrile to obtain (S)-2-(4-bromobenzenesulfonylamino)-N-(4-(carboxymethyl) phenyl)-3-phenylpropanamide (1.10 g).

$[α]_D^{27}$+52.4° (c 0.38, THF)

Melting point: 224°–224.5° C.

IR νmax cm$^{-1}$ (KBr): 3361, 1716, 1684, 1525, 1322, 1167, 739, 613

$^1$H-NMR δ ppm (DMSO-d$_6$): 2.785 (1H, dd, J=13.8 Hz, J=8.9 Hz), 2.953 (1H, dd, J=13.8 Hz, J=5.7 Hz), 3.486 (2H, s), 3.603 (1H, dd, J=5.7 Hz, J=8.9 Hz), 7.08–7.30 (9H, m), 7.527 (4H, s), 9.757 (1H, s)

$^{13}$C-NMR δ ppm (DMSO-d$_6$): 38.88, 39.99, 58.19, 119.38, 124.62, 125.63, 126.12, 127.76, 128.05, 129.00, 129.12, 130.04, 131.48, 136.57, 140.14, 168.48, 172.20

Fab-MS m/z: 517 (MH$^+$)

Example 253

Preparation of (R)-2-(4-bromobenzenesulfonylamino)-N-(4-(carboxymethyl)phenyl)-3-phenylpropanamide The procedure described in Example 225 was repeated, except that (R)-2-(4-bromobenzenesulfonylamino)-N-(4-(ethoxycarbonylmethyl)phenyl)-3-phenylpropanamide (398 mg) was hydrolyzed and recrystallized from acetonitrile to obtain (R)-2-(4-bromobenzenesulfonylamino)-N-(4-(carboxymethyl)phenyl)-3-phenylpropanamide (344 mg).

$[α]_D^{26}$ −51.4° (c 1.06, THF)

Melting point: 223.5°–224° C.

The various spectra (IR, $^1$H-NMR, $^{13}$C-NMR, Fab-MS) were found to be identical to those of the S-form of Example 252.

Example 254

Preparation of (S)-2-(4-bromobenzenesulfonylamino)-N-(4-(2-carboxyethyl)phenyl)-3-phenylpropanamide The procedure described in Example 225 was repeated, except that (S)-2-(4-bromobenzenesulfonylamino)-N-(4-(2-methoxycarbonylethyl)phenyl)-3-phenylpropanamide (19.4 g) was hydrolyzed and recrystallized from acetonitrile to obtain (S)-2-(4-bromobenzenesulfonylamino)-N-(4-(2-carboxyethyl)phenyl)-3-phenylpropanamide (17.1 g).

$[α]_D^{28}$ +52.4° (c 0.38, THF)

Melting point: 208°–209° C.

IR vmax cm$^{-1}$ (KBr): 3331, 3267, 1703, 1655, 1527, 1338, 1165, 748, 613

$^1$H-NMR δ ppm (DMSO-d$_6$): 2.745 (2H, d, J=3.0 Hz), 2.786 (2H, d, J=3.0 Hz), 2.791 (1H, dd, J=13.7 Hz, J=4.9 Hz), 2.949 (1H, dd, J=13.7 Hz, J=5.9 Hz), 4.151 (1H, q, J=6.8 Hz), 7.04–7.28 (9H, m), 7.515 (4H, s), 9.699 (1H, s)

$^{13}$C-NMR δ ppm (DMSO-d$_6$): 29.60, 35.06, 38.22, 58.17, 119.44, 124.58, 125.61, 126.08, 127.73, 127.95, 128.03, 128.98, 131.40, 135.91, 136.57, 140.09, 168.33, 173.24

Fab-MS m/z: 531 (MH$^+$)

Example 255

Preparation of (R)-2-(4-bromobenzenesulfonylamino)-N-(4-(2-carboxyethyl)phenyl)-3-phenylpropanamide The procedure described in Example 225 was repeated, except that (R)-2-(4-bromobenzenesulfonylamino)-N-(4-(2-methoxycarbonylethyl)phenyl)-3-phenylpropanamide (407 mg) was hydrolyzed and recrystallized from acetonitrile to obtain (R)-2-(4-bromobenzenesulfonylamino)-N-(4-(2-carboxyethyl)phenyl)-3-phenylpropanamide (367 mg).

$[α]_D^{26}$ −54.7° (c 1.02, THF)

Melting point: 212°–212.5° C.

The various spectra (IR, $^1$H-NMR, $^{13}$C-NMR, Fab-MS) were found to be identical to those of the S-form of Example 254.

Example 256

Preparation of (S)-2-(4-bromobenzenesulfonylamino)-N-(4-carboxyphenyl)-3-phenylpropanamide The procedure described in Example 225 was repeated, except that (S)-2-(4-bromobenzenesulfonylamino)-N-(4-ethoxycarbonylphenyl)-3-phenylpropanamide (2 13 mg) was hydrolyzed and recrystallized from acetonitrile to obtain (S)-2-(4-bromobenzenesulfonylamino)-N-(4-carboxyphenyl)-3-phenylpropanamide (170 mg).

$[α]_D^{28}$ 58.3° (c 0.63, THF)

Melting point: 300° C. (decomposition)

IR vmax cm$^{-1}$ (KBr): 3352, 1689, 1601, 1531, 1410, 1317, 1163, 1090, 741

$^1$H-NMR δ ppm (CD$_3$OD): 2.881 (1H, dd, J=13.5 Hz, J=8.2 Hz), 3.040 (1H, dd, J=13.5 Hz, J=6.8 Hz), 4.11–4.17 (1H, m), 7.13–7.24 (5H, m), 7.366 (2H, d, J=8.8 Hz), 7.455 (2H, d, J=8.8 Hz), 7.576 (2H, d, J=8.7 Hz), 7.915 (2H, d, J=8.7 Hz)

$^{13}$C-NMR δ ppm (CD$_3$OD): 40.16, 60.30, 120.29, 127.33, 127.88, 128.17, 129.46, 129.79, 130.41, 131.66, 133.16, 137.53, 140.97, 143.28, 169.36, 171.23

Fab-MS m/z: 503 (MH$^+$)

Example 257

Preparation of (S)-2-(4-bromobenzenesulfonylamino)-N-(3-carboxyphenyl)-3-phenylpropanamide The procedure described in Example 225 was repeated, except that (S)-2-(4-bromobenzenesulfonylamino)-N-(3-ethoxycarbonylphenyl)-3-phenylpropanamide (300 mg) was hydrolyzed and recrystallized from acetonitrile to obtain (S)-2-(4-bromobenzenesulfonylamino)-N-(3-carboxyphenyl)-3-phenylpropanamide (145 mg).

$[α]_D^{29}$ 38.9° (c 1.07, THF)

Melting point: 234.5°–235.5° C.

IR vmax cm$^{-1}$ (KBr): 3338, 1697, 1552, 1323, 1161, 742, 615

$^1$H-NMR δ ppm (CD$_3$OD): 2.895 (1H, dd, J=13.7 Hz, J=7.6 Hz), 3.044 (1H, dd, J=13.7 Hz, J=7.6 Hz), 4.122 (1H, t, J=7.6 Hz), 7.14–7.23 (5H, m), 7.343 (1H, t, J=7.9 Hz), 7.43–7.50 (1H, m), 7.456 (2H, d, J=8.8 Hz), 7.595 (2H, d, J=8.8 Hz), 7.730 (1H, dt, J=8.1 Hz, J=1.4 Hz), 7.898 (1H, t, J=1.7 Hz)

$^{13}$C-NMR δ ppm (CD$_3$OD): 39.87, 59.89, 122.16, 125.24, 126.30, 127.51, 127.88, 129.13, 129.46, 130.05, 132.17, 132.80, 137.20, 138.7, 140.61, 168.99, 170.68, 177.98

Fab-MS m/z: 503 (MH$^+$)

Example 258

Preparation of (S)-N-(4-(carboxymethyl) phenyl)-2-(4-chlorobenzenesulfonylamino)-3-(3-indolyl) propanamide The procedure described in Example 225 was repeated, except that (S)-2-(4-chlorobenzenesulfonylamino)-N-(4-(ethoxycarbonylmethyl)phenyl)-3-(3-indolyl)propanamide (4.01 g) was hydrolyzed and recrystallized from acetonitrile to obtain (S)-N-(4-(carboxymethyl)phenyl)-2-(4-chlorobenzenesulfonylamino)-3-(3-indolyl)propanamide (3.22 mg).

$[α]_D^{27}$ −12.6° (c 0.61, MeCN)

Melting point: 182°–183.5° C.

IR vmax cm$^{-1}$ (KBr): 3282, 1714, 1697, 1533, 1417, 1317, 1161, 750

$^1$H-NMR δ ppm (DMSO-d$_6$): 3.014 (1H, dd, J=14.4 Hz, J=8.1 Hz), 3.195 (1H, dd, J=14.4 Hz, J=6.0 Hz), 3.489 (2H, s), 4.13–4.23 (1H, m), 6.943 (1H, t, J=7.4 Hz), 7.02–7.54 (12H, m), 7.662 (1H, bs), 9.449 (1H, s), $^{13}$C-NMR δ ppm (DMSO-d$_6$): 28.46, 4012, 57.69, 108.70, 110.90, 117.76, 117.98, 119.33, 120.54, 123.44, 126.74, 127.48, 127.88, 128.87, 129.71, 135.80, 136.46, 137.16, 138.81, 168.95, 172.36

Fab-MS m/z: 512 (MH⁺)

Example 259

Preparation of (S)-N-(4-(2-carboxyethyl) phenyl)-2-(4-chlorobenzenesulfonylamino)-3-(3-indolyl) propanamide The procedure described in Example 225 was repeated, except that (S)-2-(4-chlorobenzenesulfonylamino)-3-(3-indolyl)-N-(4-(2-methoxycarbonylethyl)phenyl) propanamide (3.00 g) was hydrolyzed and recrystallized from acetonitrile to obtain (S)-N-(4-(2-carboxyethyl) phenyl)-2-(4-chlorobenzenesulfonylamino)-3-(3-indolyl) propanamide (2.68 g).

$[\alpha]_D^{30}$+83.9° (c 0.70, THF)

Melting point: 231.5°–232° C.

IR vmax cm$^{-1}$ (KBr): 3405, 1707, 1659, 1531, 1416, 1165, 1093, 756

$^1$H-NMR δ ppm (CDCl$_3$-DMSO-d$_6$): 2.501 (2H, t, J=7.6 Hz), 2.807 (2H, t, J=7.6 Hz), 2.943 (1H, dd, J=14.5 Hz, J=8.4 Hz), 3.123 (1H, dd, J=14.5 Hz, J=5.9 Hz), 4.10–4.21 (1H, m), 6.937 (1H, t, J=7.2 Hz), 7.00–7.12 (4H, m), 7.157 (2H, d, J=8.9 Hz), 7.299 (3H, t, J=8.4 Hz), 7.478 (1H, d, J=8.5 Hz), 7.520 (1H, d, J=8.5 Hz), 8.163 (2H, d, J=8.9 Hz), 9.765 (1H, s), 10.579 (1H, s)

$^{13}$C-NMR δ ppm (CDCl$_3$-DMSO-d$_6$): 28.46, 29.78, 35.32, 57.58, 108.55, 111.12, 118.05, 119.48, 120.65, 123.77, 126.85, 127.70, 127.99, 128.10, 135.87, 136.17, 136.94, 139.25, 169.10, 173.65

Fab-MS m/z: 526 (MH⁺)

Example 260

Preparation of (RS)-N-(4-(carboxymethyl) phenyl)-2-(4-chlorobenzenesulfonylamino)-3-cyclohexylpropanamide The procedure described in Example 39 was repeated, except that (RS)-2-(4-chlorobenzenesulfonylamino)-3-cyclohexyl-N-(4-(ethoxycarbonylmethyl)phenyl) propanamide (62.4 mg) was hydrolyzed to obtain (RS)-N-(4-(carboxymethyl)phenyl)-2-(4-chlorobenzenesulfonylamino)-3-cyclohexylpropanamide (30.0 mg).

Melting point: 179°–181° C.

IR vmax cm$^{-1}$ (KBr): 3236, 2924, 2852, 1711, 1668, 1606, 1518, 1416, 1325, 1163, 1093, 827, 754

$^1$H-NMR δ ppm (CD$_3$OD): 0.8–1.0 (2H, m), 1.0–1.4 (4H, m), 1.4–1.5 (1H, m), 1.5–1.7 (4H, m), 3.2–3.4 (2H, m), 3.551 (2H, s), 3.951 (1H, dd, J=9.0 Hz, J=5.9 Hz), 7.190 (2H, d, J=8.8 Hz), 7.256 (2H, d, J=8.8 Hz), 7.409 (2H, d, J=8.8 Hz), 7.808 (2H, d, J=8.8 Hz)

$^{13}$C-NMR δ ppm (CD$_3$OD): 27.07, 27.33, 27.44, 33.16, 34.77, 34.88, 41.34, 41.59, 56.44, 121.39, 121.50, 129.90, 130.63, 132.14, 139.91, 140.61, 172.07, 175.41

Fab-MS m/z: 479 (MH⁺)

Example 261

Preparation of (RS)-N-(4-(2-carboxyethyl) phenyl)-2-(4-chlorobenzenesulfonylamino)-3-cyclohexylpropanamide The procedure described in Example 39 was repeated, except that (RS)-2-(4-chlorobenzenesulfonylamino)-3-cyclohexyl-N-(4-(2-methoxycarbonylethyl)phenyl) propanamide (135.3 mg) was hydrolyzed to obtain (RS)-N-(4-(2-carboxyethyl)phenyl)-2-(4-chlorobenzenesulfonylamino)-3-cyclohexylpropanamide (112.2 mg).

Melting point: 197°–198° C.

IR vmax cm$^{-1}$ (neat): 3338, 2926, 2850, 1709, 1668, 1606, 1539, 1414, 1325, 1163, 1093, 1014, 827, 754

$^1$H-NMR δ ppm (CD$_3$OD): 0.8–1.0 (2H, m), 1.1–1.4 (4H, m), 1.5–1.6 (1H, m), 1.6–1.7 (4H, m), 2.574 (2H, t, J=7.6 Hz), 2.875 (2H, t, J=7.6 Hz), 3.3–3.4 (2H, m), 3.9–4.0 (1H, m), 4.103 (1H, q, J=7.1 Hz), 7.131 (2H, d, J=8.5 Hz), 7.211 (2H, d, J=8.5 Hz), 7.405 (2H, d, J=8.5 Hz), 7.808 (2H, d, J=8.5 Hz)

$^{13}$C-NMR δ ppm (CD$_3$OD): 20.73, 27.07, 27.29, 27.44, 31.36, 33.16, 34.85, 36.64, 41.56, 56.41, 121.50, 129.53, 129.86, 130.16, 137.01, 138.37, 139.87, 140.53, 171.96, 176.54

Fab-MS m/z: 493 (MH⁺)

Pharmacological Examples

The biological activity of the arylsulfonamide derivative of the general formula (I) of the present invention was evaluated as follows, using as a control substance 4-[2-(4-chlorobenzenesulfonylamino) ethyl ]-phenoxy acetic acid [Japanese Examined Patent Publication (Kokoku) No. 57-35910].

(1) TxA$_2$ antagonist action by binding assay

Guinea pigs (Hartley; male; body weight=approximately 500 g) were anesthetized with ether, and the blood was collected into sodium citrate (final concentration=0.38%). The preparation of platelets was carried out at room temperature. The platelet rich plasma was obtained by centrifugation at 980 rpm for 10 minutes. One tenth (1/10) amount of 77 mM-EDTA-Na (pH 7.4) was added to the platelet rich plasma, and the mixture was centrifuged for 10 minutes at 3000 rpm. The precipitate was suspended in a washing buffer (1) shown in Table 1. The suspension was again centrifuged at 3000 rpm for 10 minutes. The precipitate was further resuspended in a suspension buffer (2) shown in Table 2 to obtain washed platelets. The number of platelets was counted by an automatic blood cell counter (Sysmex Microcellcounter F-800) and the sample was diluted with the suspension buffer to 4×10$^8$ cells/ml.

The platelets, sample solution and labeled compounds were placed into plastic tubes in amounts (volumes) shown in the following Table 3, incubated for 45 minutes at 25° C., and then the mixture was filtered using a cell harvester (Brandel cell harvester M-24R) by a glass fiber filter (Whatman GF/B). After the filter was sufficiently dried, the scintillation was counted by a scintillation counter (Beckman LS5000TD). IC$_{50}$ was calculated from (binding) /(control binding) ratio in the presence of an antagonist.

TABLE 1

| (1) Washing buffer (pH 7.2) |
|---|
| 135 mM NaCl |
| 5 mM KCl |
| 8 mM Na2HPO4 |
| 2 mM NaH2PO4 |
| 10 mM EDTA |

TABLE 2

| (2) Suspension buffer (pH 7.5) |
|---|
| 135 mM NaCl |
| 5 mM MgCl |
| 1 mM EGTA |
| 25 mM Tris-HCl |

TABLE 3

| Control binding | 1 nM [³H]-SQ29, 548 10 μl |
| --- | --- |
| | Suspension buffer 10 μl |
| | Washed platelets 980 μl |
| Binding in the presence of antagonist | 1 nM [³H]-SQ29, 548 10 μl |
| | Sample 10 μl |
| | Washed platelets 980 μl |

(2) Inhibitory Activity of Vasoconstriction of Isolated Rat Artery

Rats (Wistar; male; body weight=250–300 g) were stunned by a blow to the head and exsanguinated. Then, the thoracic aorta was quickly removed, and the connective tissue and the endothelium were gently cleaned and then ring preparation was cut. The preparations were suspended in a 25 ml organ bath which was maintained at 37° C. under an aeration of 95% $O_2$-5% $CO_2$. An initial tension of 1.5 g was applied and preincubation was performed for 60 minutes. The organ bath was filled with Krebs-Henselait solution (NaCl=118, KCl=4.7, $CaCl_2$ 2.55, $MgSO_4$=1.18, $KH_2PO_4$=1.18, $NaHCO_3$=24.88, glucose=11.1). The constriction of the samples was ionotropicaly measured using an isometric transducer (UL-10GR, Minebea) and an amplifier (6M92, NEC SANEI) and recorded by a recticorder (RECTI-HORIZ-8K, NEC SANEI).

(3) Inhibitory Activity of Aggregation in Rat Platelet

The abdomen of etherized rat was open, and blood was taken from the abdominal arteries, using a sodium citrate solution (final concentration was 0.38%). The blood was centrifuged at 1100 rpm for 10 minutes, and the supernatent was separated as the platelet rich plasma. The plasma was further centrifuged at 2000 rpm for 15 minutes to obtain the supernatent as a platelet poor plasma. The platelet rich plasma (280 μl) was placed in a measuring cuvette and preincubated for 1 minute at 37° C. Then, a sample solution (10 μl) was added. After 2 minutes, an arachidonic acid solution (final concentration=0.5 mM) (10 μl) was added as an inducer. The change in light transmission was recorded for 5 minutes. The results are shown in the following Table 4.

TABLE 4

| Compound to be tested | A | B | C |
| --- | --- | --- | --- |
| Control Compound | 2.0 | 6.90 | 1.7 |
| Compound of Example 39 | 0.20 | 7.90 | — |
| Compound of Example 40 | 0.50 | 7.54 | 0.52 |
| Compound of Example 41 | 0.057 | 8.16 | 0.18 |
| Compound of Example 42 | 0.088 | 7.89 | 0.54 |
| Compound of Example 43 | — | 7.38 | — |
| Compound of Example 44 | 0.40 | 7.49 | 0.30 |
| Compound of Example 45 | 0.42 | — | 3.6 |
| Compound of Example 46 | 0.11 | — | 1.7 |
| Compound of Example 47 | — | — | 1.5 |
| Compound of Example 48 | — | — | 1.7 |
| Compound of Example 49 | 1.7 | — | 0.40 |
| Compound of Example 50 | 1.0 | — | 1.75 |
| Compound of Example 52 | 2.2 | — | 1.7 |
| Compound of Example 53 | 0.2 | — | 0.53 |
| Compound of Example 54 | 0.033 | 8.23 | 0.17 |
| Compound of Example 55 | 0.016 | 8.42 | 0.53 |
| Compound of Example 56 | 0.3 | — | 1.7 |
| Compound of Example 57 | 0.15 | — | 0.53 |
| Compound of Example 58 | 1.4 | — | 5.3 |
| Compound of Example 59 | 1.6 | — | 1.7 |
| Compound of Example 60 | 0.23 | — | 5.3 |
| Compound of Example 94 | 0.86 | — | 1.7 |
| Compound of Example 95 | 1.5 | — | 1.79 |
| Compound of Example 100 | — | — | 1.7 |
| Compound of Example 101 | 0.41 | — | 1.7 |
| Compound of Example 103 | 1.9 | — | 1.7 |
| Compound of Example 104 | 0.18 | — | 1.7 |
| Compound of Example 116 | 0.50 | — | 0.95 |
| Compound of Example 119 | — | — | 1.7 |
| Compound of Example 123 | 2.0 | — | 0.31 |
| Compound of Example 124 | 0.13 | — | 0.31 |
| Compound of Example 129 | 0.72 | — | 0.54 |
| Compound of Example 130 | 0.16 | — | 1.7 |
| Compound of Example 131 | 0.047 | — | 1.7 |
| Compound of Example 132 | 0.023 | — | 1.7 |
| Compound of Example 136 | 0.15 | — | 0.55 |
| Compound of Example 137 | 0.10 | — | 1.7 |
| Compound of Example 138 | 0.10 | — | 0.53 |
| Compound of Example 142 | 0.024 | — | 0.53 |
| Compound of Example 143 | 0.037 | — | 1.7 |
| Compound of Example 144 | 0.051 | — | 0.53 |
| Compound of Example 149 | 0.017 | — | 0.17 |
| Compound of Example 150 | 0.019 | — | 5.4 |
| Compound of Example 151 | 0.019 | — | 1.7 |
| Compound of Example 152 | 0.074 | — | 1.7 |
| Compound of Example 169 | 0.69 | — | 1.7 |
| Compound of Example 172 | 0.072 | — | 1.7 |
| Compound of Example 174 | 0.17 | — | 5.3 |
| Compound of Example 220 | — | — | 0.53 |
| Compound of Example 221 | — | — | 0.53 |
| Compound of Example 222 | — | — | 0.17 |
| Compound of Example 223 | 0.13 | — | 0.17 |
| Compound of Example 224 | 48.2 | — | 3.4 |
| Compound of Example 225 | — | — | 0.56 |
| Compound of Example 226 | 0.072 | — | 0.53 |
| Compound of Example 227 | 0.045 | — | — |
| Compound of Example 228 | 0.057 | — | — |
| Compound of Example 230 | — | — | 0.55 |
| Compound of Example 231 | — | — | 1.7 |
| Compound of Example 232 | 0.16 | — | 1.7 |
| Compound of Example 233 | 0.17 | — | 0.17 |
| Compound of Example 234 | 0.052 | — | 0.17 |
| Compound of Example 235 | 22.0 | — | 17.1 |
| Compound of Example 236 | 0.42 | — | — |
| Compound of Example 237 | 0.15 | — | 0.3 |
| Compound of Example 239 | 0.026 | — | 0.055 |
| Compound of Example 240 | 0.099 | — | 0.17 |
| Compound of Example 241 | 0.014 | — | 0.053 |
| Compound of Example 242 | 0.032 | — | 0.16 |
| Compound of Example 243 | — | — | 0.17 |
| Compound of Example 244 | 0.29 | — | 1.6 |
| Compound of Example 245 | — | — | 0.055 |
| Compound of Example 246 | 0.034 | — | — |
| Compound of Example 247 | 0.046 | — | 0.54 |
| Compound of Example 248 | 0.012 | — | 0.053 |
| Compound of Example 249 | 0.024 | — | 0.18 |
| Compound of Example 250 | 0.029 | — | 0.17 |
| Compound of Example 251 | 0.012 | — | 0.17 |
| Compound of Example 252 | 0.0071 | — | 0.055 |
| Compound of Example 253 | 1.3 | — | — |
| Compound of Example 254 | 0.005 | — | 0.051 |
| Compound of Example 256 | — | — | 0.17 |
| Compound of Example 257 | 0.0087 | — | 0.17 |
| Compound of Example 258 | — | — | 0.53 |
| Compound of Example 260 | 0.06 | — | 0.89 |
| Compound of Example 261 | — | — | 2.3 |

In Table 4, A, B, and C have the following meanings:

A: $TXA_2$ antagonist action by binding assay ($IC_{50}$; μM)

B: Inhibitory activity of vasoconstriction (rat artery) ($pA_2$)

C: Inhibitory activity of aggregation in rat platelet ($IC_{50}$; μM)

INDUSTRIAL APPLICABILITY

The arylsulfonamide derivative of the general formula (I) of the present invention exhibits an antagonism specific to a thromboxane $A_2$ ($TxA_2$) receptor, and may be used as an effective ingredient in a pharmaceutical composition based on thromboxane $A_2$ receptor antagonism, inhibitory activity of vasoconstriction and inhibitory activity of agglutinating platelets.

The reaction routes described in the above Examples will be shown schematically hereinafter by chemical structural formulas. In the following reaction routes, Me is a methyl group, Et is an ethyl group, DHP is a dihydropyran, TsOH is a toluenesulfonic acid, OTHP is a tetrahydroxypyranyloxyl group, Ph is a phenyl group, and OMs is a methanesulfonyloxyl group.

Example 1

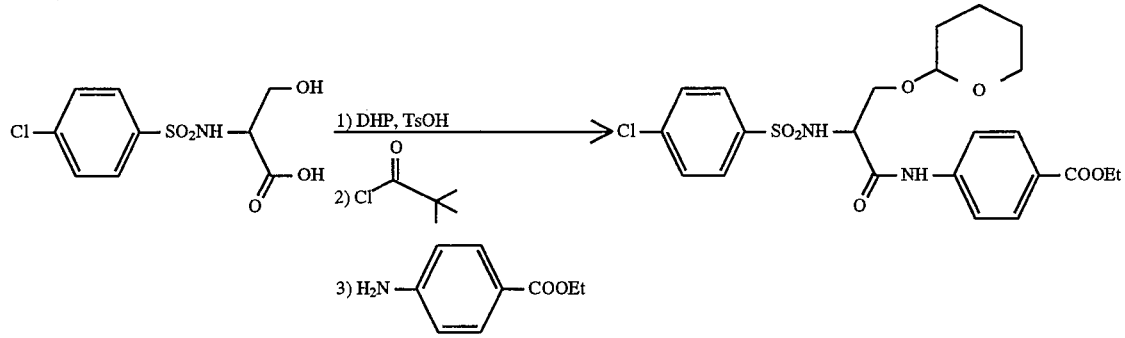

Example 2

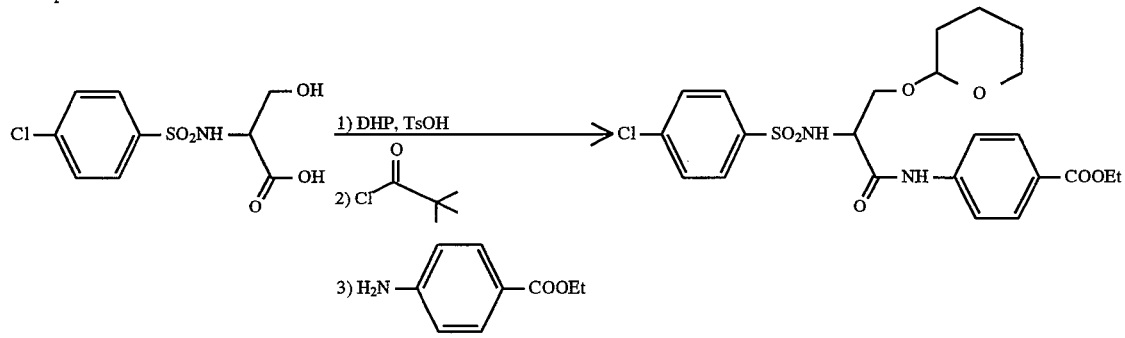

Example 3

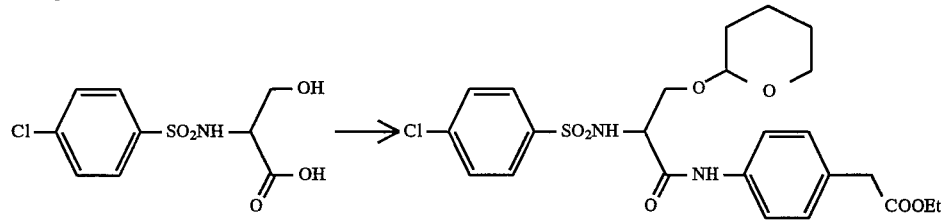

Example 4

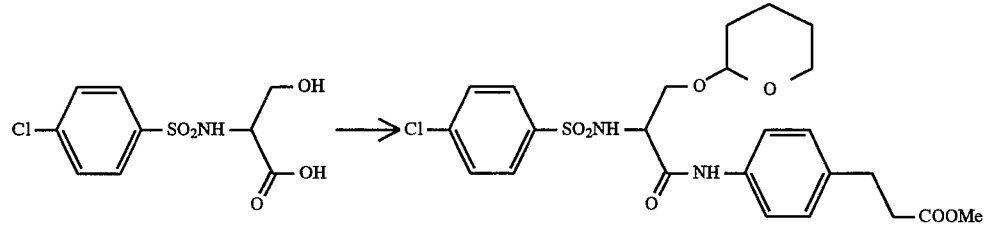

Example 5

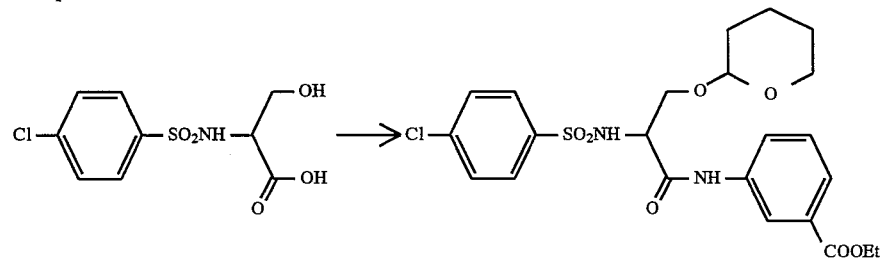

Example 6
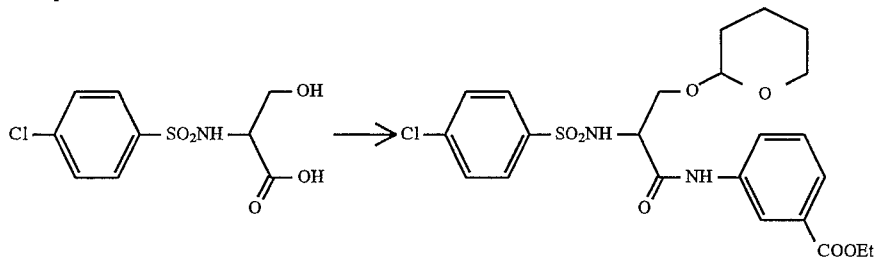
Example 7
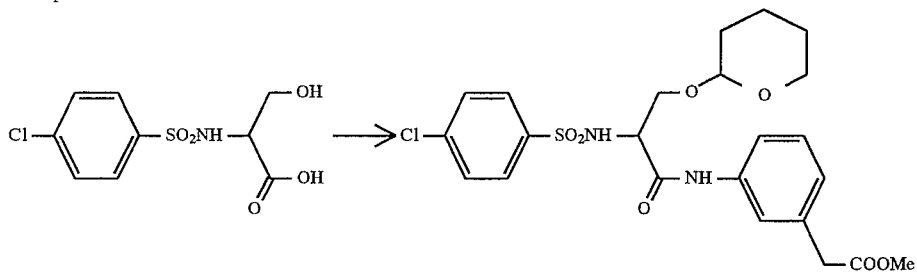
Example 8
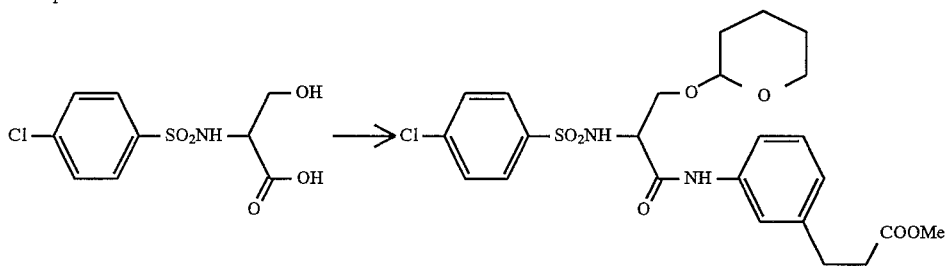
Example 9
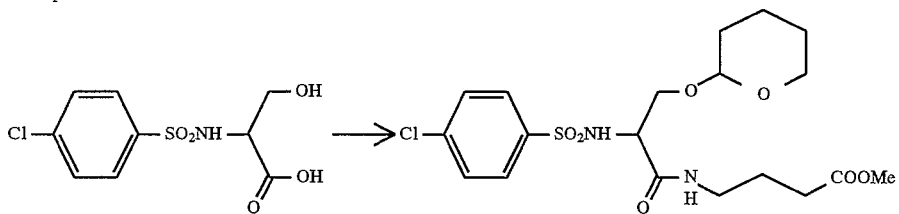
Example 10
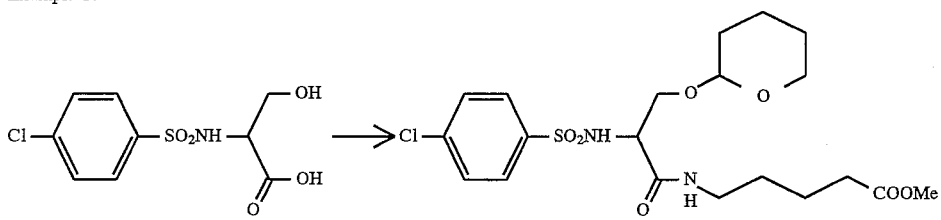
Example 11
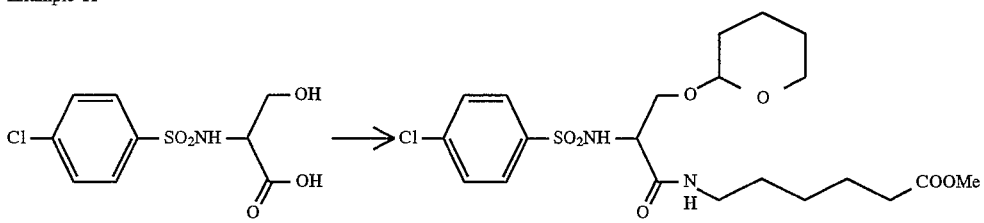

Example 12
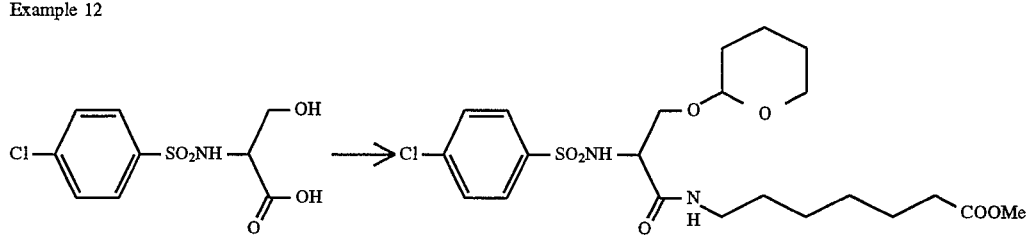
Example 13
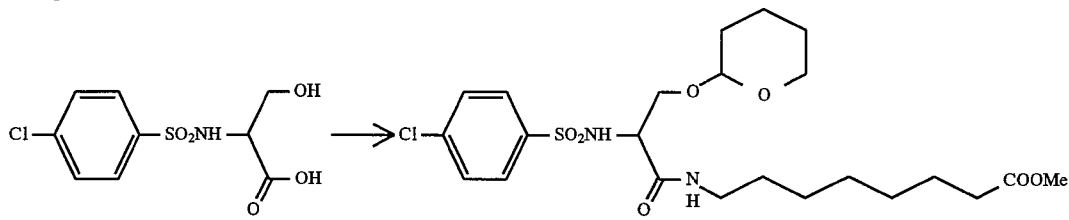
Example 14
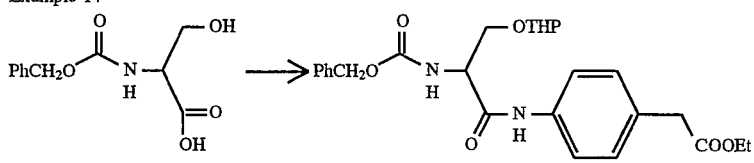
Example 15
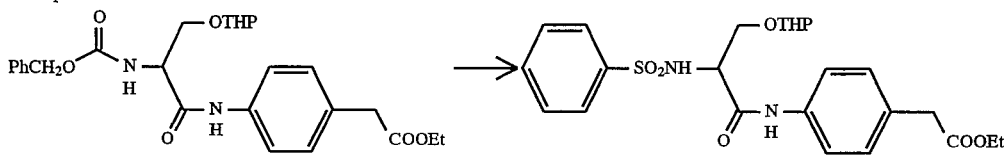
Example 16
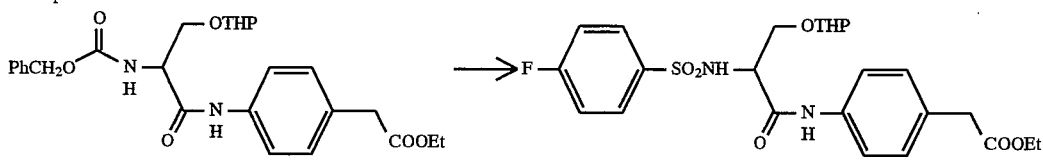
Example 17
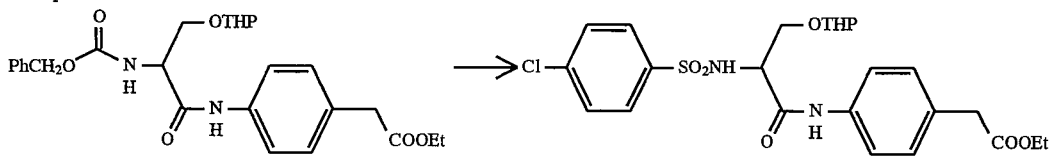
Example 18
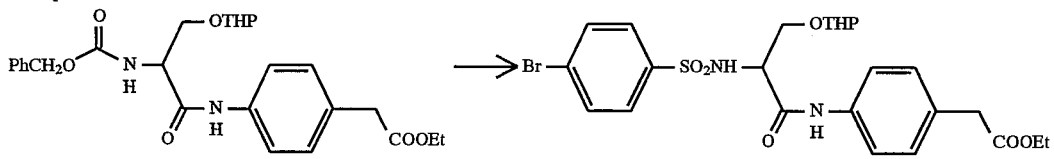
Example 19
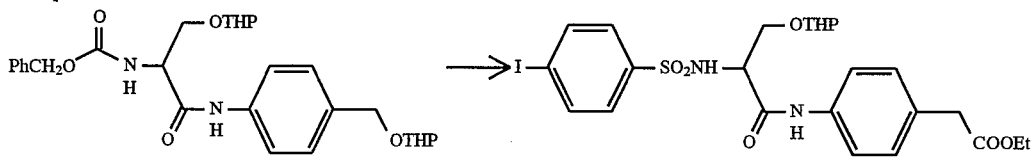

Example 20
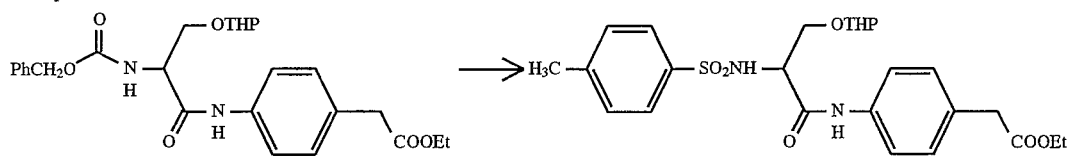
Example 21
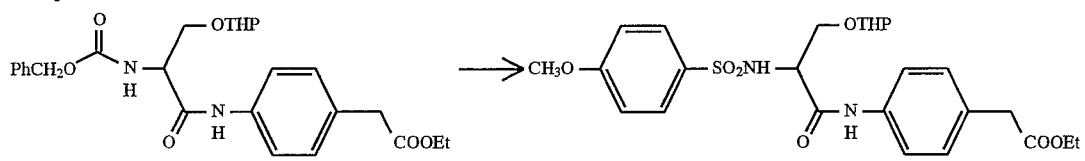
Example 22
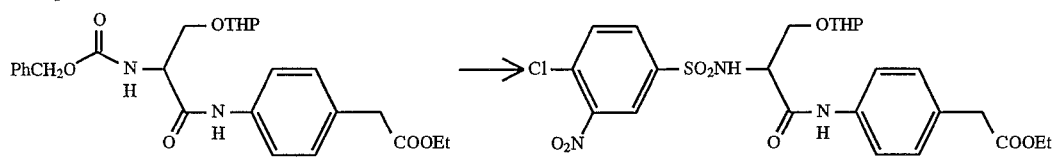
Example 24
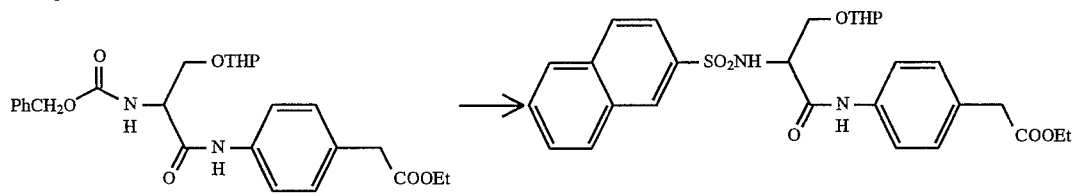
Example 25
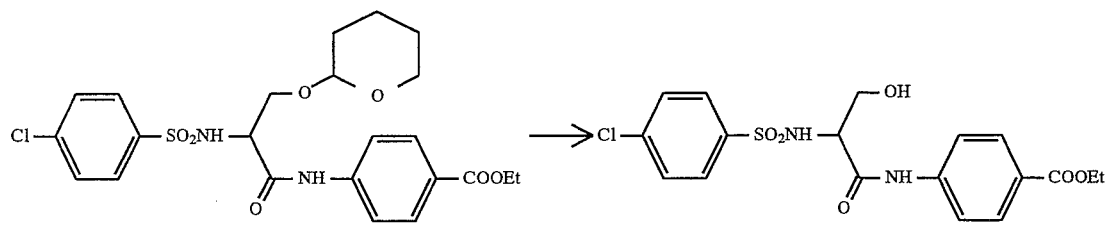
Example 26
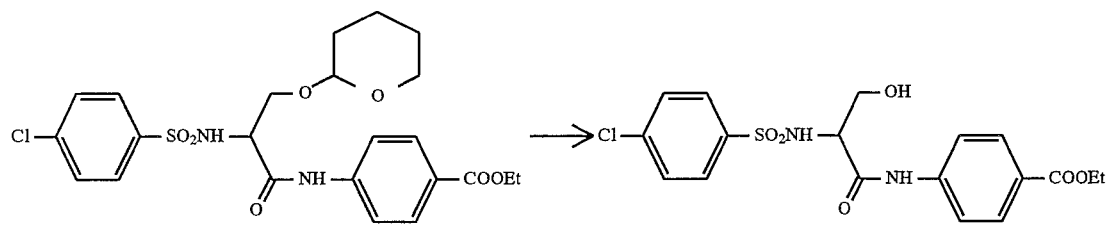
Example 27
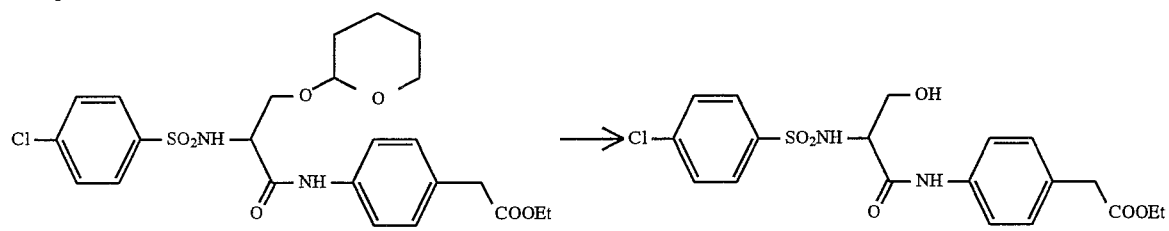

Example 28
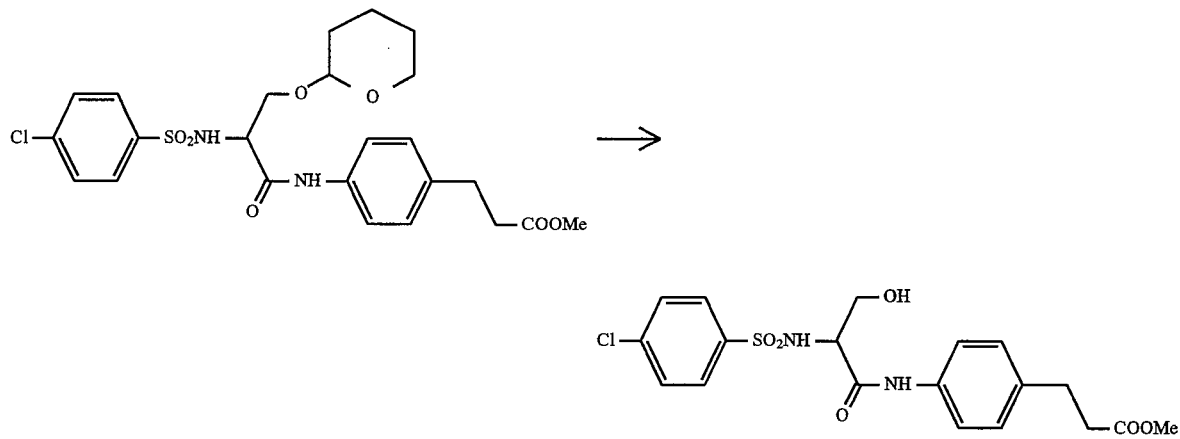
Example 29
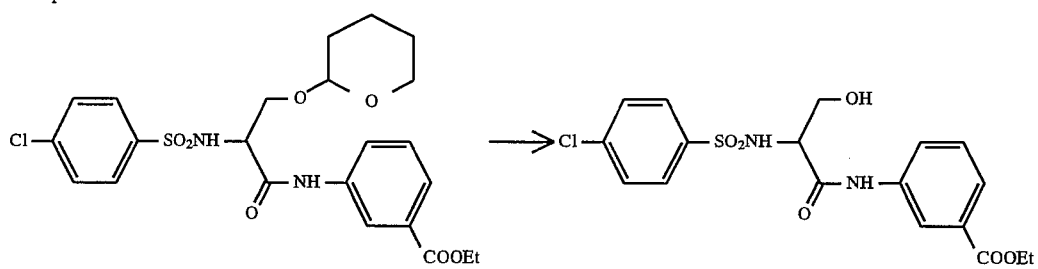
Example 30
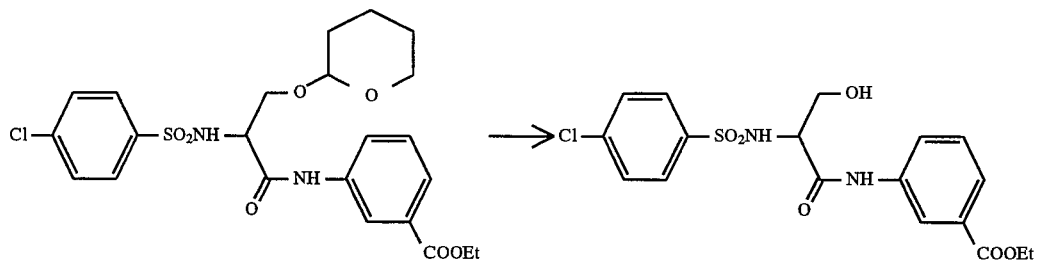
Example 31
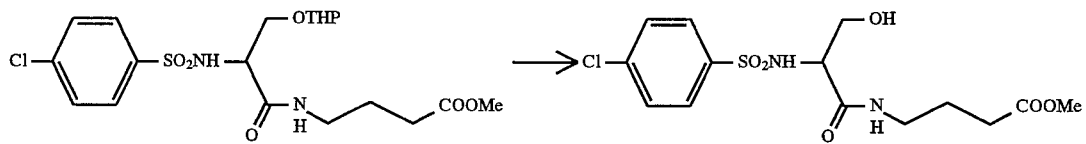
Example 32
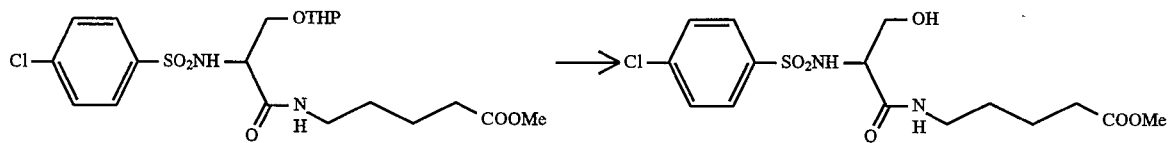
Example 33
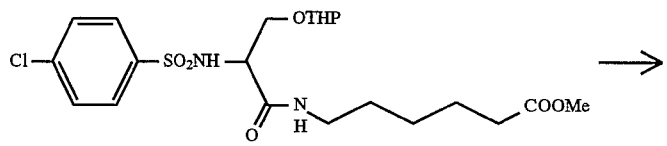

-continued
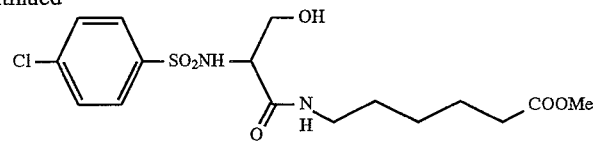
Example 34
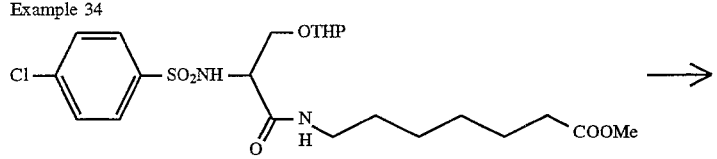 
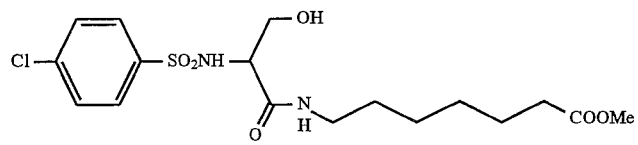
Example 35
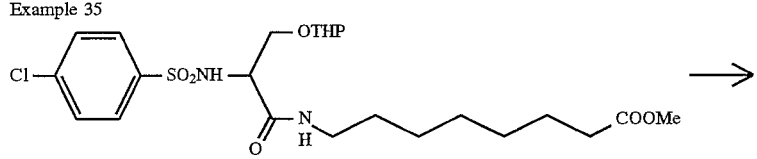 
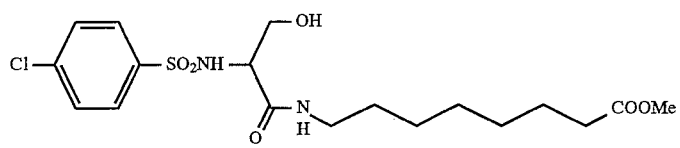
Example 36
 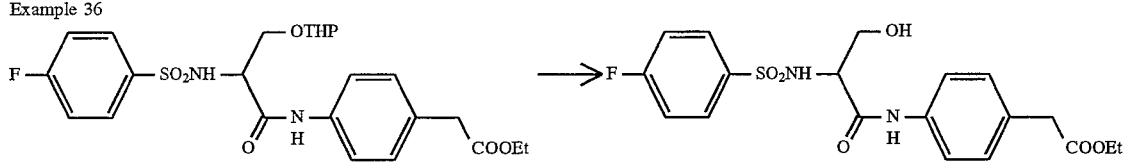 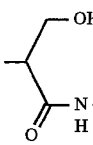
Example 37
 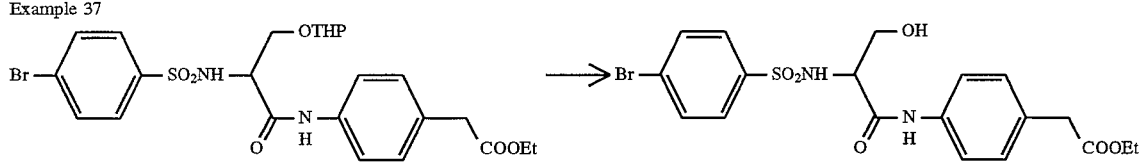 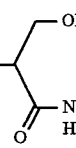
Example 38
 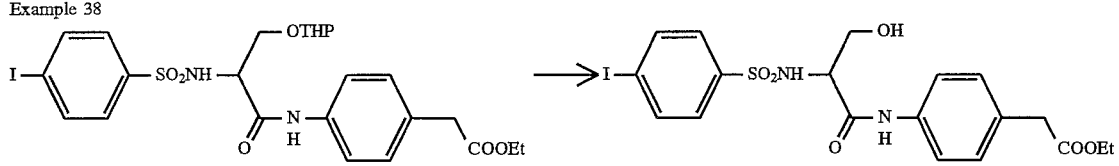 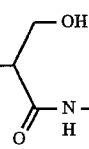
Example 39
 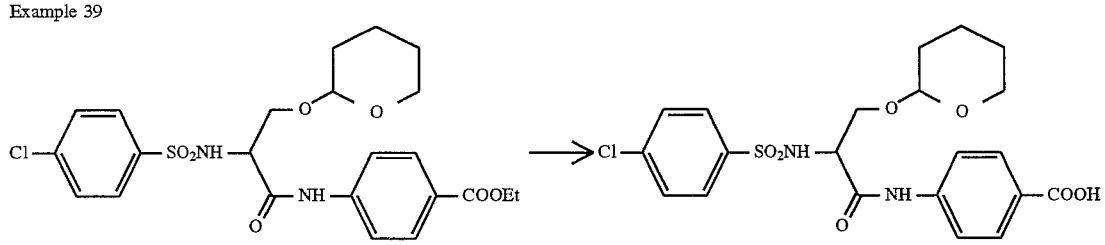 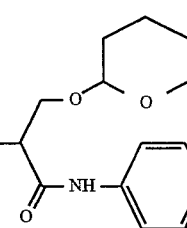

Example 40
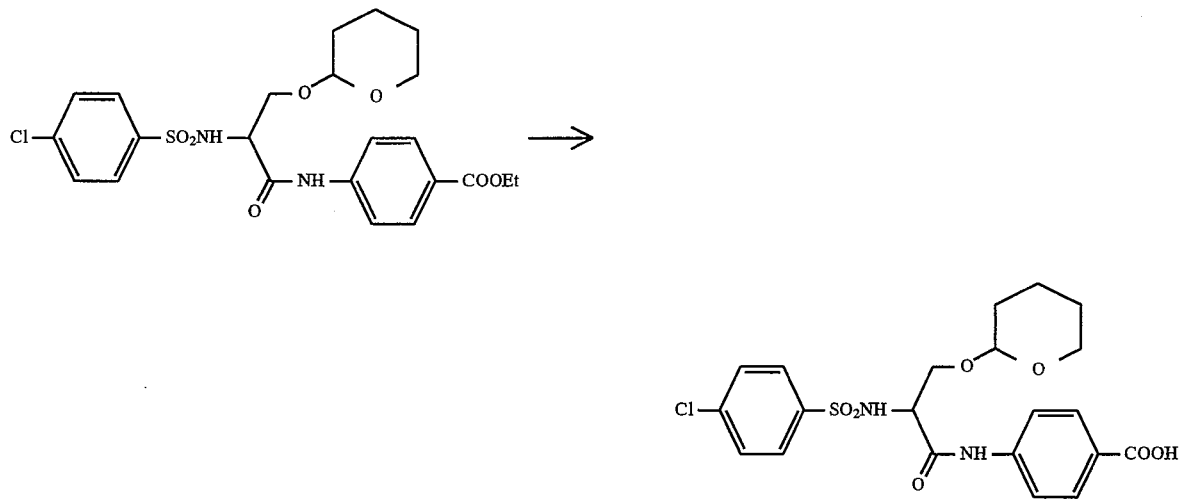
Example 41
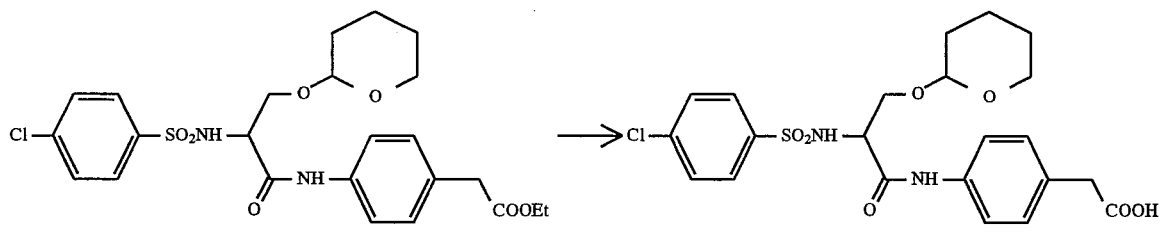
Example 42
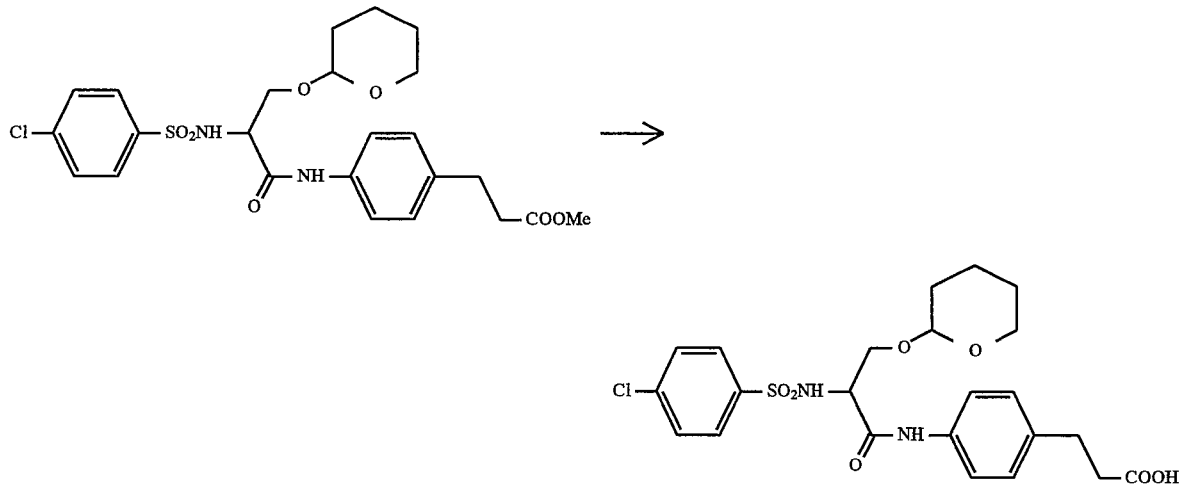
Example 43
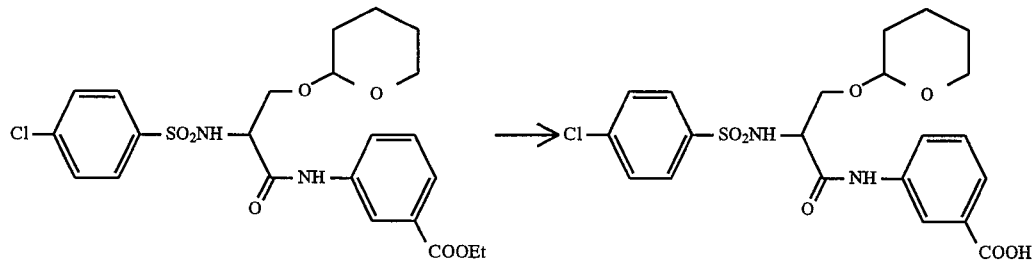

Example 44
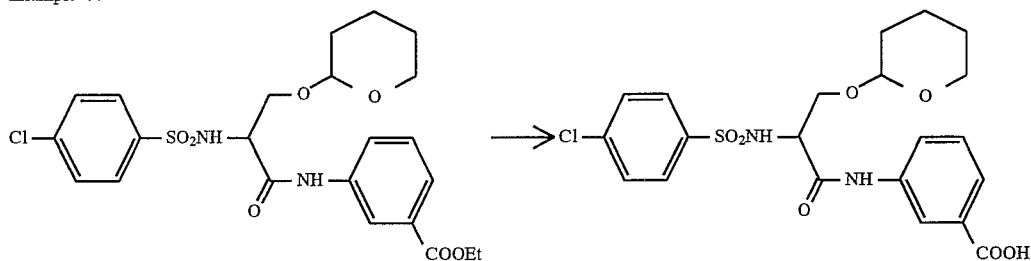
Example 45
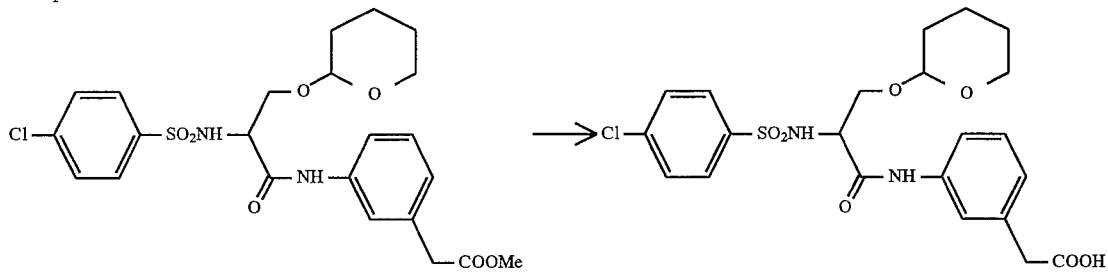
Example 46
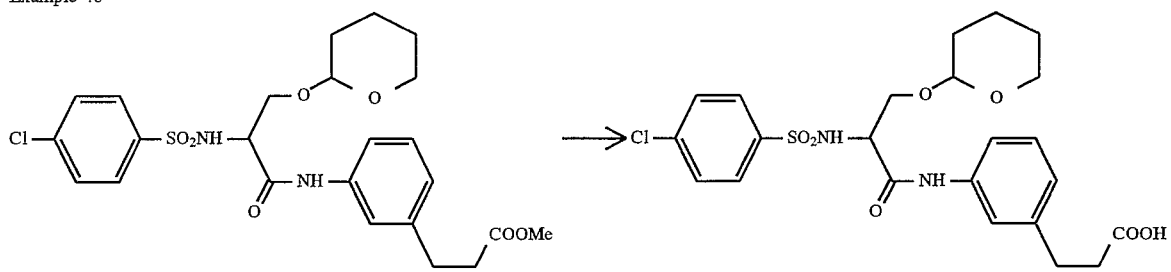
Example 47
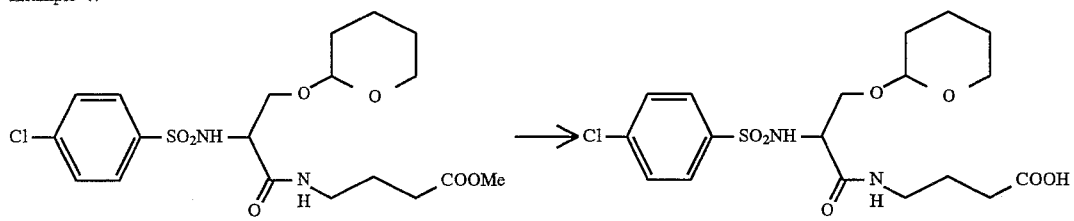
Example 48
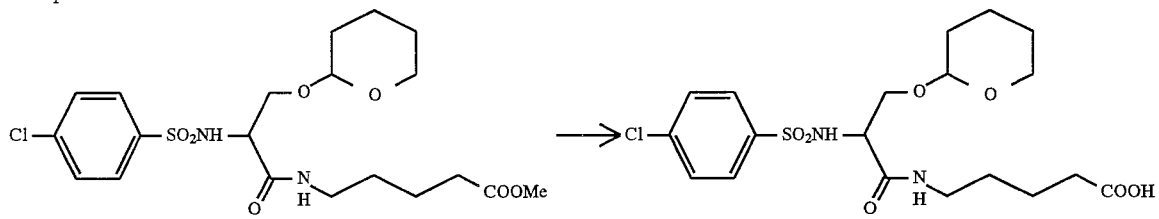
Example 49
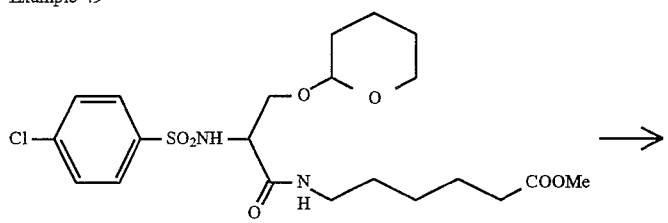

-continued
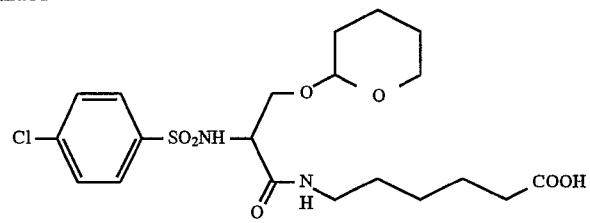
Example 50
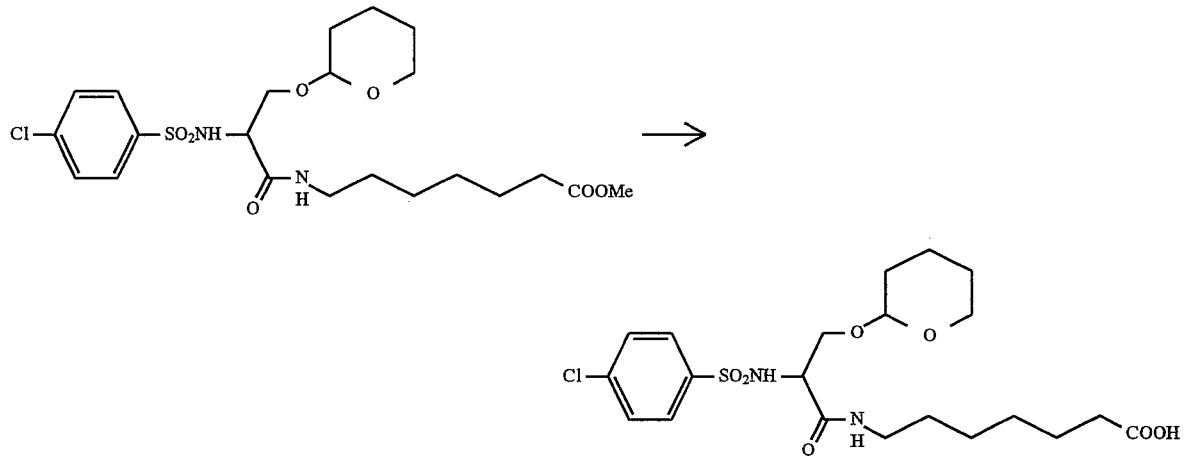
Example 51
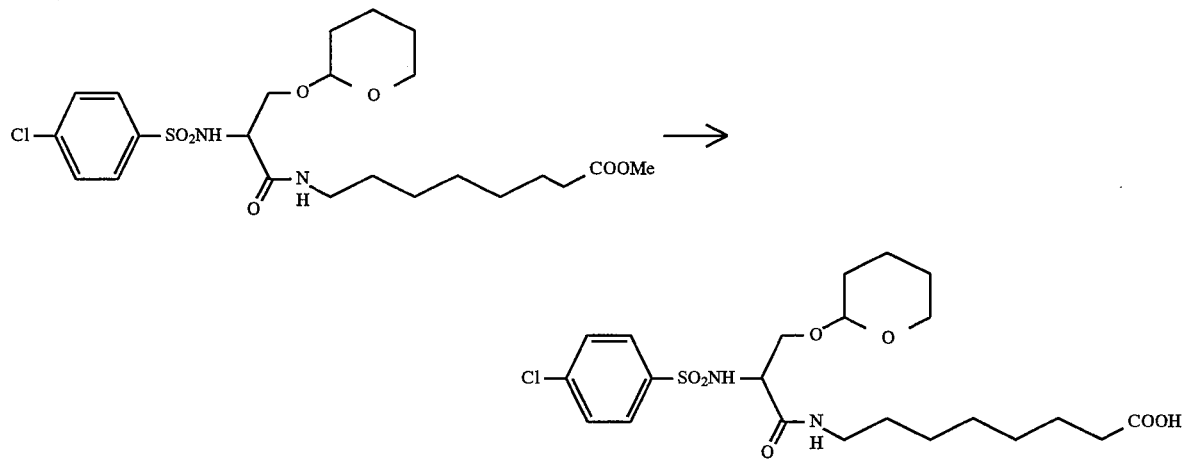
Example 52
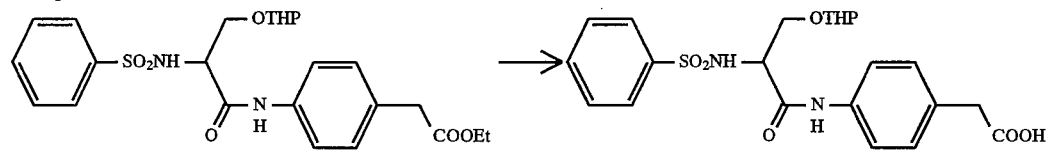
Example 53
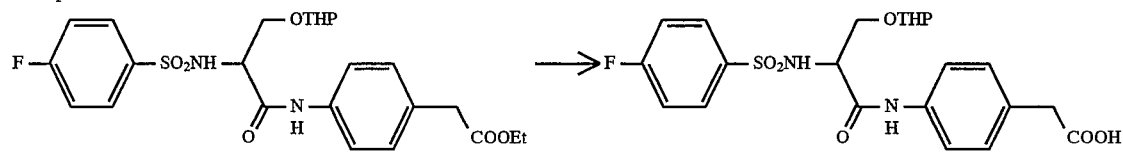

Example 54
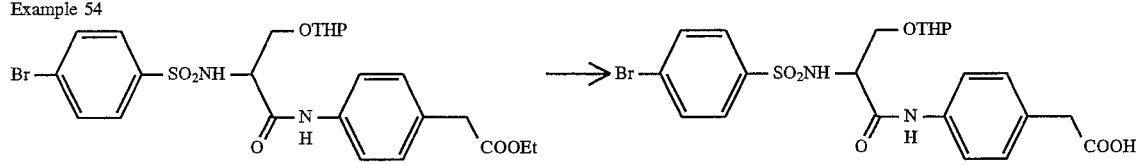
Example 55
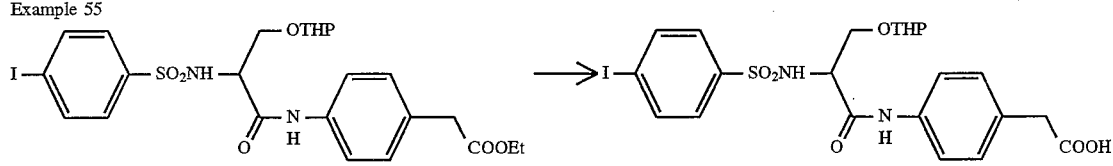
Example 56
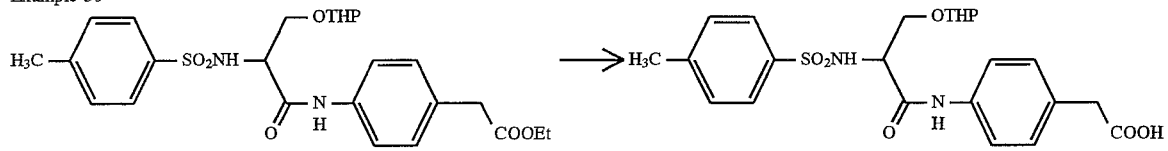
Example 57
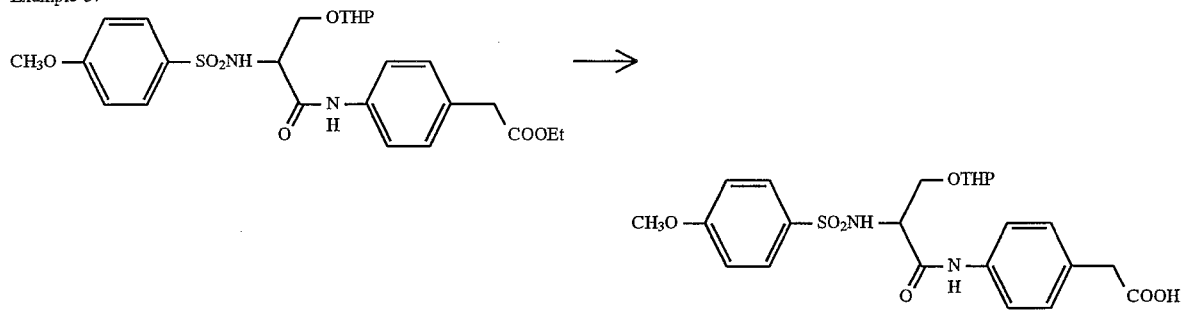
Example 58
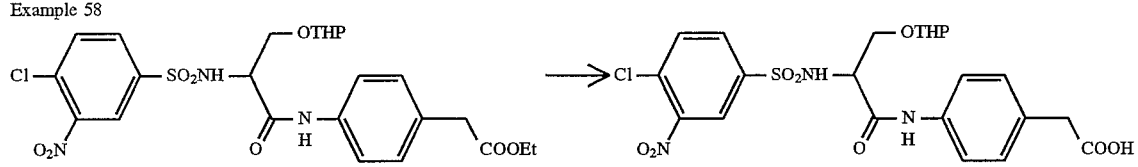
Example 60
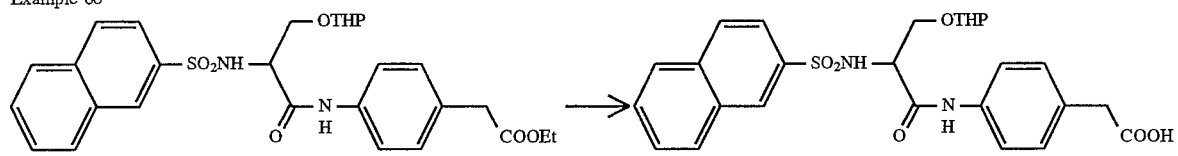
Example 61
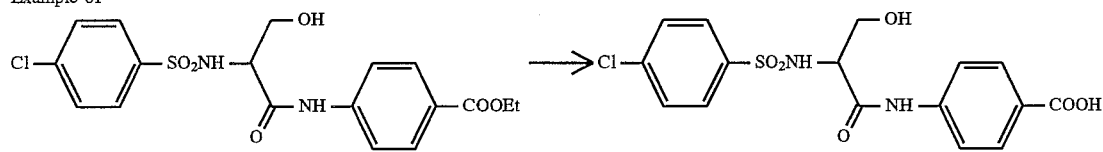
Example 62
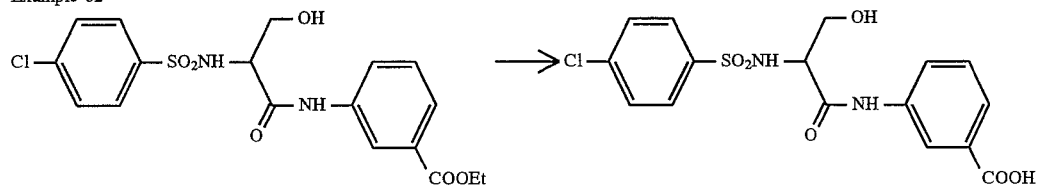

Example 63
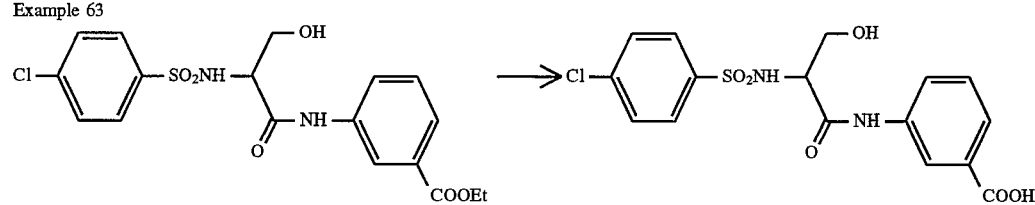
Example 64
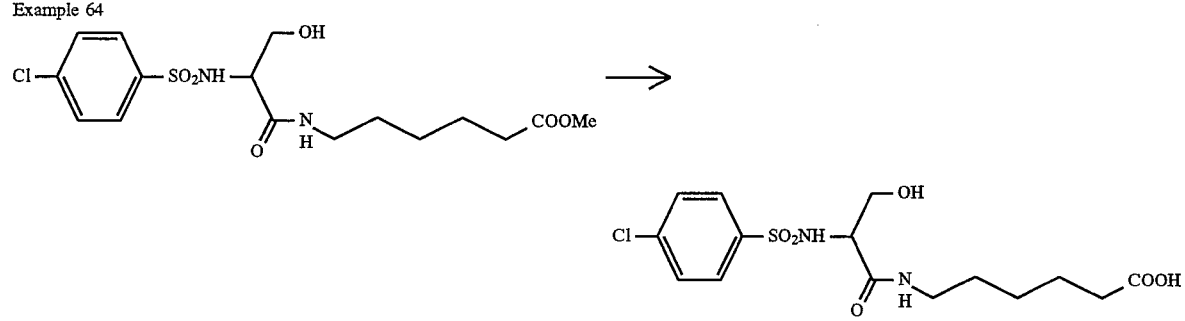
Example 65
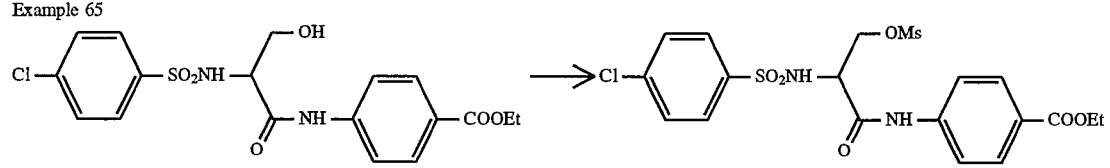
Example 66
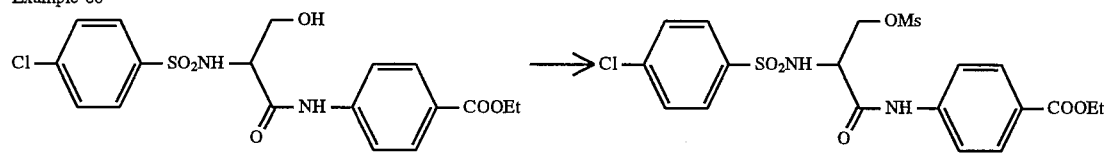
Example 67
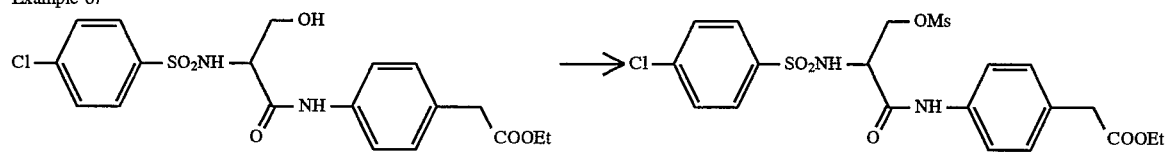
Example 68
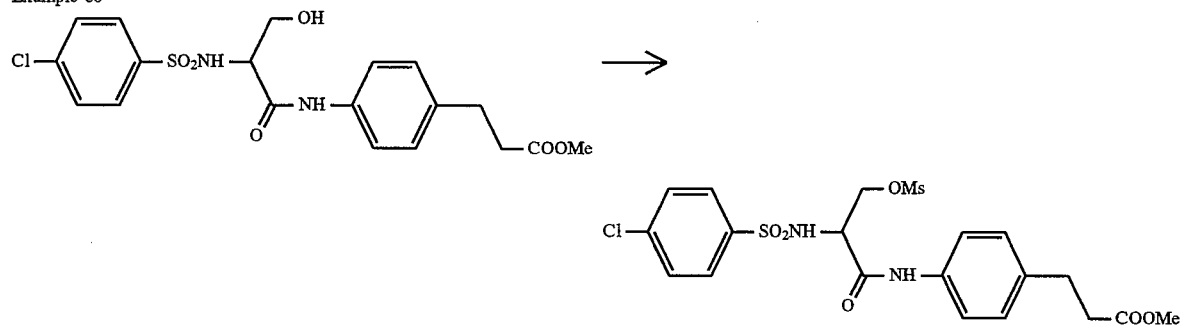
Example 69
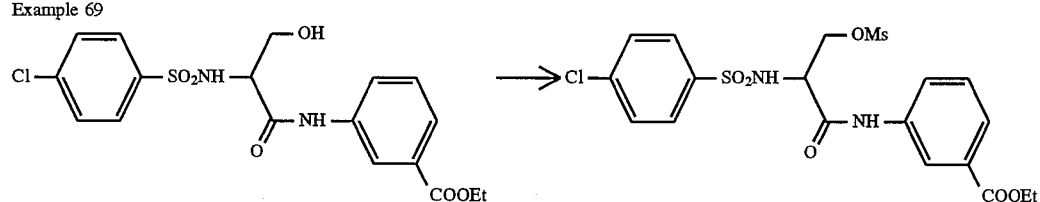

-continued
Example 70
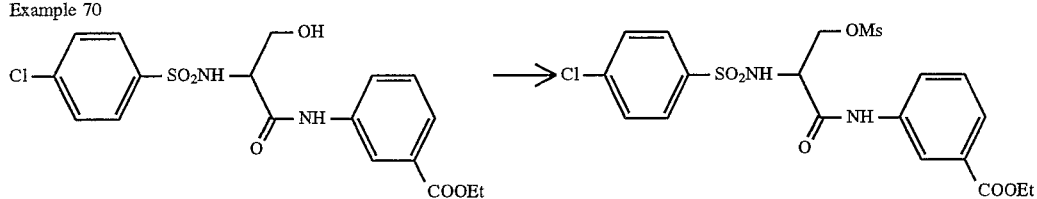
Example 71
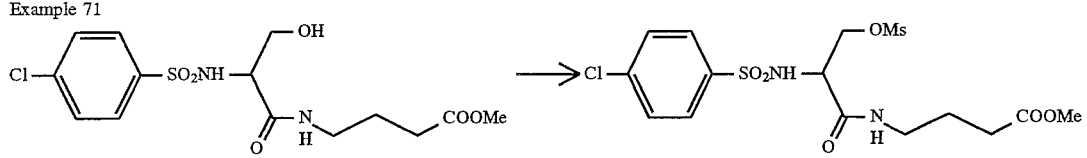
Example 72
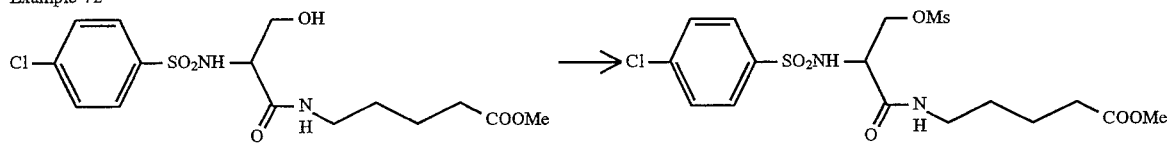
Example 73
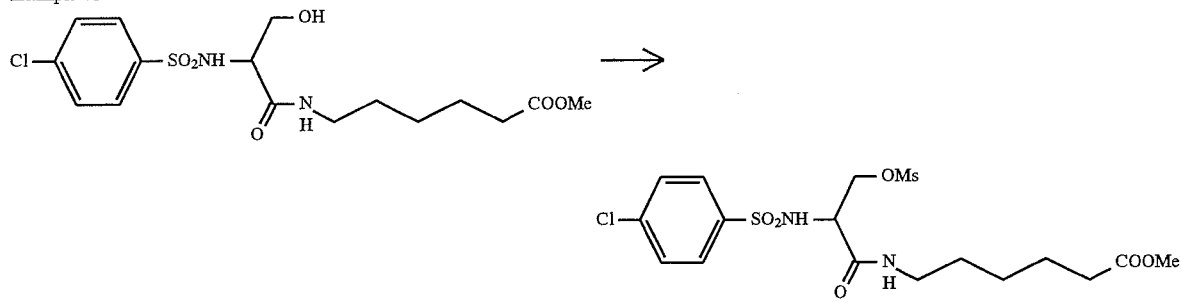
Example 74
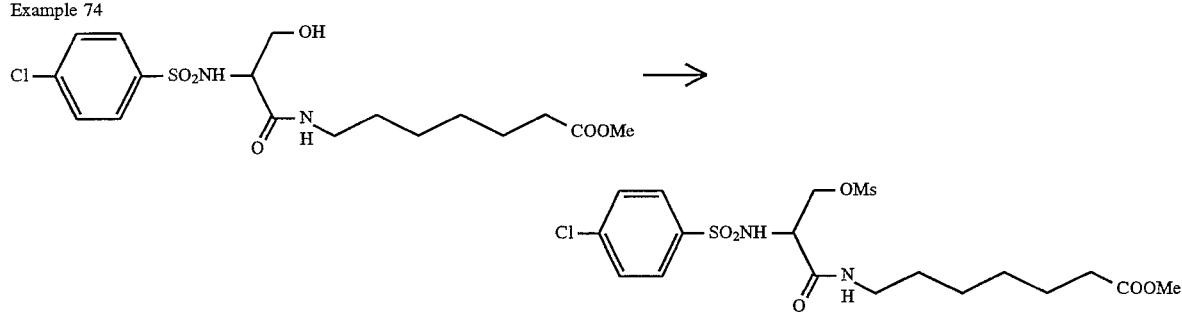
Example 75
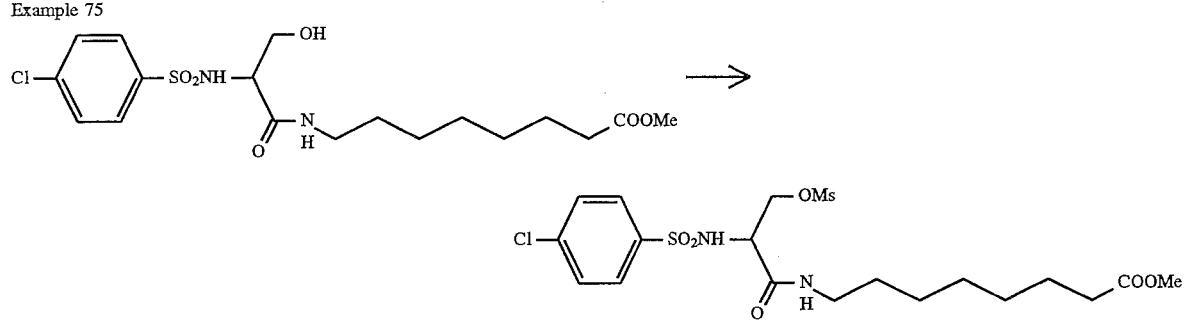

Example 76
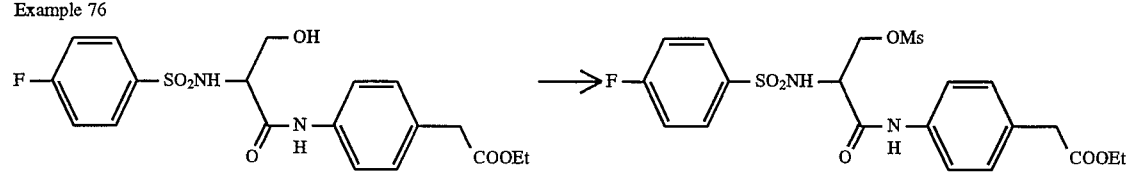
Example 77
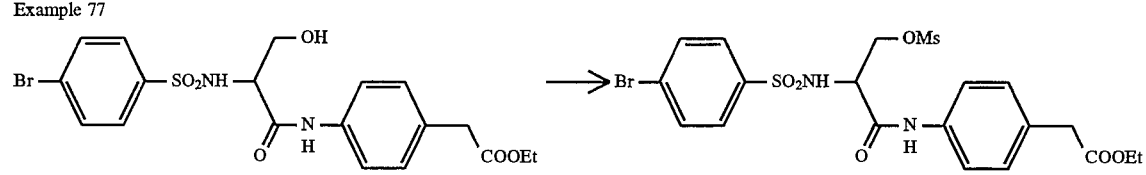
Example 78
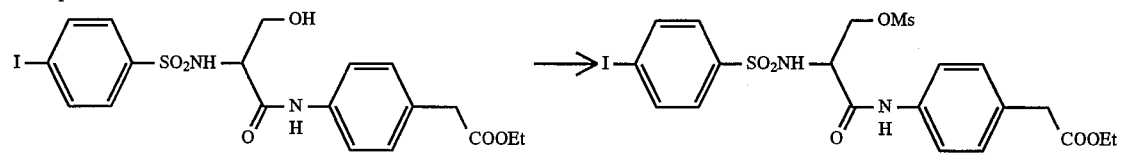
Example 79
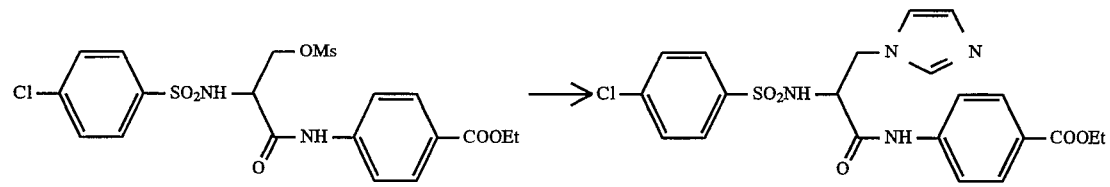
Example 80
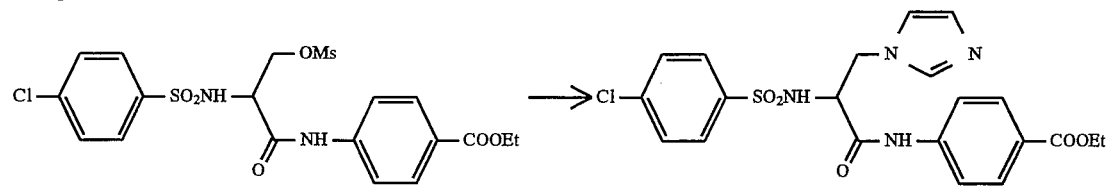
Example 81
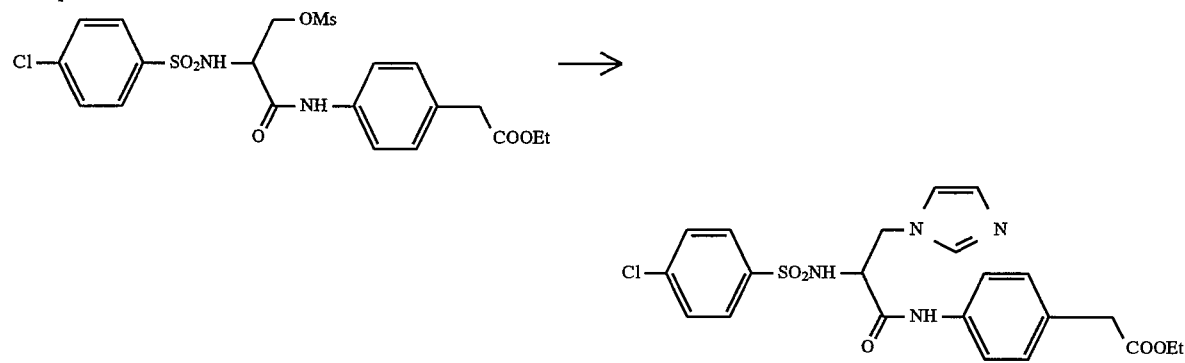
Example 82
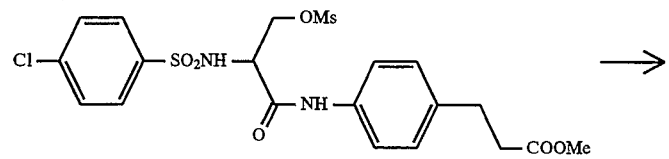

-continued
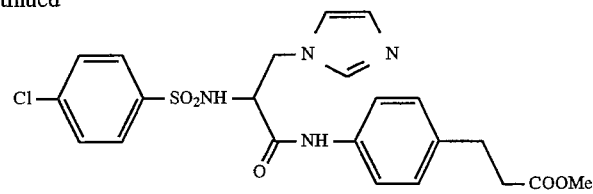
Example 83
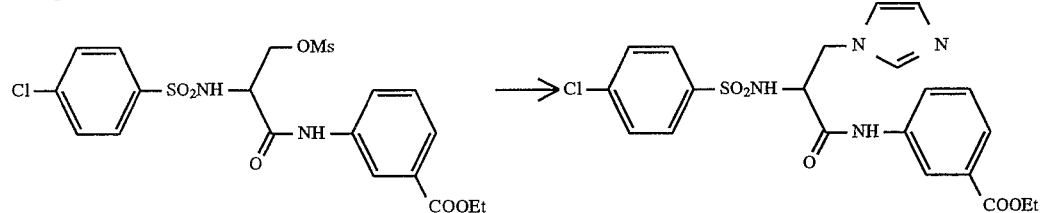
Example 84
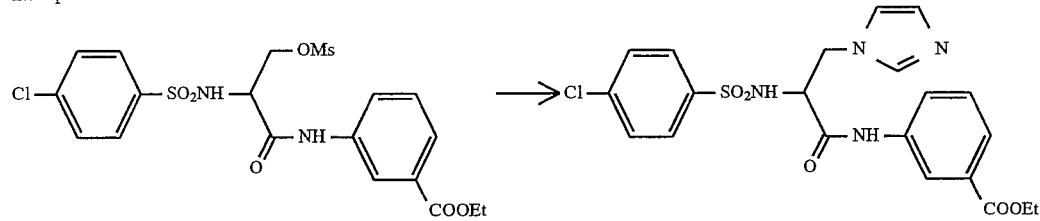
Example 85
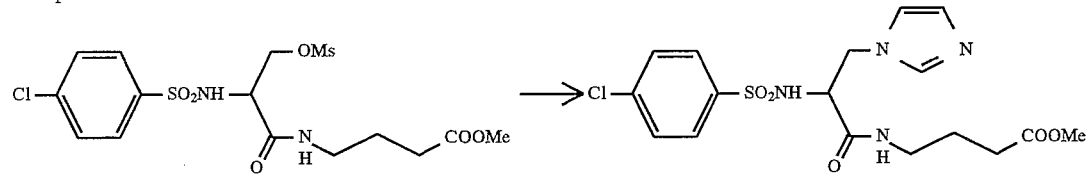
Example 86
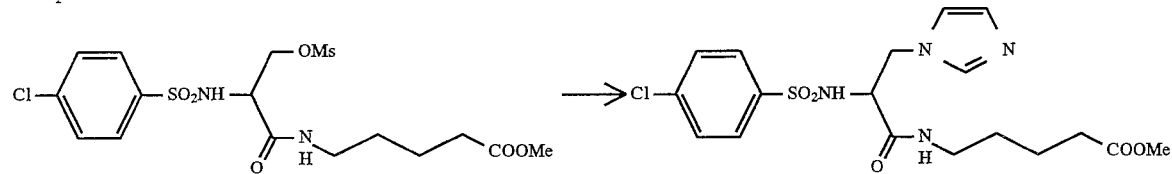
Example 87
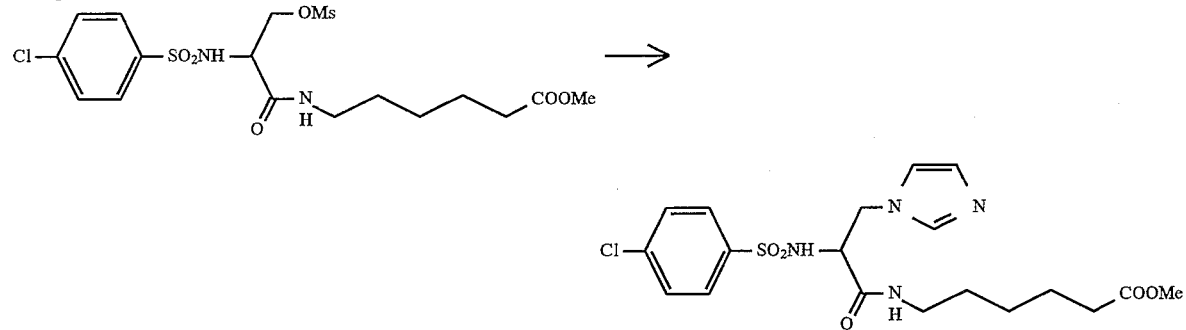
Example 88
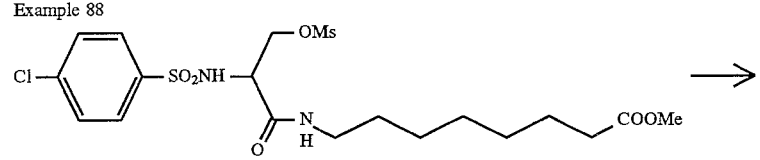

-continued
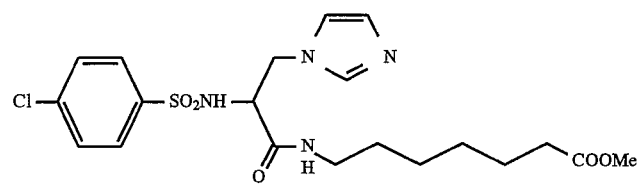
Example 89
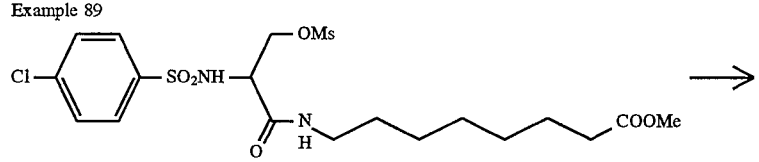
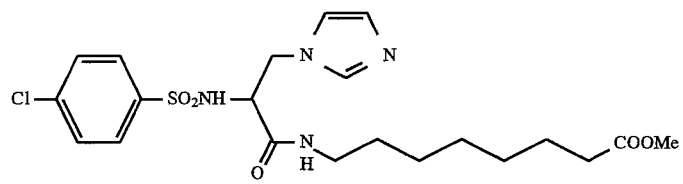
Example 90
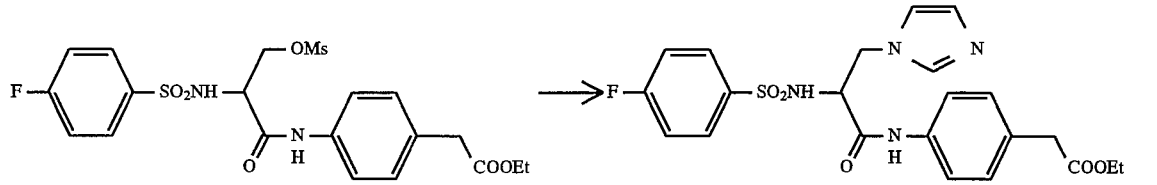
Example 91
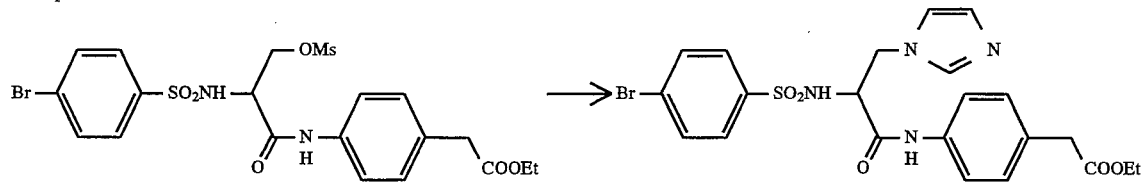
Example 92
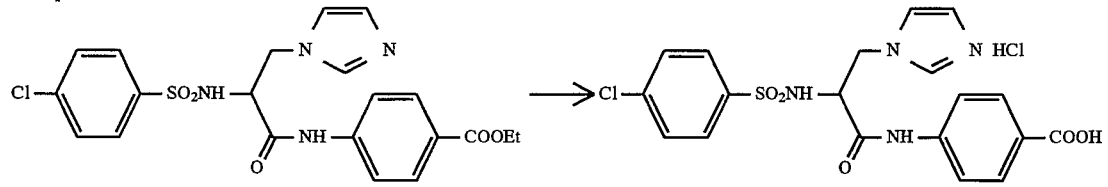
Example 93
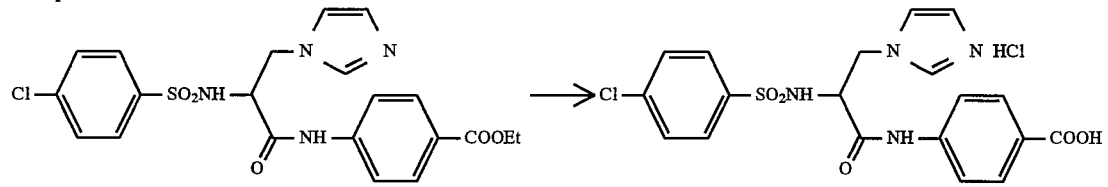
Example 94
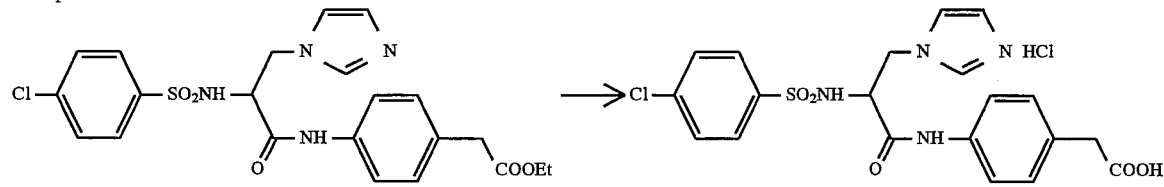

Example 95
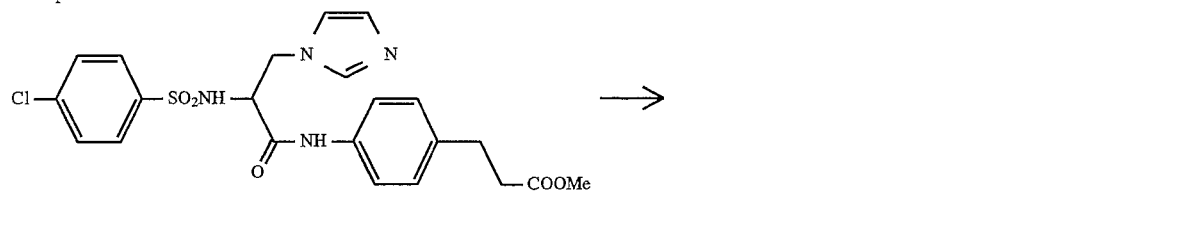
Example 96
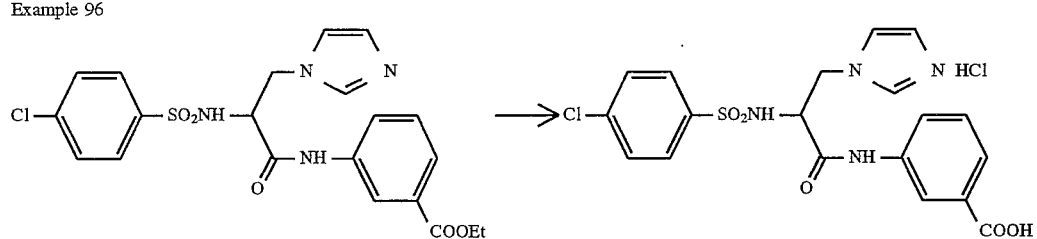
Example 97
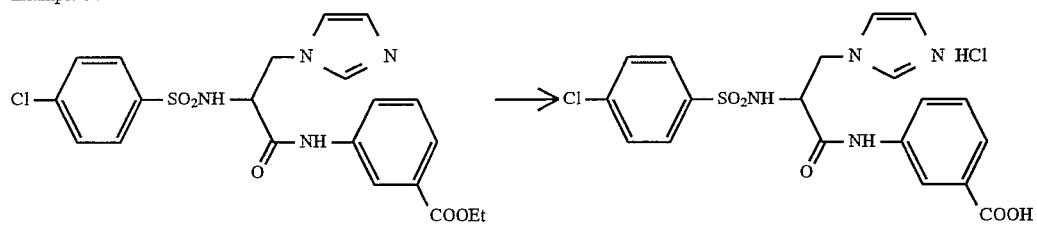
Example 98
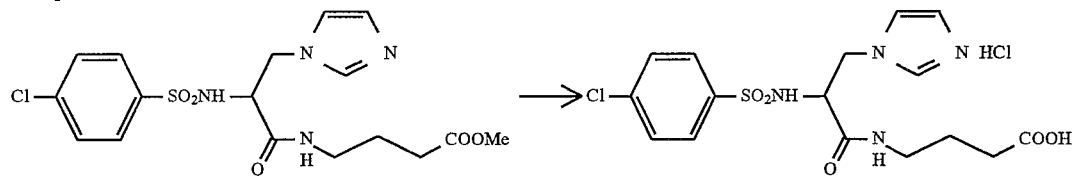
Example 99
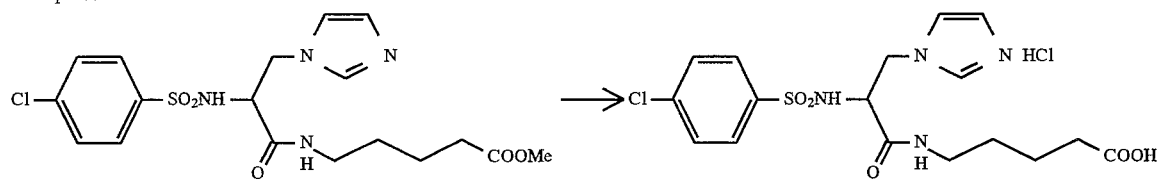
Example 100
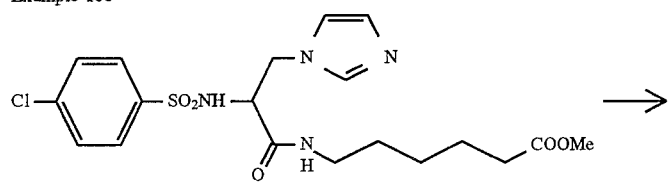

-continued
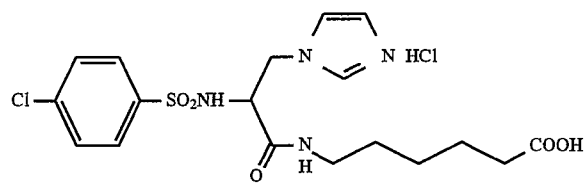
Example 101
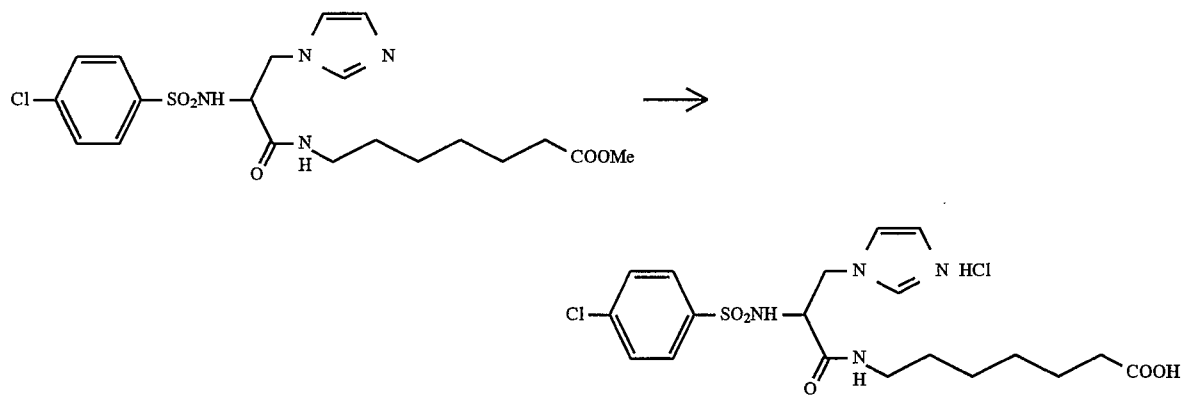
Example 102
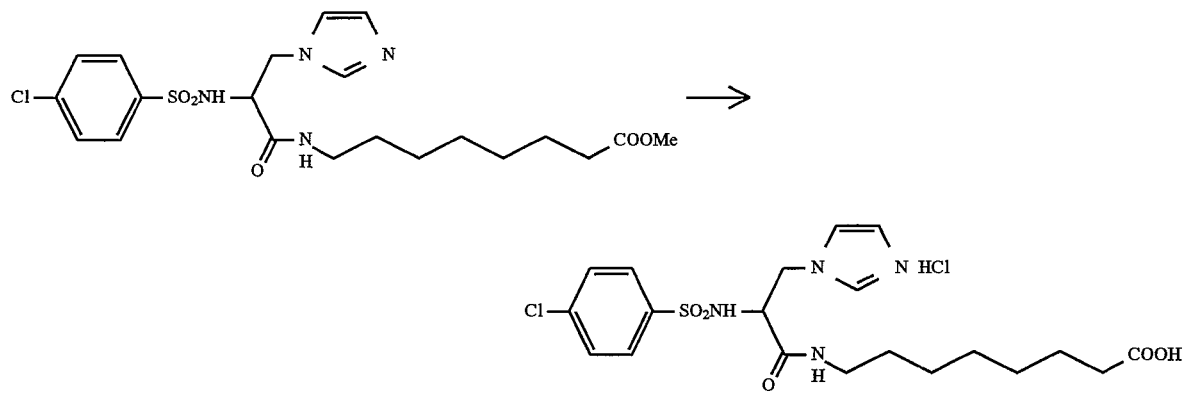
Example 103
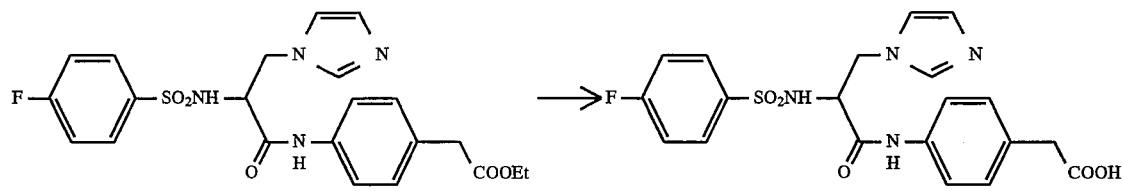
Example 104
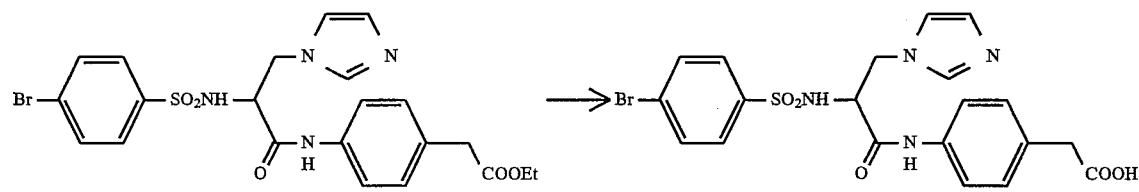

-continued
Example 105
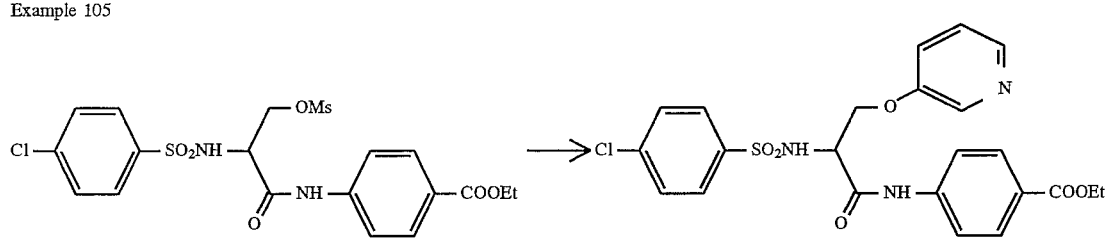
Example 106
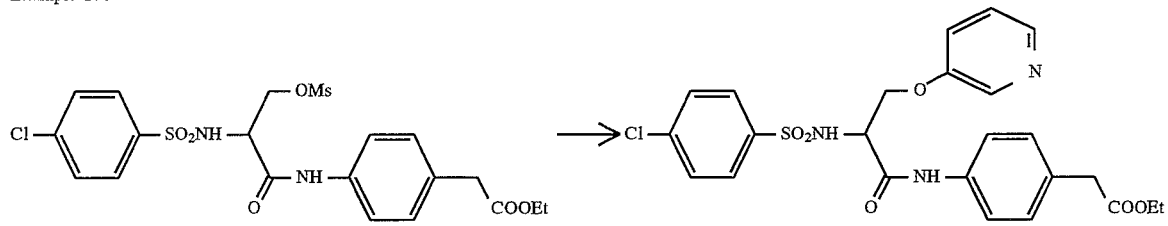
Example 107
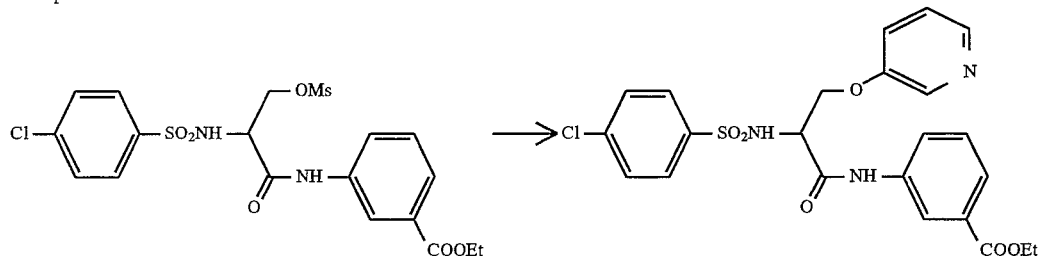
Example 108
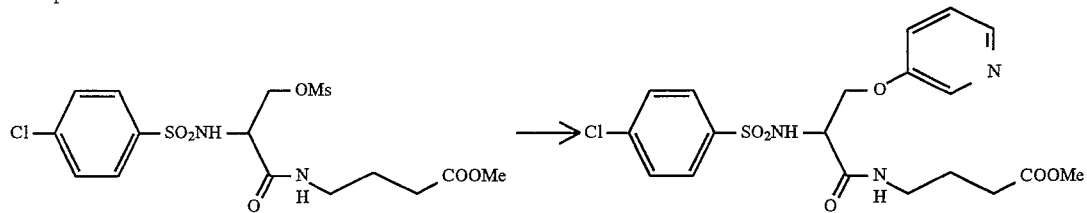
Example 109
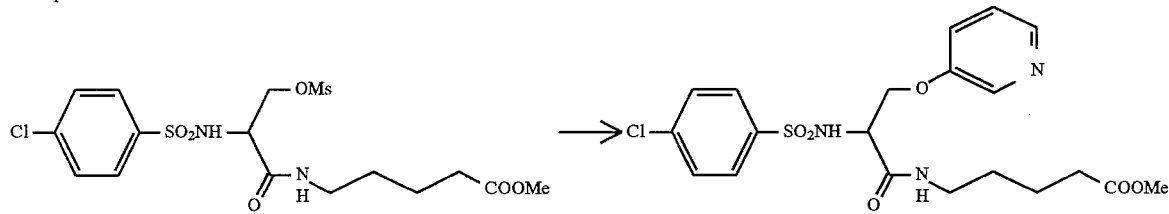
Example 110
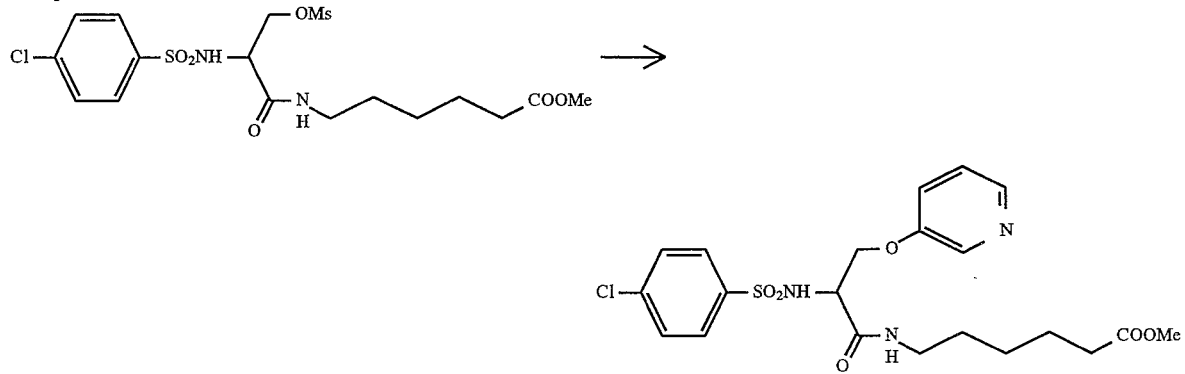

Example 111
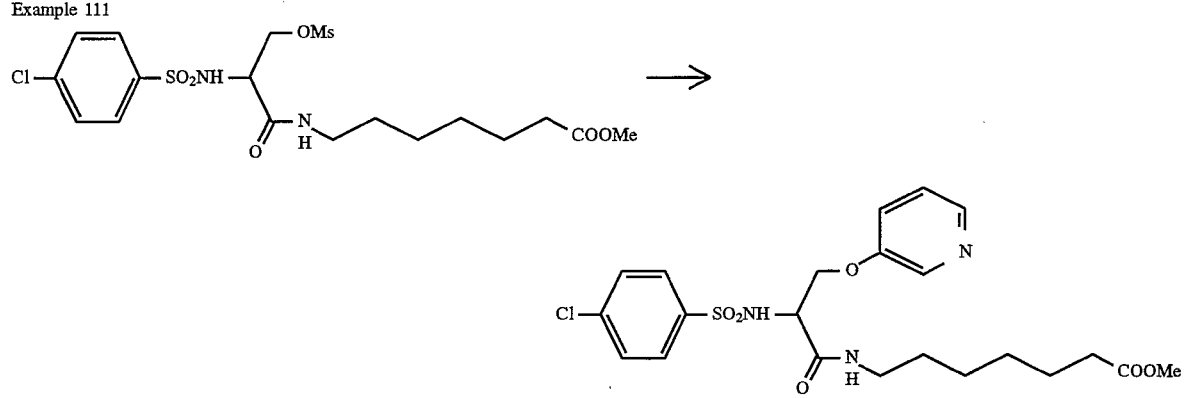
Example 112
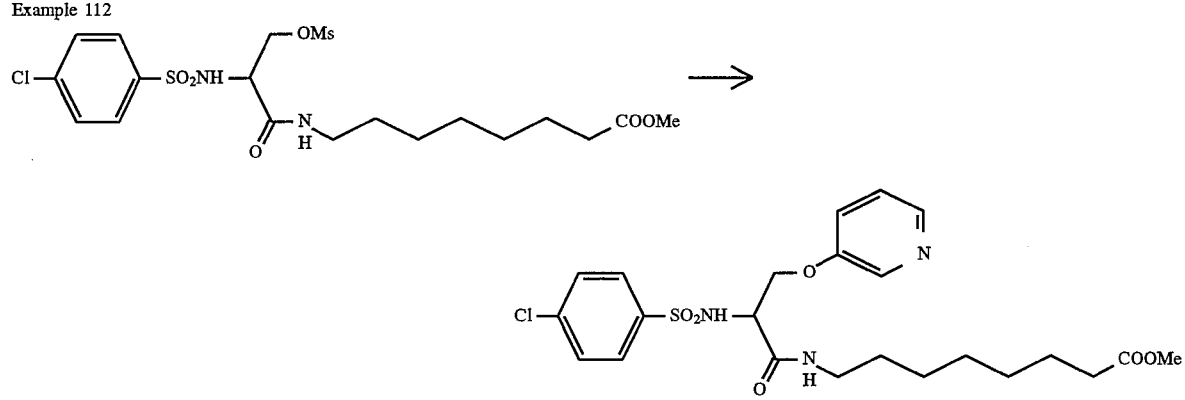
Example 113
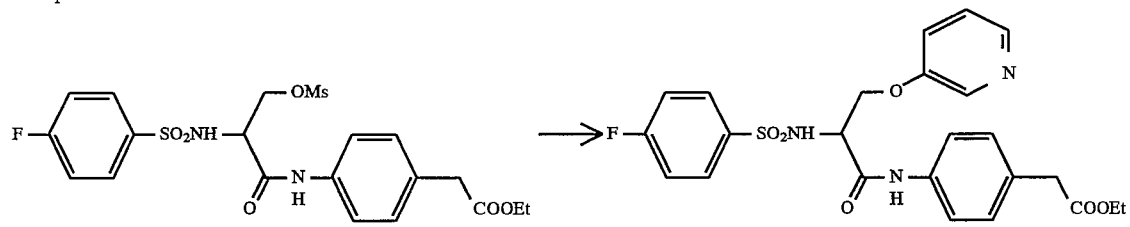
Example 114
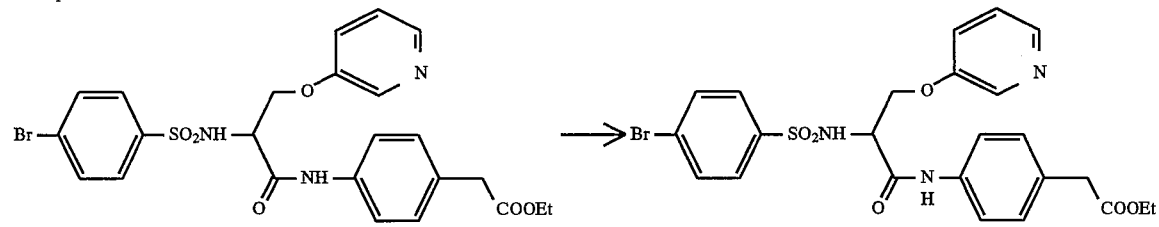
Example 115
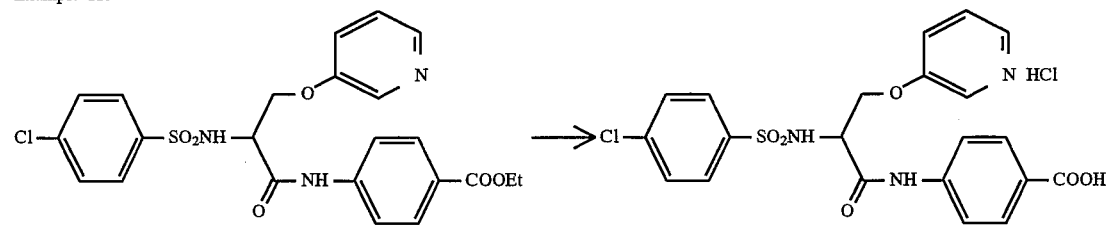

-continued
Example 116
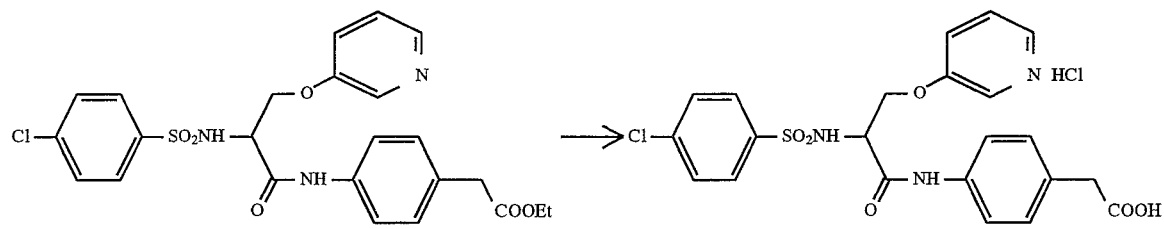
Example 117
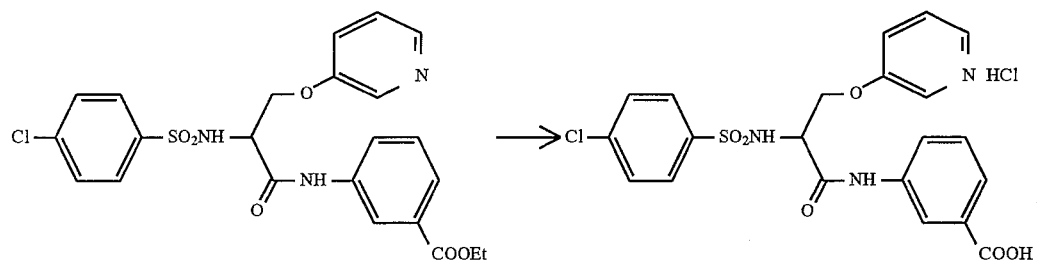
Example 118
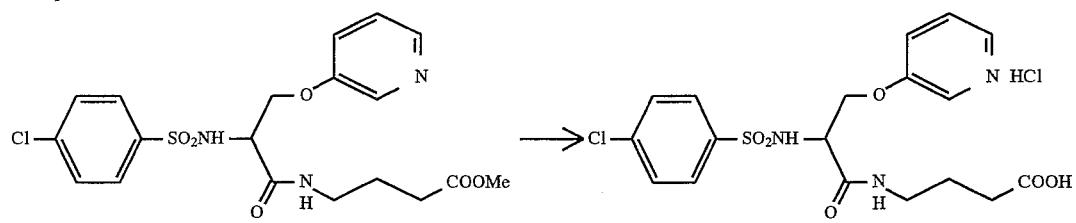
Example 119
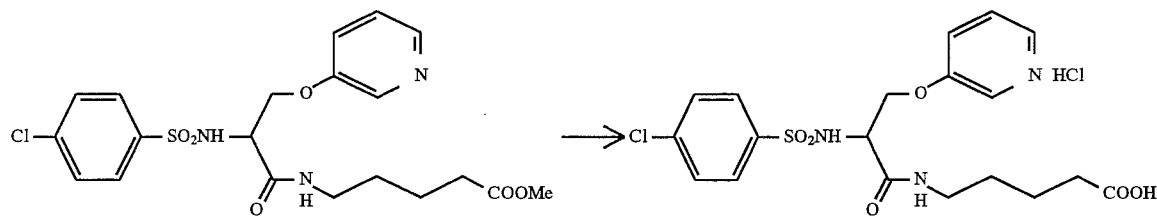
Example 120
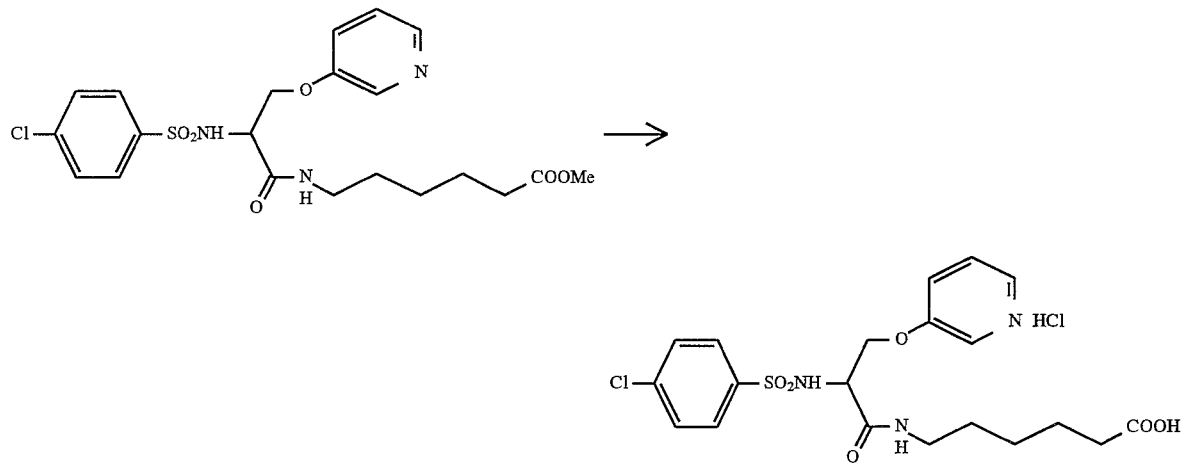

Example 121
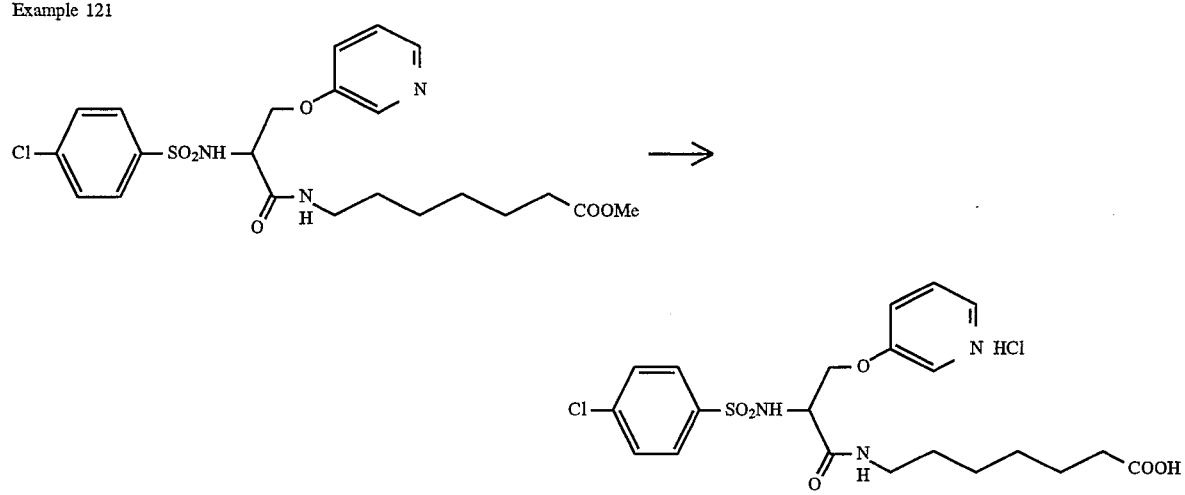
Example 122
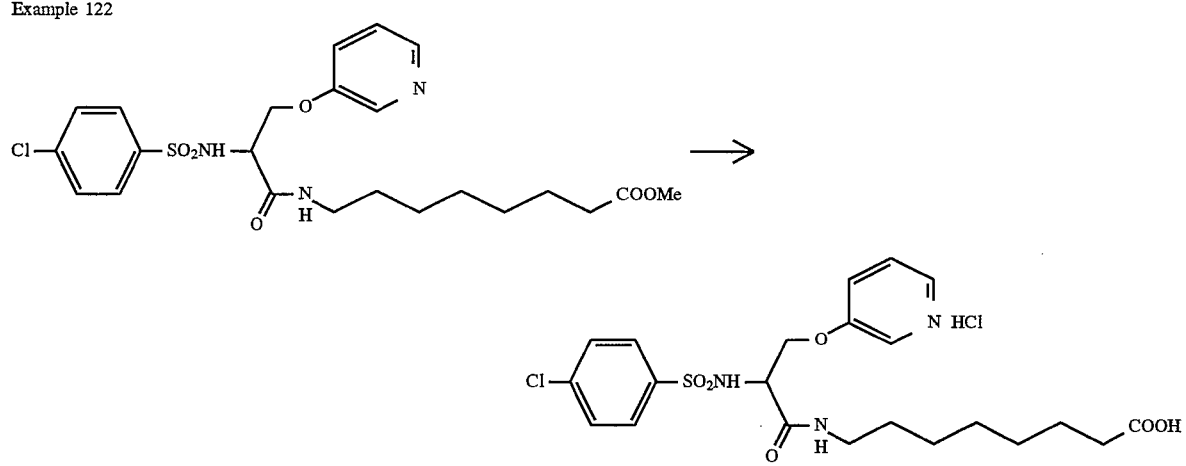
Example 123
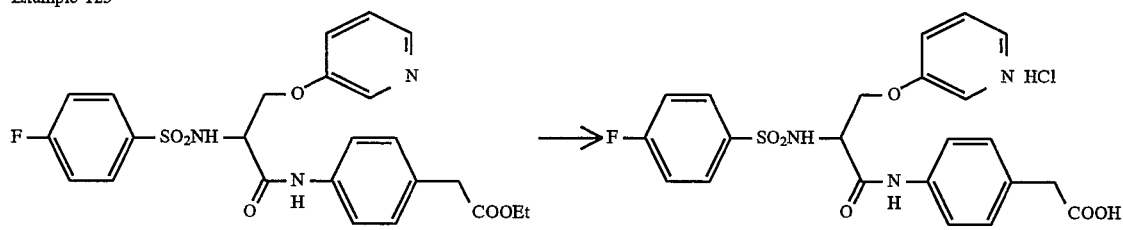
Example 124
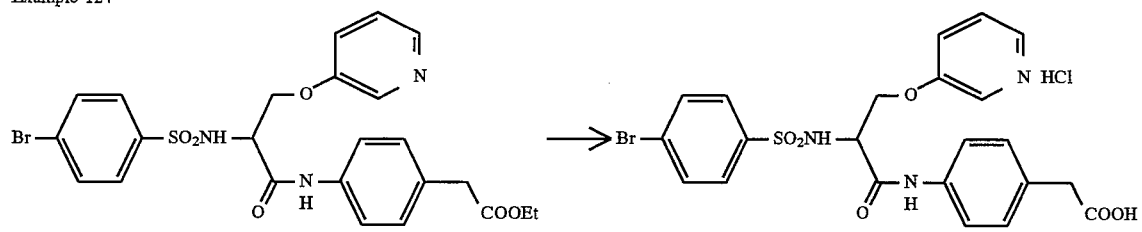
Example 125
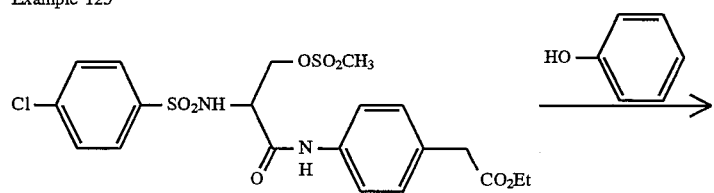

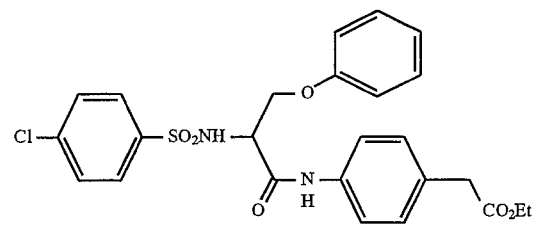
Example 126
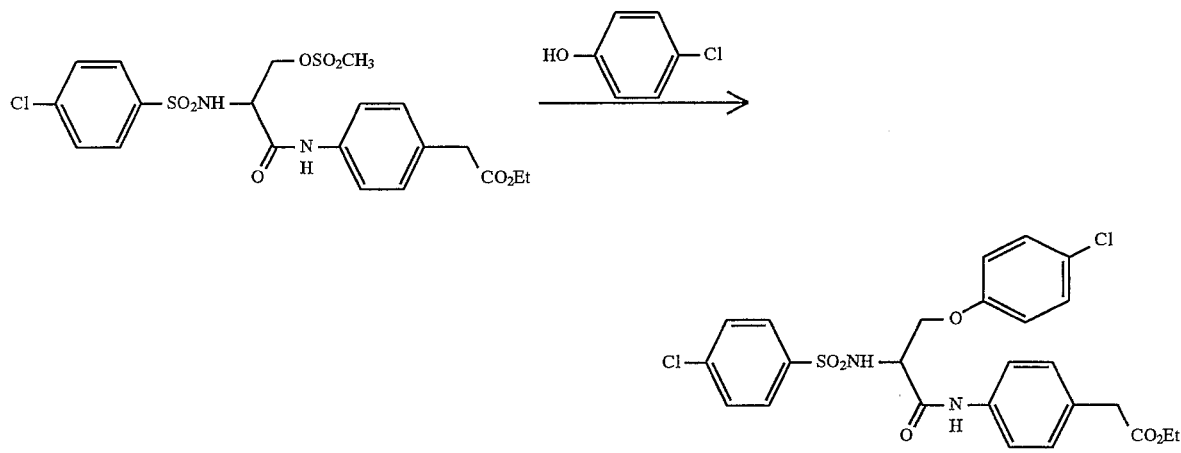
Example 127
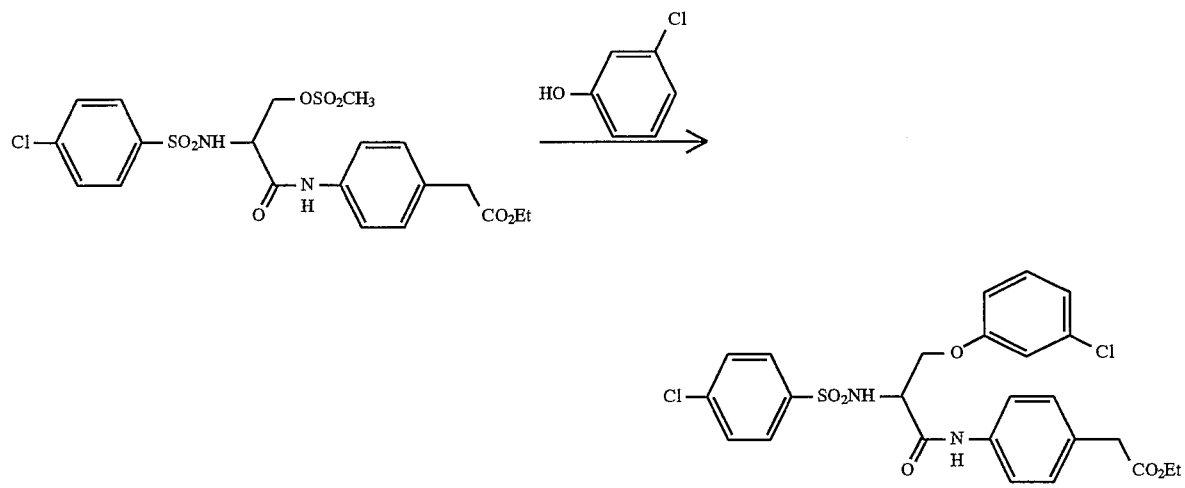
Example 128
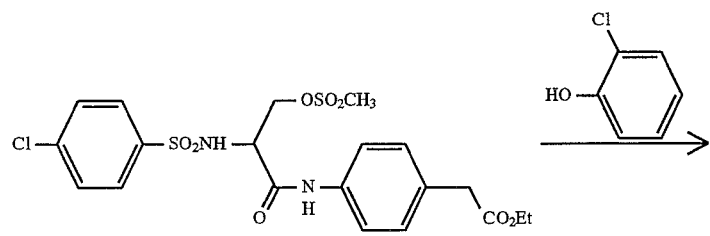

-continued
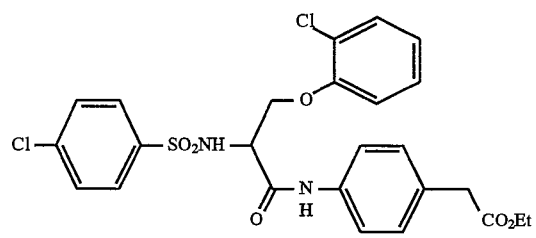
Example 129
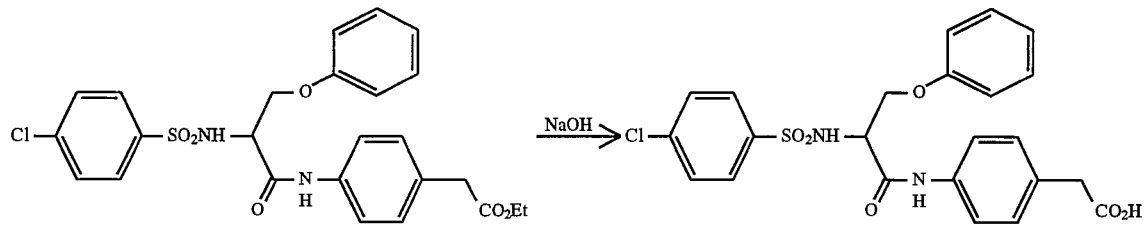
Example 130
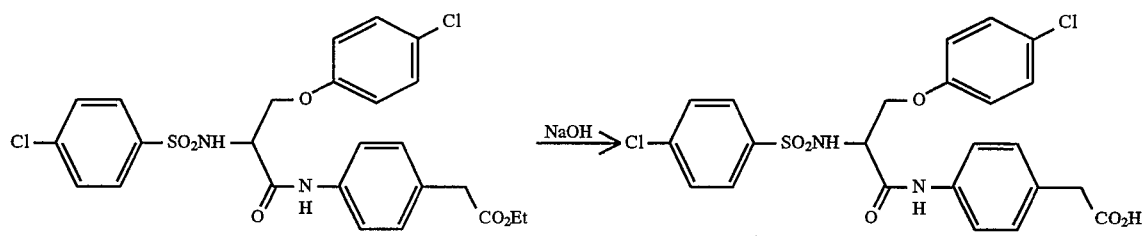
Example 131
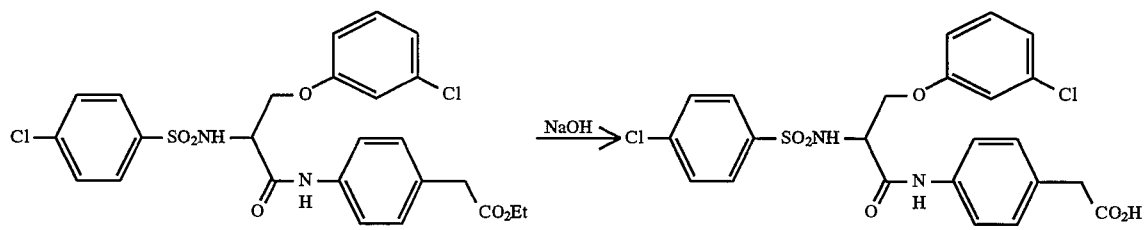
Example 132
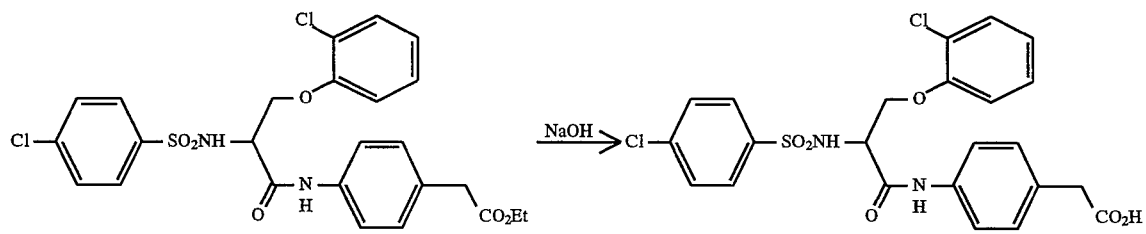
Example 133
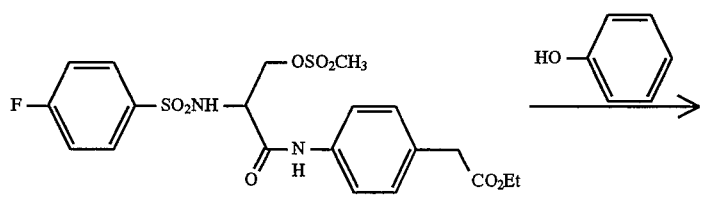

-continued
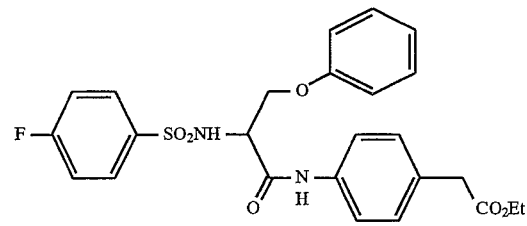
Example 134
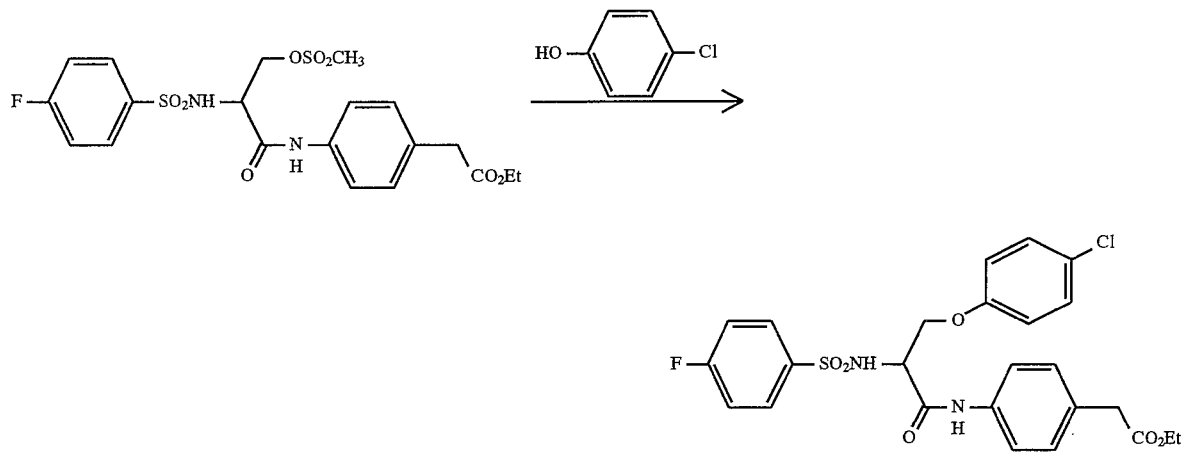
Example 135
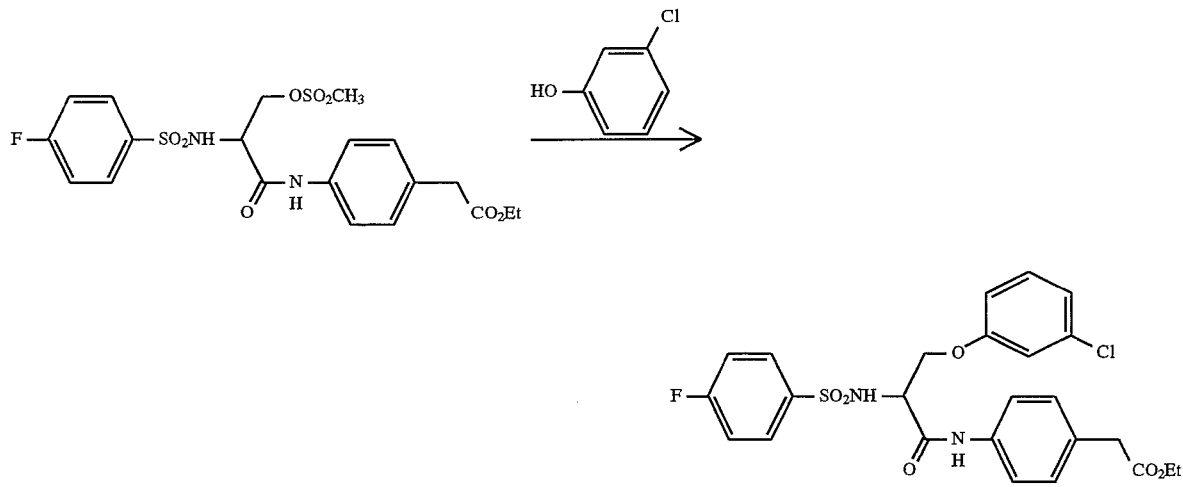
Example 136
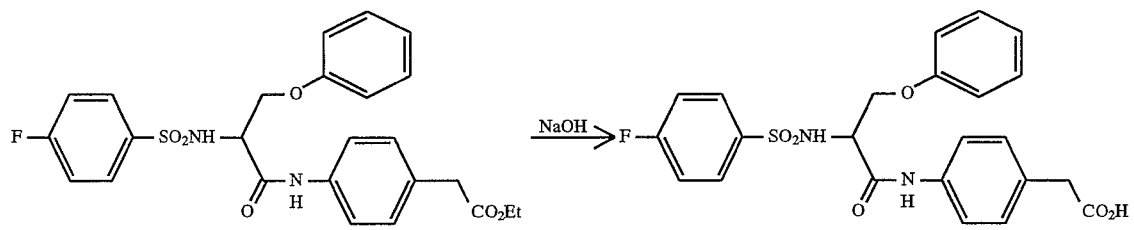

-continued
Example 137
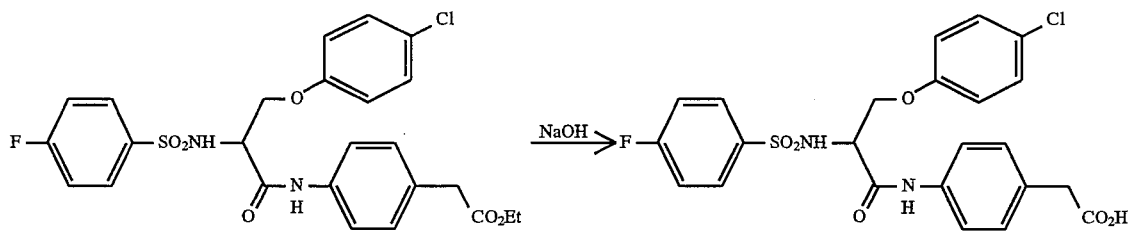
Example 138
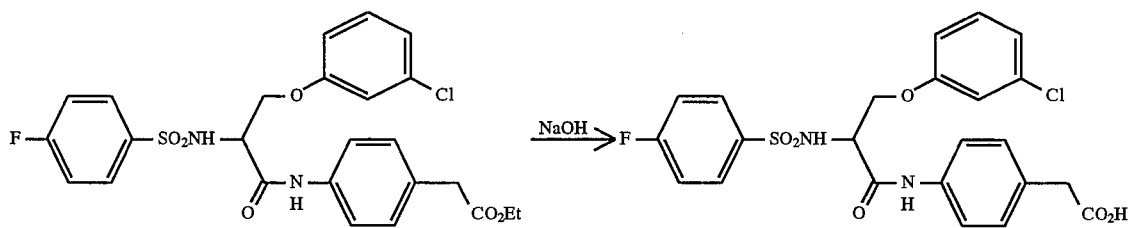
Example 139
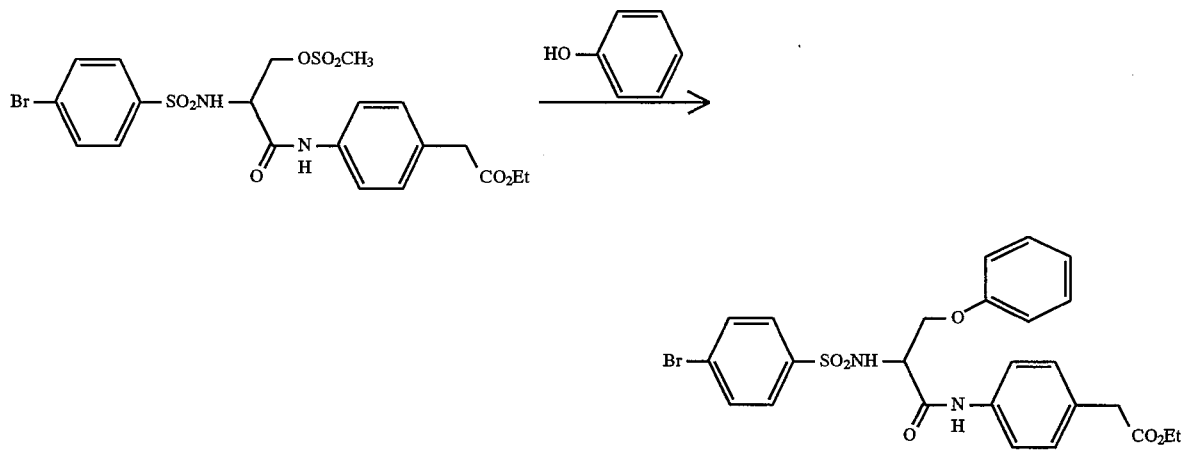
Example 140
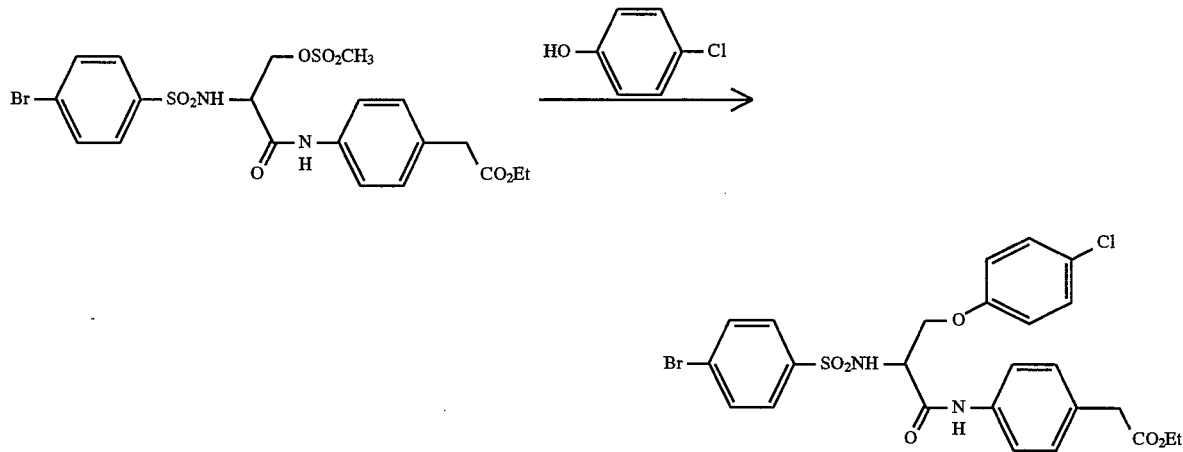

Example 141
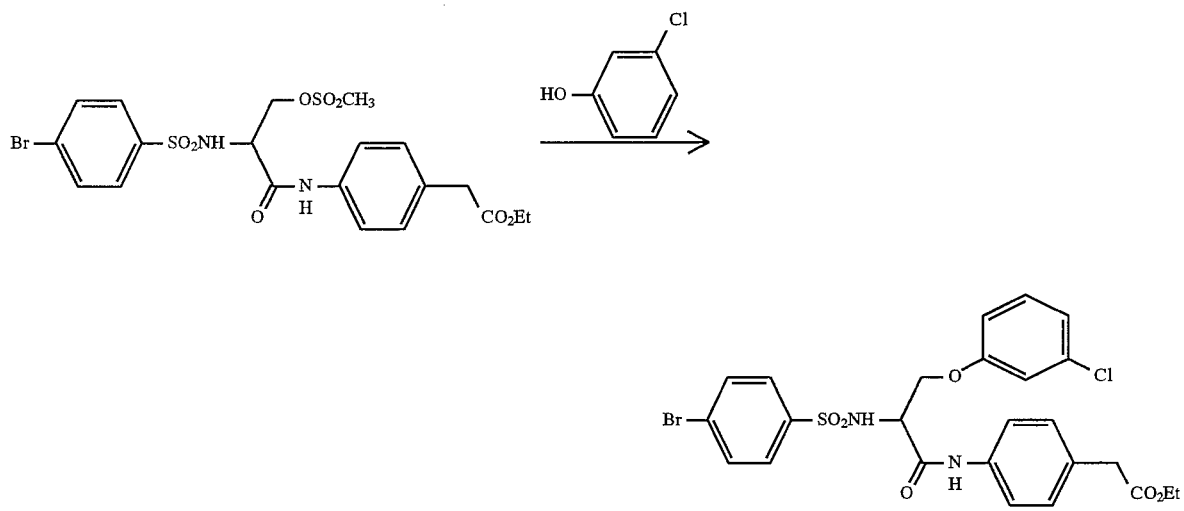
Example 142
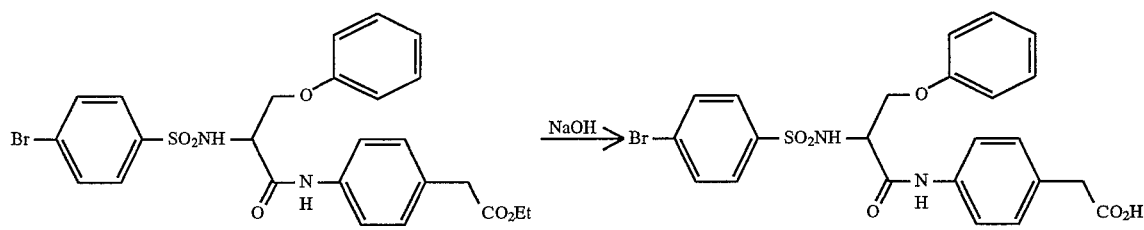
Example 143
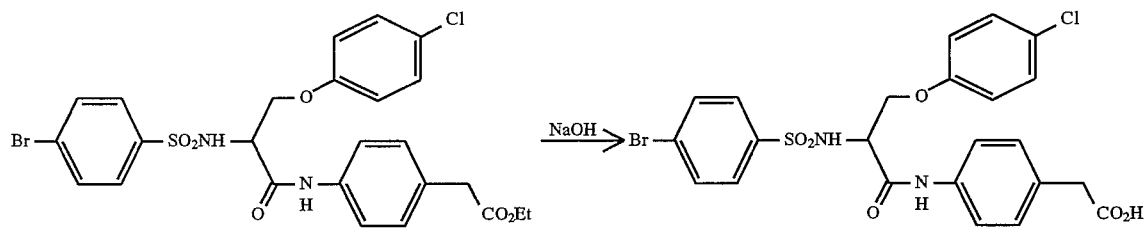
Example 144
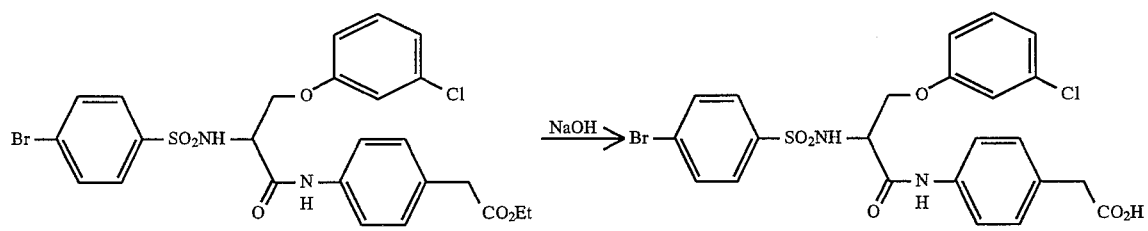
Example 145
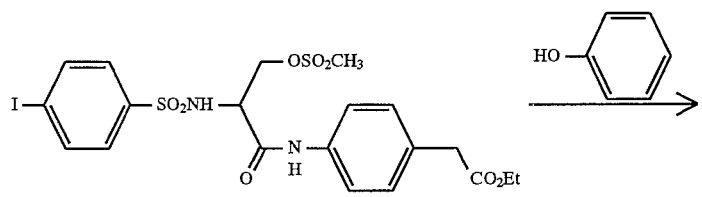

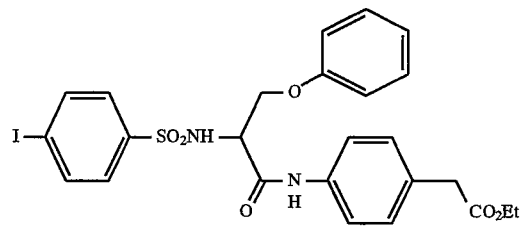
Example 146
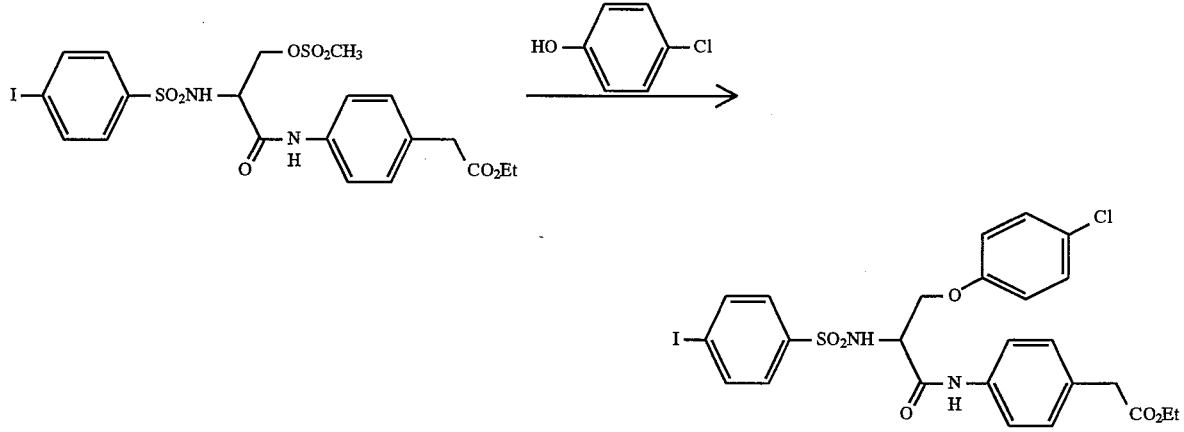
Example 147
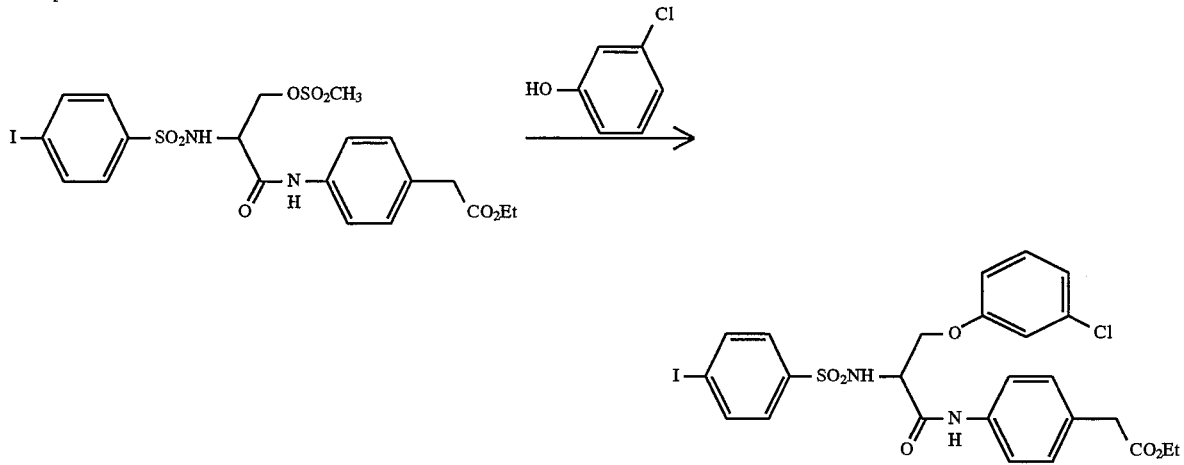
Example 148
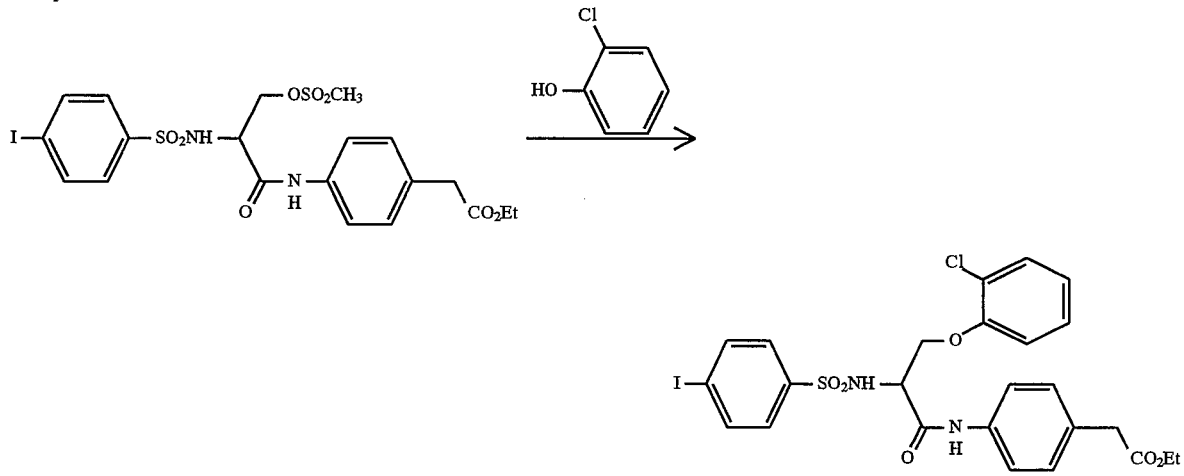

Example 149
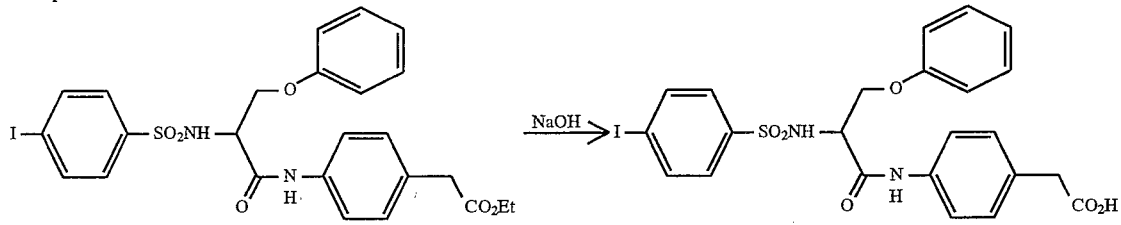
Example 150
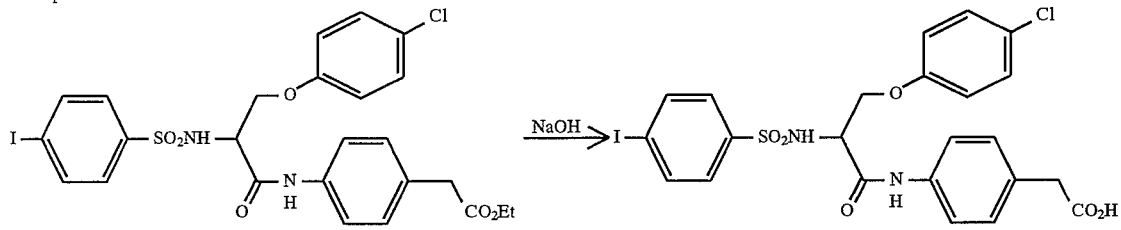
Example 151
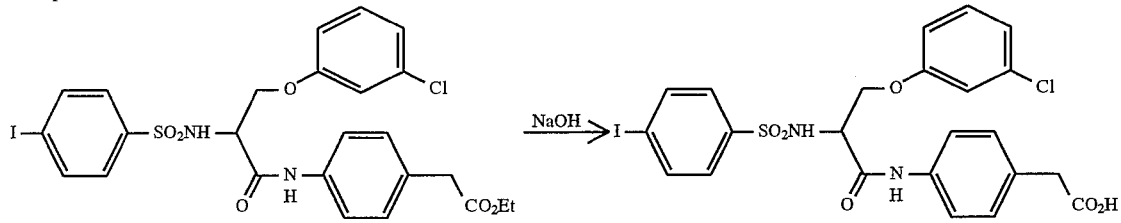
Example 152
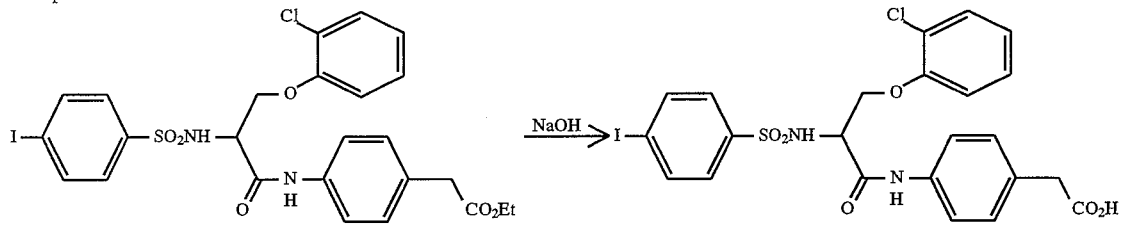
Example 153
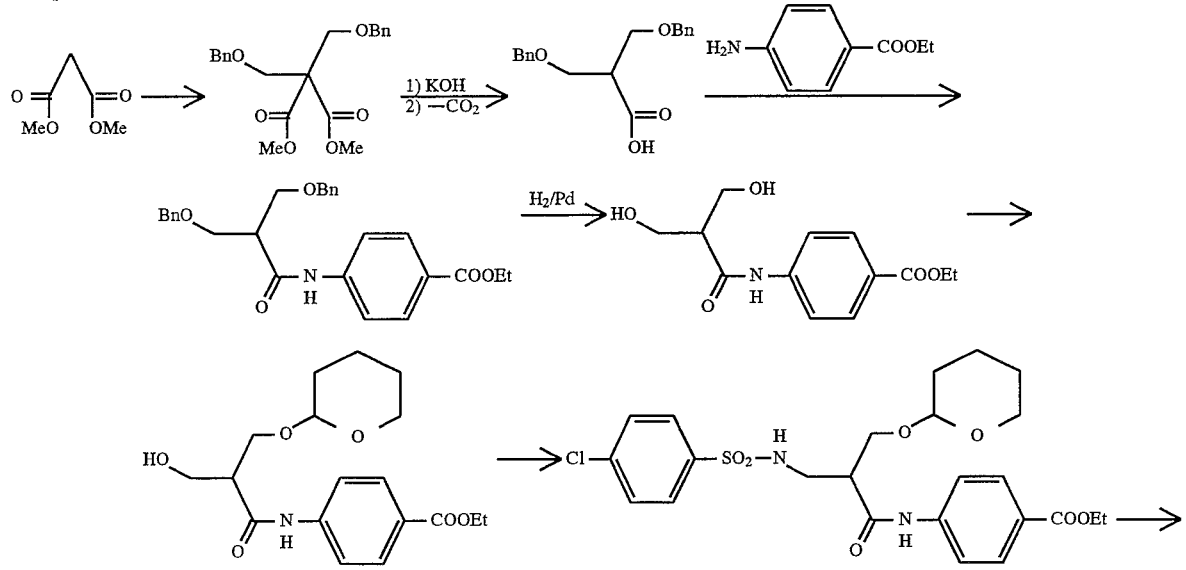

Example 154
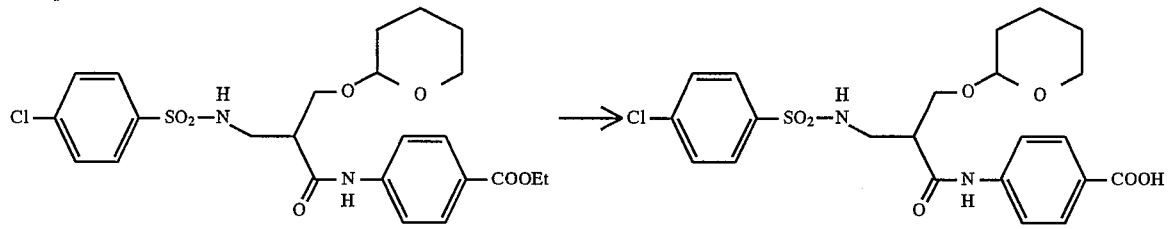
Example 155
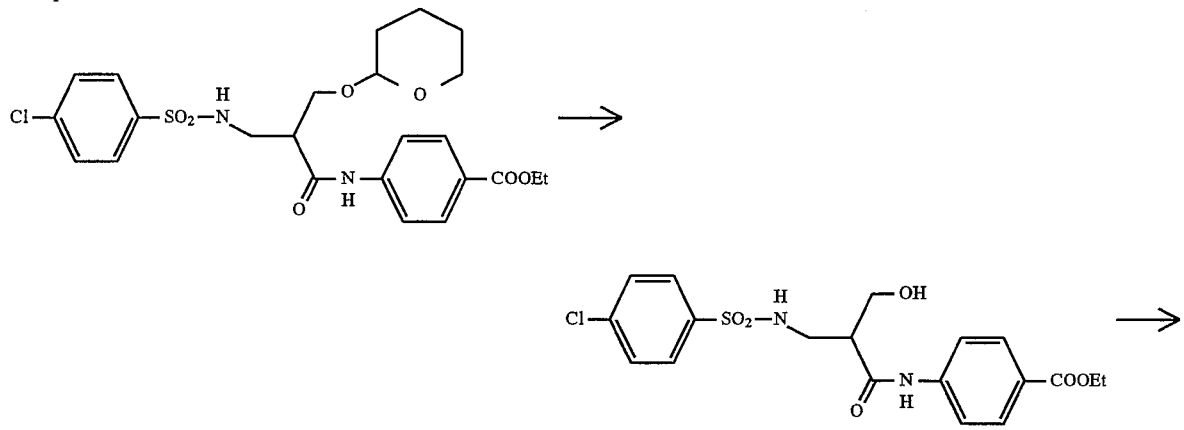
Example 156
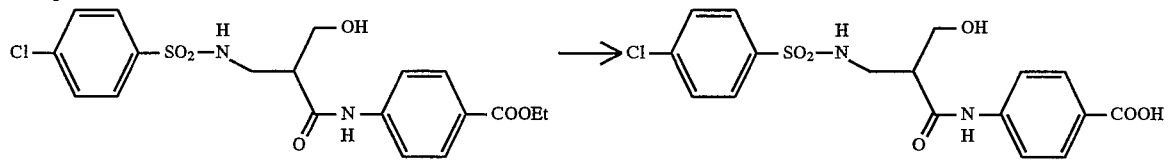
Example 157
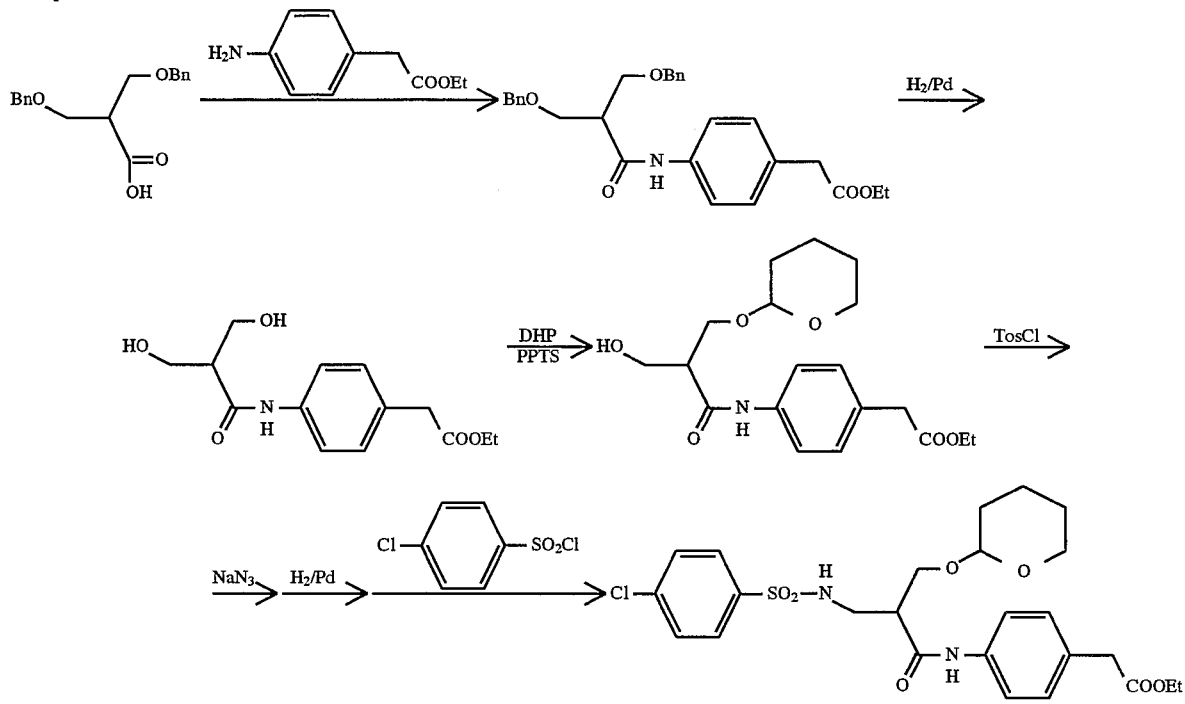

Example 158
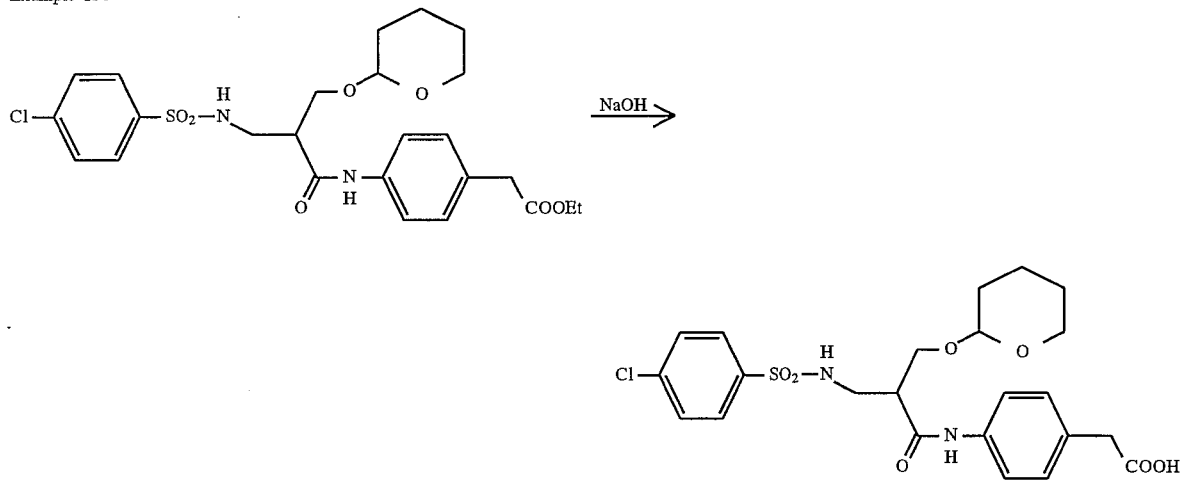
Example 159
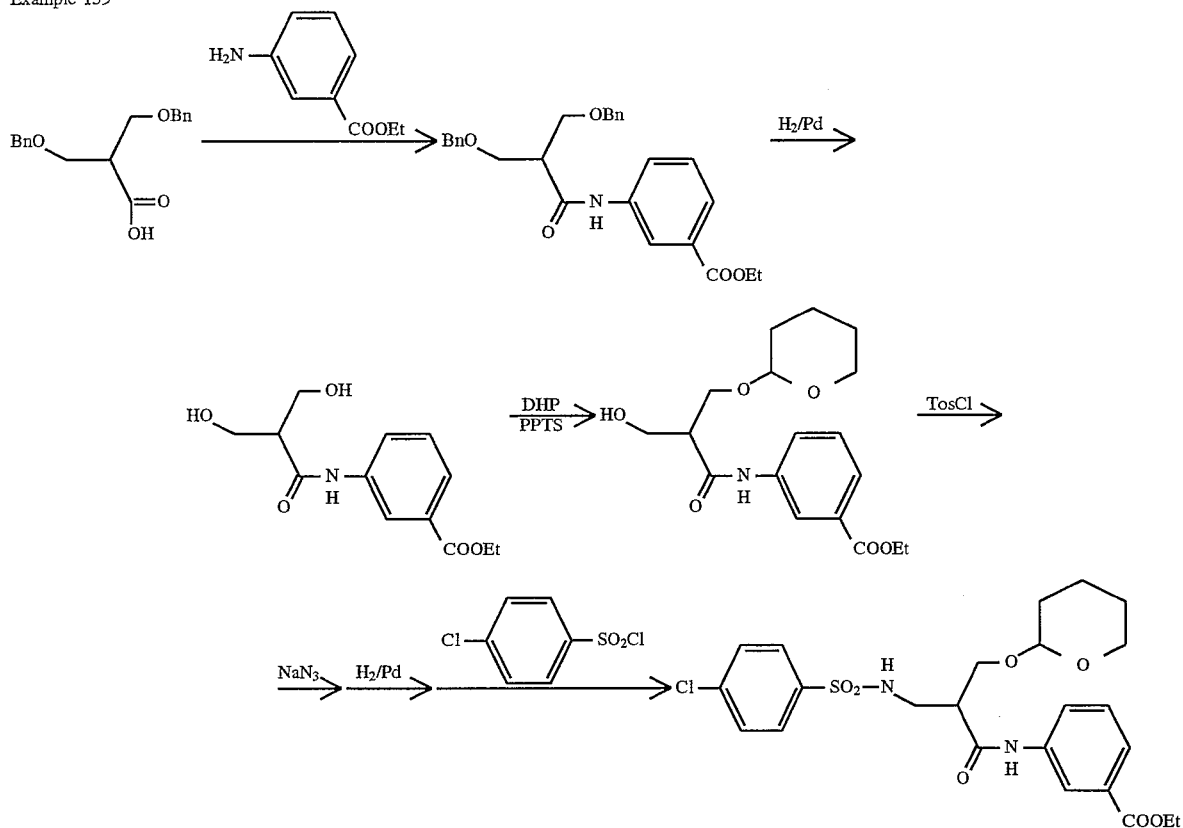
Example 160
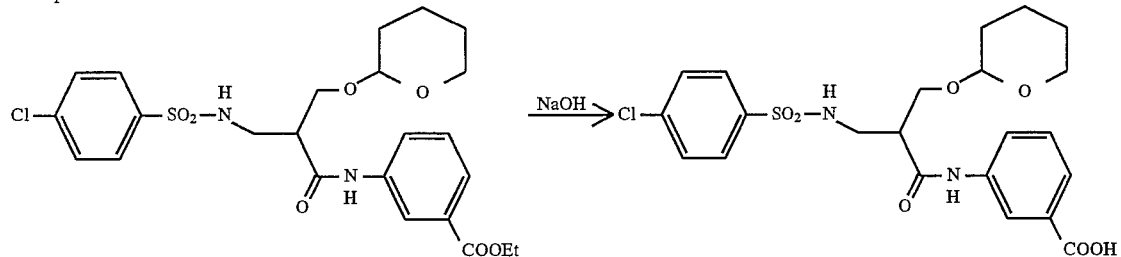

Example 161
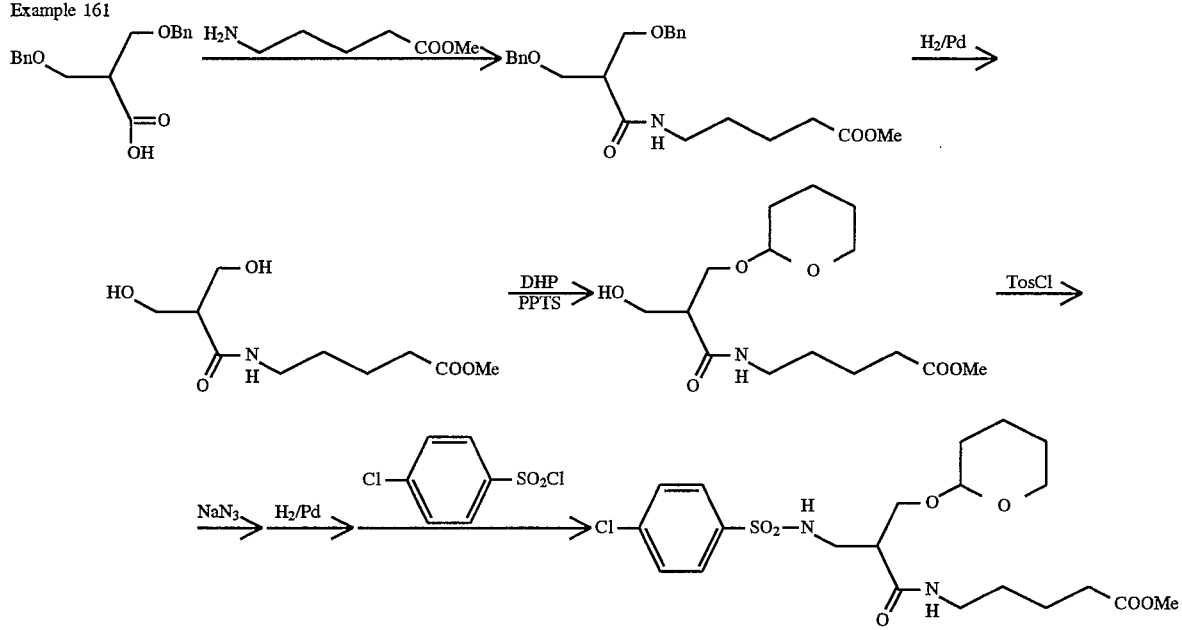
Example 162
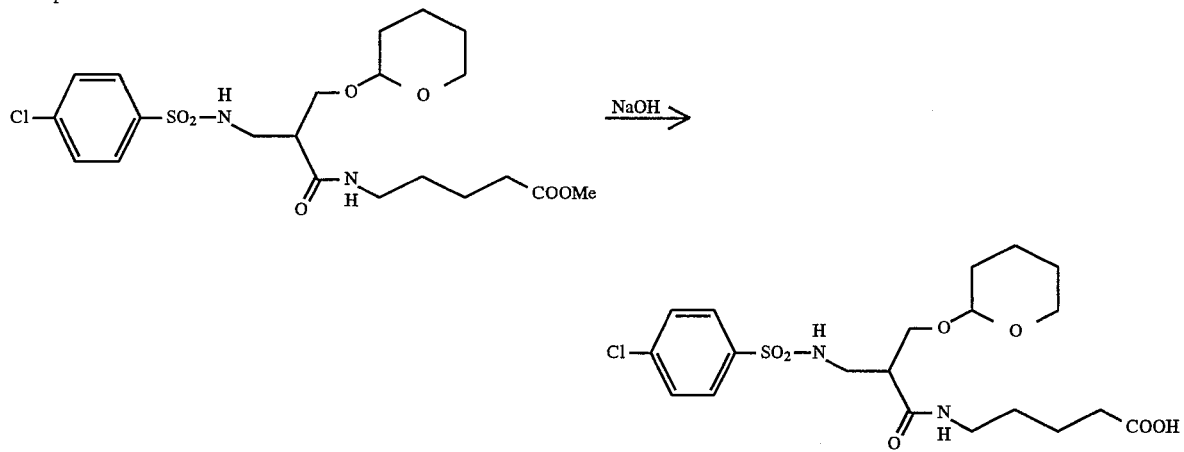
Example 163
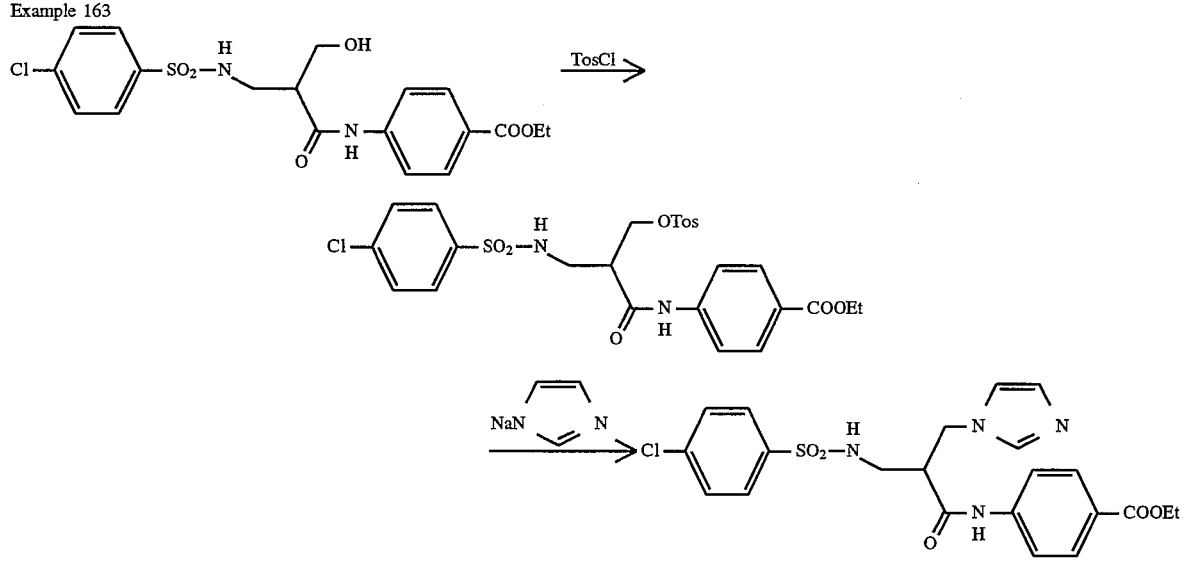

Example 164
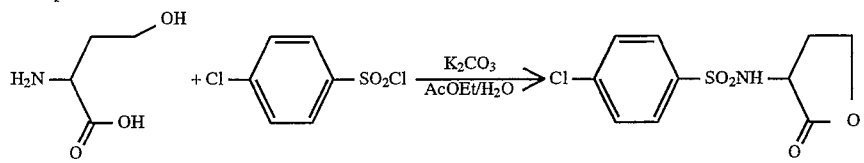
Example 165
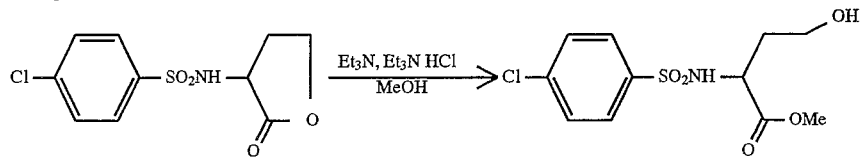
Example 166
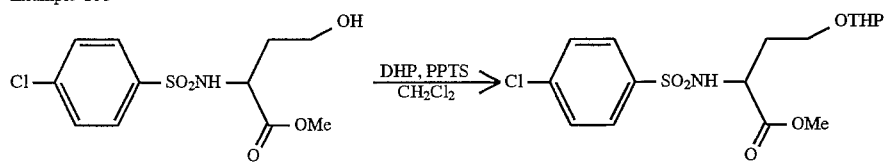
Example 167
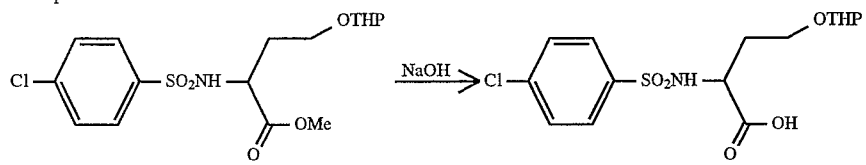
Example 168
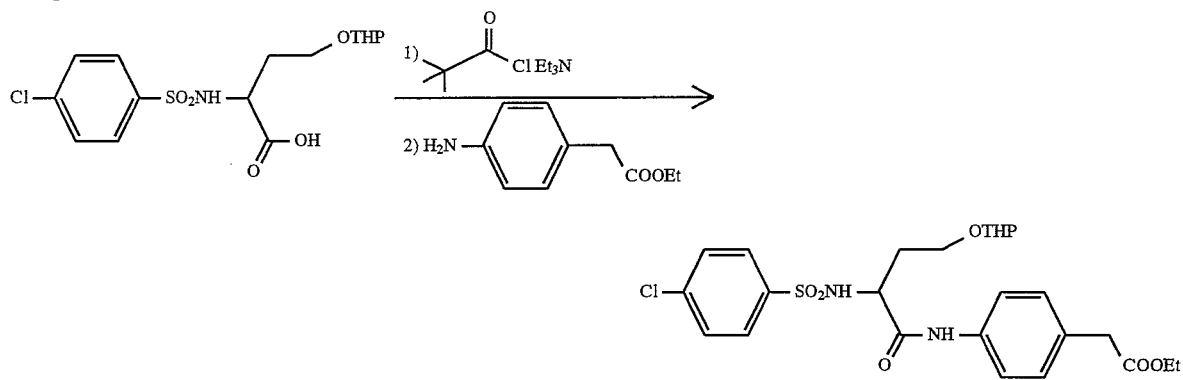
Example 169
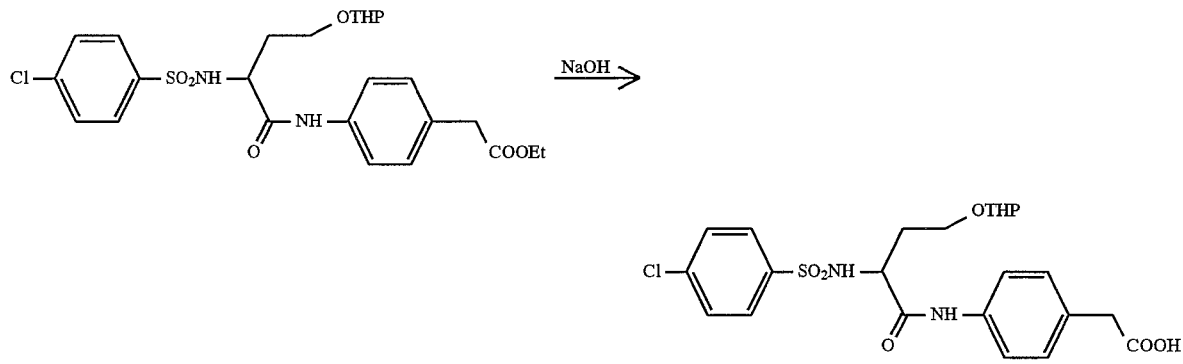

Example 170
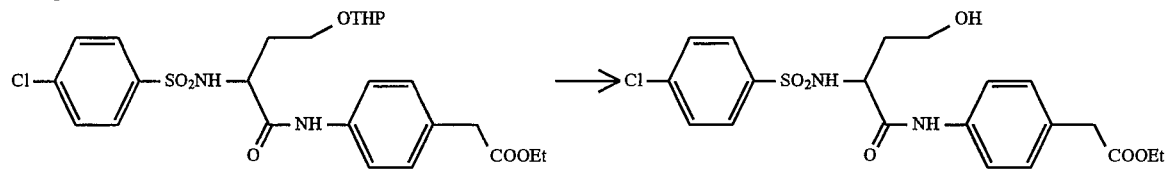
Example 171
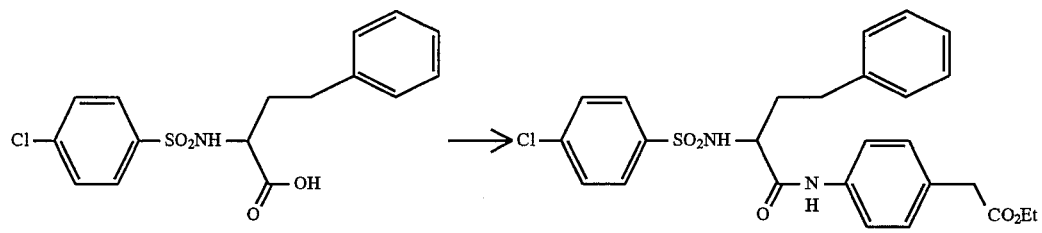
Example 172
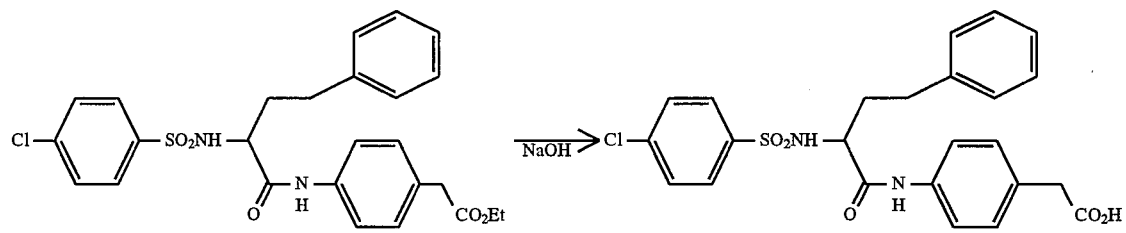
Example 173
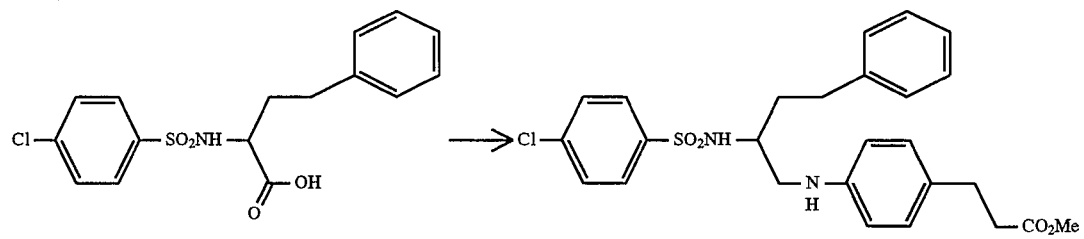
Example 174
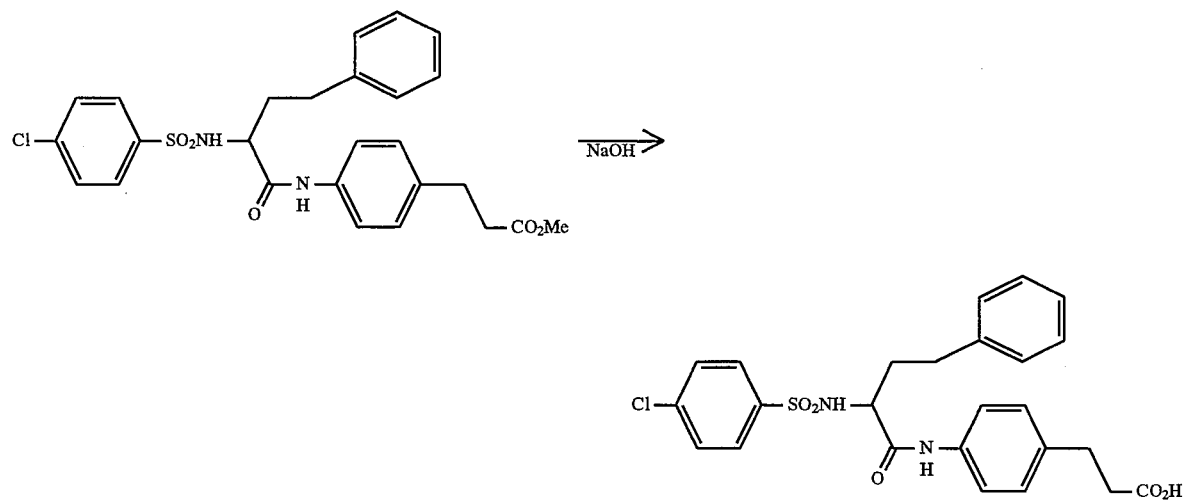

Example 175
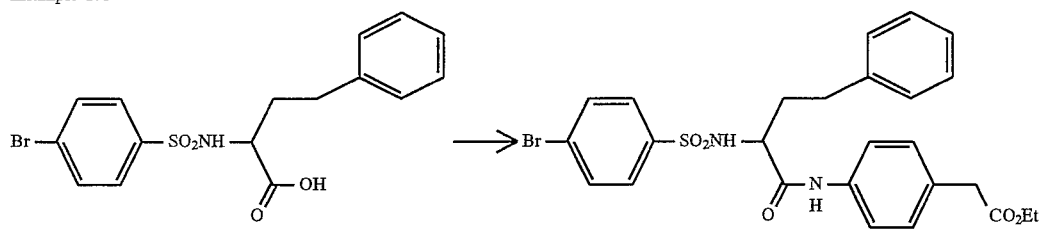
Example 176
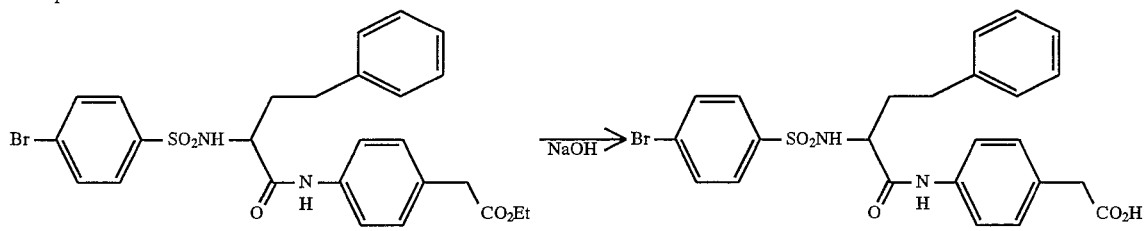
Example 177
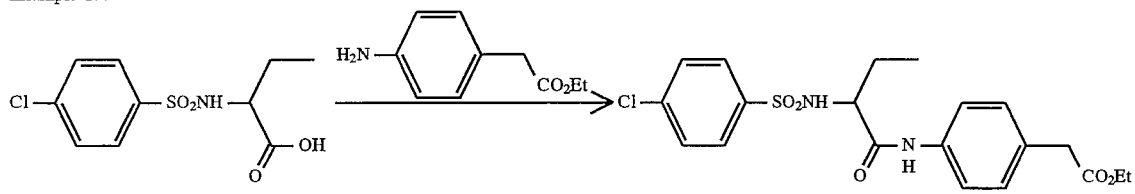
Example 178
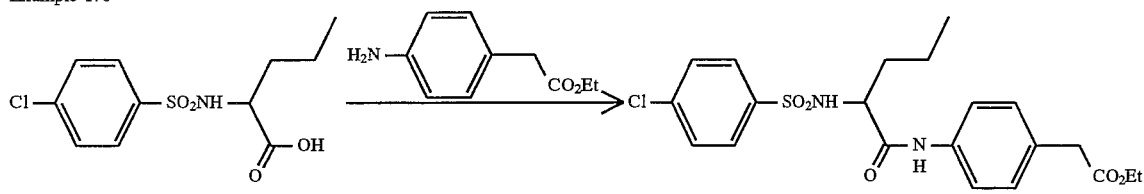
Example 179
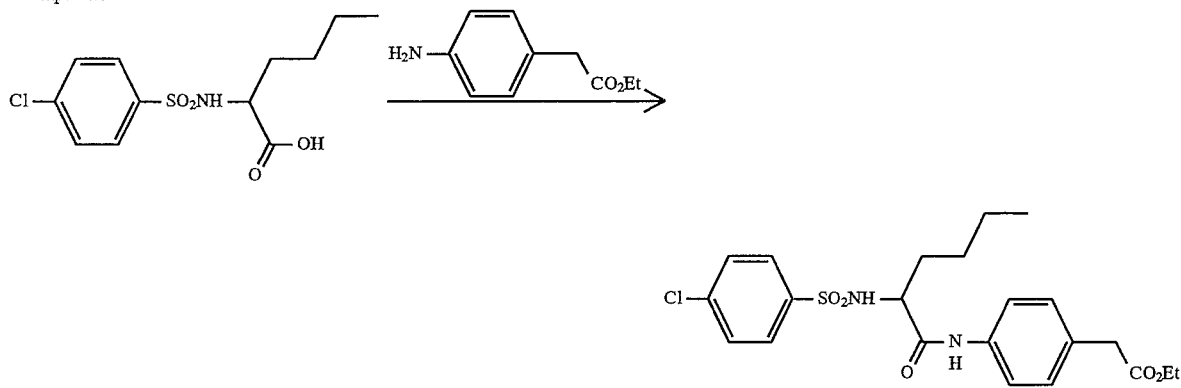
Example 180
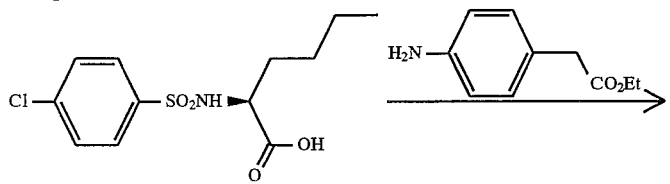

-continued
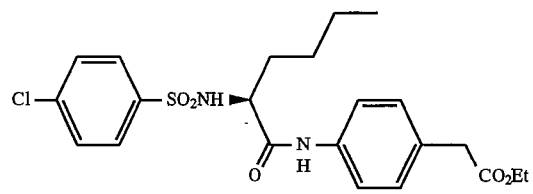
Example 181
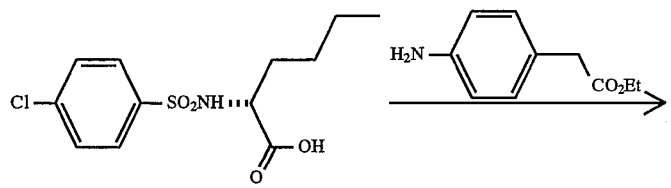
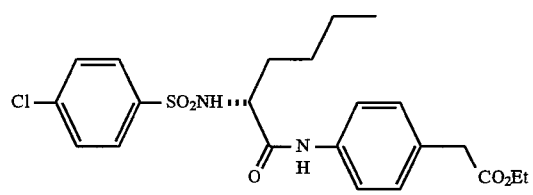
Example 182
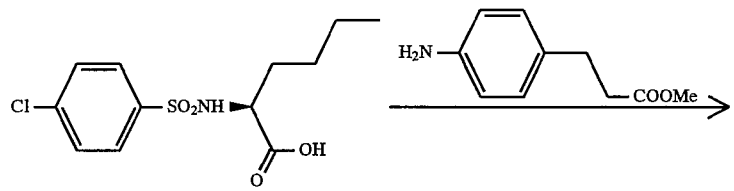
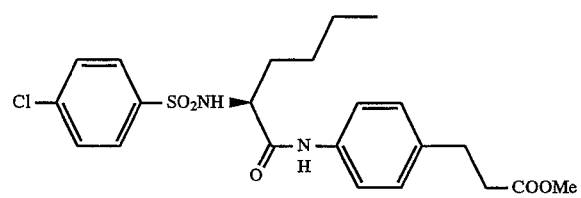
Example 183
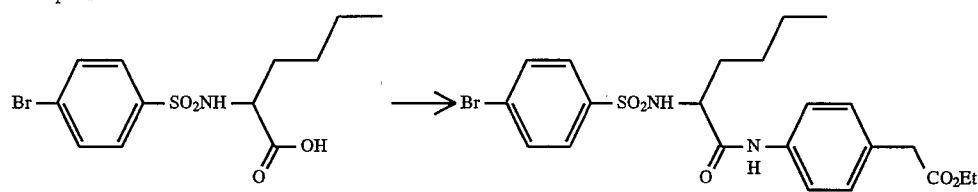
Example 184
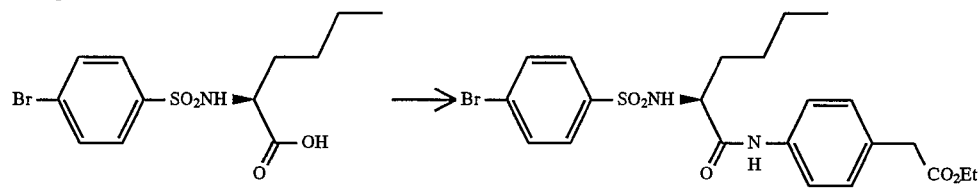

Example 185
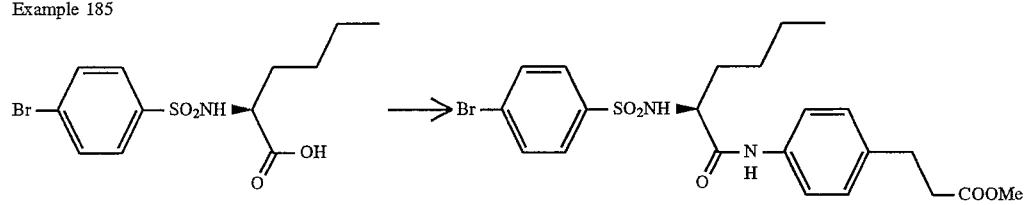
Example 186
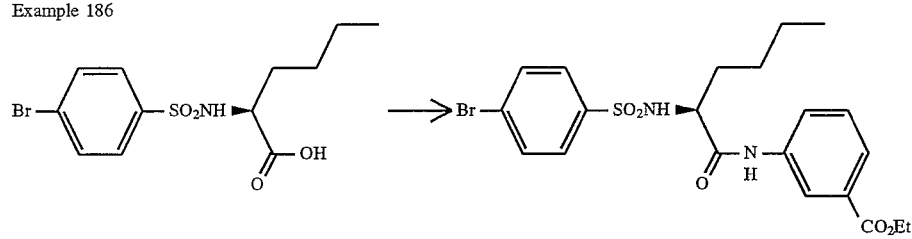
Example 187
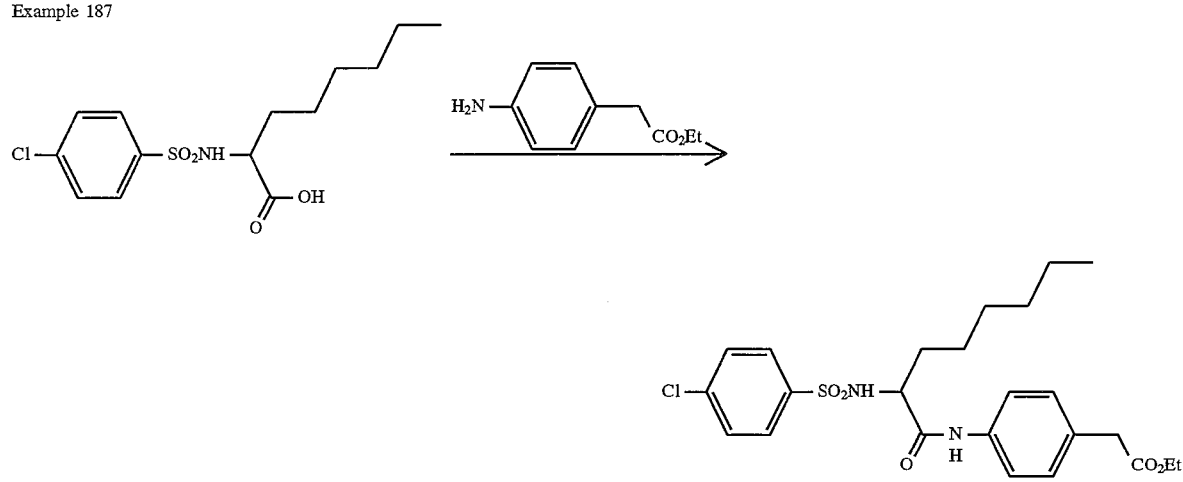
Example 188
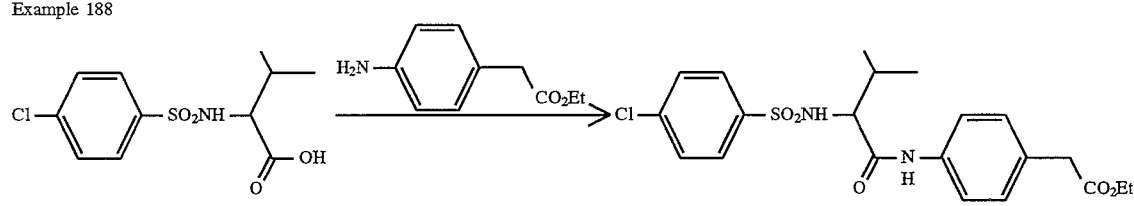
Example 189
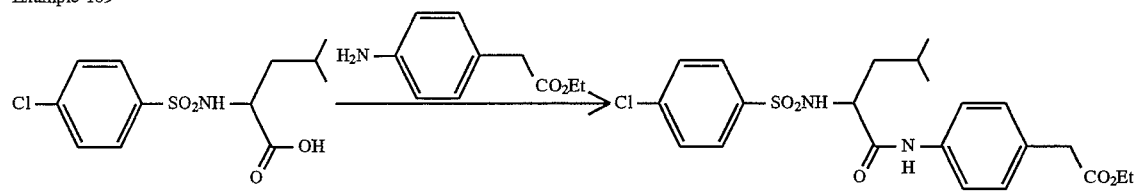
Example 190
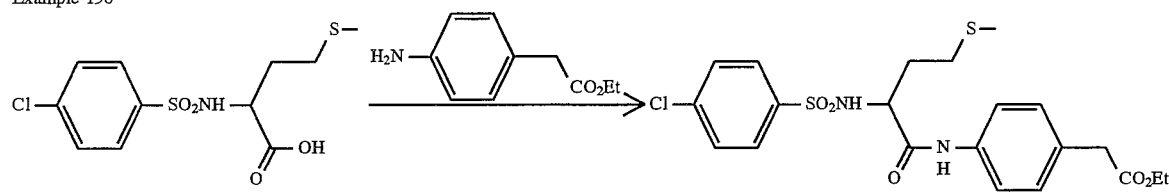

Example 191
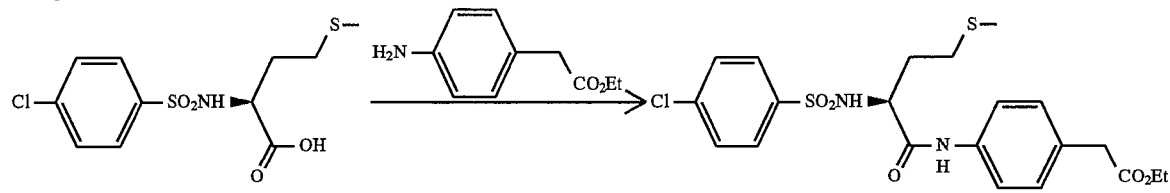
Example 192
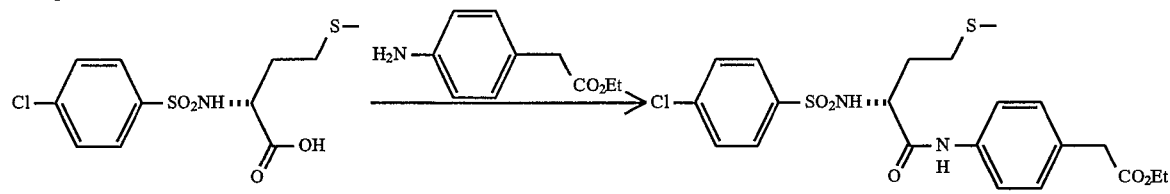
Example 193
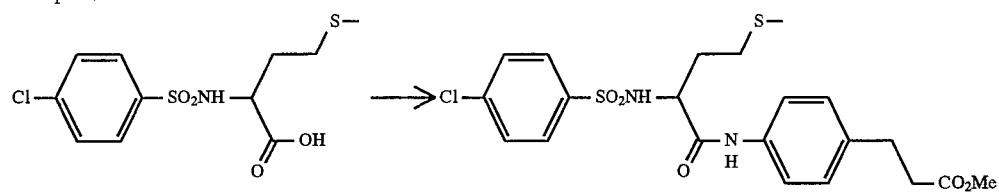
Example 194
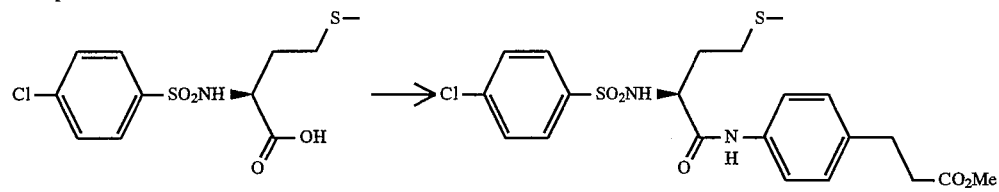
Example 195
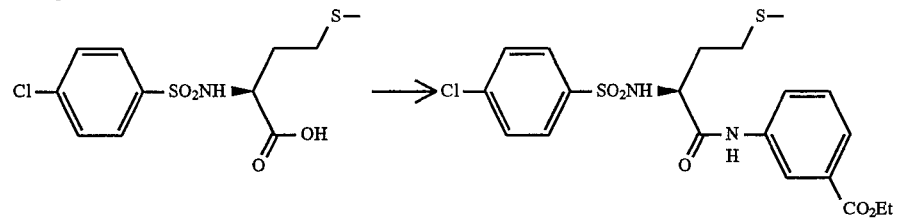
Example 196
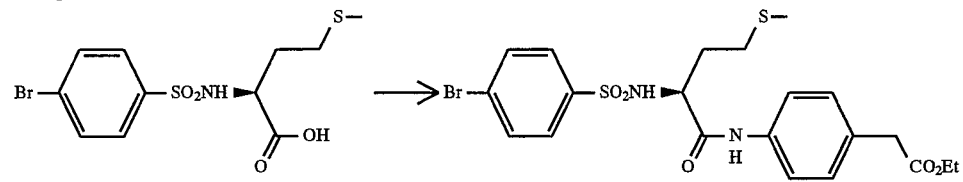
Example 197
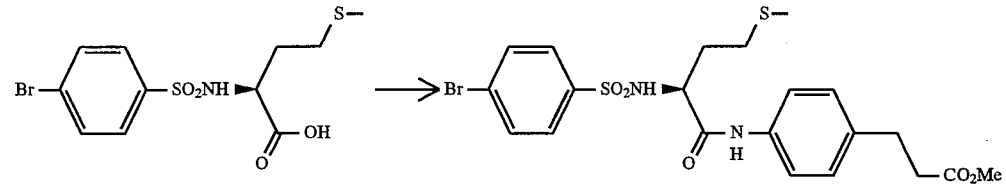

Example 198
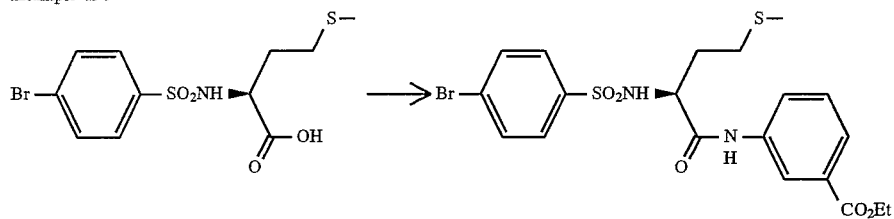
Example 199
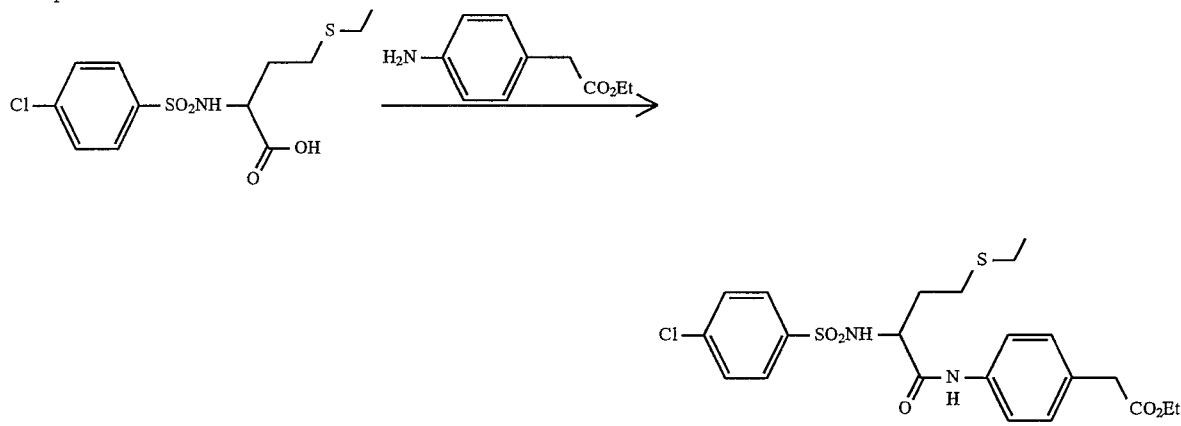
Example 200
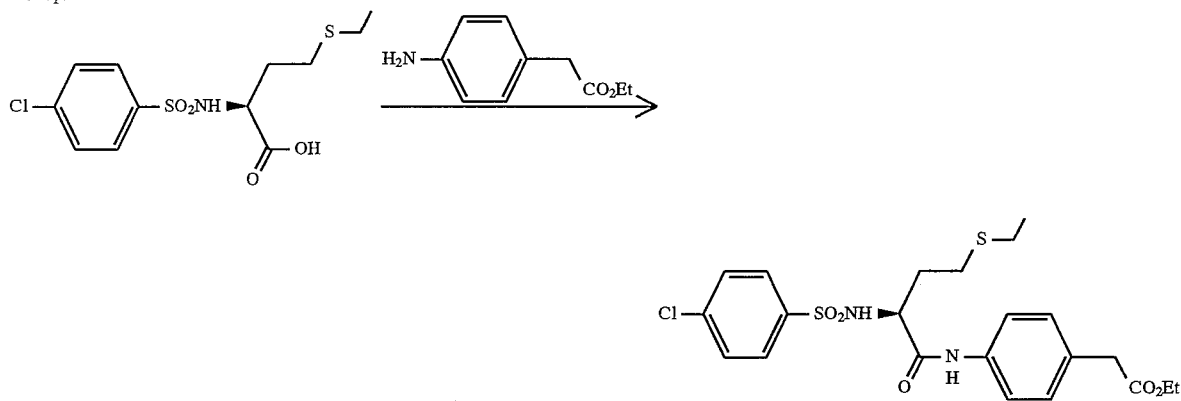
Example 201
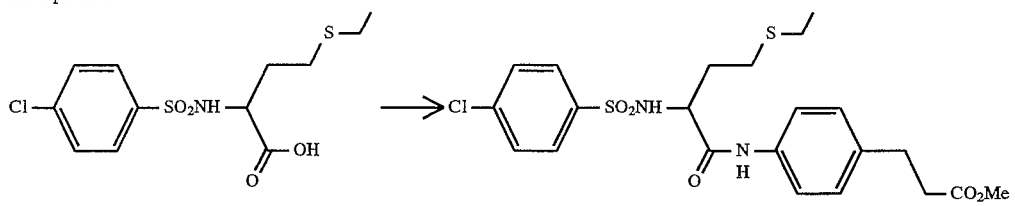
Example 202
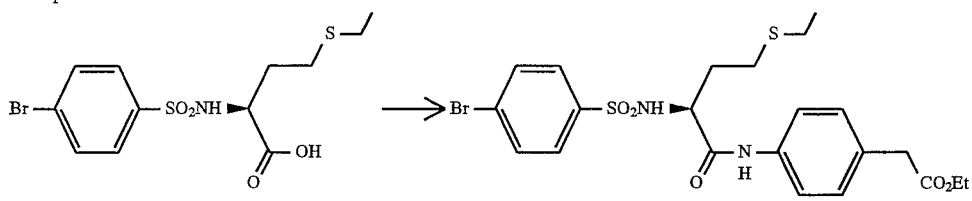

Example 203
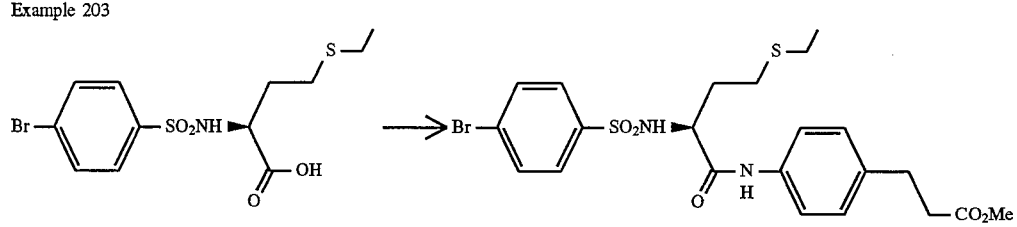
Example 204
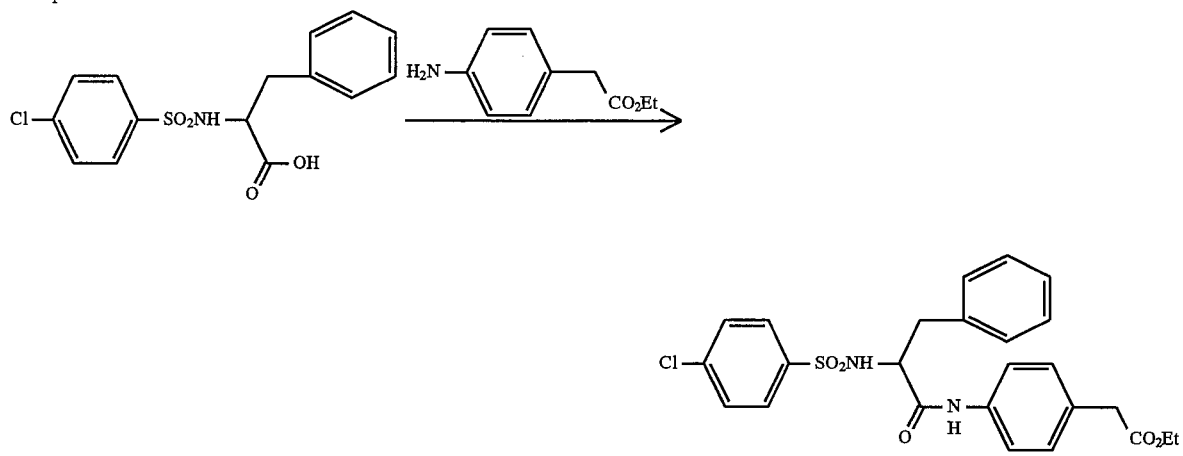
Example 205
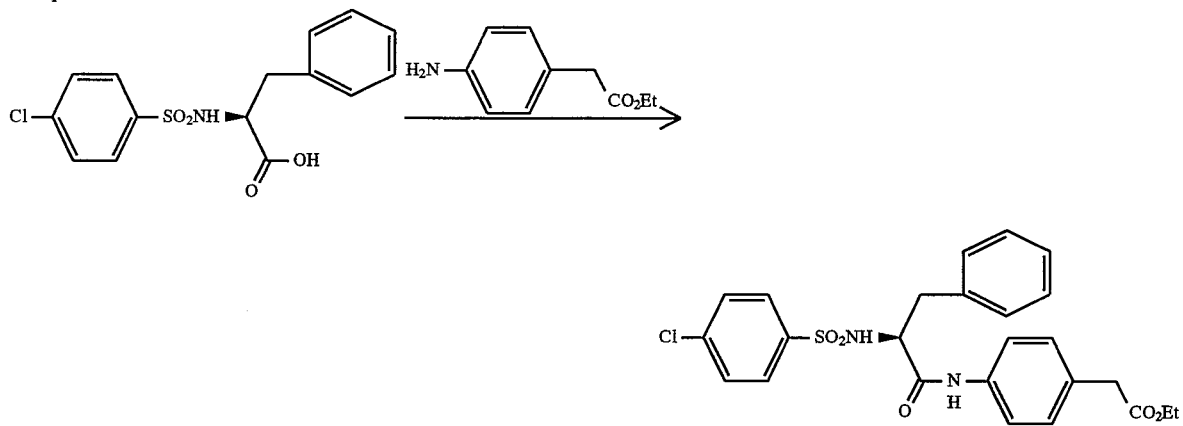
Example 206
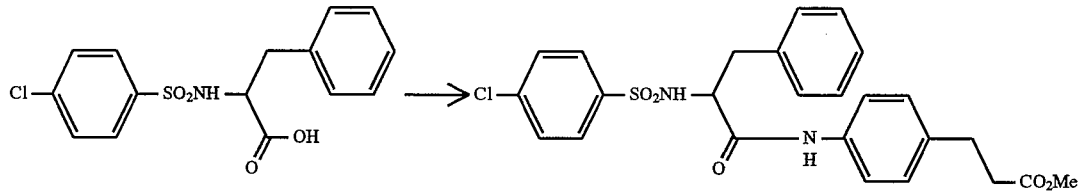
Example 207
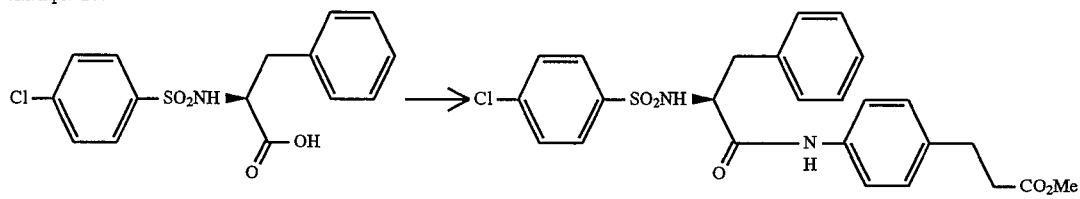

Example 208
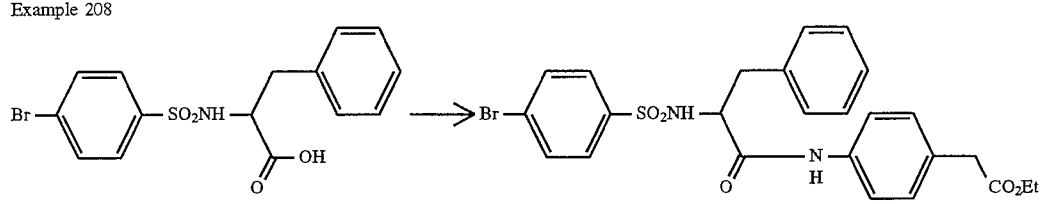
Example 209
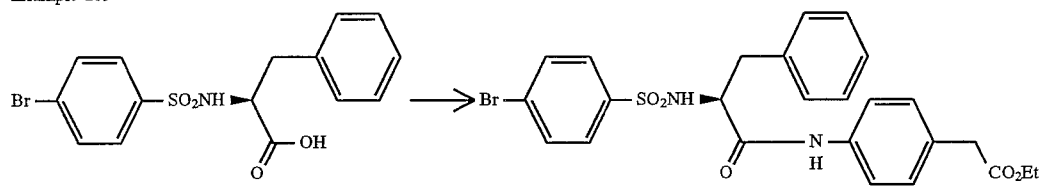
Example 210
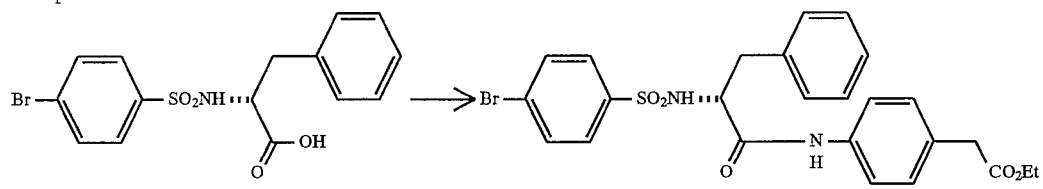
Exaqmple 211
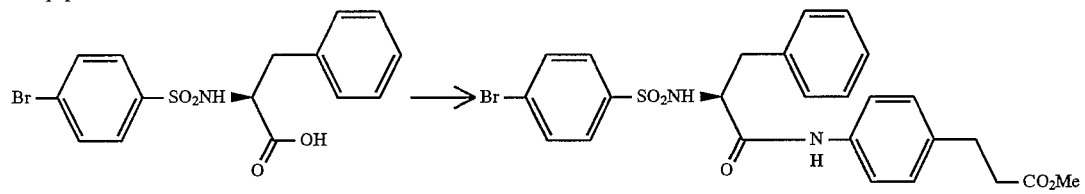
Example 212
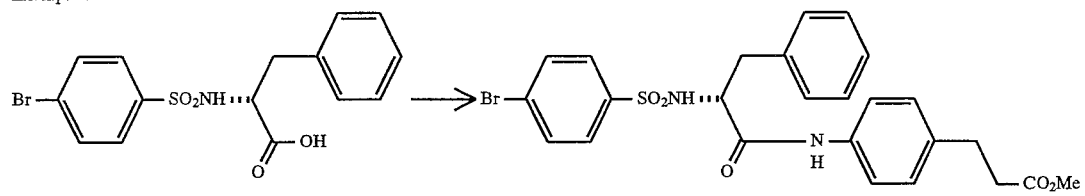
Example 213
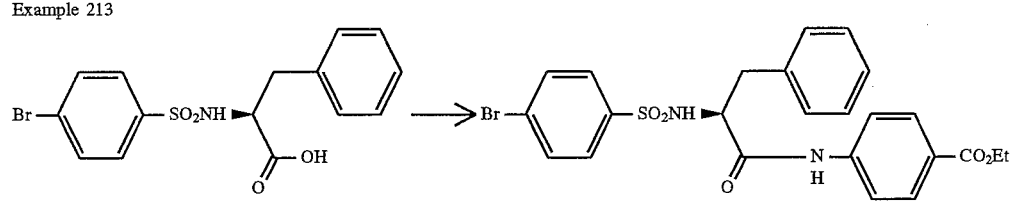
Example 214
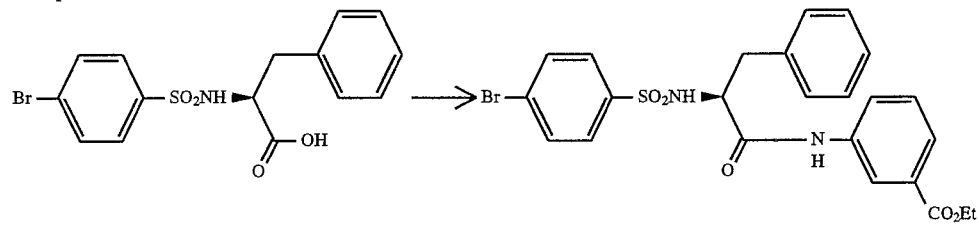

Example 215
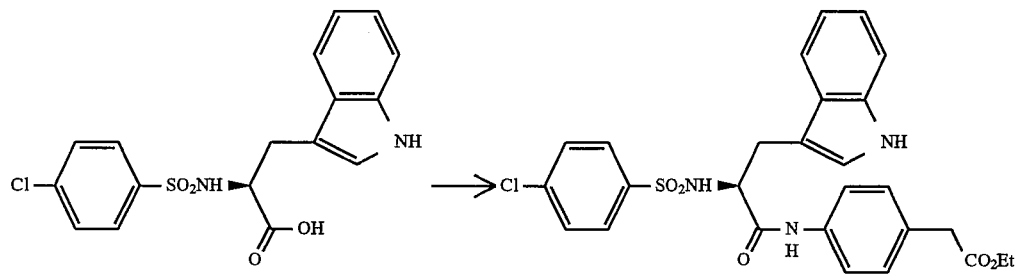
Example 216
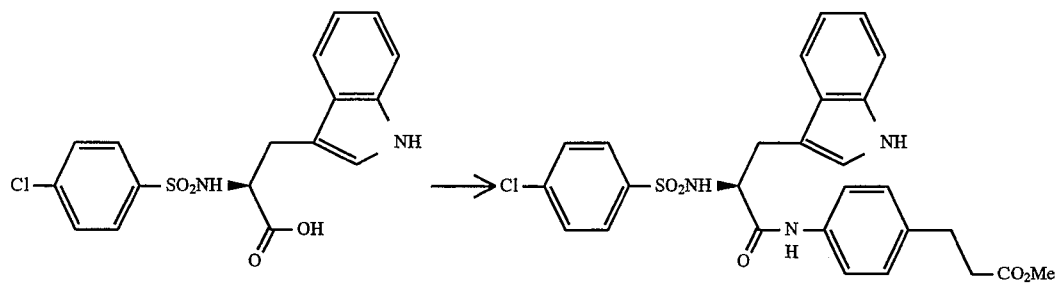
Example 217
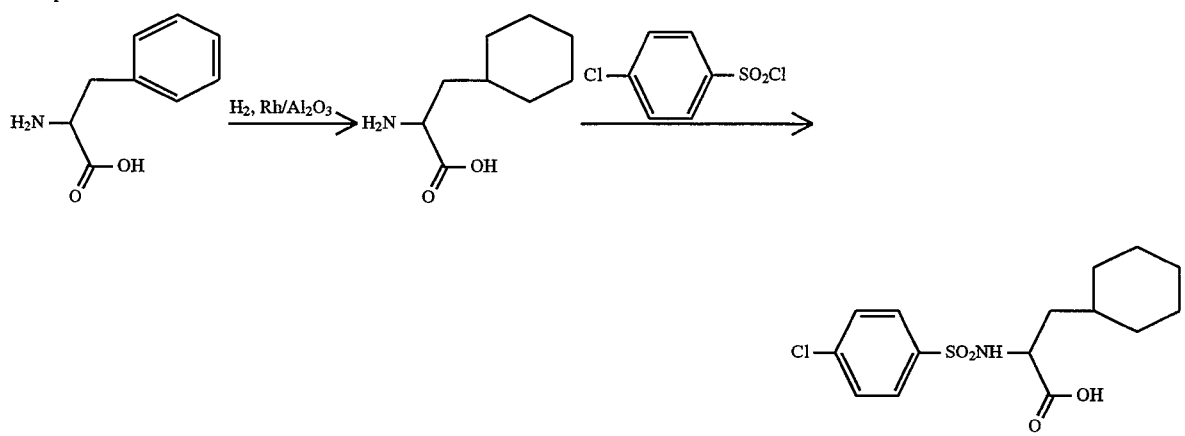
Example 218
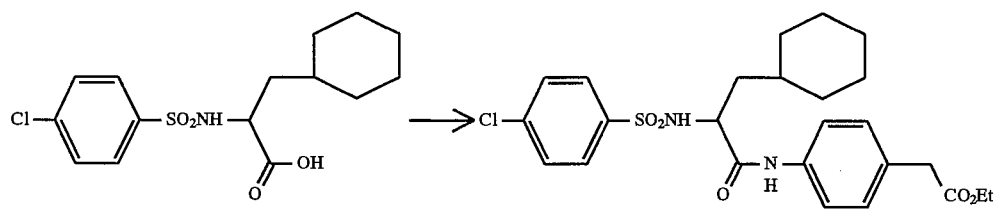
Example 219
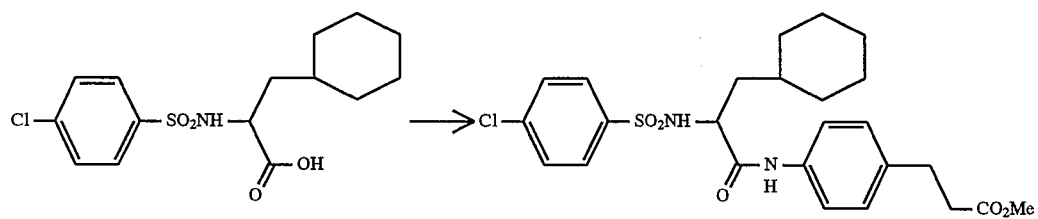

Example 220
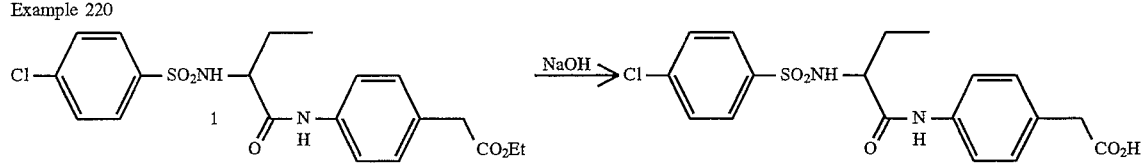
Example 221
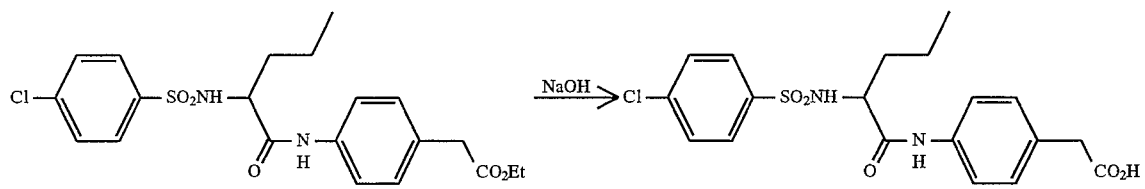
Example 222
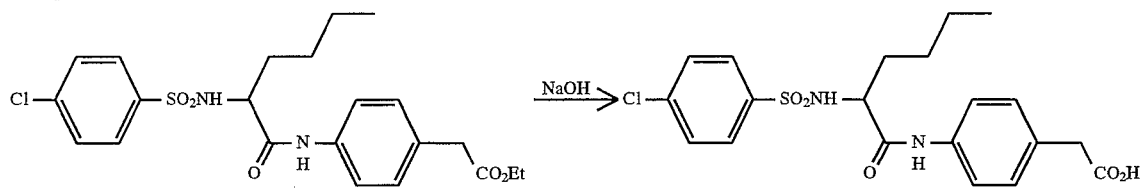
Example 223
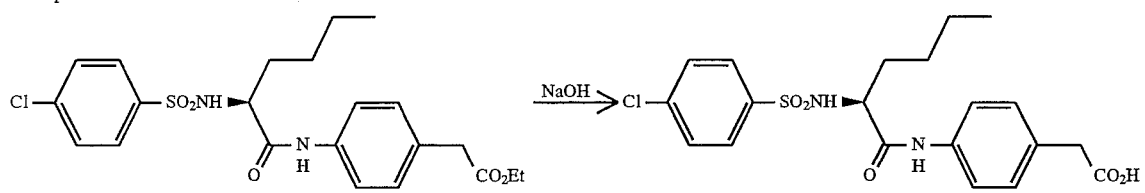
Example 224
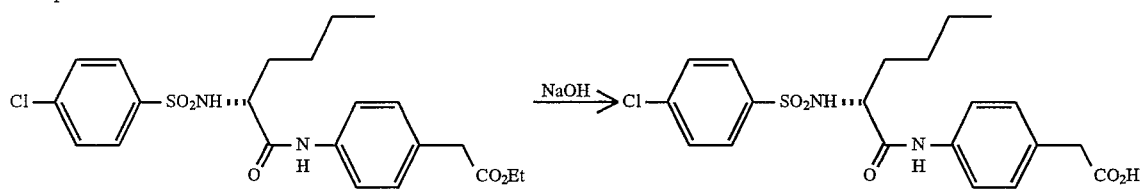
Example 225
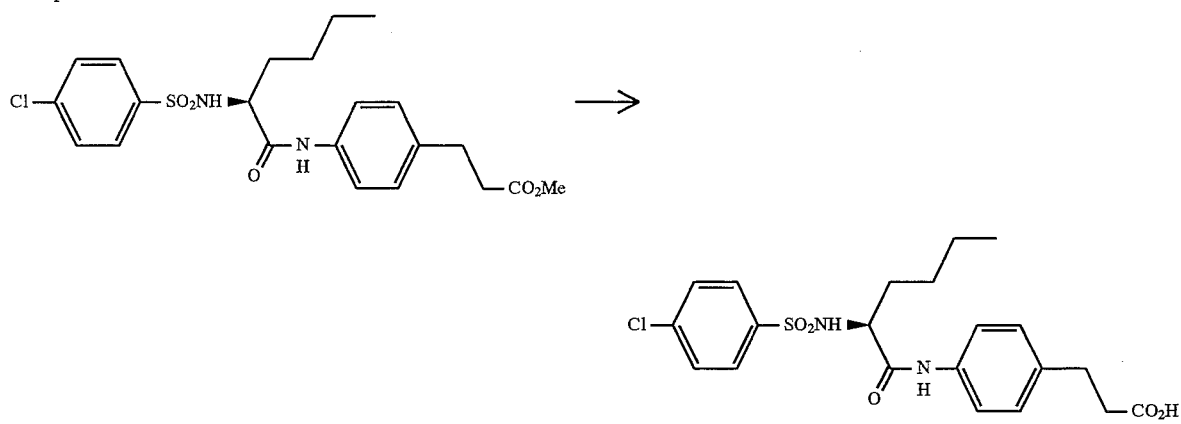

Example 226
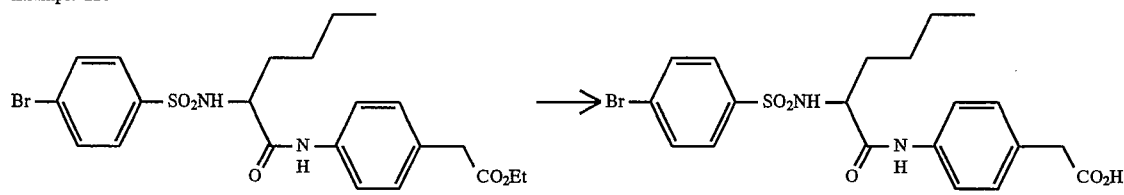
Example 227
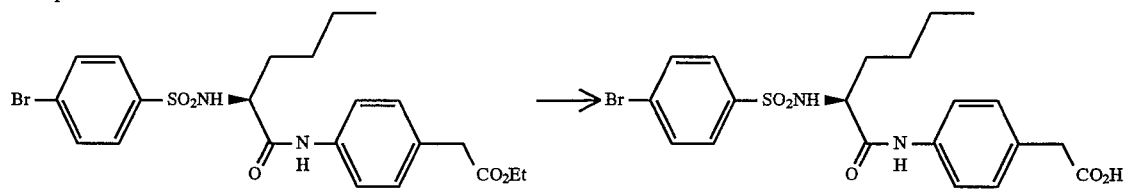
Example 228
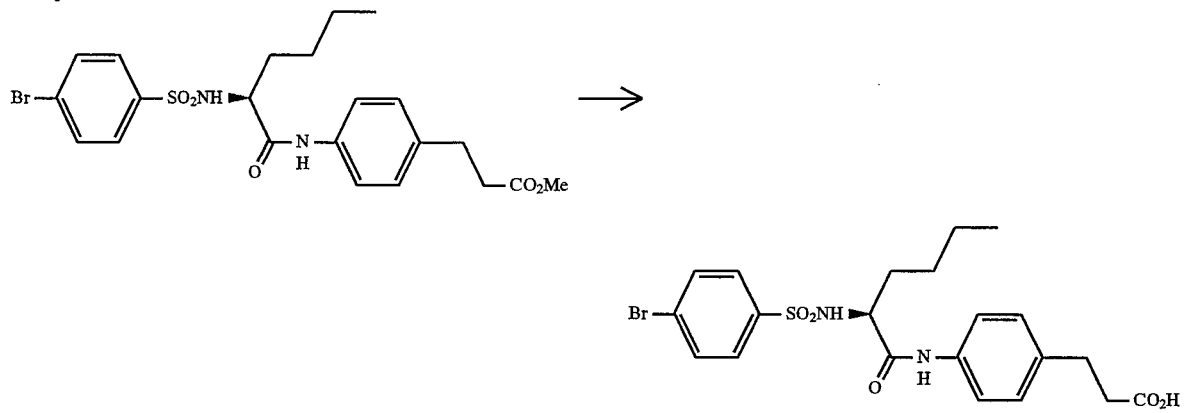
Example 229
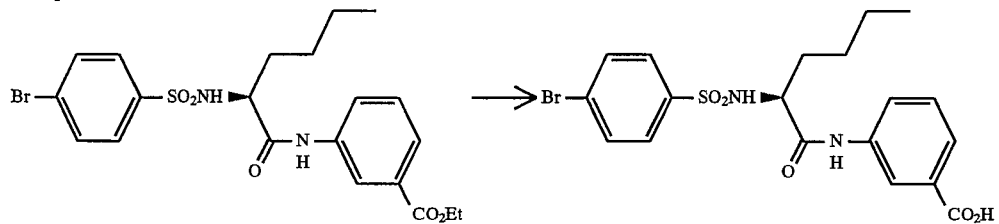
Example 230
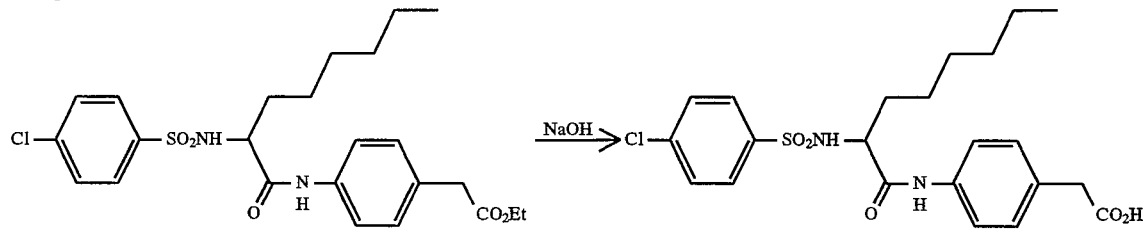
Example 231
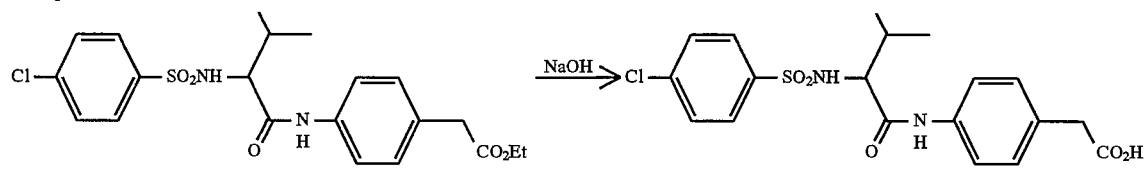

Example 232
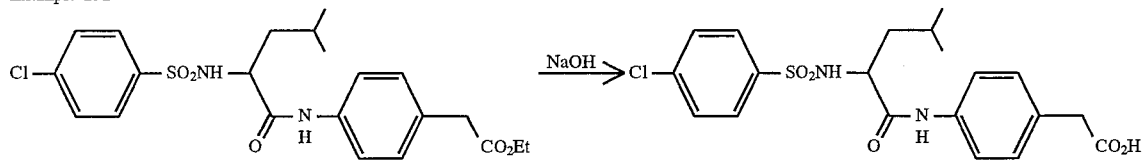
Example 233
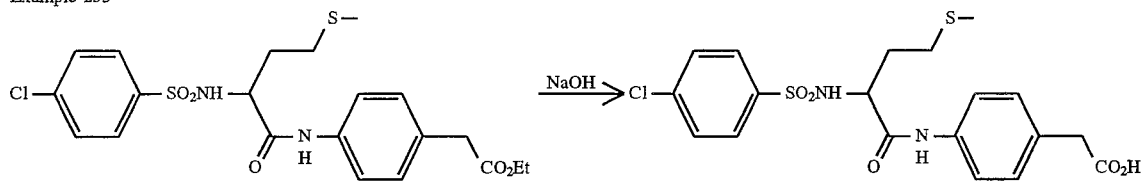
Example 234
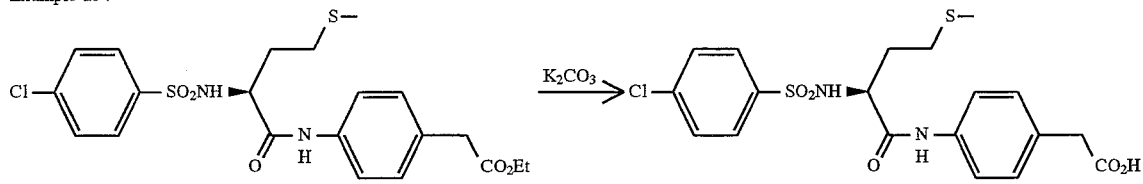
Example 235
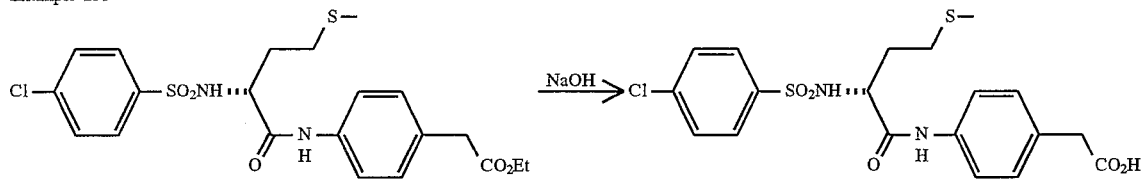
Example 236
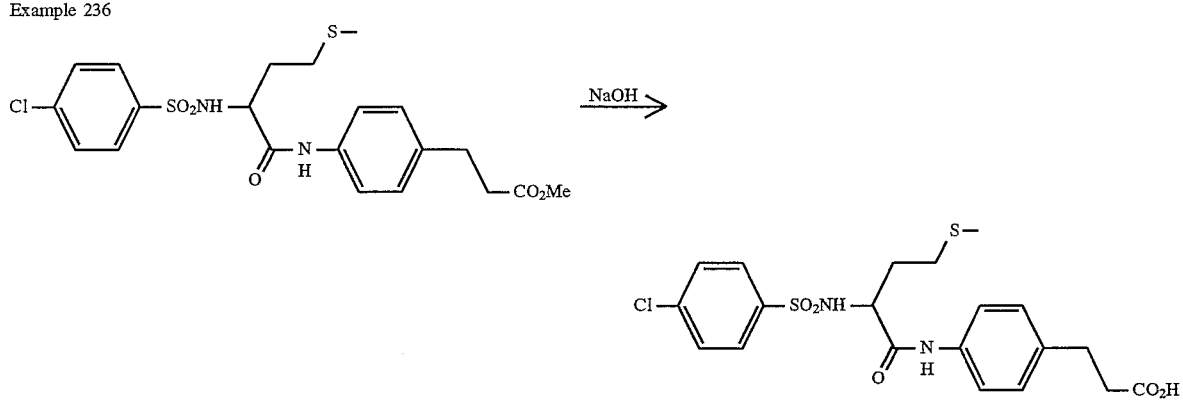
Example 237
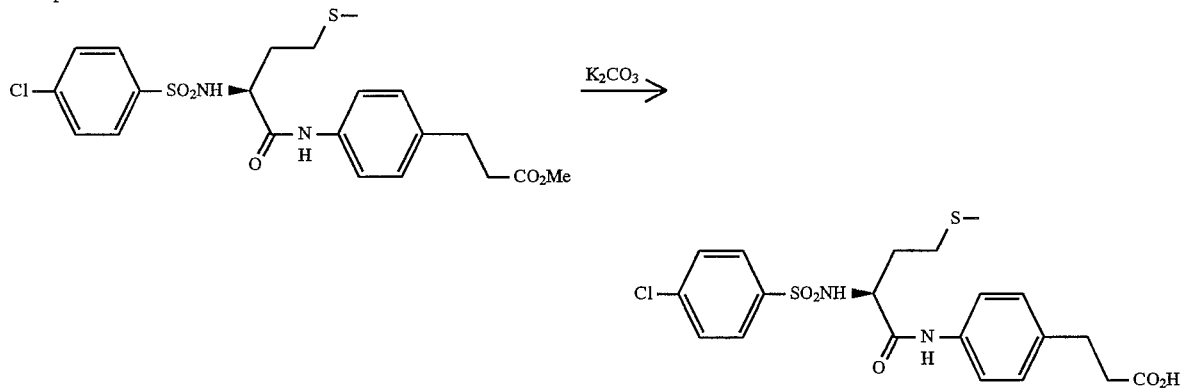

Example 238
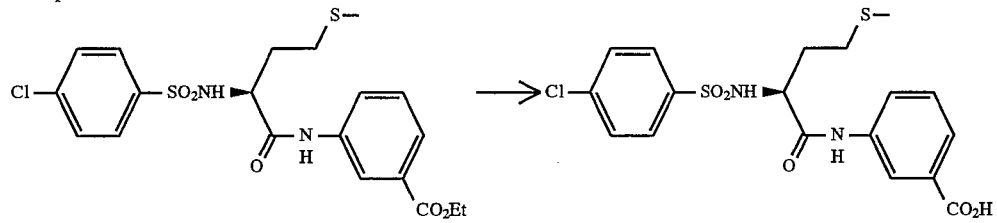
Example 239
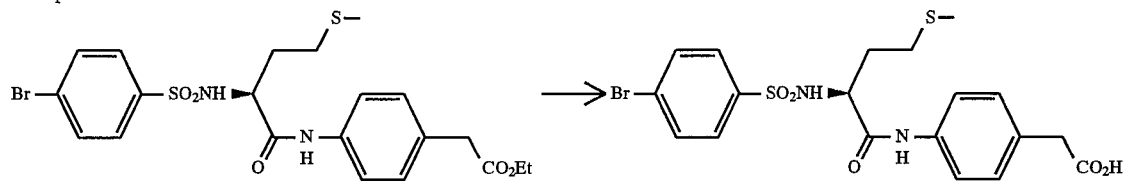
Example 240
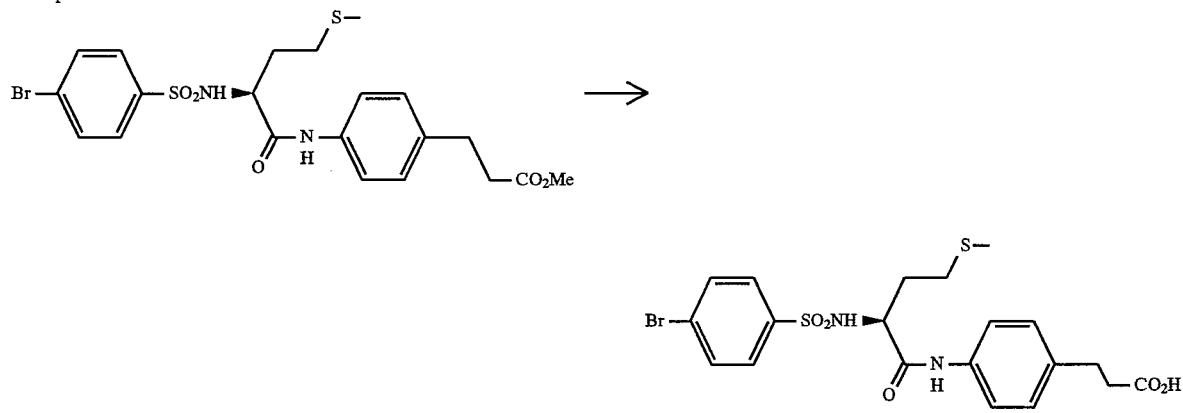
Example 241
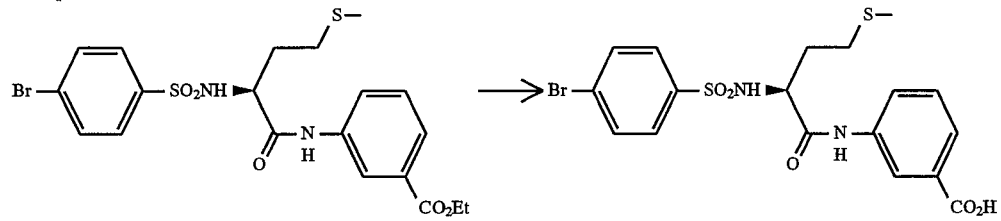
Example 242
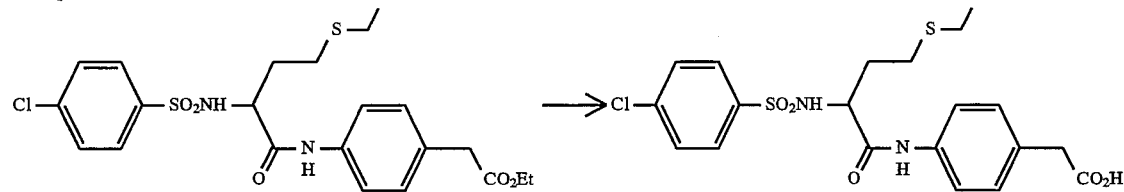
Example 243
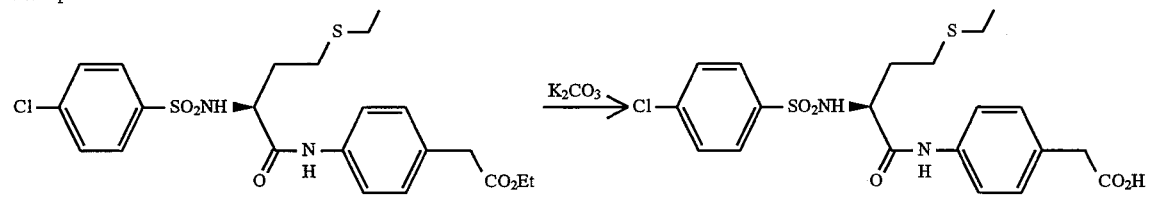

Example 244
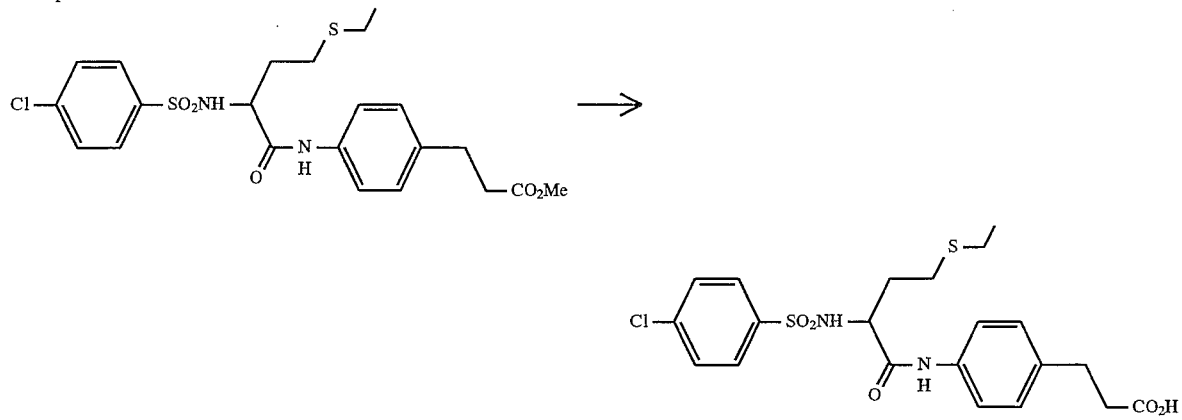
Example 245
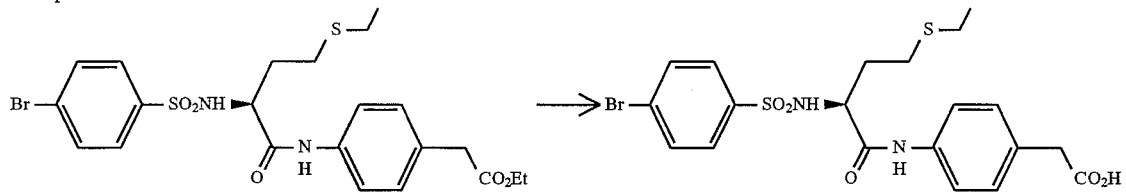
Example 246
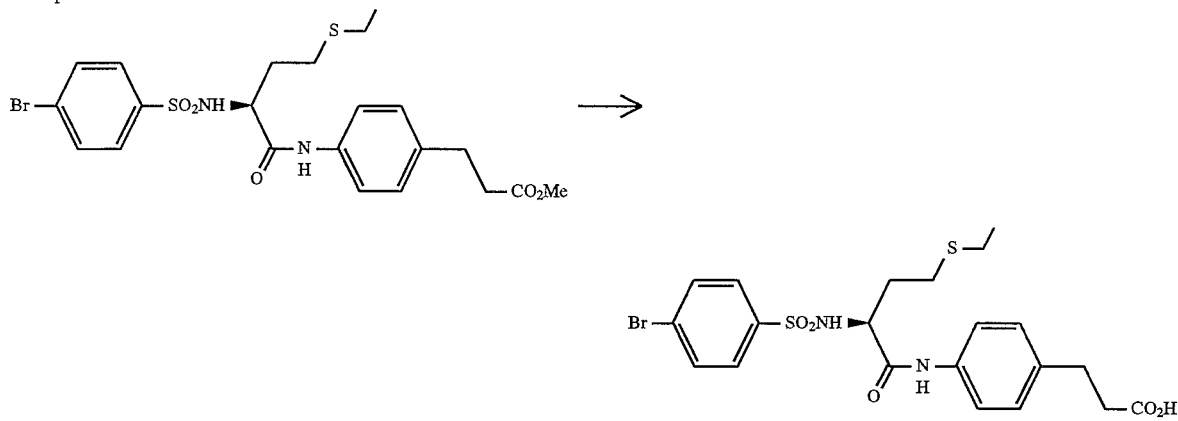
Example 247
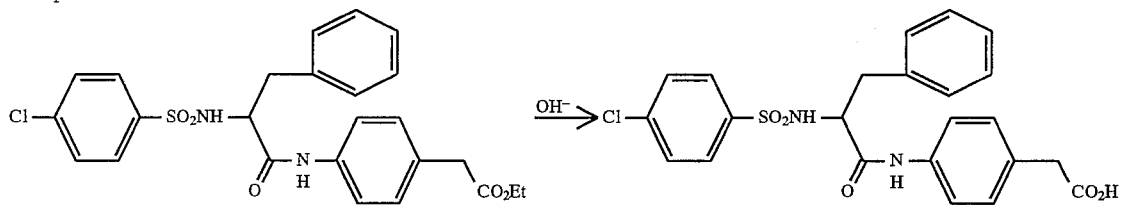
Example 248
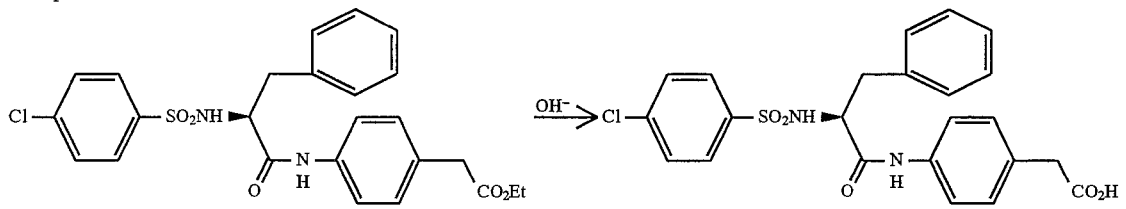

-continued
Example 249
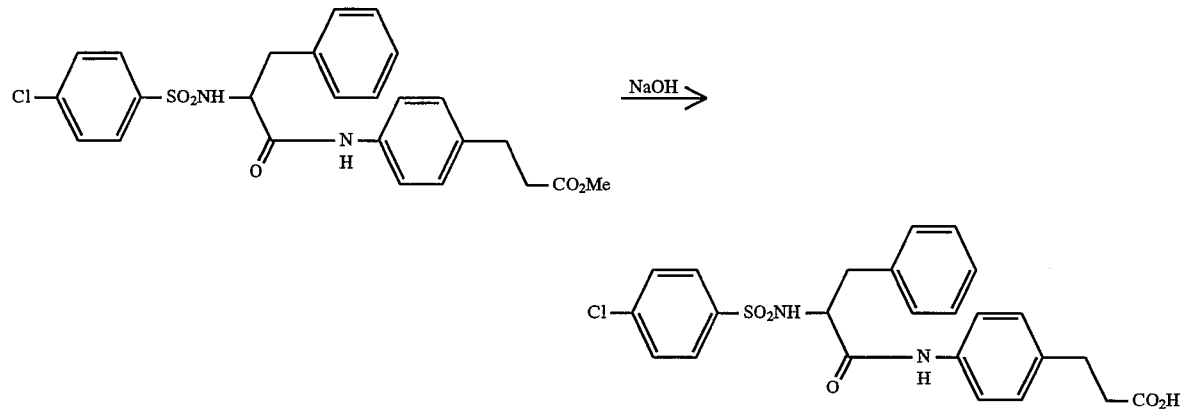
Example 250
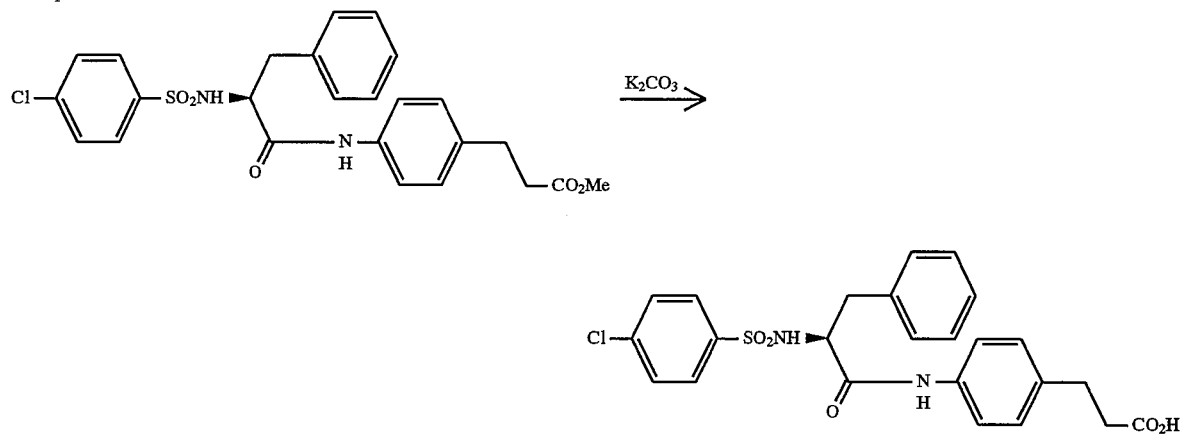
Example 251
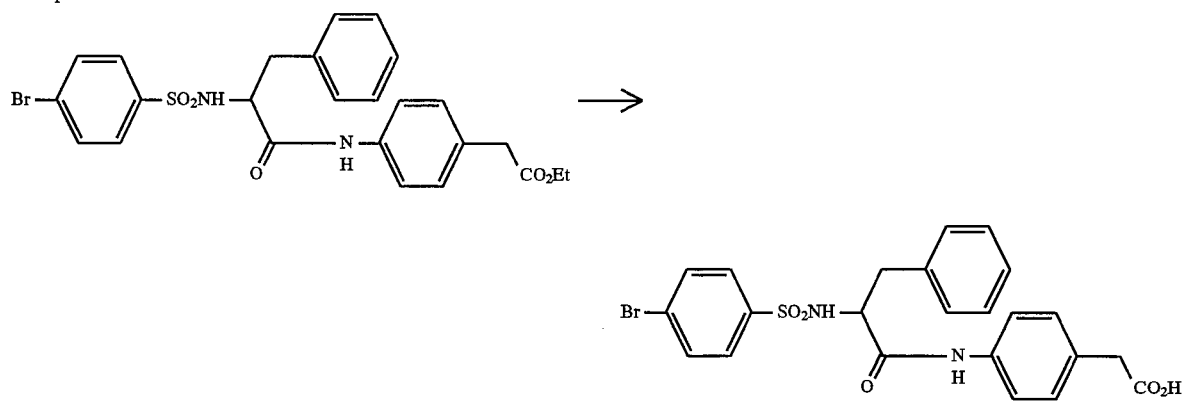
Example 252
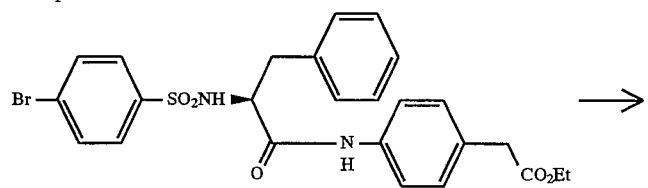

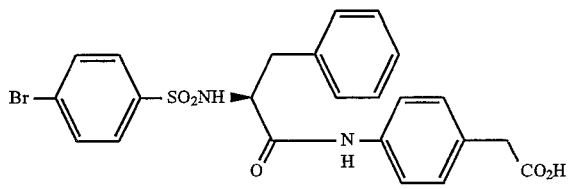
Example 253
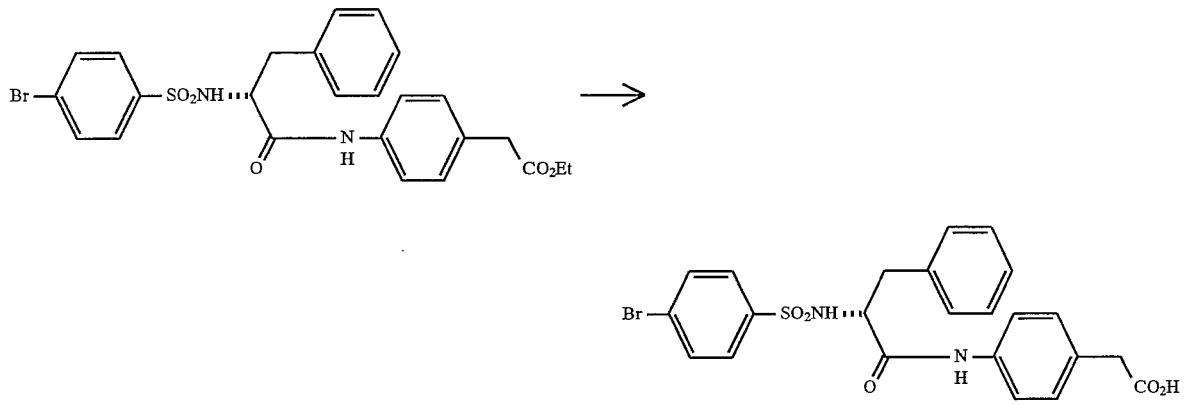
Example 254
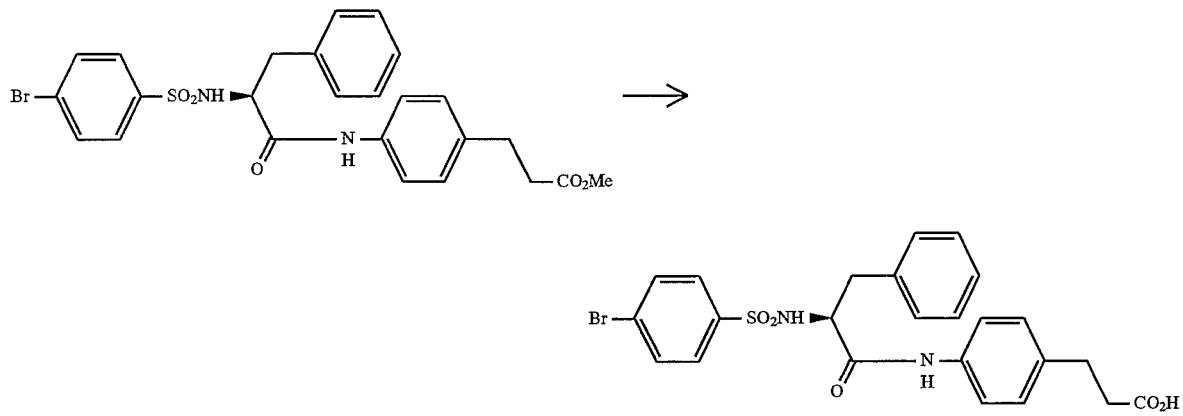
Example 255
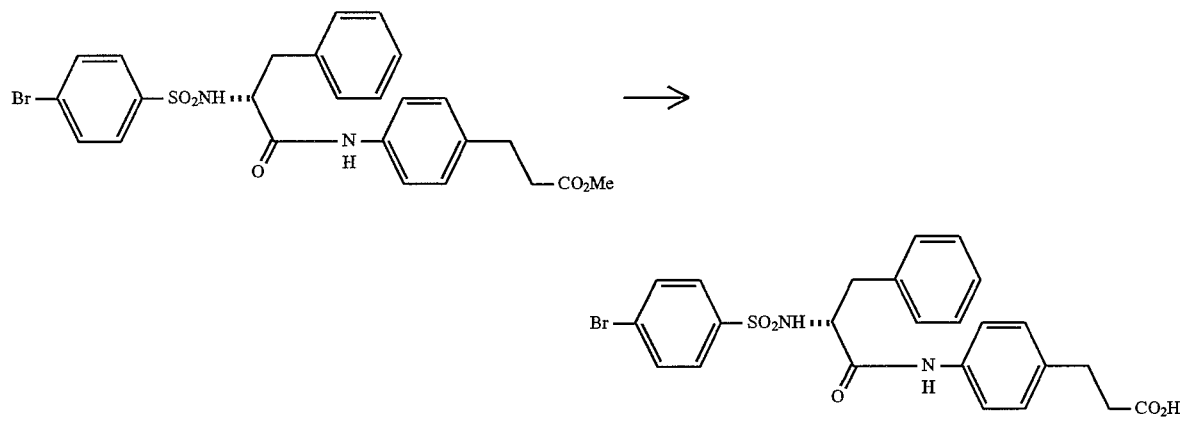

-continued
Example 256
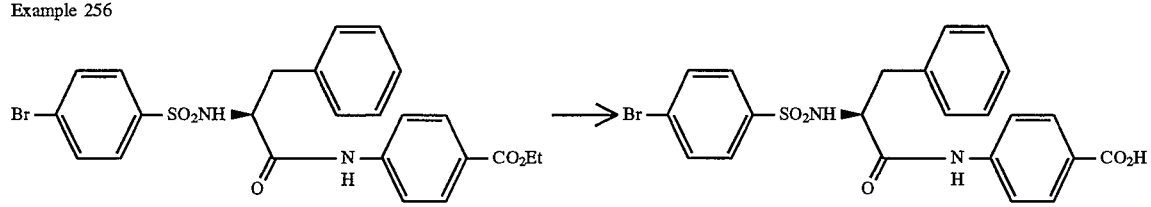
Example 257
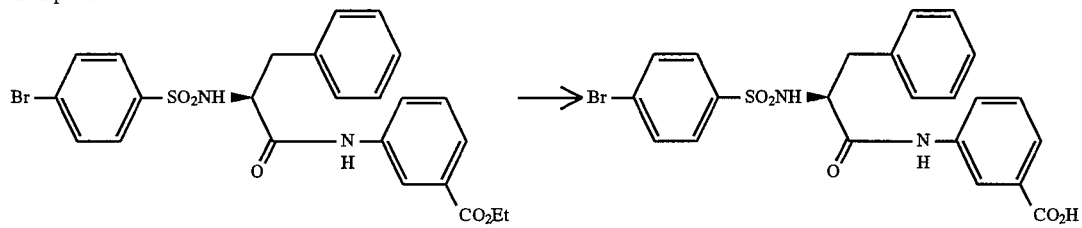
Example 258
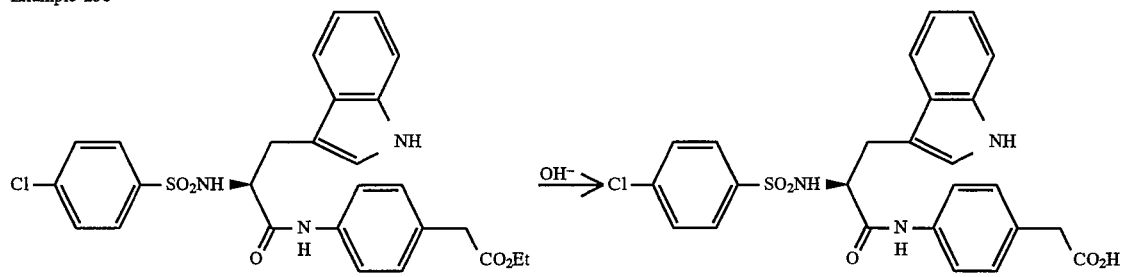
Example 259
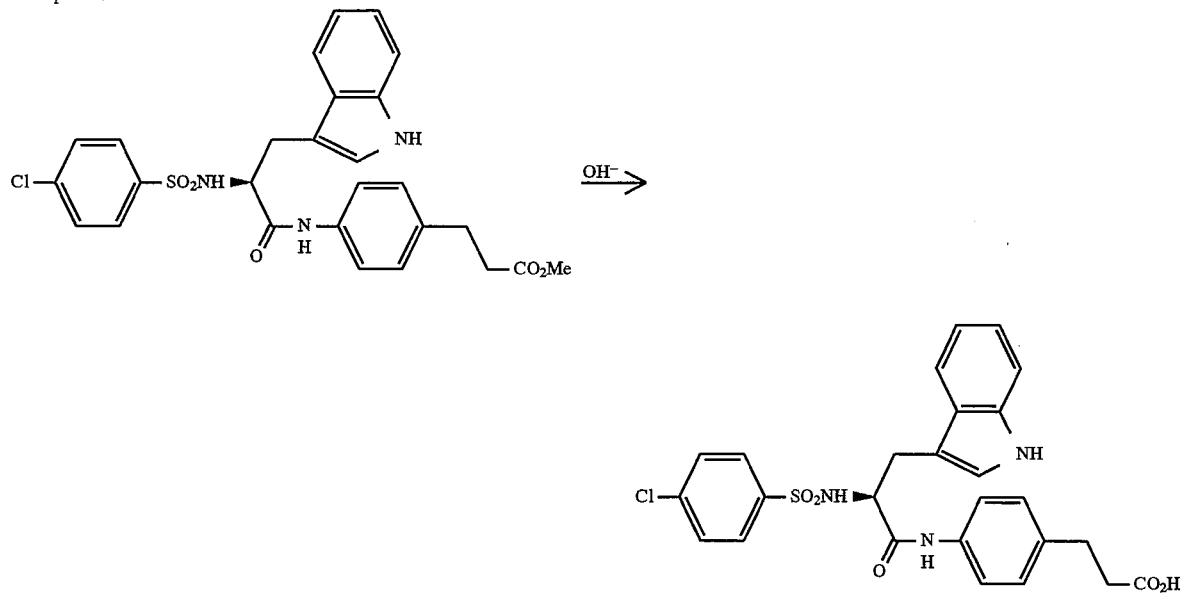
Example 260
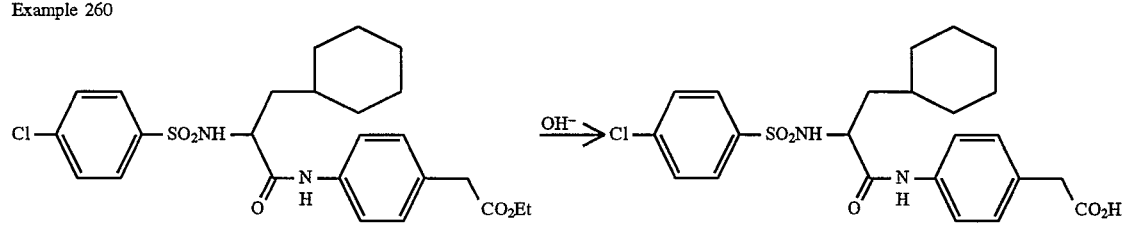

Example 261

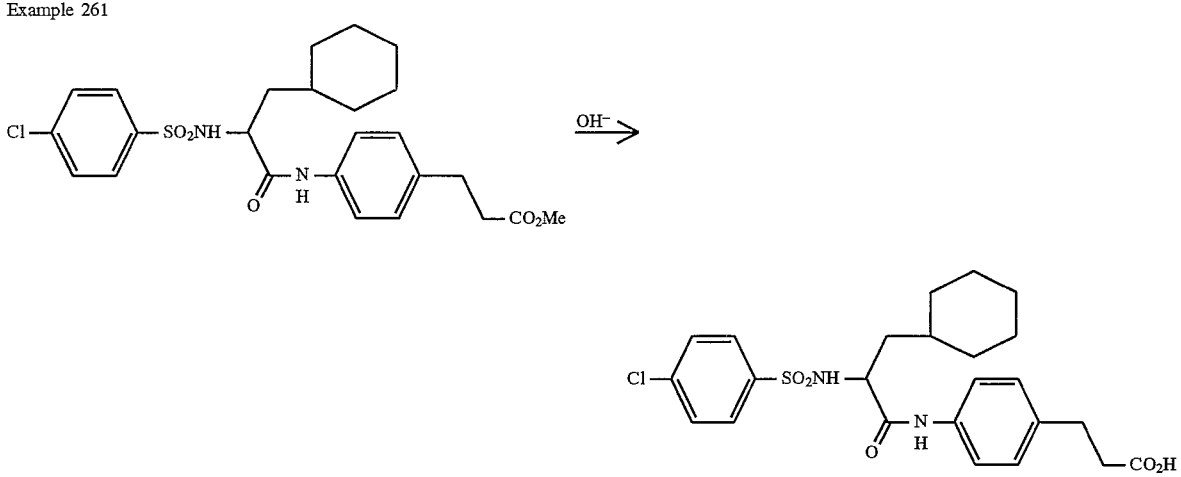

-continued

We claim:

1. An arylsulfonamide derivative of the general formula (I):

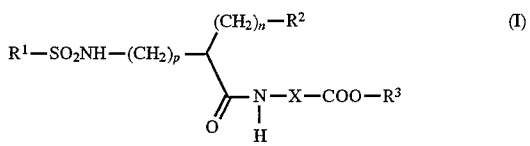

wherein $R^1$ is an unsubstituted phenyl or naphthyl group, or a phenyl group substituted by 1 to 3 same or different substituents selected from the group consisting of a halogen atom, alkyl group, nitro group and alkoxy group, $R^2$ is a straight, branched, or branched cyclic alkyl group with 1 to 15 carbon atoms, phenyl group, phenyloxyl group, phenyloxy group substituted by one or more halogen atoms, cycloalkyl group with 5 to 7 carbon atoms, indolyl group, alkylthiol group with 1 to 4 carbon atoms, hydroxyl group, protected hydroxyl group, imidazolyl group, pyridyloxyl group, or —$OSO_2R^4$ group, $R^4$ is a straight or branched alkyl group with 1 to 15 carbon atoms, or unsubstituted phenyl or thienyl group, or a phenyl or thienyl group substituted by 1 to 3 same or different substituents selected from the group consisting of a halogen atom, alkyl group, nitro group and alkoxy group, $R^3$ is a hydrogen atom or straight or branched alkyl group with 1 to 20 carbon atoms, n is an integer of 0 to 10, p is an integer of 0 to 10, X is a group of the general formula —$(CH_2)$m-A-$(CH_2)$q-, m and q are independently an integer of 0 to 8, and A is a direct bond or phenylene group, or a salt thereof.

2. An arylsulfonamide derivative or a salt thereof according to claim 1, wherein $R^1$ is an unsubstituted phenyl or naphthyl group, or a phenyl or thienyl group substituted by 1 to 3 same or different substituents selected from the group consisting of a halogen atom, straight or branched alkyl group with 1 to 10 carbon atoms, nitro group and straight or branched alkoxy group with 1 to 10 carbon atoms, $R^2$ is a straight, branched or branched cyclic alkyl group with 1 to 8 carbon atoms, phenyl, phenyloxy, phenyloxy group substituted by one or more halogen atoms, cyclohexyl, indolyl, alkylthiol group with 1 to 3 carbon atoms, hydroxyl, tetrahydropyranyloxy, imidazolyl, pyridyloxy or —$OSO_2R^4$ group, $R^4$ is a straight or branched alkyl group with 1 to 8 carbon atoms, $R^3$ is a hydrogen atom or straight or branched alkyl group with 1 to 5 carbon atoms, n is an integer of 0 to 2, p is 0 or 1, X is a group of the general formula —$(CH_2)$m-A-$(CH_2)$q-, m and q are independently an integer of 0 to 5, and A is a direct bond or 1,2-, 1,3-, or 1,4-phenylene group.

3. An arylsulfonamide derivative or a salt thereof according to claim 1, wherein $R^1$ is an unsubstituted phenyl or naphthyl group or a phenyl group substituted by 1 or 2 same or different substituents selected from the group consisting of a halogen atom, straight alkyl group with 1 to 2 carbon atoms, nitro group and straight alkoxy group with 1 to 2 carbon atoms, $R^2$ is a straight or branched alkyl group with 1 to 6 carbon atoms, phenyl, phenyloxy, phenyloxy group substituted by one or more halogen atoms, cyclohexyl, 3-indolyl, alkylthio group with 1 to 2 carbon atoms, hydroxyl, 2-tetrahydropyranyloxy, 1-imidazolyl, 3-pyridyloxy or —$OSO_2CH_3$ group, $R^3$ is a hydrogen atom or alkyl group with 1 to 3 carbon atoms, n is an integer of 0 to 2, p is 0 or 1, X is a group of the general formula —$(CH_2)$m-A-$(CH_2)$q-, m and q are independently an integer of 0 to 5, and A is a direct bond or 1,3-or 1,4-phenylene group.

4. A process for manufacturing an arylsulfonamide derivative of the general formula (I):

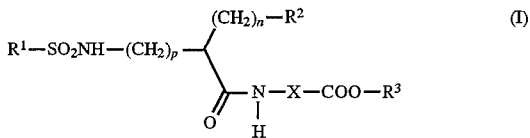

wherein $R^1$ is an unsubstituted phenyl or naphthyl group, or a phenyl group substituted by 1 to 3 same or different substituents selected from the group consisting of a halogen atom, alkyl group, nitro group and alkoxy group, $R^2$ is a straight, branched, or branched cyclic alkyl group with 1 to 15 carbon atoms, phenyl group, phenyloxyl group, phenyloxy group substituted by one or more halogen atoms, cycloalkyl group with 5 to 7 carbon atoms, indolyl group, alkylthiol group with 1 to 4 carbon atoms, hydroxyl group, protected hydroxyl group, imidazolyl group, pyridyloxyl group, or —$OSO_2R^4$ group, $R^4$ is a straight or branched alkyl group with 1 to 15 carbon atoms, or unsubstituted phenyl or thienyl group, or a phenyl or thienyl group substituted by 1 to 3 same or different substituents selected from the group consisting of a halogen atom, alkyl group, nitro group and alkoxy group, R³ is a hydrogen atom or straight or branched alkyl group with 1 to 20 carbon atoms, n is an integer of 0 to 10, p is an integer of 0 to 10, X is a group of the general formula

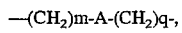

m and q are independently an integer of 0 to 8, and A is a direct bond or phenylene group, or a salt thereof, comprising reacting a sulfonylaminocarboxylic acid compound of the general formula (II):

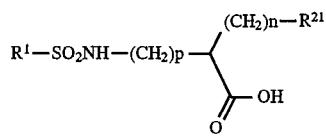

wherein $R^{21}$ is a straight, branched or branched cyclic alkyl group with 1 to 15 carbon atoms, phenyl group, cycloalkyl group with 5 to 7 carbon atoms, indolyl group, alkylthio group with 1 to 4 carbon atoms, protected hydroxyl group, or imidazolyl group, and $R^1$, n, and p have the same meanings as above, with an amino acid ester compound of the general formula (III):

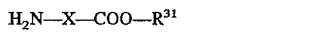

wherein $R^{31}$ is a straight or branched alkyl group with 1–20 carbon atoms, and X has the same meaning as above, to obtain the arylsulfonamide derivative of the general formula (I) wherein $R^2$ is the group $R^{21}$ and $R^3$ is the group $R^{31}$, and then, if desired, converting the group $R^{21}$ and/or $R^{31}$ into another group $R^2$ and/or $R^3$.

5. A process for manufacturing an arylsulfonamide derivative of the general formula (I):

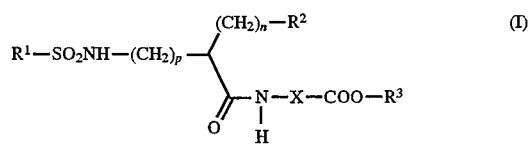

wherein $R^1$ is an unsubstituted phenyl or naphthyl group, or a phenyl group substituted by 1 to 3 same or different substituents selected from the group consisting of a halogen atom, alkyl group, nitro group and alkoxy group, $R^2$ is a straight, branched, or branched cyclic alkyl group with 1 to 15 carbon atoms, phenyl group, phenyloxyl group, phenyloxy group substituted by one or more halogen atoms, cycloalkyl group with 5 to 7 carbon atoms, indolyl group, alkylthiol group with 1 to 4 carbon atoms, hydroxyl group, protected hydroxyl group, imidazolyl group, pyridyloxyl group, or —OSO₂R⁴ group, R⁴ is a straight or branched alkyl group with 1 to 15 carbon atoms, or unsubstituted phenyl or thienyl group, or a phenyl or thienyl group substituted by 1 to 3 same or different substituents selected from the group consisting of a halogen atom, alkyl group, nitro group and alkoxy group, R³ is a hydrogen atom or straight or branched alkyl group with 1 to 20 carbon atoms, n is an integer of 0 to 10, p is an integer of 0 to 10, X is a group of the general formula

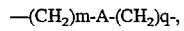

m and q are independently an integer of 0 to 8, and A is a direct bond or phenylene group, or a salt thereof, comprising reacting a carbonylaminocarboxylic acid compound of the general formula (V):

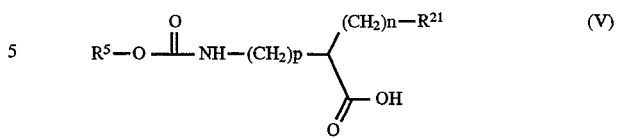

wherein $R^5$ is a straight or branched alkyl group with 1 to 20 carbon atoms, or unsubstituted benzyl group or a benzyl group substituted by 1 to 3 same or different substituents selected from the group consisting of a halogen atom, alky group, nitro group, alkoxy group or hydroxyl group, $R^{21}$ is a straight, branched or branched cyclic alkyl group with 1 to 15 carbon atoms, phenyl group, cycloalkyl group with 5 to 7 carbon atoms, indolyl group, alkylthio group with 1 to 4 carbon atoms, protected hydroxyl group, or imidazolyl group, and n and p have the same meanings as above, with an amino acid ester compound of the general formula (III):

wherein $R^{21}$ is a straight or branched alkyl group with 1–20 carbon atoms, and X has the same meaning as above, to produce a carbonylamine derivative of the general formula (VI):

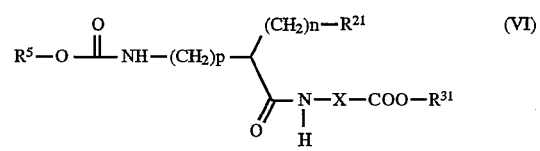

wherein $R^5$, $R^{21}$, $R^{31}$ and X have the same meanings as above, then hydrogenolyzing the carbonylamine derivative of the general formula (VI) to remove the $R^5$—O—CO— group and obtain an amine derivative of the general formula (VII):

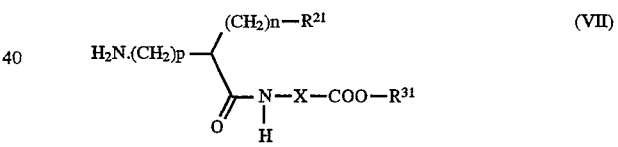

wherein $R^5$, $R^{21}$, $R^{31}$ and X have the same meanings as above, and then, sulfonating the resulting derivative with a sulfonating agent to produce the arylsulfonamide derivative of the general formula (I) wherein $R^2$ is the group $R^{21}$ and $R^3$ is the group $R^{31}$, and then, if desired, converting the group $R^{21}$ and/or $R^{31}$ into another group $R^2$ and/or $R^3$.

6. A pharmaceutical composition comprising an arylsulfonamide derivative of the general formula (I):

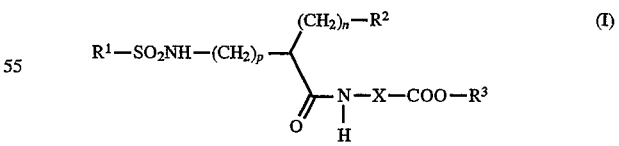

wherein $R^1$ is an unsubstituted phenyl or naphthyl group, or a phenyl group substituted by 1 to 3 same or different substituents selected from the group consisting of a halogen atom, alkyl group, nitro group and alkoxy group, $R^2$ is a straight, branched, or branched cyclic alkyl group with 1 to 15 carbon atoms, phenyl group, phenyloxyl group, phenyloxy group substituted by one or more halogen atoms, cycloalkyl group with 5 to 7 carbon atoms, indolyl group, alkylthiol group with 1 to 4 carbon atoms, hydroxyl group, protected hydroxyl group, imidazolyl group, pyridyloxyl group, or —$OSO_2R^4$ group, $R^4$ is a straight or branched alkyl group with 1 to 15 carbon atoms, or unsubstituted phenyl or thienyl group, or a phenyl or thienyl group substituted by 1 to 3 same or different substituents selected from the group consisting of a halogen atom, alkyl group, nitro group and alkoxy group, $R^3$ is a hydrogen atom or straight or branched alkyl group with 1 to 20 carbon atoms, n is an integer of 0 to 10, p is an integer of 0 to 10, X is a group of the general formula —$(CH_2)m$-A-$(CH_2)q$-, m and q are independently an integer of 0 to 8, and A is a direct bond or phenylene group, or a pharmaceutically acceptable salt thereof, and a pharmaceutically acceptable carrier.

7. A pharmaceutical composition according to claim 6, which is a thromboxane $A_2$ antagonist.

8. A method for treatment of competitive inhibitory to a thromboxane $A_2$, comprising administering to a mammal in need thereof the compound according to claim 1 in an amount effective for a thromboxane $A_2$ antagonism.

9. A method of treating at least one disease selected from the group consisting of cardiac infarction, cerebral infarction, pneumobstruction, thrombosis, renal insufficiency, gestational toxemia and asthma due to bronchoconstriction, comprising: administering to a mammal in need thereof an effective amount of the pharmaceutical composition according to claim 6.

* * * * *